US012370269B2

(12) United States Patent
Ash et al.

(10) Patent No.: US 12,370,269 B2
(45) Date of Patent: Jul. 29, 2025

(54) RETINAL PROTECTIVE FACTOR 2 (RPF2) PROTEIN DELIVERED BY ADENO-ASSOCIATED VIRUS EXPRESSION

(71) Applicant: University of Florida Research Foundation, Incorporated, Gainesville, FL (US)

(72) Inventors: John Ash, Gainesville, FL (US); Clayton Pio Santiago, Catonsville, MD (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1367 days.

(21) Appl. No.: 16/977,124

(22) PCT Filed: Mar. 2, 2019

(86) PCT No.: PCT/US2019/020454
§ 371 (c)(1),
(2) Date: Sep. 1, 2020

(87) PCT Pub. No.: WO2019/169371
PCT Pub. Date: Sep. 6, 2019

(65) Prior Publication Data
US 2021/0046193 A1 Feb. 18, 2021

Related U.S. Application Data

(60) Provisional application No. 62/637,485, filed on Mar. 2, 2018.

(51) Int. Cl.
| | | |
|---|---|---|
| *A61P 27/02* | (2006.01) | |
| *A61K 48/00* | (2006.01) | |
| *C07K 14/54* | (2006.01) | |
| *C12N 9/06* | (2006.01) | |

(52) U.S. Cl.
CPC .......... *A61K 48/0075* (2013.01); *A61P 27/02* (2018.01); *C07K 14/5415* (2013.01); *C12N 9/003* (2013.01)

(58) Field of Classification Search
CPC ...... A61P 27/02; C07K 14/5415; C12N 9/003
See application file for complete search history.

(56) References Cited

U.S. PATENT DOCUMENTS

| 5,443,825 A | 8/1995 | Gearing et al. |
| 6,346,415 B1 | 2/2002 | Feldhaus |

| 2004/0235160 A1 | 11/2004 | Nishikawa et al. |
| 2007/0292922 A1* | 12/2007 | Fang .................... C07K 14/005 435/69.6 |
| 2013/0280224 A1 | 10/2013 | Monsonego |

FOREIGN PATENT DOCUMENTS

WO WO 2011/057144 A2 5/2011

OTHER PUBLICATIONS

Quintino L, Manfré G, Wettergren EE, Namislo A, Isaksson C, Lundberg C. Functional neuroprotection and efficient regulation of GDNF using destabilizing domains in a rodent model of Parkinson's disease. Mol Ther. Dec. 2013;21(12):2169-80. (Year: 2013).*
Naso MF, Tomkowicz B, Perry WL 3rd, Strohl WR. Adeno-Associated Virus (AAV) as a Vector for Gene Therapy. BioDrugs. Aug. 2017;31(4):317-334. doi: 10.1007/s40259-017-0234-5. (Year: 2017).*
Im DS, Muzyczka N. The AAV origin binding protein Rep68 is an ATP-dependent site-specific endonuclease with DNA helicase activity. Cell. May 4, 1990;61(3):447-57. (Year: 1990).*
Leaver SG, Cui Q, Plant GW, Arulpragasam A, Hisheh S, Verhaagen J, Harvey AR. AAV-mediated expression of CNTF promotes long-term survival and regeneration of adult rat retinal ganglion cells. Gene Ther. Sep. 2006;13(18):1328-41. (Year: 2006).*
Nam JH et al. TRPV1 on astrocytes rescues nigral dopamine neurons in Parkinson's disease via CNTF. Brain. Dec. 2015;138(Pt 12):3610-22. (Year: 2015).*
International Search Report and Written Opinion mailed May 13, 2019 in connection with Application No. PCT/US2019/020454.
International Preliminary Report on Patentability mailed Sep. 17, 2020 in connection with Application No. PCT/US2019/020454.
PCT/US2019/020454, May 13, 2019, International Search Report and Written Opinion.
PCT/US2019/020454, Sep. 17, 2020, International Preliminary Report on Patentability.

* cited by examiner

*Primary Examiner* — Nicole Kinsey White
*Assistant Examiner* — Ruixue Wang
(74) *Attorney, Agent, or Firm* — Wolf, Greenfield & Sacks, P.C.

(57) ABSTRACT

In some aspects, the disclosure relates to compositions and methods useful for maintaining or improving retinal function and/or morphology. The disclosure is based, in part, on isolated nucleic acids encoding certain neurotrophic factors (e.g., leukemia inhibitory factor (LIF), etc.) and gene therapy vectors (e.g., recombinant adeno-associated virus (rAAV) vectors) encoding the same. In some embodiments, isolated nucleic acids and gene therapy vectors described by the disclosure are useful for treatment of certain diseases or disorders of the eye, for example retinal degeneration, retinitis pigmentosa (RP), age-related macular degeneration (AMD), glaucoma, etc.

6 Claims, 42 Drawing Sheets
Specification includes a Sequence Listing.

SEQUENCE LISTING

<160> NUMBER OF SEQ ID NOS: 32

<210> SEQ ID NO 1
<211> LENGTH: 609
<212> TYPE: DNA
<213> ORGANISM: Artificial Sequence
<220> FEATURE:
<223> OTHER INFORMATION: Synthetic Polynucleotide

<400> SEQUENCE: 1

```
atgaaggtct tggcggcagg agttgtgccc ctgctgttgg ttctgcactg gaaacatggg      60
gcggggagcc ccctccccat caccectgtc aacgccacct gtgccatacg ccacccatgt     120
cacaacaacc tcatgaacca gatcaggagc caactggcac agctcaatgg cagtgccaat     180
gccctctta ttctctatta cacagcccag ggggagccgt tccccaacaa cctggacaag     240
ctatgtggcc caacgtgac ggacttcccg cccttccacg ccaacggcac ggagaaggcc     300
aagctggtgg agctgtaccg catagtcgtg taccttggca cctccctggg caacatcacc     360
cgggaccaga agatcctcaa ccccagtgcc ctcagcctcc acagcaagct caacgccacc     420
gccgacatcc tgcgaggcct ccttagcaac gtgctgtgcc gctgtgcag caagtaccac      480
gtgggccatg tggacgtgac ctacggccct gacacctcgg gtaaggatgt cttccagaag      540
aagaagctgg gctgtcaact cctggggaag tataagcaga tcatcgccgt gttggcccag     600
gccttctag                                                              609
```

<210> SEQ ID NO 2
<211> LENGTH: 202
<212> TYPE: PRT
<213> ORGANISM: Artificial Sequence
<220> FEATURE:
<223> OTHER INFORMATION: Synthetic Polypeptide

<400> SEQUENCE: 2

```
Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190
```

Gln Ile Ile Ala Val Leu Ala Gln Ala Phe
        195                 200

<210> SEQ ID NO 3
<211> LENGTH: 1143
<212> TYPE: DNA
<213> ORGANISM: Artificial Sequence
<220> FEATURE:
<223> OTHER INFORMATION: Synthetic Polynucleotide

<400> SEQUENCE: 3

```
atgaaagtgc tggctgccgg cgtggttcct ctgctgctgg tacttcactg gaagcacggt      60
gccggctcac cactccccat caccccagta aacgcgacct cgctattag acacccatgt     120
cacaacaacc tgatgaacca gattcgctcc caactggccc agctgaacgg gagtgctaat    180
gctctgttca tcttgtatta cacagcccaa ggagaaccct ttcccaataa ccttgataaa    240
ctgtgcggcc ccaatgtgac cgatttcccc cccttccatg ctaacgggac ggagaaagct    300
aaactggtcg agctgtaccg gatagttgtg tacttgggca tcactcggc aacattaca     360
cgggatcaga agatcctgaa cccttctgcc ctttctttgc atagcaagct gaacgccacg    420
gctgacatac tgaggggtct gctttctaat gtgttgtgcc ggctttgctc taagtaccat    480
gtaggccatg tagatgtgac gtacggtccg gatacttcag ggaaagacgt attccagaaa    540
aagaagttgg ggtgccagct gctggggaaa tataagcaga tcatagccgt tctggcccag    600
gcttttacca gatctcgcaa gaagcgcagc accagatctc gcaagaagcg cagcggggcc    660
cccatgatat ctctgatcgc tgctcttgct gtggactacg tgattggtat ggagaatgct    720
atgccctgga atctgcctgc agacctggca tggtttaaga ggaacaccct taataaacct    780
gtaatcatgg gacgacatac atgggagagt atcggcaggc cattgcccgg gaggaagaat    840
ataattctga gttcccagcc ttctactgat gatagggtaa cttgggtcaa gagcgtcgac    900
gaggccatcg ccgcttgcgg ggatgtgcct gaaatcatgg ttatcggggg cggacgggtg    960
attgagcaat ttctgcccaa ggcacagaag ctgtatctga cccatataga cgccgaggtg   1020
gagggagata cacactttcc cgactatgag cccgatgatt gggagagtgt ctttagcgaa   1080
tttcatgacg ccgacgcaca gaattcccat agctactgct cgaaattctc gaacggcgc    1140
tag                                                                 1143
```

<210> SEQ ID NO 4
<211> LENGTH: 380
<212> TYPE: PRT
<213> ORGANISM: Artificial Sequence
<220> FEATURE:
<223> OTHER INFORMATION: Synthetic Polypeptide

<400> SEQUENCE: 4

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

```
Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
            115                 120                 125

Ser Ala Leu Ser Leu His Ser Lys Leu Asn Ala Thr Ala Asp Ile Leu
130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Leu Gly Cys Gln Leu Leu Gly Lys Tyr Lys
                180                 185                 190

Gln Ile Ile Ala Val Leu Ala Gln Ala Phe Thr Arg Ser Arg Lys Lys
                195                 200                 205

Arg Ser Thr Arg Ser Arg Lys Lys Arg Ser Gly Ala Pro Met Ile Ser
            210                 215                 220

Leu Ile Ala Ala Leu Ala Val Asp Tyr Val Ile Gly Met Glu Asn Ala
225                 230                 235                 240

Met Pro Trp Asn Leu Pro Ala Asp Leu Ala Trp Phe Lys Arg Asn Thr
                245                 250                 255

Leu Asn Lys Pro Val Ile Met Gly Arg His Thr Trp Glu Ser Ile Gly
                260                 265                 270

Arg Pro Leu Pro Gly Arg Lys Asn Ile Ile Leu Ser Ser Gln Pro Ser
            275                 280                 285

Thr Asp Asp Arg Val Thr Trp Val Lys Ser Val Asp Glu Ala Ile Ala
290                 295                 300

Ala Cys Gly Asp Val Pro Glu Ile Met Val Ile Gly Gly Gly Arg Val
305                 310                 315                 320

Ile Glu Gln Phe Leu Pro Lys Ala Gln Lys Leu Tyr Leu Thr His Ile
                325                 330                 335

Asp Ala Glu Val Glu Gly Asp Thr His Phe Pro Asp Tyr Glu Pro Asp
            340                 345                 350

Asp Trp Glu Ser Val Phe Ser Glu Phe His Asp Ala Asp Ala Gln Asn
            355                 360                 365

Ser His Ser Tyr Cys Phe Glu Ile Leu Glu Arg Arg
            370                 375                 380

<210> SEQ ID NO 5
<211> LENGTH: 414
<212> TYPE: PRT
<213> ORGANISM: Artificial Sequence
<220> FEATURE:
<223> OTHER INFORMATION: Synthetic Polypeptide

<400> SEQUENCE: 5

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
            35                  40                  45

Ser Ala Gln Gln Gln Gln Gln Gln Gln Gln Gln Gln Gln Gln Ala Pro
50                  55                  60
```

```
Gln Leu Arg Pro Ala Ala Asp Gly Gln Pro Ser Gly Gly Gly His Lys
 65                  70                  75                  80

Ser Ala Pro Lys Gln Val Lys Arg Gln Arg Ser Ser Pro Glu Leu
                 85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
            180                 185                 190

Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
210                 215                 220

Glu Glu Gln Glu Leu Leu Asp Phe Thr Asn Trp Phe Thr Arg Ser Arg
225                 230                 235                 240

Lys Lys Arg Ser Thr Arg Ser Arg Lys Lys Arg Ser Gly Ala Pro Met
                245                 250                 255

Ile Ser Leu Ile Ala Ala Leu Ala Val Asp Tyr Val Ile Gly Met Glu
            260                 265                 270

Asn Ala Met Pro Trp Asn Leu Pro Ala Asp Leu Ala Trp Phe Lys Arg
        275                 280                 285

Asn Thr Leu Asn Lys Pro Val Ile Met Gly Arg His Thr Trp Glu Ser
290                 295                 300

Ile Gly Arg Pro Leu Pro Gly Arg Lys Asn Ile Ile Leu Ser Ser Gln
305                 310                 315                 320

Pro Ser Thr Asp Asp Arg Val Thr Trp Val Lys Ser Val Asp Glu Ala
                325                 330                 335

Ile Ala Ala Cys Gly Asp Val Pro Glu Ile Met Val Ile Gly Gly Gly
            340                 345                 350

Arg Val Ile Glu Gln Phe Leu Pro Lys Ala Gln Lys Leu Tyr Leu Thr
        355                 360                 365

His Ile Asp Ala Glu Val Glu Gly Asp Thr His Phe Pro Asp Tyr Glu
370                 375                 380

Pro Asp Asp Trp Glu Ser Val Phe Ser Glu Phe His Asp Ala Asp Ala
385                 390                 395                 400

Gln Asn Ser His Ser Tyr Cys Phe Glu Ile Leu Glu Arg Arg
                405                 410

<210> SEQ ID NO 6
<211> LENGTH: 3540
<212> TYPE: DNA
<213> ORGANISM: Artificial Sequence
<220> FEATURE:
<223> OTHER INFORMATION: Synthetic Polynucleotide

<400> SEQUENCE: 6
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
```

```
gccaactcca tcactagggg ttcctcagat ctgaattcgg tacctagtta ttaatagtaa    180
tcaattacgg ggtcattagt tcatagccca tatatggagt tccgcgttac ataacttacg    240
gtaaatggcc cgcctggctg accgcccaac gaccccgcc cattgacgtc aataatgacg     300
tatgttccca tagtaacgcc aatagggact ttccattgac gtcaatgggt ggagtattta    360
cggtaaactg cccacttggc agtacatcaa gtgtatcata tgccaagtac gccccctatt    420
gacgtcaatg acggtaaatg gcccgcctgg cattatgccc agtacatgac cttatgggac    480
tttcctactt ggcagtacat ctacgtatta gtcatcgcta ttaccatggt cgaggtgagc    540
cccacgttct gcttcactct ccccatctcc cccccctccc cacccccaat tttgtattta    600 tttattttt aattattttg tgcagcgatg ggggcggggg ggggggggg gcgcgcgcca      660 ggcggggcgg ggcggggcga ggggcggggc ggggcgaggc ggagaggtgc ggcggcagcc    720
aatcagagcg gcgcgctccg aaagtttcct tttatggcga ggcggcggcg gcggcggccc    780
tataaaaagc gaagcgcgcg gcgggcggga gtcgctgcgc gctgccttcg ccccgtgccc    840
cgctccgccg ccgcctcgcg ccgcccgccc cggctctgac tgaccgcgtt actcccacag    900
gtgagcgggc gggacggccc ttctcctccg ggctgtaatt agcgcttggt ttaatgacgg    960
cttgtttctt ttctgtggct gcgtgaaagc cttgagggc tccgggaggg ccctttgtgc    1020 gggggagcg gctcgggggg tgcgtgcgtg tgtgtgtgcg tggggagcgc gcgtgcggc     1080 tccgcgctgc ccggcggctg tgagcgctgc gggcgcggcg cggggctttg tgcgctccgc    1140
agtgtgcgcg aggggagcgc ggccggggc ggtgccccgc ggtgcggggg gggctgcgag    1200
gggaacaaag gctgcgtgcg gggtgtgtgc gtgggggggt gagcaggggg tgtgggcgcg    1260
tcggtcgggc tgcaaccccc cctgcacccc cctccccgag ttgctgagca cggcccggct    1320
tcgggtgcgg ggctccgtac ggggcgtggc gcggggctcg ccgtgccggg cggggggtgg    1380
cggcaggtgg gggtgccggg cggggcgggg ccgcctcggg ccggggaggg ctcggggag    1440 gggcgcggcg gcccccggag cgccggcggc tgtcgaggcg cggcgagccg cagccattgc    1500
cttttatggt aatcgtgcga gagggcgcag ggacttcctt tgtcccaaat ctgtgcggag    1560
ccgaaatctg ggaggcgccg ccgcacccc tctagcgggc gcggggcgaa gcggtgcggc    1620
gccggcagga aggaaatggg cggggagggc cttcgtgcgt cgccgcgccg ccgtccccctt    1680 ctccctctcc agcctcgggg ctgtccgcgg gggacggct gccttcgggg gggacggggc    1740
agggcggggt tcggcttctg gcgtgtgacc ggcggctcta gagcctctgc taaccatgtt    1800
catgccttct tcttttttcct acagctcctg ggcaacgtgc tggttattgt gctgtctcat    1860
cattttggca aagaattcct cgaagatcta ggcaacgcgt ctcgaggcgg ccgccgccac    1920
catggagtct tctgctaaaa tggaaagcgg aggagcaggt cagcagccgc agccacagcc    1980
ccaacagccg tttctccctc cggccgcatg cttttttcgca acagcagccg cagctgcggc    2040
cgctgccgct gctgctgccg ctcaatcagc ccaacagcag caacaacaac agcaacagca    2100
gcaacaggcc ccacaactga gaccagcagc tgacgggcaa ccctcagggg gtggacataa    2160
gagtgcccca aagcaagtta agcgccaacg ctcaagttcc ccggagctga tgcggtgtaa    2220
gagacgcctg aactttagcg ggttcggcta cagcctgccc caacagcaac cagcagccgt    2280
agccaggaga aatgaaaggg agcgcaatcg ggttaagctc gtcaacctcg gcttcgcaac    2340
tctgcgcgaa cacgtcccaa atggagcggc taacaagaaa atgagtaaag ttgagactct    2400
ccgcagtgct gtcgaatata ttcgggcgct tcaacaactt ctcgatgagc acgatgcagt    2460
```

```
gtctgccgcg tttcaggccg gggtcttgtc tccgaccatt tccccgaact actccaatga   2520
cctgaactct atggcaggtt ctcccgtctc ttcctattct tctgatgaag gctcatacga   2580
tcctctgagt cctgaggaac aggaattgtt ggatttcacg aactggttca ccagatctcg   2640
caagaagcgc agcaccagat ctcgcaagaa gcgcagcggg gcccccatga tatctctgat   2700
cgctgctctt gctgtggact acgtgattgg tatggagaat gctatgccct ggaatctgcc   2760
tgcagacctg gcatggttta agaggaacac ccttaataaa cctgtaatca tgggacgaca   2820
tacatgggag agtatcggca ggccattgcc cgggaggaag aatataattc tgagttccca   2880
gccttctact gatgataggg taacttgggt caagagcgtc gacgaggcca tcgccgcttg   2940
cggggatgtg cctgaaatca tggttatcgg gggcggacgg gtgattgagc aatttctgcc   3000
caaggcacag aagctgtatc tgacccatat agacgccgag gtggagggag atacacactt   3060
tcccgactat gagcccgatg attgggagag tgtctttagc gaatttcatg acgccgacgc   3120
acagaattcc catagctact gcttcgaaat tctcgaacgg cgctaggcgg ccgcgcggat   3180
ccagacatga taagatacat tgatgagttt ggacaaacca caactagaat gcagtgaaaa   3240
aaatgcttta tttgtgaaat ttgtgatgct attgctttat ttgtaaccat tataagctgc   3300
aataaacaag ttaacaacaa caattgcatt cattttatgt ttcaggttca gggggaggtg   3360
tgggaggttt tttagtcgac tggggagaga tctgaggaac ccctagtgat ggagttggcc   3420
actccctctc tgcgcgctcg ctcgctcact gaggccgccc gggcaaagcc cgggcgtcgg   3480
gcgacctttg gtcgcccggc ctcagtgagc gagcgagcgc gcagagaggg agtggccaac   3540
```

<210> SEQ ID NO 7
<211> LENGTH: 378
<212> TYPE: PRT
<213> ORGANISM: Artificial Sequence
<220> FEATURE:
<223> OTHER INFORMATION: Synthetic Polypeptide

<400> SEQUENCE: 7

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175
```

```
Arg Phe Ile Ser Ser His Gln Thr Gly Ile Pro Ala Arg Gly Ser His
            180                 185                 190
Tyr Ile Ala Asn Asn Lys Lys Met Thr Arg Ser Arg Lys Lys Arg Ser
        195                 200                 205
Thr Arg Ser Arg Lys Lys Arg Ser Gly Ala Pro Met Ile Ser Leu Ile
    210                 215                 220
Ala Ala Leu Ala Val Asp Tyr Val Ile Gly Met Glu Asn Ala Met Pro
225                 230                 235                 240
Trp Asn Leu Pro Ala Asp Leu Ala Trp Phe Lys Arg Asn Thr Leu Asn
                245                 250                 255
Lys Pro Val Ile Met Gly Arg His Thr Trp Glu Ser Ile Gly Arg Pro
            260                 265                 270
Leu Pro Gly Arg Lys Asn Ile Ile Leu Ser Ser Gln Pro Ser Thr Asp
        275                 280                 285
Asp Arg Val Thr Trp Val Lys Ser Val Asp Glu Ala Ile Ala Ala Cys
    290                 295                 300
Gly Asp Val Pro Glu Ile Met Val Ile Gly Gly Arg Val Ile Glu
305                 310                 315                 320
Gln Phe Leu Pro Lys Ala Gln Lys Leu Tyr Leu Thr His Ile Asp Ala
                325                 330                 335
Glu Val Glu Gly Asp Thr His Phe Pro Asp Tyr Glu Pro Asp Asp Trp
            340                 345                 350
Glu Ser Val Phe Ser Glu Phe His Asp Ala Asp Ala Gln Asn Ser His
        355                 360                 365
Ser Tyr Cys Phe Glu Ile Leu Glu Arg Arg
    370                 375
```

<210> SEQ ID NO 8
<211> LENGTH: 3432
<212> TYPE: DNA
<213> ORGANISM: Artificial Sequence
<220> FEATURE:
<223> OTHER INFORMATION: Synthetic Polynucleotide

<400> SEQUENCE: 8

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctcagat ctgaattcgg tacctagtta ttaatagtaa     180
tcaattacgg ggtcattagt tcatagccca tatatggagt tccgcgttac ataacttacg     240
gtaaatggcc cgcctggctg accgcccaac gacccccgcc cattgacgtc aataatgacg     300
tatgttccca tagtaacgcc aatagggact ttccattgac gtcaatgggt ggagtattta     360
cggtaaactg cccacttggc agtacatcaa gtgtatcata tgccaagtac gccccctatt     420
gacgtcaatg acggtaaatg gcccgcctgg cattatgccc agtacatgac cttatgggac     480
tttcctactt ggcagtacat ctacgtatta gtcatcgcta ttaccatggt cgaggtgagc     540
cccacgttct gcttcactct ccccatctcc cccccctccc cacccccaat tttgtattta     600
tttatttttt aattattttg tgcagcgatg ggggcggggg ggggggggggg gcgcgcgcca     660
ggcggggcgg ggcggggcga ggggcggggc ggggcgaggc ggagaggtgc ggcggcagcc     720
aatcagagcg gcgcgctccg aaagtttcct tttatggcga ggcggcggcg gcggcggccc     780
tataaaaagc gaagcgcgcg gcgggcggga gtcgctgcgc gctgccttcg ccccgtgccc     840
cgctccgccg ccgcctcgcg ccgcccgccc cggctctgac tgaccgcgtt actcccacag     900
```

-continued

```
gtgagcgggc gggacggccc ttctcctccg ggctgtaatt agcgcttggt ttaatgacgg    960
cttgtttctt ttctgtggct gcgtgaaagc cttgaggggc tccgggaggg ccctttgtgc   1020 gggggggagcg gctcgggggg tgcgtgcgtg tgtgtgtgcg tggggagcgc cgcgtgcggc   1080
tccgcgctgc ccggcggctg tgagcgctgc gggcgcggcg cggggctttg tgcgctccgc   1140
agtgtgcgcg aggggagcgc ggccggggc ggtgccccgc ggtgcggggg gggctgcgag    1200
gggaacaaag gctgcgtgcg gggtgtgtgc gtgggggggt gagcagggg tgtgggcgcg    1260 tcggtcgggc tgcaaccccc cctgcacccc cctccccgag ttgctgagca cggcccggct   1320
tcgggtgcgg ggctccgtac ggggcgtggc gcggggctcg ccgtgccggg cgggggtgg    1380 cggcaggtgg gggtgccggg cggggcgggg ccgcctcggg ccggggaggg ctcggggag    1440 gggcgcggcg ccccccggag cgccggcggc tgtcgaggcg cggcgagccg cagccattgc   1500
cttttatggt aatcgtgcga gagggcgcag ggacttcctt tgtcccaaat ctgtgcggag   1560
ccgaaatctg ggaggcgccg ccgcaccccc tctagcgggc gcggggcgaa gcggtgcggc   1620
gccggcagga aggaaatggg cggggagggc cttcgtgcgt cgccgcgccg ccgtcccctt   1680
ctccctctcc agcctcgggg ctgtccgcgg ggggacggct gccttcgggg gggacggggc   1740
agggcggggt tcggcttctg gcgtgtgacc ggcggctcta gagcctctgc taaccatgtt   1800
catgccttct tcttttttcct acagctcctg ggcaacgtgc tggttattgt gctgtctcat   1860
cattttggca aagaattcct cgaagatcta ggcaacgcgt ctcgaggcgg ccgccgccac   1920
catggccttt actgagcata gccccttgac accgcacaga agggatcttt gctccaggtc   1980
catctggctc gcacggaaga tcaggtcaga cctgacagcc ctgaccgaat catatgtaaa   2040
gcaccagggc ctgaataaaa acattaacct cgacagcgca gacggaatgc cggtggcctc   2100
aacagatcag tggtccgaac tgacggaggc ggagcggttg caagaaaact tgcaggcgta   2160
tcgaacgttt cacgtcctgc ttgcccggct tcttgaagac cagcaggttc atttcacgcc   2220
tacagaggga gatttccatc aagcaatcca cactttgctc ctgcaagtcg cggcctttgc   2280
ctatcagatt gaggaactca tgattcttct cgaatataag attccacgga atgaggcgga   2340
tgggatgccg attaacgtgg gcgacggagg gttgtttgag aaaaaactct ggggtttgaa   2400
agttctgcaa gaattgagtc agtggactgt gcgatctatc cacgacttga ggttcatctc   2460
atcccatcaa acaggataca ctgcaagagg ctctcattat atagcgaata ataaaaaaat   2520
gaccagatct cgcaagaagc gcagcaccag atctcgcaag aagcgcagcg ggcccccat    2580 gatatctctg atcgctgctc ttgctgtgga ctacgtgatt ggtatggaga atgctatgcc   2640
ctggaatctg cctgcagacc tggcatggtt taagaggaac accctaata aacctgtaat    2700 catgggacga catacatggg agagtatcgg caggccattg cccgggagga agaatataat   2760
tctgagttcc cagccttcta ctgatgatag ggtaacttgg gtcaagagcg tcgacgaggc   2820
catcgccgct tgcggggatg tgcctgaaat catggttatc gggggcgac  gggtgattga    2880 gcaatttctg cccaaggcac agaagctgta tctgacccat atagacgccg aggtggaggg   2940
agatacacac tttcccgact atgagcccga tgattgggag agtgtctta gcgaatttca    3000 tgacgccgac gcacagaatt cccatagcta ctgcttcgaa attctcgaac ggcgctaggc   3060
ggccgcgcgg atccagacat gataagatac attgatgagt ttggacaaac cacaactaga   3120
atgcagtgaa aaaatgcttt tatttgtgaa atttgtgatg ctattgcttt atttgtaacc   3180
attataagct gcaataaaca agttaacaac aacaattgca ttcatttat gtttcaggtt    3240 caggggagg tgtgggaggt ttttagtcg actgggagaa gatctgagga accctagtg     3300
```

```
atggagttgg ccactccctc tctgcgcgct cgctcgctca ctgaggccgc ccgggcaaag    3360 cccggcgtc gggcgacctt tggtcgcccg gcctcagtga gcgagcgagc gcgcagagag     3420
ggagtggcca ac                                                        3432
```

<210> SEQ ID NO 9
<211> LENGTH: 510
<212> TYPE: PRT
<213> ORGANISM: Artificial Sequence
<220> FEATURE:
<223> OTHER INFORMATION: Synthetic Polypeptide

<400> SEQUENCE: 9

```
Met Ile Ser Leu Ile Ala Ala Leu Ala Val Asp Tyr Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg Gly
145                 150                 155                 160

Ala Pro Lys Lys Lys Arg Lys Val Ser Asn Leu Leu Thr Val His Gln
                165                 170                 175

Asn Leu Pro Ala Leu Pro Val Asp Ala Thr Ser Asp Glu Val Arg Lys
            180                 185                 190

Asn Leu Met Asp Met Phe Arg Asp Arg Gln Ala Phe Ser Glu His Thr
        195                 200                 205

Trp Lys Met Leu Leu Ser Val Cys Arg Ser Trp Ala Ala Trp Cys Lys
    210                 215                 220

Leu Asn Asn Arg Lys Trp Phe Pro Ala Glu Pro Glu Asp Val Arg Asp
225                 230                 235                 240

Tyr Leu Leu Tyr Leu Gln Ala Arg Gly Leu Ala Val Lys Thr Ile Gln
                245                 250                 255

Gln His Leu Gly Gln Leu Asn Met Leu His Arg Arg Ser Gly Leu Pro
            260                 265                 270

Arg Pro Ser Asp Ser Asn Ala Val Ser Leu Val Met Arg Arg Ile Arg
        275                 280                 285

Lys Glu Asn Val Asp Ala Gly Glu Arg Ala Lys Gln Ala Leu Ala Phe
    290                 295                 300

Glu Arg Thr Asp Phe Asp Gln Val Arg Ser Leu Met Glu Asn Ser Asp
305                 310                 315                 320

Arg Cys Gln Asp Ile Arg Asn Leu Ala Phe Leu Gly Ile Ala Tyr Asn
                325                 330                 335
```

```
Thr Leu Leu Arg Ile Ala Glu Ile Ala Arg Ile Arg Val Lys Asp Ile
            340                 345                 350

Ser Arg Thr Asp Gly Gly Arg Met Leu Ile His Ile Gly Arg Thr Lys
        355                 360                 365

Thr Leu Val Ser Thr Ala Gly Val Glu Lys Ala Leu Ser Leu Gly Val
    370                 375                 380

Thr Lys Leu Val Glu Arg Trp Ile Ser Val Ser Gly Val Ala Asp Asp
385                 390                 395                 400

Pro Asn Asn Tyr Leu Phe Cys Arg Val Arg Lys Asn Gly Val Ala Ala
                405                 410                 415

Pro Ser Ala Thr Ser Gln Leu Ser Thr Arg Ala Leu Glu Gly Ile Phe
            420                 425                 430

Glu Ala Thr His Arg Leu Ile Tyr Gly Ala Lys Asp Asp Ser Gly Gln
        435                 440                 445

Arg Tyr Leu Ala Trp Ser Gly His Ser Ala Arg Val Gly Ala Ala Arg
    450                 455                 460

Asp Met Ala Arg Ala Gly Val Ser Ile Pro Glu Ile Met Gln Ala Gly
465                 470                 475                 480

Gly Trp Thr Asn Val Asn Ile Val Met Asn Tyr Ile Arg Asn Leu Asp
                485                 490                 495

Ser Glu Thr Gly Ala Met Val Arg Leu Leu Glu Asp Gly Asp
            500                 505                 510

<210> SEQ ID NO 10
<211> LENGTH: 3838
<212> TYPE: DNA
<213> ORGANISM: Artificial Sequence
<220> FEATURE:
<223> OTHER INFORMATION: Synthetic Polynucleotide

<400> SEQUENCE: 10
ttggccactc cctctctgcg cgctcgctcg ctcactgagg ccgggcgacc aaaggtcgcc      60
cgacgcccgg gctttgcccg gcggcctca  gtgagcgagc gagcgcgcag agagggagtg     120
gccaactcca tcactagggg ttcctcagat ctgaattcgg tacctagtta ttaatagtaa     180
tcaattacgg ggtcattagt tcatagccca tatatggagt tccgcgttac ataacttacg     240
gtaaatggcc cgcctggctg accgcccaac gacccccgcc cattgacgtc aataatgacg     300
tatgttccca tagtaacgcc aatagggact ttccattgac gtcaatgggt ggagtattta     360
cggtaaactg cccacttggc agtacatcaa gtgtatcata tgccaagtac gccccctatt     420
gacgtcaatg acggtaaatg gcccgcctgg cattatgccc agtacatgac cttatgggac     480
tttcctactt ggcagtacat ctacgtatta gtcatcgcta ttaccatggt cgaggtgagc     540
cccacgttct gcttcactct ccccatctcc cccctccc  acccccaat tttgtattta      600 tttatttttt aattattttg tgcagcgatg ggggcggggg gggggggggg gcgcgcgcca     660 ggcgggcgg  ggcgggcga ggggcgggc  ggggcgaggc ggagaggtgc ggcggcagcc     720
aatcagagcg gcgcgctccg aaagtttcct tttatggcga ggcggcggcg gcggcggccc     780
tataaaaagc gaagcgcgcg gcgggcggga gtcgctgcgc gctgccttcg ccccgtgccc     840
cgctccgccg ccgcctcgcg ccgcccgccc cggctctgac tgaccgcgtt actcccacag     900
gtgagcgggc gggacggccc ttctcctccg ggctgtaatt agcgcttggt ttaatgacgg     960
cttgtttctt ttctgtggct gcgtgaaagc cttgaggggc tccggagggc cctttgtgc    1020 gggggagcg  gctcgggggg tgcgtgcgtg tgtgtgtgcg tggggagcgc cgcgtgcggc    1080
```

```
tccgcgctgc ccggcggctg tgagcgctgc gggcgcggcg cggggctttg tgcgctccgc    1140
agtgtgcgcg aggggagcgc ggccgggggc ggtgccccgc ggtgcggggg gggctgcgag    1200
gggaacaaag gctgcgtgcg gggtgtgtgc gtggggggt gagcaggggg tgtgggcgcg     1260
tcggtcgggc tgcaaccccc cctgcacccc cctcccccgag ttgctgagca cggcccggct   1320
tcgggtgcgg ggctccgtac ggggcgtggc gcggggctcg ccgtgccggg cgggggtgg    1380 cggcaggtgg gggtgccggg cggggcgggg ccgcctcggg ccggggaggg ctcggggag    1440 gggcgcggcg gccccccggag cgccggcggc tgtcgaggcg cggcgagccg cagccattgc    1500
cttttatggt aatcgtgcga gagggcgcag ggacttcctt tgtcccaaat ctgtgcggag    1560
ccgaaatctg ggaggcgccg ccgcacccccc tctagcgggc gcggggcgaa gcggtgcggc    1620
gccggcagga aggaaatggg cggggagggc cttcgtgcgt cgccgcgccg ccgtccccctt    1680 ctccctctcc agcctcgggg ctgtccgcgg ggggacggct gccttcgggg gggacgggc     1740 agggcggggt tcggcttctg gcgtgtgacc ggcggctcta gagcctctgc taaccatgtt    1800
catgccttct tctttttcct acagctcctg gcaacgtgc tggttattgt gctgtctcat     1860
cattttggca aagaattcct cgaagatcta ggcctgcagg cggccgccgc caccatgatc    1920
tctctgattg ccgctctggc cgtggactac gtgatcggga tggaaaacgc tatgccatgg    1980
aatctgcccg ccgatctggc ttggttcaag aggaacaccc tgaacaagcc agtgatcatg    2040
ggcagacaca cttgggagtc cattggccgg ccctgcctg gacgcaagaa catcattctg     2100
agctcccagc cctctaccga cgacagggtg acatgggtga aaagtgtgga cgaagccatt    2160
gccgcttgcg gagatgtgcc cgagatcatg gtcatcggcg gagggagagt gatcgagcag    2220
ttcctgccta aggcccagaa actgtacctg actcacattg acgctgaggt ggaaggggac    2280
acccattttc ctgattatga ccagacgat tgggaaagcg tgttctccga gtttcacgac    2340
gccgatgctc agaattctca tagttattgc tttgagatcc tggaaaggag aggcgcgcct    2400
aagaagaaga ggaaggtgtc caatttactg accgtacacc aaaatttgcc tgcattaccg    2460
gtcgatgcaa cgagtgatga ggttcgcaag aacctgatgg acatgttcag ggatcgccag    2520
gcgttttctg agcatacctg gaaaatgctt ctgtccgttt ccggtcgtg ggcggcatgg     2580 tgcaagttga ataaccggaa atggtttccc gcagaacctg aagatgttcg cgattatctt    2640
ctatatcttc aggcgcgcgg tctggcagta aaaactatcc agcaacattt gggccagcta    2700
aacatgcttc atcgtcggtc cgggctgcca cgaccaagtg acagcaatgc tgtttcactg    2760
gttatgcggc ggatccgaaa agaaaacgtt gatgccggtg aacgtgcaaa acaggctcta    2820
gcgttcgaac gcactgattt cgaccaggtt cgttcactca tggaaaatag cgatcgctgc    2880
caggatatac gtaatctggc atttctgggg attgcttata acaccctgtt acgtatagcc    2940
gaaattgcca ggatcagggt taaagatatc tcacgtactg acggtgggag aatgttaatc    3000
catattggca gaacgaaaac gctggttagc accgcaggtg tagagaaggc acttagcctg    3060
ggggtaacta aactggtcga gcgatggatt tccgtctctg gtgtagctga tgatccgaat    3120
aactacctgt tttgccgggt cagaaaaaat ggtgttgccg cgccatctgc caccagccag    3180
ctatcaactc gcgccctgga agggattttt gaagcaactc atcgattgat ttacggcgct    3240
aaggatgact ctggtcagag ataccctggcc tggtctggac acagtgcccg tgtcggagcc    3300
gcgcgagata tggcccgcgc tggagtttca ataccggaga tcatgcaagc tggtggctgg    3360
accaatgtaa atattgtcat gaactatatc cgtaacctgg atagtgaaac aggggcaatg    3420
```

-continued

```
gtgcgcctgc tggaagatgg cgattaggtc gactagagct cgctgatcag cctcgactgt    3480
gccttctagt tgccagccat ctgttgtttg cccctccccc gtgccttcct tgaccctgga    3540
aggtgccact cccactgtcc tttcctaata aaatgaggaa attgcatcgc attgtctgag    3600
taggtgtcat tctattctgg ggggtggggt ggggcaggac agcaaggggg aggattggga    3660
agacaatagc aggcatgctg gggagagatc tgaggaaccc ctagtgatgg agttggccac    3720
tccctctctg cgcgctcgct cgctcactga ggccgcccgg gcaaagcccg ggcgtcgggc    3780
gacctttggt cgcccggcct cagtgagcga gcagcgcgc agagagggag tggccaac     3838
```

<210> SEQ ID NO 11
<211> LENGTH: 356
<212> TYPE: PRT
<213> ORGANISM: Artificial Sequence
<220> FEATURE:
<223> OTHER INFORMATION: Synthetic Polypeptide

<400> SEQUENCE: 11

```
Met Val Ser Val Pro Thr Thr Trp Cys Ser Val Ala Leu Ala Leu Leu
1               5                   10                  15

Val Ala Leu His Glu Gly Lys Gly Gln Ala Ala Ala Thr Leu Glu Gln
            20                  25                  30

Pro Ala Ser Ser His Ala Gln Gly Thr His Leu Arg Leu Arg Arg
        35                  40                  45

Cys Ser Cys Ser Ser Trp Leu Asp Lys Glu Cys Val Tyr Phe Cys His
    50                  55                  60

Leu Asp Ile Ile Trp Val Asn Thr Pro Glu Gln Thr Ala Pro Tyr Gly
65                  70                  75                  80

Leu Gly Asn Pro Pro Arg Arg Arg Arg Ser Leu Pro Arg Arg Cys
                85                  90                  95

Gln Cys Ser Ser Ala Arg Asp Pro Ala Cys Ala Thr Phe Cys Leu Arg
            100                 105                 110

Arg Pro Trp Thr Glu Ala Gly Ala Val Pro Ser Arg Lys Ser Pro Ala
        115                 120                 125

Asp Val Phe Gln Thr Gly Lys Thr Gly Ala Thr Thr Gly Glu Leu Leu
    130                 135                 140

Gln Arg Leu Arg Asp Ile Ser Thr Val Lys Ser Leu Phe Ala Lys Arg
145                 150                 155                 160

Gln Gln Glu Ala Met Arg Glu Pro Arg Ser Thr His Ser Arg Trp Arg
                165                 170                 175

Lys Arg Thr Arg Ser Arg Lys Lys Arg Ser Thr Arg Ser Arg Lys Lys
            180                 185                 190

Arg Ser Gly Ala Pro Met Ile Ser Leu Ile Ala Ala Leu Ala Val Asp
        195                 200                 205

Tyr Val Ile Gly Met Glu Asn Ala Met Pro Trp Asn Leu Pro Ala Asp
    210                 215                 220

Leu Ala Trp Phe Lys Arg Asn Thr Leu Asn Lys Pro Val Ile Met Gly
225                 230                 235                 240

Arg His Thr Trp Glu Ser Ile Gly Arg Pro Leu Pro Gly Arg Lys Asn
                245                 250                 255

Ile Ile Leu Ser Ser Gln Pro Ser Thr Asp Asp Arg Val Thr Trp Val
            260                 265                 270

Lys Ser Val Asp Glu Ala Ile Ala Ala Cys Gly Asp Val Pro Glu Ile
        275                 280                 285

Met Val Ile Gly Gly Gly Arg Val Ile Glu Gln Phe Leu Pro Lys Ala
```

|  |  |  | 290 |  |  |  | 295 |  |  |  | 300 |  |  |
|---|---|---|---|---|---|---|---|---|---|---|---|---|---|

Gln Lys Leu Tyr Leu Thr His Ile Asp Ala Glu Val Glu Gly Asp Thr
305                 310                 315                 320

His Phe Pro Asp Tyr Glu Pro Asp Asp Trp Glu Ser Val Phe Ser Glu
                325                 330                 335

Phe His Asp Ala Asp Ala Gln Asn Ser His Ser Tyr Cys Phe Glu Ile
            340                 345                 350

Leu Glu Arg Arg
        355

<210> SEQ ID NO 12
<211> LENGTH: 3366
<212> TYPE: DNA
<213> ORGANISM: Artificial Sequence
<220> FEATURE:
<223> OTHER INFORMATION: Synthetic Polynucleotide

<400> SEQUENCE: 12

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctcagat | ctgaattcgg | tacctagtta | ttaatagtaa | 180 |
| tcaattacgg | ggtcattagt | tcatagccca | tatatggagt | tccgcgttac | ataacttacg | 240 |
| gtaaatggcc | cgcctggctg | accgcccaac | gacccccgcc | cattgacgtc | aataatgacg | 300 |
| tatgttccca | tagtaacgcc | aatagggact | ttccattgac | gtcaatgggt | ggagtattta | 360 |
| cggtaaactg | cccacttggc | agtacatcaa | gtgtatcata | tgccaagtac | gccccctatt | 420 |
| gacgtcaatg | acggtaaatg | gcccgcctgg | cattatgccc | agtacatgac | cttatgggac | 480 |
| tttcctactt | ggcagtacat | ctacgtatta | gtcatcgcta | ttaccatggt | cgaggtgagc | 540 |
| cccacgttct | gcttcactct | ccccatctcc | cccccctccc | cacccccaat | tttgtattta | 600 |
| tttattttt | aattatttg | tgcagcgatg | ggggcggggg | ggggggggg | gcgcgcgcca | 660 |
| ggcggggcgg | ggcggggcga | ggggcggggc | ggggcgaggc | ggagaggtgc | ggcggcagcc | 720 |
| aatcagagcg | gcgcgctccg | aaagtttcct | tttatggcga | ggcggcggcg | gcggcggccc | 780 |
| tataaaaagc | gaagcgcgcg | gcgggcggga | gtcgctgcgc | gctgccttcg | ccccgtgccc | 840 |
| cgctccgccg | cctcgcg | ccgcccgcc | cggctctgac | tgaccgcgtt | actcccacag | 900 |
| gtgagcgggc | gggacggccc | ttctcctccg | ggctgtaatt | agcgcttggt | ttaatgacgg | 960 |
| cttgtttctt | ttctgtggct | gcgtgaaagc | cttgaggggc | tccggagggc | ccctttgtgc | 1020 |
| gggggagcg | gctcgggggg | tgcgtgcgtg | tgtgtgtgcg | tggggagcgc | cgcgtgcggc | 1080 |
| tccgcgctgc | ccggcggctg | tgagcgctgc | gggcgcggcg | cggggctttg | tgcgctccgc | 1140 |
| agtgtgcgcg | aggggagcgc | ggccggggc | ggtgccccgc | ggtgcggggg | gggctgcgag | 1200 |
| gggaacaaag | gctgcgtgcg | gggtgtgtgc | gtgggggggt | gagcagggg | tgtgggcgcg | 1260 |
| tcggtcgggc | tgcaaccccc | cctgcacccc | cctccccgag | ttgctgagca | cggcccggct | 1320 |
| tcgggtgcgg | ggctccgtac | ggggcgtggc | gcggggctcg | ccgtgccggg | cgggggtgg | 1380 |
| cggcaggtgg | gggtgccggg | cggggcgggg | ccgcctcggg | ccggggaggg | ctcggggag | 1440 |
| gggcgcggcg | gcccccggag | cgccggcggc | tgtcgaggcg | cggcgagccg | cagccattgc | 1500 |
| cttttatggt | aatcgtgcga | gagggcgcag | ggacttcctt | tgtcccaaat | ctgtgcggag | 1560 |
| ccgaaatctg | ggaggcgccg | ccgcaccccc | tctagcgggc | gcggggcgaa | gcggtgcggc | 1620 |
| gccggcagga | aggaaatggg | cggggagggc | cttcgtgcgt | cgccgcgccg | ccgtccccctt | 1680 |

```
ctccctctcc agcctcgggg ctgtccgcgg ggggacggct gccttcgggg gggacggggc      1740
agggcggggt tcggcttctg gcgtgtgacc ggcggctcta gagcctctgc taaccatgtt      1800
catgccttct tcttttcct acagctcctg ggcaacgtgc tggttattgt gctgtctcat       1860
cattttggca aagaattcct cgaagatcta ggcaacgcgt ctcgaggcgg ccgccgccac      1920
catggtgagc gttcctacga catggtgctc agtagctctt gcgcttctgg tagcgctcca     1980
tgaaggcaaa ggccaagcgg ccgcaaccct cgagcagccg gcttcatcct cccacgccca    2040
aggcacgcac ctcagactca gaaggtgttc ctgttcctca tggctggata agaatgtgt      2100 ttattttgc catttggata ttatttgggt caatacgcca gaacaaacgg ccccttacgg       2160
gcttggtaat ccgccacgac ggagaaggag gagtctccct cgcagatgcc aatgctcatc    2220
tgcacgcgac cctgcatgcg ctacgttctg cctcagacga ccgtggactg aagctggtgc    2280
agtgccaagc cgcaaatccc ctgccgatgt gttccaaacg gggaagaccg gggctaccac     2340
tggagaactt ctgcaacgct tgcgggacat ttctacagtc aaatccctgt ttgcaaaaag    2400
gcaacaggag gcgatgcgcg agccccgatc tacccatagc cggtggcgga aaagaaccag     2460
atctcgcaag aagcgcagca ccagatctcg caagaagcgc agcggggccc ccatgatatc    2520
tctgatcgct gctcttgctg tggactacgt gattggtatg gagaatgcta tgccctggaa    2580
tctgcctgca gacctggcat ggtttaagag gaacacccctt aataaacctg taatcatggg    2640
acgacataca tgggagagta tcggcaggcc attgcccggg aggaagaata taattctgag     2700 ttccagcct tctactgatg ataggtaac ttgggtcaag agcgtcgacg aggccatcgc         2760
cgcttgcggg gatgtgcctg aaatcatggt tatcgggggc ggacgggtga ttgagcaatt    2820
tctgcccaag gcacagaagc tgtatctgac ccatatagac gccgaggtgg agggagatac    2880
acactttccc gactatgagc ccgatgattg ggagagtgtc tttagcgaat tcatgacgc     2940 cgacgcacag aattcccata gctactgctt cgaaattctc gaacggcgct aggcggccgc    3000
gcggatccag acatgataag atacattgat gagtttggac aaaccacaac tagaatgcag    3060
tgaaaaaaat gctttatttg tgaaatttgt gatgctattg ctttatttgt aaccattata    3120
agctgcaata aacaagttaa caacaacaat tgcattcatt ttatgtttca ggttcagggg    3180
gaggtgtggg aggttttta gtcgactggg gagagatctg aggaacccct agtgatggag     3240
ttggccactc cctctctgcg cgctcgctcg ctcactgagg ccgcccgggc aaagcccggg    3300
cgtcgggcga cctttggtcg cccggcctca gtgagcgagc gagcgcgcag agagggagtg    3360
gccaac                                                                3366
```

<210> SEQ ID NO 13
<211> LENGTH: 386
<212> TYPE: PRT
<213> ORGANISM: Artificial Sequence
<220> FEATURE:
<223> OTHER INFORMATION: Synthetic Polypeptide

<400> SEQUENCE: 13

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
                20                  25                  30

Leu Ala Ala Gly Thr Ser Asn Pro Asp Pro Pro Thr Val Ser Thr Asp
            35                  40                  45

Gln Leu Leu Pro Leu Gly Gly Gly Arg Asp Arg Lys Val Arg Asp Leu

```
                50             55              60
        Gln Glu Ala Asp Leu Asp Leu Leu Arg Val Thr Leu Ser Ser Lys Pro
        65              70                      75                  80

Gln Ala Leu Ala Thr Pro Asn Lys Glu Glu His Gly Lys Arg Lys Lys
                        85                  90                  95

Lys Gly Lys Gly Leu Gly Lys Lys Arg Asp Pro Cys Leu Arg Lys Tyr
                    100                 105                 110

Lys Asp Phe Cys Ile His Gly Glu Cys Lys Tyr Val Lys Glu Leu Arg
                    115                 120                 125

Ala Pro Ser Cys Ile Cys His Pro Gly Tyr His Gly Glu Arg Cys His
                    130                 135                 140

Gly Leu Ser Leu Pro Val Glu Asn Arg Leu Tyr Thr Tyr Asp His Thr
        145                 150                 155                 160

Thr Ile Leu Ala Val Val Ala Val Val Leu Ser Ser Val Cys Leu Leu
                        165                 170                 175

Val Ile Val Gly Leu Leu Met Phe Arg Tyr His Arg Arg Gly Gly Tyr
                    180                 185                 190

Asp Val Glu Asn Glu Glu Lys Val Lys Leu Gly Met Thr Asn Ser His
                    195                 200                 205

Thr Arg Ser Arg Lys Lys Arg Ser Thr Arg Ser Arg Lys Lys Arg Ser
        210                 215                 220

Gly Ala Pro Met Ile Ser Leu Ile Ala Ala Leu Ala Val Asp Tyr Val
        225                 230                 235                 240

Ile Gly Met Glu Asn Ala Met Pro Trp Asn Leu Pro Ala Asp Leu Ala
                        245                 250                 255

Trp Phe Lys Arg Asn Thr Leu Asn Lys Pro Val Ile Met Gly Arg His
                    260                 265                 270

Thr Trp Glu Ser Ile Gly Arg Pro Leu Pro Gly Arg Lys Asn Ile Ile
                    275                 280                 285

Leu Ser Ser Gln Pro Ser Thr Asp Asp Arg Val Thr Trp Val Lys Ser
        290                 295                 300

Val Asp Glu Ala Ile Ala Ala Cys Gly Asp Val Pro Glu Ile Met Val
        305                 310                 315                 320

Ile Gly Gly Gly Arg Val Ile Glu Gln Phe Leu Pro Lys Ala Gln Lys
                        325                 330                 335

Leu Tyr Leu Thr His Ile Asp Ala Glu Val Glu Gly Asp Thr His Phe
                    340                 345                 350

Pro Asp Tyr Glu Pro Asp Asp Trp Glu Ser Val Phe Ser Glu Phe His
                    355                 360                 365

Asp Ala Asp Ala Gln Asn Ser His Ser Tyr Cys Phe Glu Ile Leu Glu
                    370                 375                 380

Arg Arg
        385

<210> SEQ ID NO 14
<211> LENGTH: 3456
<212> TYPE: DNA
<213> ORGANISM: Artificial Sequence
<220> FEATURE:
<223> OTHER INFORMATION: Synthetic Polynucleotide

<400> SEQUENCE: 14
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
```

```
gccaactcca tcactagggg ttcctcagat ctgaattcgg tacctagtta ttaatagtaa    180
tcaattacgg ggtcattagt tcatagccca tatatggagt tccgcgttac ataacttacg    240
gtaaatggcc cgcctggctg accgcccaac gacccccgcc cattgacgtc aataatgacg    300
tatgttccca gtaacgcc aatagggact ttccattgac gtcaatgggt ggagtattta    360
cggtaaactg cccacttggc agtacatcaa gtgtatcata tgccaagtac gccccctatt    420
gacgtcaatg acggtaaatg gcccgcctgg cattatgccc agtacatgac cttatgggac    480
tttcctactt ggcagtacat ctacgtatta gtcatcgcta ttaccatggt cgaggtgagc    540
cccacgttct gcttcactct ccccatctcc ccccccctccc cacccccaat tttgtattta    600 tttattttt aattattttg tgcagcgatg ggggcggggg ggggggggggg gcgcgcgcca    660 ggcggggcgg ggcggggcga ggggcggggc ggggcgaggc ggagaggtgc ggcggcagcc    720
aatcagagcg gcgcgctccg aaagtttcct tttatggcga ggcggcggcg gcggcggccc    780
tataaaaagc gaagcgcgcg gcgggcggga gtcgctgcgc gctgccttcg ccccgtgccc    840
cgctccgccg ccgcctcgcg ccgcccgccc cggctctgac tgaccgcgtt actcccacag    900
gtgagcgggc gggacggccc ttctcctccg gctgtaatt agcgcttggt ttaatgacgg    960
cttgtttctt ttctgtggct gcgtgaaagc cttgaggggc tccggagggg cccttttgtgc   1020 ggggggagcg gctcgggggg tgcgtgcgtg tgtgtgtgcg tggggagcgc gcgtgcggc    1080 tccgcgctgc ccggcggctg tgagcgctgc gggcgcggcg cggggctttg tgcgctccgc    1140
agtgtgcgcg aggggagcgc ggccgggggc ggtgccccgc ggtgcggggg gggctgcgag   1200
gggaacaaag gctgcgtgcg gggtgtgtgc gtggggggggt gagcagggg tgtgggcgcg   1260 tcggtcgggc tgcaaccccc cctgcaccc cctccccgag ttgctgagca cggcccggct    1320
tcgggtgcgg ggctccgtac ggggcgtggc gcggggctcg ccgtgccggg cggggggtgg    1380
cggcaggtgg gggtgccggg cggggcgggg ccgcctcggg ccgggagggg ctcgggggag   1440
gggcgcggcg gccccggag cgccggcggc tgtcgaggcg cggcgagccg cagccattgc    1500 ctttatggt aatcgtgcga gagggcgcag ggacttcctt tgtcccaaat ctgtgcggag   1560
ccgaaatctg ggaggcgccg ccgcaccccc tctagcgggc gcggggcgaa gcggtgcggc    1620
gccggcagga aggaaatggg cggggagggc cttcgtgcgt cgccgcgccg ccgtcccctt    1680
ctccctctcc agcctcgggg ctgtccgcgc ggggacggct gccttcgggg gggacgggc   1740 agggcgggt tcggcttctg gcgtgtgacc ggcggctcta gagcctctgc taaccatgtt    1800
catgccttct tctttttcct acagctcctg ggcaacgtgc tggttattgt gctgtctcat    1860
cattttggca aagaattcct cgaagatcta ggcaacgcgt ctcgaggcgg ccgccgccac    1920
catgaaactc ctgccgtctg tagtcctgaa actgtttctg gctgctgtgt tgagtgctct    1980
cgttacggga gagtccttgg agaggcttcg acgcggtttg gcagcaggta cgtcaaaccc    2040
agatccccct accgtgagta cggatcagct tctgccgctc ggcggaggaa gggaccgcaa    2100
ggtgcgcgat ctgcaggagg cggaccttga cctgcttcga gttacattgt cctctaagcc    2160
tcaagctctg gcgacgccga acaaagagga gcatggtaag cgaaagaaga aaggcaaagg    2220
gctgggaaaa aaacgcgacc cctgtcttcg caagtataag gacttctgta ttcatggaga    2280
gtgtaagtat gttaaagagc ttcgagctcc cagttgcatt tgccaccctg gtatcacgg    2340 ggaacgctgt catggcttgt cattgccagt tgaaaatcgc ttgtatacgt atgaccatac    2400
cactatcctc gcagtagtag ctgttgtcct ttccagcgtt tgtttgctgg tcatcgtcgg    2460
cttgctgatg tttcggtacc accgacgggg aggttacgat gtagagaacg aggagaaagt    2520
```

-continued

```
caagctgggc atgacaaata gccataccag atctcgcaag aagcgcagca ccagatctcg    2580
caagaagcgc agcggggccc ccatgatatc tctgatcgct gctcttgctg tggactacgt    2640
gattggtatg gagaatgcta tgccctggaa tctgcctgca gacctggcat ggtttaagag    2700
gaacacccct aataaacctg taatcatggg acgacataca tgggagagta tcggcaggcc    2760
attgcccggg aggaagaata taattctgag ttcccagcct tctactgatg atagggtaac    2820
ttgggtcaag agcgtcgacg aggccatcgc cgcttgcggg gatgtgcctg aaatcatggt    2880 tatcggggc ggacgggtga ttgagcaatt tctgcccaag gcacagaagc tgtatctgac    2940
ccatatagac gccgaggtgg agggagatac acactttccc gactatgagc ccgatgattg    3000
ggagagtgtc tttagcgaat tcatgacgc cgacgcacag aattcccata gctactgctt    3060
cgaaattctc gaacggcgct aggcggccgc gcggatccag acatgataag atacattgat    3120
gagtttggac aaaccacaac tagaatgcag tgaaaaaaat gctttatttg tgaaatttgt    3180
gatgctattg ctttatttgt aaccattata agctgcaata aacaagttaa caacaacaat    3240
tgcattcatt ttatgtttca ggttcagggg gaggtgtggg aggttttta gtcgactggg    3300 gagagatctg aggaacccct agtgatgag ttggccactc cctctctgcg cgctcgctcg    3360
ctcactgagg ccgcccgggc aaagcccggg cgtcgggcga cctttggtcg cccggcctca    3420
gtgagcgagc gagcgcgcag agagggagtg gccaac                             3456
```

<210> SEQ ID NO 15
<211> LENGTH: 783
<212> TYPE: PRT
<213> ORGANISM: Artificial Sequence
<220> FEATURE:
<223> OTHER INFORMATION: Synthetic Polypeptide

<400> SEQUENCE: 15

```
Met Met Asp Leu Glu Leu Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190
```

```
Ser Ile Pro Glu Leu Gln Cys Leu Asn Ile Glu Asn Asp Lys Leu Val
        195                 200                 205
Glu Thr Thr Met Val Pro Ser Pro Glu Ala Lys Leu Thr Glu Val Asp
210                 215                 220
Asn Tyr His Phe Tyr Ser Ser Ile Pro Ser Met Glu Lys Glu Val Gly
225                 230                 235                 240
Asn Cys Ser Pro His Phe Leu Asn Ala Phe Glu Asp Ser Phe Ser Ser
                245                 250                 255
Ile Leu Ser Thr Glu Asp Pro Asn Gln Leu Thr Val Asn Ser Leu Asn
            260                 265                 270
Ser Asp Ala Thr Val Asn Thr Asp Phe Gly Asp Glu Phe Tyr Ser Ala
        275                 280                 285
Phe Ile Ala Glu Pro Ser Ile Ser Asn Ser Met Pro Ser Pro Ala Thr
290                 295                 300
Leu Ser His Ser Leu Ser Glu Leu Leu Asn Gly Pro Ile Asp Val Ser
305                 310                 315                 320
Asp Leu Ser Leu Cys Lys Ala Phe Asn Gln Asn His Pro Glu Ser Thr
                325                 330                 335
Ala Glu Phe Asn Asp Ser Asp Ser Gly Ile Ser Leu Asn Thr Ser Pro
            340                 345                 350
Ser Val Ala Ser Pro Glu His Ser Val Glu Ser Ser Tyr Gly Asp Asp
        355                 360                 365
Thr Leu Leu Gly Leu Ser Asp Ser Glu Val Glu Glu Leu Asp Ser Ala
370                 375                 380
Pro Gly Ser Val Lys Gln Asn Gly Pro Lys Thr Pro Val His Ser Ser
385                 390                 395                 400
Gly Asp Met Val Gln Pro Leu Ser Pro Ser Gln Gly Gln Ser Thr His
                405                 410                 415
Val His Asp Ala Gln Cys Glu Asn Thr Pro Glu Lys Glu Leu Pro Val
            420                 425                 430
Ser Pro Gly His Arg Lys Thr Pro Phe Thr Lys Asp Lys His Ser Ser
        435                 440                 445
Arg Leu Glu Ala His Leu Thr Arg Asp Glu Leu Arg Ala Lys Ala Leu
450                 455                 460
His Ile Pro Phe Pro Val Glu Lys Ile Ile Asn Leu Pro Val Val Asp
465                 470                 475                 480
Phe Asn Glu Met Met Ser Lys Glu Gln Phe Asn Glu Ala Gln Leu Ala
                485                 490                 495
Leu Ile Arg Asp Ile Arg Arg Arg Gly Lys Asn Lys Val Ala Ala Gln
            500                 505                 510
Asn Cys Arg Lys Arg Lys Leu Glu Asn Ile Val Glu Leu Glu Gln Asp
        515                 520                 525
Leu Asp His Leu Lys Asp Glu Lys Glu Lys Leu Leu Lys Glu Lys Gly
530                 535                 540
Glu Asn Asp Lys Ser Leu His Leu Leu Lys Lys Gln Leu Ser Thr Leu
545                 550                 555                 560
Tyr Leu Glu Val Phe Ser Met Leu Arg Asp Glu Asp Gly Lys Pro Tyr
                565                 570                 575
Ser Pro Ser Glu Tyr Ser Leu Gln Gln Thr Arg Asp Gly Asn Val Phe
            580                 585                 590
Leu Val Pro Lys Ser Lys Lys Pro Asp Val Lys Lys Asn Thr Arg Ser
        595                 600                 605
Arg Lys Lys Arg Ser Thr Arg Ser Arg Lys Lys Arg Ser Gly Ala Pro
```

```
              610              615              620
Met Ile Ser Leu Ile Ala Ala Leu Ala Val Asp Tyr Val Ile Gly Met
625                 630                 635                 640

Glu Asn Ala Met Pro Trp Asn Leu Pro Ala Asp Leu Ala Trp Phe Lys
                645                 650                 655

Arg Asn Thr Leu Asn Lys Pro Val Ile Met Gly Arg His Thr Trp Glu
            660                 665                 670

Ser Ile Gly Arg Pro Leu Pro Gly Arg Lys Asn Ile Ile Leu Ser Ser
                675                 680                 685

Gln Pro Ser Thr Asp Asp Arg Val Thr Trp Val Lys Ser Val Asp Glu
        690                 695                 700

Ala Ile Ala Ala Cys Gly Asp Val Pro Glu Ile Met Val Ile Gly Gly
705                 710                 715                 720

Gly Arg Val Ile Glu Gln Phe Leu Pro Lys Ala Gln Lys Leu Tyr Leu
                725                 730                 735

Thr His Ile Asp Ala Glu Val Glu Gly Asp Thr His Phe Pro Asp Tyr
                740                 745                 750

Glu Pro Asp Asp Trp Glu Ser Val Phe Ser Glu Phe His Asp Ala Asp
            755                 760                 765

Ala Gln Asn Ser His Ser Tyr Cys Phe Glu Ile Leu Glu Arg Arg
        770                 775                 780
```

<210> SEQ ID NO 16
<211> LENGTH: 4647
<212> TYPE: DNA
<213> ORGANISM: Artificial Sequence
<220> FEATURE:
<223> OTHER INFORMATION: Synthetic Polynucleotide

<400> SEQUENCE: 16

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctcagat ctgaattcgg tacctagtta ttaatagtaa     180
tcaattacgg ggtcattagt tcatagccca tatatggagt tccgcgttac ataacttacg     240
gtaaatggcc cgcctggctg accgcccaac gacccccgcc cattgacgtc aataatgacg     300
tatgttccca tagtaacgcc aatagggact ttccattgac gtcaatgggt ggagtattta     360
cggtaaactg cccacttggc agtacatcaa gtgtatcata tgccaagtac gccccctatt     420
gacgtcaatg acggtaaatg gcccgcctgg cattatgccc agtacatgac cttatgggac     480
tttcctactt ggcagtacat ctacgtatta gtcatcgcta ttaccatggt cgaggtgagc     540
cccacgttct gcttcactct ccccatctcc cccccctccc cacccccaat tttgtattta     600
tttatttttt aattattttg tgcagcgatg ggggcggggg ggggggggg gcgcgcgcca     660
ggcggggcgg ggcggggcga ggggcggggc ggggcgaggc ggagaggtgc ggcggcagcc     720
aatcagagcg gcgcgctccg aaagtttcct tttatggcga ggcggcggcg gcggcggccc     780
tataaaaagc gaagcgcgcg gcgggcggga gtcgctgcgc gctgccttcg ccccgtgccc     840
cgctccgccg ccgcctcgcg ccgcccgccc ggctctgact gaccgcgtt actcccacag     900
gtgagcgggc gggacggccc ttctcctccg gctgtaatt agcgcttggt ttaatgacgg     960
cttgtttctt ttctgtggct gcgtgaaagc cttgagggc tccgggaggg ccctttgtgc    1020
gggggagcg gctcggggg tgcgtgcgtg tgtgtgtgcg tggggagcgc gcgtgcggg    1080
tccgcgctgc ccggcggctg tgagcgctgc gggcgcggcg cggggctttg tgcgctccgc    1140
```

```
agtgtgcgcg aggggagcgc ggccgggggc ggtgccccgc ggtgcggggg gggctgcgag   1200
gggaacaaag gctgcgtgcg gggtgtgtgc gtggggggt gagcagggg tgtgggcgcg    1260 tcggtcgggc tgcaaccccc cctgcacccc cctccccgag ttgctgagca cggcccggct   1320
tcgggtgcgg ggctccgtac ggggcgtggc gcggggctcg ccgtgccggg cggggggtgg   1380
cggcaggtgg gggtgccggg cggggcgggg ccgcctcggg ccggggaggg ctcgggggag   1440
gggcgcggcg gccccggag cgccggcggc tgtcgaggcg cggcgagccg cagccattgc    1500
cttttatggt aatcgtgcga gagggcgcag ggacttcctt tgtcccaaat ctgtgcggag   1560
ccgaaatctg ggaggcgccg ccgcacccc tctagcgggc gcgggggcgaa gcggtgcggc   1620 gccggcagga aggaaatggg cggggagggc cttcgtgcgt cgccgcgccg ccgtcccctt   1680
ctccctctcc agcctcgggg ctgtccgcgc ggggacggct gccttcgggg gggacggggc   1740 agggcgggt tcggcttctg gcgtgtgacc ggcggctcta gagcctctgc taaccatgtt   1800
catgccttct tcttttcct acagctcctg ggcaacgtgc tggttattgt gctgtctcat    1860
cattttggca aagaattcct cgaagatcta ggcaacgcgt ctcgaggcgg ccgccgccac   1920
catgatggat ctcgaacttc cccctccagg cctgcctagc cagcaagaca tggaccttat   1980
cgacatcctg tggcgccagg atattgatct cggtgtgtct agggaagtct ttgactttc    2040 ccaaaggagg aaggaatatg agcttgagaa acaaaagaag cttgaaaagg aacggcaaga   2100
gcagcttcaa aaggagcagg aaaaagcatt ctttgcgcaa ttgcagcttg atgaagaaac   2160
cggcgaattc cttccaatac aaccagctca acatatccaa tccgagacct caggttccgc   2220
aaattactcc caagtggcac atataccgaa atccgacgcg ttgtacttcg acgattgtat   2280
gcagctgctc gcacaaacgt tccctttcgt ggacgataac gaagtgagtt ctgctacttt   2340
ccagtcactt gttccagaca tccccggaca tattgaatcc ccagtgttta tagcgacaaa   2400
ccaagcccaa tcacctgaga cgagtgtcgc ccaagtagcc ccagtcgatc tggatggtat   2460
gcaacaggac attgaacaag tctgggaaga gctgcttagc attcctgaac tgcagtgcct   2520
gaacatcgaa aacgacaaat tggtagagac aactatggta ccctcacctg aggccaagtt   2580
gaccgaggtg gacaattatc attttactc ttcaatacct agtatggaga aagaagtcgg    2640
taattgttcc cctcatttcc tgaacgcgtt cgaagacagc tttagcagca tcttgtccac   2700
agaagaccca aatcaattga cggtaaactc cttgaactca gacgcgacag tgaataccga   2760
ttttggtgat gaattttatt cagcatttat agccgagcca agcatcagta attctatgcc   2820
cagccccgca actctctccc acagtctttc agaattgctc aacggaccca tcgatgtgag   2880
tgatctgtcc ctctgcaaag cgtttaacca aaaccatccg agagtacgg ccgagttcaa    2940 cgacagtgat agtggtattt cactcaatac ctcacccctcc gtggccagtc cggagcacag   3000
tgttgaatca agctcctacg gggacacatt gctgggcctc tcagacagcg aagtcgaaga   3060
acttgacagc gccccccggat ccgtaaagca aaatgggccg aaaactccgg tgcattcatc   3120
aggtgatatg gtacagccac tttcaccaag tcagggacaa agtacgcacg tccatgacgc   3180
gcaatgtgaa aatactcctg agaaagagct cccggtatca ccggggcacc ggaagacccc   3240
ttttactaag gacaaacata gtagtcgctt ggaggctcat ttgactcgag atgagctccg   3300
cgcaaaagca ctccatattc catttcccgt tgaaaagatt attaacctcc cggtagtgga   3360
cttcaacgag atgatgtcta aggagcagtt taatgaggcg cagcttgcac tgataaggga   3420
catacgacgc agaggtaaga ataaggtggc tgcccaaaac tgcaggaagc gaaagctcga   3480
```

| | | |
|---|---|---|
| gaacattgta gaacttgagc aggaccttga tcacctgaaa gatgagaagg aaaaattgct | 3540 |
| taaagagaaa ggtgagaatg ataaaagctt gcatcttctc aaaaaacagc tgagcacatt | 3600 |
| gtatcttgag gtcttcagca tgctcagaga tgaagatggg aaaccgtatt ctccgagcga | 3660 |
| atacagtctg cagcagaccc gggatggcaa tgtgttcctc gtacccaaaa gcaaaaaacc | 3720 |
| tgatgttaag aagaatacca gatctcgcaa gaagcgcagc accagatctc gcaagaagcg | 3780 |
| cagcggggcc cccatgatat ctctgatcgc tgctcttgct gtggactacg tgattggtat | 3840 |
| ggagaatgct atgccctgga atctgcctgc agacctggca tggtttaaga ggaacaccct | 3900 |
| taataaacct gtaatcatgg gacgacatac atgggagagt atcggcaggc cattgcccgg | 3960 |
| gaggaagaat ataattctga gttcccagcc ttctactgat gatagggtaa cttgggtcaa | 4020 |
| gagcgtcgac gaggccatcg ccgcttgcgg ggatgtgcct gaaatcatgg ttatcggggg | 4080 |
| cggacgggtg attgagcaat ttctgcccaa ggcacagaag ctgtatctga cccatataga | 4140 |
| cgccgaggtg gagggagata cacactttcc cgactatgag cccgatgatt gggagagtgt | 4200 |
| ctttagcgaa tttcatgacg ccgacgcaca gaattcccat agctactgct tcgaaattct | 4260 |
| cgaacggcgc taggcggccg cgcggatcca gacatgataa gatacattga tgagtttgga | 4320 |
| caaaccacaa ctagaatgca gtgaaaaaaa tgctttattt gtgaaatttg tgatgctatt | 4380 |
| gctttatttg taaccattat aagctgcaat aaacaagtta acaacaacaa ttgcattcat | 4440 |
| tttatgtttc aggttcaggg ggaggtgtgg gaggttttt agtcgactgg ggagagatct | 4500 |
| gaggaaccccc tagtgatgga gttggccact ccctctctgc gcgctcgctc gctcactgag | 4560 |
| gccgcccggg caaagcccgg gcgtcgggcg acctttggtc gcccggcctc agtgagcgag | 4620 |
| cgagcgcgca gagagggagt ggccaac | 4647 |

<210> SEQ ID NO 17
<211> LENGTH: 430
<212> TYPE: PRT
<213> ORGANISM: Artificial Sequence
<220> FEATURE:
<223> OTHER INFORMATION: Synthetic Polypeptide

<400> SEQUENCE: 17

```
Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160
```

Asp Thr Ala Glu Pro Thr Lys Ala Gly Arg Gly Ala Ser Gln Pro Pro
            165                 170                 175

Thr Pro Thr Pro Ala Ser Asp Ala Phe Gln Arg Lys Leu Glu Gly Cys
        180                 185                 190

Arg Phe Leu His Gly Tyr His Arg Phe Met His Ser Val Gly Arg Val
            195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg Thr Arg Ser Arg
                245                 250                 255

Lys Lys Arg Ser Thr Arg Ser Arg Lys Lys Arg Ser Gly Ala Pro Met
            260                 265                 270

Ile Ser Leu Ile Ala Ala Leu Ala Val Asp Tyr Val Ile Gly Met Glu
        275                 280                 285

Asn Ala Met Pro Trp Asn Leu Pro Ala Asp Leu Ala Trp Phe Lys Arg
    290                 295                 300

Asn Thr Leu Asn Lys Pro Val Ile Met Gly Arg His Thr Trp Glu Ser
305                 310                 315                 320

Ile Gly Arg Pro Leu Pro Gly Arg Lys Asn Ile Ile Leu Ser Ser Gln
                325                 330                 335

Pro Ser Thr Asp Asp Arg Val Thr Trp Val Lys Ser Val Asp Glu Ala
            340                 345                 350

Ile Ala Ala Cys Gly Asp Val Pro Glu Ile Met Val Ile Gly Gly Gly
        355                 360                 365

Arg Val Ile Glu Gln Phe Leu Pro Lys Ala Gln Lys Leu Tyr Leu Thr
    370                 375                 380

His Ile Asp Ala Glu Val Glu Gly Asp Thr His Phe Pro Asp Tyr Glu
385                 390                 395                 400

Pro Asp Asp Trp Glu Ser Val Phe Ser Glu Phe His Asp Ala Asp Ala
                405                 410                 415

Gln Asn Ser His Ser Tyr Cys Phe Glu Ile Leu Glu Arg Arg
            420                 425                 430

<210> SEQ ID NO 18
<211> LENGTH: 3588
<212> TYPE: DNA
<213> ORGANISM: Artificial Sequence
<220> FEATURE:
<223> OTHER INFORMATION: Synthetic Polynucleotide

<400> SEQUENCE: 18
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg      120
gccaactcca tcactagggg ttcctcagat ctgaattcgg tacctagtta ttaatagtaa      180
tcaattacgg ggtcattagt tcatagccca tatatggagt tccgcgttac ataacttacg      240
gtaaatggcc cgcctggctg accgcccaac gacccccgcc cattgacgtc aataatgacg      300
tatgttccca tagtaacgcc aatagggact ttccattgac gtcaatgggt ggagtattta      360
cggtaaactg cccacttggc agtacatcaa gtgtatcata tgccaagtac gccccctatt      420
gacgtcaatg acggtaaatg gcccgcctgg cattatgccc agtacatgac cttatgggac      480
tttcctactt ggcagtacat ctacgtatta gtcatcgcta ttaccatggt cgaggtgagc      540

```
cccacgttct gcttcactct ccccatctcc cccccctccc cacccccaat tttgtattta      600
tttatttttt aattattttg tgcagcgatg ggggcggggg ggggggggggg gcgcgcgcca      660
ggcggggcgg ggcggggcga ggggcggggc ggggcgaggc ggagaggtgc ggcggcagcc      720
aatcagagcg gcgcgctccg aaagtttcct tttatggcga ggcggcggcg gcggcggccc      780
tataaaaagc gaagcgcgcg gcgggcggga gtcgctgcgc gctgccttcg ccccgtgccc      840
cgctccgccg ccgcctcgcg ccgcccgccc cggtctgac tgaccgcgtt actcccacag       900
gtgagcgggc gggacggccc ttctcctccg ggctgtaatt agcgcttggt ttaatgacgg      960
cttgtttctt ttctgtggct gcgtgaaagc cttgaggggc tccggagggg ccctttgtgc     1020
gggggagcg gctcgggggg tgcgtgcgtg tgtgtgtgcg tggggagcgc cgcgtgcggc      1080
tccgcgctgc ccggcggctg tgagcgctgc gggcgcggcg cggggctttg tgcgctccgc     1140
agtgtgcgcg aggggagcgc ggccgggggc ggtgccccgc ggtgcggggg gggctgcgag     1200
gggaacaaag gctgcgtgcg gggtgtgtgc gtgggggggt gagcagggg tgtgggcgcg      1260
tcggtcgggc tgcaaccccc cctgcacccc cctccccgag ttgctgagca cggcccggct     1320
tcgggtgcgg ggctccgtac ggggcgtggc gcggggctcg ccgtgccggg cgggggtgg      1380
cggcaggtgg gggtgccggg cggggcgggg ccgcctcggg ccggggaggg ctcggggggag    1440
gggcgcggcg gcccccggag cgccggcggc tgtcgaggcg cggcgagccg cagccattgc     1500
cttttatggt aatcgtgcga gagggcgcag ggacttcctt tgtcccaaat ctgtgcggag     1560
ccgaaatctg ggaggcgccg ccgcaccccc tctagcgggc gcggggcgaa gcggtgcggc    1620
gccggcagga aggaaatggg cggggagggc cttcgtgcgt cgccgcgccg ccgtcccctt    1680
ctccctctcc agcctcgggg ctgtccgcgg ggggacggct gccttcgggg gggacggggc    1740
agggcgggt tcggcttctg gcgtgtgacc ggcggctcta gagcctctgc taaccatgtt     1800
catgccttct tcttttttcct acagctcctg gcaacgtgc tggttattgt gctgtctcat     1860
cattttggca aagaattcct cgaagatcta ggcaacgcgt ctcgaggcgg ccgccgccac     1920
catgggggtg cttttgacac agcgcacact cctgagcttg gttctggctc tcctgttccc     1980
gtcaatggct tctatggcgg ccataggctc atgttctaaa gaataccgag tgcttctggg     2040
ccaacttcag aagcagacgg acctcatgca ggatacaagc cgccttttgg acccatatat     2100
aaggatccaa gggttggatg tgccgaagct gagggaacac tgtcgagaac gacctggagc    2160
ttttccaagc gaagaaaccc tcagaggtct tgggaggagg ggcttttttgc agacgctcaa     2220
cgcgaccctg gggtgtgtgc tccaccgact tgcagatctc gagcagcgcc tgccaaaagc    2280
acaggatctg gagcggagtg gacttaacat cgaagacctg gaaaaattgc agatggctcg    2340
accgaacatt cttggccttc gaaacaacat ctactgtatg gcacagctgc tggataactc    2400
agatacagcc gaacctacaa agcagggcg gggcgcgtcc caaccaccta ctcccacacc     2460
agcctccgat gcctttcaga gaaagcttga agggtgtagg tttctccacg gctatcatcg    2520
cttcatgcat tcagtaggga ggtgttctc aaaatgggga gagtcaccta atcgatcaag     2580
gaggcactca ccccatcagg ctcttcggaa gggcgttcgg cgcactcgcc cgagcaggaa    2640
gggtaaaagg ctgatgactc ggggtcaact gccaaggacc agatctcgca agaagcgcag    2700
caccagatct cgcaagaagc gcagcgggc cccatgata tctctgatcg ctgctcttgc     2760
tgtggactac gtgattggta tggagaatgc tatgccctgg aatctgcctg cagacctggc    2820
atggtttaag aggaacaccc ttaataaacc tgtaatcatg ggacgacata catgggagag    2880
```

-continued

```
tatcggcagg ccattgcccg ggaggaagaa tataattctg agttcccagc cttctactga    2940
tgatagggta acttgggtca agagcgtcga cgaggccatc gccgcttgcg gggatgtgcc    3000
tgaaatcatg gttatcgggg gcggacgggt gattgagcaa tttctgccca aggcacagaa    3060
gctgtatctg acccatatag acgccgaggt ggagggagat acacactttc ccgactatga    3120
gcccgatgat tgggagagtg tctttagcga atttcatgac gccgacgcac agaattccca    3180
tagctactgc ttcgaaattc tcgaacggcg ctaggcggcc gcgcggatcc agacatgata    3240
agatacattg atgagtttgg acaaaccaca actagaatgc agtgaaaaaa atgctttatt    3300
tgtgaaattt gtgatgctat tgctttattt gtaaccatta taagctgcaa taaacaagtt    3360
aacaacaaca attgcattca ttttatgttt caggttcagg gggaggtgtg ggaggttttt    3420
tagtcgactg gggagagatc tgaggaaccc ctagtgatgg agttggccac tccctctctg    3480
cgcgctcgct cgctcactga ggccgcccgg gcaaagcccg ggcgtcgggc gacctttggt    3540
cgcccggcct cagtgagcga gcgagcgcgc agagagggag tggccaac              3588
```

<210> SEQ ID NO 19
<211> LENGTH: 415
<212> TYPE: PRT
<213> ORGANISM: Artificial Sequence
<220> FEATURE:
<223> OTHER INFORMATION: Synthetic Polypeptide

<400> SEQUENCE: 19

```
Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
                20                  25                  30

Lys Glu Tyr Arg Val Leu Leu Gly Gln Leu Gln Lys Gln Thr Asp Leu
            35                  40                  45

Met Gln Asp Thr Ser Arg Leu Leu Asp Pro Tyr Ile Arg Ile Gln Gly
        50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Gly Gly Gly Asn Ile Glu Asp Leu Glu Lys Leu
        115                 120                 125

Gln Met Ala Arg Pro Asn Ile Leu Gly Leu Arg Asn Asn Ile Tyr Cys
    130                 135                 140

Met Ala Gln Leu Leu Asp Asn Ser Asp Thr Ala Glu Pro Thr Lys Ala
145                 150                 155                 160

Gly Arg Gly Ala Ser Gln Pro Pro Thr Pro Thr Pro Ala Ser Asp Ala
                165                 170                 175

Phe Gln Arg Lys Leu Glu Gly Cys Arg Phe Leu His Gly Tyr His Arg
            180                 185                 190

Phe Met His Ser Val Gly Arg Val Phe Ser Lys Trp Gly Glu Ser Pro
        195                 200                 205

Asn Arg Ser Arg Arg His Ser Pro His Gln Ala Leu Arg Lys Gly Val
    210                 215                 220

Arg Arg Thr Arg Pro Ser Arg Lys Gly Lys Arg Leu Met Thr Arg Ser
225                 230                 235                 240
```

```
Arg Lys Lys Arg Ser Thr Arg Ser Arg Lys Arg Ser Gly Ala Pro
                245                 250                 255

Met Ile Ser Leu Ile Ala Ala Leu Ala Val Asp Tyr Val Ile Gly Met
            260                 265                 270

Glu Asn Ala Met Pro Trp Asn Leu Pro Ala Asp Leu Ala Trp Phe Lys
        275                 280                 285

Arg Asn Thr Leu Asn Lys Pro Val Ile Met Gly Arg His Thr Trp Glu
    290                 295                 300

Ser Ile Gly Arg Pro Leu Pro Gly Arg Lys Asn Ile Ile Leu Ser Ser
305                 310                 315                 320

Gln Pro Ser Thr Asp Asp Arg Val Thr Trp Val Lys Ser Val Asp Glu
                325                 330                 335

Ala Ile Ala Ala Cys Gly Asp Val Pro Glu Ile Met Val Ile Gly Gly
            340                 345                 350

Gly Arg Val Ile Glu Gln Phe Leu Pro Lys Ala Gln Lys Leu Tyr Leu
        355                 360                 365

Thr His Ile Asp Ala Glu Val Glu Gly Asp Thr His Phe Pro Asp Tyr
    370                 375                 380

Glu Pro Asp Asp Trp Glu Ser Val Phe Ser Glu Phe His Asp Ala Asp
385                 390                 395                 400

Ala Gln Asn Ser His Ser Tyr Cys Phe Glu Ile Leu Glu Arg Arg
                405                 410                 415

<210> SEQ ID NO 20
<211> LENGTH: 3543
<212> TYPE: DNA
<213> ORGANISM: Artificial Sequence
<220> FEATURE:
<223> OTHER INFORMATION: Synthetic Polynucleotide

<400> SEQUENCE: 20
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctcagat ctgaattcgg tacctagtta ttaatagtaa    180
tcaattacgg ggtcattagt tcatagccca tatatggagt tccgcgttac ataacttacg    240
gtaaatggcc cgcctggctg accgcccaac gacccccgcc cattgacgtc aataatgacg    300
tatgttccca tagtaacgcc aatagggact ttccattgac gtcaatgggt ggagtattta    360
cggtaaactg cccacttggc agtacatcaa gtgtatcata tgccaagtac gccccctatt    420
gacgtcaatg acggtaaatg gcccgcctgg cattatgccc agtacatgac cttatgggac    480
tttcctactt ggcagtacat ctacgtatta gtcatcgcta ttaccatggt cgaggtgagc    540
cccacgttct gcttcactct ccccatctcc cccccctccc cacccccaat tttgtattta    600 tttattttt aattattttg tgcagcgatg ggggcggggg ggggggggg gcgcgcgcca    660 ggcggggcgg ggcggggcga ggggcggggc ggggcgaggc ggagaggtgc ggcggcagcc    720
aatcagagcg gcgcgctccg aaagtttcct tttatggcga ggcggcggcg gcggcggccc    780
tataaaaagc gaagcgcgcg gcgggcggga gtcgctgcgc gctgccttcg ccccgtgccc    840
cgctccgccg ccgcctcgcg ccgcccgccc cggctctgac tgaccgcgtt actcccacag    900
gtgagcgggc gggacggccc ttctcctccg gctgtaatt agcgcttggt ttaatgacgg    960
cttgtttctt ttctgtggct gcgtgaaagc cttgagggc tccggagggg cccttttgtgc   1020 gggggagcg gctcgggggg tgcgtgcgtg tgtgtgtgcg tggggagcgc gcgtgcggc    1080
```

```
tccgcgctgc ccggcggctg tgagcgctgc gggcgcggcg cggggctttg tgcgctccgc    1140
agtgtgcgcg aggggagcgc ggccgggggc ggtgccccgc ggtgcggggg gggctgcgag    1200
gggaacaaag gctgcgtgcg gggtgtgtgc gtgggggggt gagcaggggg tgtgggcgcg    1260
tcggtcgggc tgcaaccccc cctgcacccc cctccccgag ttgctgagca cggcccggct    1320
tcgggtgcgg ggctccgtac ggggcgtggc gcggggctcg ccgtgccggg cgggggtgg     1380
cggcaggtgg gggtgccggg cggggcgggg ccgcctcggg ccggggaggg ctcggggag     1440
gggcgcggcg gcccccggag cgccggcggc tgtcgaggcg cggcgagccg cagccattgc    1500
cttttatggt aatcgtgcga gagggcgcag ggacttcctt tgtcccaaat ctgtgcggag    1560
ccgaaatctg ggaggcgccg ccgcaccccc tctagcgggc gcggggcgaa gcggtgcggc    1620
gccggcagga aggaaatggg cggggagggc cttcgtgcgt cgccgcgccg ccgtcccctt    1680
ctccctctcc agcctcgggg ctgtccgcgg ggggacgggct gccttcgggg gggacggggc   1740
agggcggggt tcggcttctg gcgtgtgacc ggcggctcta gagcctctgc taaccatgtt    1800
catgccttct tcttttttcct acagctcctg ggcaacgtgc tggttattgt gctgtctcat   1860
cattttggca aagaattcct cgaagatcta ggcaacgcgt tcgaggcgg ccgccgccac    1920
catgggtgtg ttgctcactc aaaggacctt gttgtccctg gtcctggcac tcttgttccc    1980
atctatggcg agtatggcgg ctattggctc atgctctaaa gagtacagag ttctgctcgg    2040
tcaactgcaa aagcaaacgg acctgatgca agatacgtcc aggttgctcg acccttatat    2100
taggatccag ggactcgacg ttccgaagct tagagagcac tgtcgcgagc gaccaggtgc    2160
ctttcccagt gaagaaacac tgaggggttt ggcaggcgc ggtttcttgc agacccttaa     2220
tgctacattg gggtgcgtat tgcatcgcct ggcagatctc gagcaaagac tcggaggtgg    2280
caatatcgag gatcttgaaa agctccagat ggctcgcccg aacatactcg ggctgaggaa    2340
taatatatat tgtatggctc aactcctcga caactcagac actgcggagc ctacgaaagc    2400
aggaaggggc gcatcacaac cacctacacc tactcctgcc agtgatgcct ttcagcgcaa    2460
gcttgagggc tgccgatttc tccacggcta tcatcggttc atgcactccg ttggccgagt    2520
gttttcaaaa tggggggaat ctcctaaccg atctagaagg cactcacctc accaggcact    2580
gcggaaaggc gttaggagaa cccggccaag ccgcaaagga aagcgcctga tgaccagatc    2640
tcgcaagaag cgcagcacca gatctcgcaa gaagcgcagc ggggccccca tgatatctct    2700
gatcgctgct cttgctgtgg actacgtgat tggtatggag aatgctatgc cctggaatct    2760
gcctgcagac ctggcatggt ttaagaggaa cacccttaat aaacctgtaa tcatgggacg    2820
acatacatgg gagagtatcg gcaggccatt gcccgggagg aagaatataa ttctgagttc    2880
ccagccttct actgatgata gggtaacttg ggtcaagagc gtcgacgagg ccatcgccgc    2940
ttgcggggat gtgcctgaaa tcatggttat cggggcgga cgggtgattg agcaatttct    3000
gcccaaggca cagaagctgt atctgaccca tatagacgcc gaggtggagg gagatacaca    3060
ctttcccgac tatgagcccg atgattggga gagtgtcttt agcgaatttc atgacgccga    3120
cgcacagaat tcccatagct actgcttcga aattctcgaa cggcgctagg cggccgcgcg    3180
gatccagaca tgataagata cattgatgag tttggacaaa ccacaactag aatgcagtga    3240
aaaaaatgct ttatttgtga aatttgtgat gctattgctt tatttgtaac cattataagc    3300
tgcaataaac aagttaacaa caacaattgc attcatttta tgtttcaggt tcaggggagag   3360
gtgtgggagg ttttttagtc gactgggag agatctgagg aacccctagt gatggagttg    3420
gccactccct ctctgcgcgc tcgctcgctc actgaggccg cccgggcaaa gcccgggcgt    3480
```

```
cgggcgacct tggtcgccc ggcctcagtg agcgagcgag cgcgcagaga gggagtggcc    3540
aac                                                                 3543
```

<210> SEQ ID NO 21
<211> LENGTH: 948
<212> TYPE: PRT
<213> ORGANISM: Artificial Sequence
<220> FEATURE:
<223> OTHER INFORMATION: Synthetic Polypeptide

<400> SEQUENCE: 21

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
```

```
              340                 345                 350
Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
        370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765
```

```
Pro Met Thr Arg Ser Arg Lys Lys Arg Ser Arg Lys Lys
    770                 775                 780

Arg Ser Gly Ala Pro Met Ile Ser Leu Ile Ala Leu Ala Val Asp
785                 790                 795                 800

Tyr Val Ile Gly Met Glu Asn Ala Met Pro Trp Asn Leu Pro Ala Asp
                    805                 810                 815

Leu Ala Trp Phe Lys Arg Asn Thr Leu Asn Lys Pro Val Ile Met Gly
                820                 825                 830

Arg His Thr Trp Glu Ser Ile Gly Arg Pro Leu Pro Gly Arg Lys Asn
            835                 840                 845

Ile Ile Leu Ser Ser Gln Pro Ser Thr Asp Asp Arg Val Thr Trp Val
        850                 855                 860

Lys Ser Val Asp Glu Ala Ile Ala Ala Cys Gly Asp Val Pro Glu Ile
865                 870                 875                 880

Met Val Ile Gly Gly Gly Arg Val Ile Glu Gln Phe Leu Pro Lys Ala
                885                 890                 895

Gln Lys Leu Tyr Leu Thr His Ile Asp Ala Glu Val Glu Gly Asp Thr
                900                 905                 910

His Phe Pro Asp Tyr Glu Pro Asp Asp Trp Glu Ser Val Phe Ser Glu
            915                 920                 925

Phe His Asp Ala Asp Ala Gln Asn Ser His Ser Tyr Cys Phe Glu Ile
    930                 935                 940

Leu Glu Arg Arg
945

<210> SEQ ID NO 22
<211> LENGTH: 5142
<212> TYPE: DNA
<213> ORGANISM: Artificial Sequence
<220> FEATURE:
<223> OTHER INFORMATION: Synthetic Polynucleotide

<400> SEQUENCE: 22
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctcagat ctgaattcgg tacctagtta ttaatagtaa     180
tcaattacgg ggtcattagt tcatagccca tatatggagt tccgcgttac ataacttacg     240
gtaaatggcc cgcctggctg accgcccaac gacccccgcc cattgacgtc aataatgacg     300
tatgttccca tagtaacgcc aatagggact ttccattgac gtcaatgggt ggagtattta     360
cggtaaactg cccacttggc agtacatcaa gtgtatcata tgccaagtac gccccctatt     420
gacgtcaatg acggtaaatg gcccgcctgg cattatgccc agtacatgac cttatgggac     480
tttcctactt ggcagtacat ctacgtatta gtcatcgcta ttaccatggt cgaggtgagc     540
cccacgttct gcttcactct ccccatctcc cccccctccc cacccccaat tttgtattta     600
tttatttttt aattattttg tgcagcgatg ggggcggggg ggggggggcg cgcgccca      660 ggcggggcgg ggcggggcga ggggcggggc ggggcgaggc ggagaggtgc ggcggcagcc     720
aatcagagcg gcgcgctccg aaagtttcct tttatggcga ggcggcggcg gcggcggccc     780
tataaaaagc gaagcgcgcg gcgggcggga gtcgctgcgc gctgccttcg ccccgtgccc     840
cgctccgccg ccgcctcgcg ccgcccgccc ggctctgac tgaccgcgtt actcccacag     900
gtgagcgggc gggacggccc ttctcctccg ggctgtaatt agcgcttggt ttaatgacgg     960
```

```
cttgtttctt ttctgtggct gcgtgaaagc cttgaggggc tccgggaggg ccctttgtgc   1020 gggggagcg gctcgggggg tgcgtgcgtg tgtgtgtgcg tggggagcgc gcgtgcggc    1080 tccgcgctgc ccggcggctg tgagcgctgc gggcgcggcg cggggctttg tgcgctccgc   1140
agtgtgcgcg aggggagcgc ggccgggggc ggtgccccgc ggtgcggggg gggctgcgag   1200
gggaacaaag gctgcgtgcg gggtgtgtgc gtggggggt gagcagggg tgtgggcgcg    1260 tcggtcgggc tgcaaccccc cctgcacccc cctccccgag ttgctgagca cggcccggct   1320
tcgggtgcgg ggctccgtac ggggcgtggc gcggggctcg ccgtgccggg cgggggtgg    1380 cggcaggtgg gggtgccggg cggggcgggg ccgcctcggg ccggggaggg ctcggggag    1440 gggcgcggcg gccccggag cgccggcggc tgtcgaggcg cggcgagccg cagccattgc    1500
cttttatggt aatcgtgcga gagggcgcag ggacttcctt tgtcccaaat ctgtgcggag   1560
ccgaaatctg ggaggcgccg ccgcaccccc tctagcgggc gcggggcgaa gcggtgcggc   1620
gccggcagga aggaaatggg cggggagggc cttcgtgcgt cgccgcgccg ccgtcccctt   1680
ctccctctcc agcctcgggg ctgtccgcgg ggggacggct gccttcgggg gggacgggc    1740 agggcggggt tcggcttctg gcgtgtgacc ggcggctcta gagcctctgc taaccatgtt   1800
catgccttct tcttttcct acagctcctg ggcaacgtgc tggttattgt gctgtctcat    1860
cattttggca aagaattcct cgaagatcta ggcaacgcgt ctcgaggcgg ccgccgccac   1920 catgctcaa tggaaccaat tgcaacaact tgatactcga tacctggagc aactccatca   1980
gctgtactca gattcatttc cgatggagct ccggcagttt ctggctccat ggatagaatc   2040
acaggattgg gcctacgcgg cttcaaagga aagtcacgcg accctcgtat ttcacaacct   2100
cctgggggaa attgatcagc aatatagtcg gtttctgcaa gaaagcaacg tcttgtacca   2160
acataacttg aggaggatta agcaatttct ccaaagccgg tacttggaga agcctatgga   2220
aatcgctcgc attgtagcga ggtgcctgtg ggaggagagt cgccttctgc agaccgccgc   2280
cacagccgct caacaaggtg ggcaggctaa tcatcccacc gctgctgtgg tcaccgaaaa   2340
gcagcagatg ctcgagcaac accttcagga cgtcagaaag agggttcagg atctggaaca   2400
aaagatgaaa gtcgtggaga atttgcagga tgattttgat tttaactaca agaccttgaa   2460
atcccaaggc gatatgcaag atcttaatgg aaacaaccag tcagtgacca ggcagaagat   2520
gcaacaactt gaacaaatgt tgactgccct cgatcaaatg agacgcagta tagtaagcga   2580
gttggccggt cttctctcag cgatggagta cgtacagaaa acgctgactg atgaagagct   2640
ggctgactgg aagcggcggc agcagatagc ttgcatcggt gggcccccaa atatatgcct   2700
ggatcgcctg gagaactgga taacgagtct ggccgagagt cagctgcaga ctcgccagca   2760
gatcaaaaaa ctgaagaac tccagcaaaa agtttcatac aagggagatc cgattgtaca   2820
gcatcgcccc atgctggaag agcgaattgt tgaactcttt agaaatttga tgaagagcgc   2880
gttcgttgta gagcggcagc cgtgtatgcc tatgcacccg gaccggccac ttgtgataaa   2940
gaccggagtt cagtttacaa caaaggtccg actgcttgtc aaatttccgg aattgaacta   3000
tcaattgaag atcaaggttt gcatcgataa ggattctggc gatgttgcgg cgttgcgcgg   3060
cagccgcaag tttaacatac ttggcactaa taccaaggtt atgaacatgg aggagtccaa   3120
caacggctca ctcagtgctg aattcaagca ccttacgctg agagaacaga gatgcggtaa   3180
cgggggacgc gccaactgtg atgcctcact tattgtcact gaagagcttc acctgataac   3240
gttcgaaact gaggtttacc atcaaggcct gaaaatagat ctggagactc attctctgcc   3300
cgttgtcgtt atttctaaca tttgccagat gcccaatgca tgggcgagca ttctgtggta   3360
```

```
taatatgctg acaaacaatc cgaagaacgt caacttcttc acgaagccgc cgatcggtac   3420
ctgggatcag gtggcggaag tccttagctg gcagttcagc tccaccacca agaggggttt   3480
gtcaatagag caattgacta cgttggctga gaagctcctg ggacctggag taaattacag   3540
tgggtgtcag atcacatggg ctaaattttg caaggaaaac atggcaggta agggtttttc   3600
cttttgggtc tggcttgata acataataga tctcgtcaaa aagtacatac tcgcgctgtg   3660
gaacgagggt tacataatgg gttttatatc taaagaaagg gagagagcga ttttgtccac   3720
taaaccaccg ggcacgtttc ttctccgatt ttccgagtca gcaaagaag gtggcgtaac   3780 atttacctgg gtcgaaaagg acattagtgg aaagacgcaa attcaaagtg tggaacctta   3840
tacgaaacag caactgaata acatgtcctt tgcggagata ataatggggt acaaaattat   3900
ggatgctact aatatactcg ttagccctct ggtctacctt tacccagaca tccccaagga   3960
ggaggcgttc ggaaagtatt gccgaccgga atcccaagag catcccgaag cggaccccgg   4020
tagtgccgca ccctacctta aaactaagtt catttgcgtc accccaacga cgtgcagcaa   4080
cacaatagac ttgccgatga gtccccgaac gctcgatagt ctcatgcagt tcggaaacaa   4140
tggcgaggga gctgagccct ccgccggcgg acaatttgag agcctcacct ttgacatgga   4200
gcttacatca gagtgcgcga caagcccgat gaccagatct cgcaagaagc gcagcaccag   4260
atctcgcaag aagcgcagcg gggccccat gatatctctg atcgctgctc ttgctgtgga   4320
ctacgtgatt ggtatggaga atgctatgcc ctggaatctg cctgcagacc tggcatggtt   4380
taagaggaac acccttaata aacctgtaat catgggacga catacatggg agagtatcgg   4440
caggccattg cccgggagga agaatataat tctgagttcc cagccttcta ctgatgatag   4500
ggtaacttgg gtcaagagcg tcgacgaggc catcgccgct tgcggggatg tgcctgaaat   4560
catggttatc gggggcggac gggtgattga gcaatttctg cccaaggcac agaagctgta   4620
tctgacccat atagacgccg aggtggaggg agatacacac tttcccgact atgagcccga   4680
tgattgggag agtgtctta gcgaatttca tgacgccgac gcacagaatt cccatagcta   4740
ctgcttcgaa attctcgaac ggcgctaggc ggccgcgcgg atccagacat gataagatac   4800
attgatgagt ttgacaaaac cacaactaga atgcagtgaa aaaatgctt tatttgtgaa   4860 atttgtgatg ctattgcttt atttgtaacc attataagct gcaataaaca agttaacaac   4920
aacaattgca ttcatttta gtttcaggtt caggggggag tgtgggaggt ttttagtcg   4980 actggggaga gatctgagga accctagtg atggagttgg ccactccctc tctgcgcgct   5040
cgctcgctca ctgaggccgc ccgggcaaag cccgggcgtc gggcgaccttt tggtcgcccg   5100 gcctcagtga gcgagcgagc gcgcagagag ggagtggcca ac                      5142
```

<210> SEQ ID NO 23
<211> LENGTH: 948
<212> TYPE: PRT
<213> ORGANISM: Artificial Sequence
<220> FEATURE:
<223> OTHER INFORMATION: Synthetic Polypeptide

<400> SEQUENCE: 23

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

-continued

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                    85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Gln Gln Gly Gly Gln
            115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
                180                 185                 190

Gln Ser Val Thr Arg Gln Lys Met Gln Gln Leu Glu Gln Met Leu Thr
            195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
                260                 265                 270

Ser Gln Leu Gln Thr Arg Gln Gln Ile Lys Lys Leu Glu Glu Leu Gln
            275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Val Ile
    450                 455                 460

```
Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
        610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
            675                 680                 685

Pro Glu Ser Gln Glu His Pro Glu Ala Asp Pro Gly Ser Ala Ala Pro
        690                 695                 700

Phe Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met Thr Arg Ser Arg Lys Lys Arg Ser Thr Arg Ser Arg Lys Lys
770                 775                 780

Arg Ser Gly Ala Pro Met Ile Ser Leu Ile Ala Ala Leu Ala Val Asp
785                 790                 795                 800

Tyr Val Ile Gly Met Glu Asn Ala Met Pro Trp Asn Leu Pro Ala Asp
                805                 810                 815

Leu Ala Trp Phe Lys Arg Asn Thr Leu Asn Lys Pro Val Ile Met Gly
                820                 825                 830

Arg His Thr Trp Glu Ser Ile Gly Arg Pro Leu Pro Gly Arg Lys Asn
            835                 840                 845

Ile Ile Leu Ser Ser Gln Pro Ser Thr Asp Asp Arg Val Thr Trp Val
        850                 855                 860

Lys Ser Val Asp Glu Ala Ile Ala Ala Cys Gly Asp Val Pro Glu Ile
865                 870                 875                 880

Met Val Ile Gly Gly Gly Arg Val Ile Glu Gln Phe Leu Pro Lys Ala
```

|   |   |   | 885 |   |   |   | 890 |   |   |   | 895 |   |
|---|---|---|---|---|---|---|---|---|---|---|---|---|
| Gln | Lys | Leu | Tyr | Leu | Thr | His | Ile | Asp | Ala | Glu | Val | Glu | Gly | Asp | Thr |
|   |   |   | 900 |   |   |   | 905 |   |   |   | 910 |   |

| His | Phe | Pro | Asp | Tyr | Glu | Pro | Asp | Asp | Trp | Glu | Ser | Val | Phe | Ser | Glu |
|---|---|---|---|---|---|---|---|---|---|---|---|---|---|---|---|
|   |   |   | 915 |   |   |   | 920 |   |   |   | 925 |   |

| Phe | His | Asp | Ala | Asp | Ala | Gln | Asn | Ser | His | Ser | Tyr | Cys | Phe | Glu | Ile |
|---|---|---|---|---|---|---|---|---|---|---|---|---|---|---|---|
|   |   |   | 930 |   |   |   | 935 |   |   |   | 940 |   |

Leu Glu Arg Arg
945

<210> SEQ ID NO 24
<211> LENGTH: 5142
<212> TYPE: DNA
<213> ORGANISM: Artificial Sequence
<220> FEATURE:
<223> OTHER INFORMATION: Synthetic Polynucleotide

<400> SEQUENCE: 24

| ttggccactc | cctctctgcg | cgctcgctcg | ctcactgagg | ccgggcgacc | aaaggtcgcc | 60 |
|---|---|---|---|---|---|---|
| cgacgcccgg | gctttgcccg | ggcggcctca | gtgagcgagc | gagcgcgcag | agagggagtg | 120 |
| gccaactcca | tcactagggg | ttcctcagat | ctgaattcgg | tacctagtta | ttaatagtaa | 180 |
| tcaattacgg | ggtcattagt | tcatagccca | tatatggagt | tccgcgttac | ataacttacg | 240 |
| gtaaatggcc | cgcctggctg | accgcccaac | gacccccgcc | cattgacgtc | aataatgacg | 300 |
| tatgttccca | tagtaacgcc | aatagggact | ttccattgac | gtcaatgggt | ggagtattta | 360 |
| cggtaaactg | cccacttggc | agtacatcaa | gtgtatcata | tgccaagtac | gccccctatt | 420 |
| gacgtcaatg | acggtaaatg | gcccgcctgg | cattatgccc | agtacatgac | cttatgggac | 480 |
| tttcctactt | ggcagtacat | ctacgtatta | gtcatcgcta | ttaccatggt | cgaggtgagc | 540 |
| cccacgttct | gcttcactct | ccccatctcc | cccccctccc | cacccccaat | tttgtattta | 600 |
| tttattttt | aattattttg | tgcagcgatg | ggggcggggg | gggggggggg | gcgcgcgcca | 660 |
| ggcggggcgg | ggcggggcga | ggggcggggc | ggggcgaggc | ggagaggtgc | ggcggcagcc | 720 |
| aatcagagcg | gcgcgctccg | aaagtttcct | tttatggcga | ggcggcggcg | gcggcggccc | 780 |
| tataaaaagc | gaagcgcgcg | gcgggcggga | gtcgctgcgc | gctgccttcg | ccccgtgccc | 840 |
| cgctccgccg | ccgcctcgcg | ccgcccgccc | ggctctgac | tgaccgcgtt | actcccacag | 900 |
| gtgagcgggc | gggacggccc | ttctcctccg | ggctgtaatt | agcgcttggt | ttaatgacgg | 960 |
| cttgtttctt | ttctgtggct | gcgtgaaagc | cttgaggggc | tccggagggg | ccctttgtgc | 1020 |
| gggggagcg | gctcggggg | tgcgtgcgtg | tgtgtgtgcg | tggggagcgc | cgcgtgcggc | 1080 |
| tccgcgctgc | ccggcggctg | tgagcgctgc | gggcgcggcg | cggggctttg | tgcgctccgc | 1140 |
| agtgtgcgcg | aggggagcgc | ggccggggc | ggtgccccgc | ggtgcggggg | gggctgcgag | 1200 |
| gggaacaaag | gctgcgtgcg | gggtgtgtgc | gtggggggt | gagcaggggg | tgtgggcgcg | 1260 |
| tcggtcgggc | tgcaaccccc | cctgcacccc | cctccccgag | ttgctgagca | cggcccggct | 1320 |
| tcgggtgcgg | ggctccgtac | ggggcgtggc | gcggggctcg | ccgtgccggg | cggggggtgg | 1380 |
| cggcaggtgg | gggtgccggg | cggggcgggg | ccgcctcggg | ccggggaggg | ctcggggag | 1440 |
| gggcgcggcg | gcccccggag | ccgccggcggc | tgtcgaggcg | cggcgagccg | cagccattgc | 1500 |
| cttttatggt | aatcgtgcga | gagggcgcag | ggacttcctt | tgtcccaaat | ctgtgcggag | 1560 |
| ccgaaatctg | ggaggcgccg | ccgcacccc | tctagcgggc | gcggggcgaa | gcggtgcggc | 1620 |
| gccggcagga | aggaaatggg | cggggagggc | cttcgtgcgt | cgccgcgccg | ccgtcccctt | 1680 |

```
ctccctctcc agcctcgggg ctgtccgcgg ggggacggct gccttcgggg gggacggggc    1740
agggcggggt tcggcttctg gcgtgtgacc ggcggctcta gagcctctgc taaccatgtt    1800
catgccttct tcttttcct acagctcctg ggcaacgtgc tggttattgt gctgtctcat     1860
cattttggca aagaattcct cgaagatcta ggcaacgcgt ctcgaggcgg ccgccgccac    1920
catggcccag tggaatcaac ttcaacaact tgatacccgc tacctggaac aacttcatca    1980
actctacagt gatagctttc ctatggagct cagacagttc ctcgcgccgt ggattgaaag    2040
ccaggactgg gcgtatgctg cttcaaagga gagtcatgca actctcgtat tccataatct    2100
gctcggagag atcgatcaac aatacagcag gtttctgcag gaatctaacg tgctttatca    2160
acacaatctg aggcggatta acaattcct gcaatctcga tatcttgaaa acccatgga     2220 gattgcccgg atcgtcgcac gctgtctgtg ggaagagagt cgactgttgc agacggcagc    2280
tactgctgcc cagcagggcg gacaggcgaa tcatccgact gccgctgtag tgacggaaaa    2340
acaacaaatg ctggagcaac atctgcaaga cgtcagaaaa cgagtacagg acctcgaaca    2400
gaagatgaaa gtggtcgaaa acttgcaaga cgacttcgat tttaattata aaacgctgaa    2460
atcccagggg gatatgcaag accttaacgg caataatcag tctgttacca gacagaaaat    2520
gcagcagctc gagcaaatgc tgacggctct tgaccagatg agaagaagca tagtctcaga    2580
attggcaggc ctcctctctg ccatggagta cgtacagaag acgttgacag atgaggaact    2640
cgctgattgg aagagacgcc aacagattgc ttgcataggg ggtccaccta atatatgcct    2700
cgaccggttg gaaaactgga taacatcttt ggctgaatct cagctccaaa cacgccagca    2760
aataaaaaag cttgaggagt tgcagcagaa ggttagttac aagggagatc ccattgtgca    2820
gcataggcca atgctggaag agaggattgt tgagctgttt aggaatctga tgaaaagtgc    2880
cttcgtagtg gagagacagc catgcatgcc aatgcatcct gacagaccac tggttataaa    2940
gactggagtt caatttacaa caaaagttag actcctggtc aagttcccgg agctcaacta    3000
tcaactgaag ataaaagtct gtattgacaa ggatagtggc gatgttgcag ccttgagggg    3060
tagccgaaaa tttaacattc tcggaacgaa cacaaaagtg atgaacatgg aggaatcaaa    3120
taatggttct ctctccgcag agtttaagca ccttactctg cgcgaacaac gctgcggaaa    3180
cggcggccgg gccaattgcg atgccagcct tatagtgacg gaagagctgc atctgataac    3240
tttcgagacg gaagtctatc atcaaggcct caaaattgac ttggagactc actccttgcc    3300
cgtagtggtt atttcaaata tatgccaaat gcctaatgca tgggcatcaa tcctttggta    3360
caatatgctt actaataacc caagaacgt taatttcttc actaaacctc caattggtac    3420
ttgggaccaa gttgccgagg tattgagttg gcagttttcc tcaacaacta agagagggtt    3480
gagcatagaa cagctgacca cactggcgga gaaacttctg ggacccggcg tcaactattc    3540
tggatgtcag attacctggg ccaaattctg caaagaaaat atggctggca agggtttcag    3600
cttctgggta tggcttgaca atataattga cctcgtaaaa aagtacatcc tcgctctttg    3660
gaatgaaggt tatattatgg gctttataag taaagagcga gagcgggcta tcttgtcaac    3720
gaagcccccg ggtacgttcc tgttgcgatt ctcagagagc tctaaggagg gtggcgtgac    3780
tttcacgtgg gtagagaaag acatctctgg taagactcaa atccaatcag ttgaaccgta    3840
cacaaagcaa caactgaata acatgtcctt cgcagaaatt atcatggggt acaagattat    3900
ggacgcgacc aacatcctgg tcagtccgct cgtttatctc tatcccgata tacctaaaga    3960
agaagcattt ggaaagtact gccggccaga atcacaagag catcctgagg ctgatcctgg    4020
```

```
ttccgctgca ccgttcttga aaacgaaatt catatgtgtc actcctacaa cctgttcaaa    4080
cacgatagac cttccaatgt ctcctaggac gttggacagc cttatgcagt ttggtaataa    4140
tggggagggg gccgagccgt ccgcgggggg tcagtttgag agccttacat tcgatatgga    4200
gctgacctct gagtgtgcaa cttctccgat gaccagatct cgcaagaagc gcagcaccag    4260
atctcgcaag aagcgcagcg ggcccccat gatatctctg atcgctgctc ttgctgtgga     4320
ctacgtgatt ggtatggaga atgctatgcc ctggaatctg cctgcagacc tggcatggtt    4380
taagaggaac acccttaata aacctgtaat catgggacga catacatggg agagtatcgg    4440
caggccattg cccgggagga agaatataat tctgagttcc cagccttcta ctgatgatag    4500
ggtaacttgg gtcaagagcg tcgacgaggc catcgccgct tgcggggatg tgcctgaaat    4560
catggttatc gggggcggac gggtgattga gcaatttctg cccaaggcac agaagctgta    4620
tctgacccat atagacgccg aggtggaggg agatacacac tttcccgact atgagcccga    4680
tgattgggag agtgtcttta gcgaatttca tgacgccgac gcacagaatt cccatagcta    4740
ctgcttcgaa attctcgaac ggcgctaggc ggccgcgcgg atccagacat gataagatac    4800
attgatgagt ttggacaaac cacaactaga atgcagtgaa aaaatgctt tatttgtgaa     4860 atttgtgatg ctattgcttt atttgtaacc attataagct gcaataaaca gttaacaac     4920 aacaattgca ttcattttat gtttcaggtt caggggagg tgtgggaggt tttttagtcg     4980
actggggaga gatctgagga acccctagtg atggagttgg ccactccctc tctgcgcgct    5040
cgctcgctca ctgaggccgc ccgggcaaag cccgggcgtc gggcgacctt tggtcgcccg    5100
gcctcagtga gcgagcgagc gcgcagagag ggagtggcca ac                       5142
```

<210> SEQ ID NO 25
<211> LENGTH: 948
<212> TYPE: PRT
<213> ORGANISM: Artificial Sequence
<220> FEATURE:
<223> OTHER INFORMATION: Synthetic Polypeptide

<400> SEQUENCE: 25

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
            35                  40                  45

Lys Glu Ser His Ala Thr Leu Val Phe His Asn Leu Leu Gly Glu Ile
        50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
        130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
```

```
                165                 170                 175
Lys Thr Leu Lys Ser Gln Gly Asp Met Gln Asp Leu Asn Gly Asn Asn
                180                 185                 190

Gln Ser Val Thr Arg Gln Lys Met Gln Gln Leu Glu Gln Met Leu Thr
                195                 200                 205

Ala Leu Asp Gln Met Arg Arg Ser Ile Val Ser Glu Leu Ala Gly Leu
            210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
                260                 265                 270

Ser Gln Leu Gln Thr Arg Gln Gln Ile Lys Lys Leu Glu Glu Leu Gln
                275                 280                 285

Gln Lys Val Ser Tyr Lys Gly Asp Pro Ile Val Gln His Arg Pro Met
            290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
            530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590
```

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Ala Phe Gly Lys Tyr Cys Arg
        675                 680                 685

Pro Glu Ser Gln Glu His Pro Glu Ala Asp Pro Gly Ser Ala Ala Pro
        690                 695                 700

Tyr Leu Lys Thr Lys Phe Ile Cys Val Thr Pro Thr Thr Cys Ser Asn
705                 710                 715                 720

Thr Ile Asp Leu Pro Met Glu Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met Thr Arg Ser Arg Lys Lys Arg Ser Thr Arg Ser Arg Lys Lys
        770                 775                 780

Arg Ser Gly Ala Pro Met Ile Ser Leu Ile Ala Leu Ala Val Asp
785                 790                 795                 800

Tyr Val Ile Gly Met Glu Asn Ala Met Pro Trp Asn Leu Pro Ala Asp
            805                 810                 815

Leu Ala Trp Phe Lys Arg Asn Thr Leu Asn Lys Pro Val Ile Met Gly
        820                 825                 830

Arg His Thr Trp Glu Ser Ile Gly Arg Pro Leu Pro Gly Arg Lys Asn
    835                 840                 845

Ile Ile Leu Ser Ser Gln Pro Ser Thr Asp Asp Arg Val Thr Trp Val
850                 855                 860

Lys Ser Val Asp Glu Ala Ile Ala Ala Cys Gly Asp Val Pro Glu Ile
865                 870                 875                 880

Met Val Ile Gly Gly Gly Arg Val Ile Glu Gln Phe Leu Pro Lys Ala
            885                 890                 895

Gln Lys Leu Tyr Leu Thr His Ile Asp Ala Glu Val Glu Gly Asp Thr
        900                 905                 910

His Phe Pro Asp Tyr Glu Pro Asp Asp Trp Glu Ser Val Phe Ser Glu
        915                 920                 925

Phe His Asp Ala Asp Ala Gln Asn Ser His Ser Tyr Cys Phe Glu Ile
930                 935                 940

Leu Glu Arg Arg
945

<210> SEQ ID NO 26
<211> LENGTH: 5142
<212> TYPE: DNA
<213> ORGANISM: Artificial Sequence
<220> FEATURE:
<223> OTHER INFORMATION: Synthetic Polynucleotide

<400> SEQUENCE: 26

```
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg  120
gccaactcca tcactagggg ttcctcagat ctgaattcgg tacctagtta ttaatagtaa  180
tcaattacgg ggtcattagt tcatagccca tatatggagt tccgcgttac ataacttacg  240
gtaaatggcc cgcctggctg accgcccaac gaccccgcc cattgacgtc aataatgacg  300
tatgttccca tagtaacgcc aatagggact ttccattgac gtcaatgggt ggagtattta  360
cggtaaactg cccacttggc agtacatcaa gtgtatcata tgccaagtac gccccctatt  420
gacgtcaatg acggtaaatg gcccgcctgg cattatgccc agtacatgac cttatgggac  480
tttcctactt ggcagtacat ctacgtatta gtcatcgcta ttaccatggt cgaggtgagc  540
cccacgttct gcttcactct ccccatctcc cccctccc cacccccaat tttgtattta  600
tttatttttt aattatttg tgcagcgatg ggggcggggg ggggggggg gcgcgcgcca  660
ggcggggcgg ggcggggcga ggggcggggc ggggcgaggc ggagaggtgc ggcggcagcc  720
aatcagagcg gcgcgctccg aaagtttcct tttatggcga ggcggcggcg cggcggccc  780
tataaaaagc gaagcgcgcg gcgggcggga gtcgctgcgc gctgccttcg ccccgtgccc  840
cgctccgccg ccgcctcgcg ccgcccgccc cggctctgac tgaccgcgtt actcccacag  900
gtgagcgggc gggacggccc ttctcctccg ggctgtaatt agcgcttggt ttaatgacgg  960
cttgtttctt ttctgtggct gcgtgaaagc cttgaggggc tccgggaggg cccttgtgc 1020
gggggagcg gctcggggg tgcgtgcgtg tgtgtgtgcg tggggagcgc cgcgtgcggc 1080
tccgcgctgc ccggcggctg tgagcgctgc gggcgcggcg cggggctttg tgcgctccgc 1140
agtgtgcgcg aggggagcgc ggccgggggc ggtgccccgc ggtgcgggg gggctgcgag 1200
gggaacaaag gctgcgtgcg gggtgtgtgc gtgggggggt gagcaggggg tgtgggcgcg 1260
tcggtcgggc tgcaacccc cctgcacccc cctccccgag ttgctgagca cggcccggct 1320
tcgggtgcgg ggctccgtac ggggcgtggc gcggggctcg ccgtgccggg cggggggtgg 1380
cggcaggtgg gggtgccggg cggggcgggg ccgcctcggg ccggggaggg ctcgggggag 1440
gggcgcggcg gcccccggag cgccggcggc tgtcgaggcg cggcgagccg cagccattgc 1500
cttttatggt aatcgtgcga gagggcgcag ggacttcctt tgtcccaaat ctgtgcggag 1560
ccgaaatctg ggaggcgccg ccgcaccccc tctagcgggc gcggggcgaa gcggtgcggc 1620
gccggcagga aggaaatggg cggggagggc cttcgtgcgt cgccgcgccg ccgtccccctt 1680
ctccctctcc agcctcgggg ctgtccgcgc ggggacggct gccttcgggg gggacggggc 1740
agggcggggt tcggcttctg gcgtgtgacc ggcggctcta gagcctctgc taaccatgtt 1800
catgccttct tcttttttcct acagctcctg ggcaacgtgc tggttattgt gctgtctcat 1860
cattttggca aagaattcct cgaagatcta ggcaacgcgt ctcgaggcgg ccgccgccac 1920
catggctcaa tggaaccagc tccaacagct cgacaccagg tacctggagc aattgcatca 1980
actctatagt gatagcttcc ccatggaact gagacaattc cttgcaccat ggatagagtc 2040
acaggattgg gcgtacgctg caagcaaaga atctcatgca accctcgtat ttcataatct 2100
cctcggtgag atcgaccagc aatactcacg gttccttcag gagtctaatg tgctttatca 2160
acacaacctt cgccggatta agcagttctt gcagagccga tatctcgaga agcctatgga 2220
aatagctagg atcgttgcaa ggtgcttgtg gaagaaagt agacttctcc aaactgcagc 2280
aacggctgcg cagcagggtg gccaggccaa ccacccgaca gccgccgtgg taacggaaaa 2340
```

```
acagcagatg cttgaacaac accttcagga cgtccgcaaa agagtacagg acctggaaca    2400
aaaaatgaag gtcgtcgaaa accttcagga tgacttcgat tttaactata aaaccctcaa    2460
atctcaggga gatatgcaag acctcaacgg taataatcag agcgtcactc gacagaagat    2520
gcagcaactt gagcaaatgc ttacggcact ggatcagatg cgaaggtcca ttgtctccga    2580
acttgccggg ctcctgtcag ccatggagta tgtacagaaa actttgaccg acgaggagtt    2640
ggcagactgg aagaggaggc aacagatagc ctgcattggc gggcccccta acatttgcct    2700
tgacaggttg gaaaactgga ttacatctct ggcggagagt caactgcaga cacggcagca    2760
aataaaaaaa ctggaagagc tccagcgaaa ggtgagttac aaggggggacc caattgtgca    2820 gcatcgccca atgctggaag aacggattgt tgaattgttt aggaacctca tgaaatccgc    2880
gtttgtcgta gagagacagc cctgtatgcc gatgcatcct gatcgacccc tcgtgatcaa    2940
aactggtgta caattcacaa caaaagtgag gttgctggtc aagttccctg aactcaacta    3000
ccaactgaag attaaagtgt gcattgacaa ggattctgga gacgtggcgg cacttcgcgg    3060
ttcaagaaag tttaacatac tcggcactaa tacaaaagtt atgaatatgg aggagtccaa    3120
caacgggtca ctgtccgccg aatttaagca cttgacgctt cgcgagcaac gatgtggcaa    3180
tgggggcaga gcaaattgcg acgcttcttt gattgtcact gaggaacttc acctgattac    3240
cttcgaaacc gaggtatacc accaagggct gaaaattgac ttggaaaccc atagtctccc    3300
cgtggtggtc attagtaaca tttgccagat gcctaatgct gggcaagca tcctttggta    3360 caacatgctt acaaacaatc cgaagaacgt caacttcttt accaagccgc ccattggaac    3420
atgggatcaa gtggcggaag tcctcagttg gcagttttcc agtaccacga agcgaggact    3480
ttctatcgag caactgacga cgctggcgga aaaactcttg ggacctggag ttaattactc    3540
cgggtgtcag ataacatggg ccaaattctg caaggagaac atggcgggga aaggtttcag    3600
cttttgggtt tggttggata acataattga tctcgtaaag aaatacatac tggccctctg    3660
gaatgaaggt tatatcatgg gcttcattag taaagaacgg gagagggcca tacttagcac    3720
taagcctcca ggaacgtttc ttctcagatt ttctgagtct tcaaaggagg gaggcgtgac    3780
cttcacctgg gttgaaaaag atatctcagg aaagacacag attcagtccg tcgaaccata    3840
tacgaaacag caactcaata acatgagttt cgcagaaata atcatgggat ataagattat    3900
ggacgcaact aatatactgg tgagtccact cgtttatctc taccccgata tcccgaagga    3960
ggaagcattc ggaaaatact gcagacctga atcccaggaa catccagagg ccgacccagg    4020
ctctgccgct ccatatttga aaactaaatt tatctgcgta acacctacaa cttgcagcaa    4080
tacgatcgat ttgcccatgg aaccacgcac cctcgatagc cttatgcaat tcgggaataa    4140 tgggggaagga gcagaaccct ctgcaggagg acaatttgag agcctcacat tcgatatgga    4200
gttgacgtca gaatgcgcaa ccagtccaat gaccagatct cgcaagaagc gcagcaccag    4260
atctcgcaag aagcgcagcg gggcccccat gatatctctg atcgctgctc ttgctgtgga    4320
ctacgtgatt ggtatggaga atgctatgcc ctggaatctg cctgcagacc tggcatggtt    4380
taagaggaac acccttaata aacctgtaat catgggacga catacatggg agagtatcgg    4440
caggccattg cccgggagga agaatataat tctgagttcc cagccttcta ctgatgatag    4500
ggtaacttgg gtcaagagcg tcgacgaggc catcgccgct tgcgggatg tgcctgaaat    4560 catggttatc gggggcggac gggtgattga gcaattcctg cccaaggcac agaagctgta    4620
tctgacccat atagacgccg aggtggaggg agatacacac tttcccgact atgagcccga    4680
tgattgggag agtgtcttta gcgaatttca tgacgccgac gcacagaatt cccatagcta    4740
```

```
ctgcttcgaa attctcgaac ggcgctaggc ggccgcgcgg atccagacat gataagatac    4800
attgatgagt ttggacaaac cacaactaga atgcagtgaa aaaatgctt tatttgtgaa     4860 atttgtgatg ctattgcttt atttgtaacc attataagct gcaataaaca agttaacaac    4920
aacaattgca ttcattttat gtttcaggtt caggggagg tgtgggaggt tttttagtcg     4980
actggggaga gatctgagga accctagtg atggagttgg ccactccctc tctgcgcgct     5040
cgctcgctca ctgaggccgc ccgggcaaag cccgggcgtc gggcgacctt tggtcgcccg    5100
gcctcagtga gcgagcgagc gcgcagagag ggagtggcca ac                       5142
```

<210> SEQ ID NO 27
<211> LENGTH: 498
<212> TYPE: PRT
<213> ORGANISM: Artificial Sequence
<220> FEATURE:
<223> OTHER INFORMATION: Synthetic Polypeptide

<400> SEQUENCE: 27

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285
```

```
Leu Ser Thr Leu Thr Ile Asp Gly Val Thr Arg Ser Asp Gln Gly Leu
290                 295                 300
Tyr Thr Cys Ala Ala Ser Ser Gly Leu Met Thr Lys Lys Asn Ser Thr
305                 310                 315                 320
Thr Arg Ser Arg Lys Lys Arg Ser Thr Arg Ser Arg Lys Lys Arg Ser
                325                 330                 335
Gly Ala Pro Met Ile Ser Leu Ile Ala Ala Leu Ala Val Asp Tyr Val
            340                 345                 350
Ile Gly Met Glu Asn Ala Met Pro Trp Asn Leu Pro Ala Asp Leu Ala
                355                 360                 365
Trp Phe Lys Arg Asn Thr Leu Asn Lys Pro Val Ile Met Gly Arg His
370                 375                 380
Thr Trp Glu Ser Ile Gly Arg Pro Leu Pro Gly Arg Lys Asn Ile Ile
385                 390                 395                 400
Leu Ser Ser Gln Pro Ser Thr Asp Asp Arg Val Thr Trp Val Lys Ser
                405                 410                 415
Val Asp Glu Ala Ile Ala Ala Cys Gly Asp Val Pro Glu Ile Met Val
            420                 425                 430
Ile Gly Gly Gly Arg Val Ile Glu Gln Phe Leu Pro Lys Ala Gln Lys
                435                 440                 445
Leu Tyr Leu Thr His Ile Asp Ala Glu Val Glu Gly Asp Thr His Phe
450                 455                 460
Pro Asp Tyr Glu Pro Asp Asp Trp Glu Ser Val Phe Ser Glu Phe His
465                 470                 475                 480
Asp Ala Asp Ala Gln Asn Ser His Ser Tyr Cys Phe Glu Ile Leu Glu
                485                 490                 495
Arg Arg

<210> SEQ ID NO 28
<211> LENGTH: 3792
<212> TYPE: DNA
<213> ORGANISM: Artificial Sequence
<220> FEATURE:
<223> OTHER INFORMATION: Synthetic Polynucleotide

<400> SEQUENCE: 28
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctcagat ctgaattcgg tacctagtta ttaatagtaa   180
tcaattacgg ggtcattagt tcatagccca tatatggagt tccgcgttac ataacttacg   240
gtaaatggcc cgcctggctg accgcccaac gacccccgcc cattgacgtc aataatgacg   300
tatgttccca tagtaacgcc aatagggact ttccattgac gtcaatgggt ggagtattta   360
cggtaaactg cccacttggc agtacatcaa gtgtatcata tgccaagtac gccccctatt   420
gacgtcaatg acggtaaatg gcccgcctgg cattatgccc agtacatgac cttatgggac   480
tttcctactt ggcagtacat ctacgtatta gtcatcgcta ttaccatggt cgaggtgagc   540
cccacgttct gcttcactct ccccatctcc cccccctccc cacccccaat tttgtattta   600
tttattttt aattatttg tgcagcgatg ggggcggggg gggggggggg gcgcgcgcca   660
ggcgggcgg ggcggggcga gggcgtgggc ggggcgaggc ggagaggtgc ggcggcagcc   720
aatcagagcg gcgcgctccg aaagtttcct tttatggcga ggcggcggcg gcggcggccc   780
tataaaaagc gaagcgcgcg gcgggcggga gtcgctgcgc gctgccttcg ccccgtgccc   840
```

| | |
|---|---|
| cgctccgccg ccgcctcgcg ccgcccgccc cggctctgac tgaccgcgtt actcccacag | 900 |
| gtgagcgggc gggacggccc ttctcctccg ggctgtaatt agcgcttggt ttaatgacgg | 960 |
| cttgtttctt ttctgtggct gcgtgaaagc cttgaggggc tccgggaggg ccctttgtgc | 1020 |
| gggggagcg gctcgggggg tgcgtgcgtg tgtgtgtgcg tgggagcgc cgcgtgcggc | 1080 |
| tccgcgctgc ccggcggctg tgagcgctgc gggcgcggcg cggggctttg tgcgctccgc | 1140 |
| agtgtgcgcg aggggagcgc ggccgggggc ggtgccccgc ggtgcggggg gggctgcgag | 1200 |
| gggaacaaag gctgcgtgcg gggtgtgtgc gtggggggt gagcaggggg tgtgggcgcg | 1260 |
| tcggtcgggc tgcaaccccc cctgcacccc cctccccgag ttgctgagca cggcccggct | 1320 |
| tcgggtgcgg ggctccgtac ggggcgtggc gcggggctcg ccgtgccggg cggggggtgg | 1380 |
| cggcaggtgg gggtgccggg cggggcgggg ccgcctcggg ccggggaggg ctcggggag | 1440 |
| gggcgcggcg gcccccggag cgccggcggc tgtcgaggcg cggcgagccg cagccattgc | 1500 |
| cttttatggt aatcgtgcga gagggcgcag ggacttcctt tgtcccaaat ctgtgcggag | 1560 |
| ccgaaatctg ggaggcgccg ccgcacccc tctagcgggc gcggggcgaa gcggtgcggc | 1620 |
| gccggcagga aggaaatggg cggggagggc cttcgtgcgt cgccgcgccg ccgtcccctt | 1680 |
| ctccctctcc agcctcgggg ctgtccgcgg gggacggct gccttcgggg gggacggggc | 1740 |
| agggcggggt tcggcttctg gcgtgtgacc ggcggctcta gagcctctgc taaccatgtt | 1800 |
| catgccttct tctttttcct acagctcctg ggcaacgtgc tggttattgt gctgtctcat | 1860 |
| cattttggca aagaattcct cgaagatcta ggcaacgcgt ctcgaggcgg ccgccgccac | 1920 |
| catgcaatca aaggtgttgc tggcggtggc cctttggttg tgtgtcgaga cccgagcggc | 1980 |
| ctccgtgggt cttccctccg tttctctcga tctccctcgg ttgagcatcc aaaaagacat | 2040 |
| ccttaccata aaagcaaaca ctaccttgca gatcacatgc agaggtcaga gagatctcga | 2100 |
| ttggttgtgg cccaataatc agagcgggtc cgaacagcgg gttgaggtga ccgagtgctc | 2160 |
| agatggactt ttctgtaaga ccctcacgat acccaaagtt ataggcaacg atactggtgc | 2220 |
| ctacaagtgc ttctaccgag aaacggattt ggcctcagtt atatacgttt atgtgcaaga | 2280 |
| ttaccgctcc ccattcatag cgtcagtcag cgaccaacac ggcgttgtct acattacgga | 2340 |
| aaacaagaat aagacggtcg tgataccgtg tctcggaagc atctcaaatc tgaatgtctc | 2400 |
| cctgtgcgct cgctaccctg agaaaaggtt tgttcctgac ggtaacagaa tatcctggga | 2460 |
| tagtaaaaaa ggttttacga ttccctccta tatgattagt tatgctggca tggtgttttg | 2520 |
| cgaggctaaa atcaacgatg agtcctacca gtcaataatg tatattgtgg tggttgtggg | 2580 |
| ctacaggatc tacgatgtgg ttttgtctcc cagccatgga atcgagttgt ctgtagggga | 2640 |
| aaaactggtg cttaactgca cagcgagaac cgaactcaac gttggaatag acttcaactg | 2700 |
| ggagtacccg agttccaaac accaacacaa aaaactcgta acagggatc tgaagaccca | 2760 |
| gtcagggtct gagatgaaaa aatttctttc tactctgaca atagatggag tcacccgctc | 2820 |
| cgatcaaggg ctctacactt gtgcggcttc ttcagggctg atgaccaaaa aaaattcaac | 2880 |
| taccagatct cgcaagaagc gcagcaccag atctcgcaag aagcgcagcg ggcccccat | 2940 |
| gatatctctg atcgctgctc ttgctgtgga ctacgtgatt ggtatggaga atgctatgcc | 3000 |
| ctggaatctg cctgcagacc tggcatggtt taagaggaac acccttaata aacctgtaat | 3060 |
| catgggacga catacatggg agagtatcgg caggccattg cccgggagga agaatataat | 3120 |
| tctgagttcc cagccttcta ctgatgatag ggtaacttgg gtcaagagcg tcgacgaggc | 3180 |
| catcgccgct tgcggggatg tgcctgaaat catggttatc gggggcggac gggtgattga | 3240 |

```
gcaatttctg cccaaggcac agaagctgta tctgacccat atagacgccg aggtggaggg    3300
agatacacac tttcccgact atgagcccga tgattgggag agtgtcttta gcgaatttca    3360
tgacgccgac gcacagaatt cccatagcta ctgcttcgaa attctcgaac ggcgctaggc    3420
ggccgcgcgg atccagacat gataagatac attgatgagt ttggacaaac cacaactaga    3480
atgcagtgaa aaaatgctt tatttgtgaa atttgtgatg ctattgcttt atttgtaacc     3540
attataagct gcaataaaca agttaacaac aacaattgca ttcatttat gtttcaggtt     3600 caggggagg tgtgggaggt tttttagtcg actggggaga gatctgagga accctagtg      3660 atggagttgg ccactccctc tctgcgcgct cgctcgctca ctgaggccgc ccgggcaaag    3720 cccggcgtc gggcgaccttt tggtcgcccg gcctcagtga gcgagcgagc gcgcagagag    3780
ggagtggcca ac                                                        3792
```

<210> SEQ ID NO 29
<211> LENGTH: 931
<212> TYPE: PRT
<213> ORGANISM: Artificial Sequence
<220> FEATURE:
<223> OTHER INFORMATION: Synthetic Polypeptide

<400> SEQUENCE: 29

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255
```

```
Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
        370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
        610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
```

|     |     |     |     | 675 |     |     |     | 680 |     |     |     | 685 |     |     |
| --- | --- | --- | --- | --- | --- | --- | --- | --- | --- | --- | --- | --- | --- | --- |

Thr Ala Ser Gly Asn Pro Pro Gln Ile Met Trp Phe Lys Asp Asn
            690                695              700

Glu Thr Leu Val Glu Asp Ser Gly Ile Val Leu Lys Asp Gly Asn Arg
705              710              715              720

Asn Leu Thr Ile Arg Arg Val Arg Lys Glu Asp Gly Leu Tyr Thr
            725              730            735

Cys Gln Ala Cys Ser Val Leu Gly Cys Ala Lys Val Glu Ala Phe Phe
        740              745            750

Ile Thr Arg Ser Arg Lys Lys Arg Ser Thr Arg Ser Arg Lys Lys Arg
        755              760            765

Ser Gly Ala Pro Met Ile Ser Leu Ile Ala Ala Leu Ala Val Asp Tyr
    770              775            780

Val Ile Gly Met Glu Asn Ala Met Pro Trp Asn Leu Pro Ala Asp Leu
785              790              795              800

Ala Trp Phe Lys Arg Asn Thr Leu Asn Lys Pro Val Ile Met Gly Arg
            805              810            815

His Thr Trp Glu Ser Ile Gly Arg Pro Leu Pro Gly Arg Lys Asn Ile
        820              825            830

Ile Leu Ser Ser Gln Pro Ser Thr Asp Asp Arg Val Thr Trp Val Lys
    835              840            845

Ser Val Asp Glu Ala Ile Ala Ala Cys Gly Asp Val Pro Glu Ile Met
850              855              860

Val Ile Gly Gly Gly Arg Val Ile Glu Gln Phe Leu Pro Lys Ala Gln
865              870              875              880

Lys Leu Tyr Leu Thr His Ile Asp Ala Glu Val Glu Gly Asp Thr His
            885              890            895

Phe Pro Asp Tyr Glu Pro Asp Asp Trp Glu Ser Val Phe Ser Glu Phe
        900              905            910

His Asp Ala Asp Ala Gln Asn Ser His Ser Tyr Cys Phe Glu Ile Leu
        915              920            925

Glu Arg Arg
    930

<210> SEQ ID NO 30
<211> LENGTH: 5091
<212> TYPE: DNA
<213> ORGANISM: Artificial Sequence
<220> FEATURE:
<223> OTHER INFORMATION: Synthetic Polynucleotide

<400> SEQUENCE: 30

```
ttggccactc cctctctgcg cgctcgctcg ctcactgagg ccgggcgacc aaaggtcgcc    60
cgacgcccgg gctttgcccg gcggcctcca gtgagcgagc gagcgcgcag agagggagtg   120
gccaactcca tcactagggg ttcctcagat ctgaattcgg tacctagtta ttaatagtaa   180
tcaattacgg ggtcattagt tcatagccca tatatggagt tccgcgttac ataacttacg   240
gtaaatggcc cgcctggctg accgcccaac gaccccccgcc cattgacgtc aataatgacg   300
tatgttccca gtaacgcc aatagggact ttccattgac gtcaatgggt ggagtattta   360
cggtaaactg cccacttggc agtacatcaa gtgtatcata tgccaagtac gccccctatt   420
gacgtcaatg acggtaaatg gcccgcctgg cattatgccc agtacatgac cttatgggac   480
tttcctactt ggcagtacat ctacgtatta gtcatcgcta ttaccatggt cgaggtgagc   540
cccacgttct gcttcactct ccccatctcc cccccctccc caccccaat tttgtattta   600
```

```
tttattttt  aattattttg  tgcagcgatg  ggggcggggg  ggggggggggg  gcgcgcgcca     660 ggcggggcgg  ggcggggcga  ggggcggggc  ggggcgaggc  ggagaggtgc  ggcggcagcc     720
aatcagagcg  gcgcgctccg  aaagtttcct  tttatggcga  ggcggcggcg  gcggcggccc     780
tataaaaagc  gaagcgcgcg  gcgggcggga  gtcgctgcgc  gctgccttcg  ccccgtgccc     840
cgctccgccg  ccgcctcgcg  ccgcccgccc  cggctctgac  tgaccgcgtt  actcccacag     900
gtgagcgggc  gggacggccc  ttctcctccg  ggctgtaatt  agcgcttggt  ttaatgacgg     960
cttgtttctt  ttctgtggct  gcgtgaaagc  cttgaggggc  tccgggaggg  ccctttgtgc    1020 gggggagcg   gctcgggggg  tgcgtgcgtg  tgtgtgtgcg  tggggagcgc  cgcgtgcggc    1080
tccgcgctgc  ccggcggctg  tgagcgctgc  gggcgcggcg  cggggctttg  tgcgctccgc    1140
agtgtgcgcg  aggggagcgc  ggccggggc   ggtgccccgc  ggtgcggggg  gggctgcgag    1200
gggaacaaag  gctgcgtgcg  gggtgtgtgc  gtggggggggt  gagcagggggg  tgtgggcgcg    1260 tcggtcgggc  tgcaaccccc  cctgcacccc  cctccccgag  ttgctgagca  cggcccggct    1320
tcgggtgcgg  ggctccgtac  ggggcgtggc  gcggggctcg  ccgtgccggg  cgggggtgg    1380 cggcaggtgg  gggtgccggg  cggggcgggg  ccgcctcggg  ccggggaggg  ctcggggag    1440 gggcgcggcg  gcccccggag  cgccggcggc  tgtcgaggcg  cggcgagccg  cagccattgc    1500
cttttatggt  aatcgtgcga  gagggcgcag  ggacttcctt  tgtcccaaat  ctgtgcggag    1560
ccgaaatctg  ggaggcgccg  ccgcaccccc  tctagcgggc  gcggggcgaa  gcggtgcggc    1620
gccggcagga  aggaaatggg  cggggagggc  cttcgtgcgt  cgccgcgccg  ccgtcccctt    1680
ctccctctcc  agcctcgggg  ctgtccgcgg  ggggacggct  gccttcgggg  gggacggggc    1740
agggcggggt  tcggcttctg  gcgtgtgacc  ggcggctcta  gagcctctgc  taaccatgtt    1800
catgccttct  tcttttttcct  acagctcctg  ggcaacgtgc  tggttattgt  gctgtctcat    1860
cattttggca  aagaattcct  cgaagatcta  ggcaacgcgt  ctcgaggcgg  ccgccgccac    1920
catgcagtca  aaggtccttc  tcgcggtagc  tctgtggttg  tgcgtagaga  cacgggccgc    1980
ttcagtgggg  ctgccttcag  taagcctcga  tttgccccgg  ctttcaatac  agaaagatat    2040
tctcacaatc  aaggctaata  ccactctgca  aattacctgt  cgcggccaaa  gggatctgga    2100
ttggctctgg  ccgaataatc  aatcagggag  tgaacagcgg  gtcgaagtga  ccgagtgttc    2160
tgacggactt  ttttgcaaaa  cacttactat  cccaaaagta  atcgggaacg  ataccggggc    2220
ttacaagtgt  ttctacagag  agacagatct  tgctagtgtg  atttacgtat  atgtgcaaga    2280
ttaccgcagc  ccttttcatag  catccgtatc  agaccaacat  ggagttgtat  acattacaga    2340
gaacaagaac  aaaactgtag  ttattcccctg  tttggggtct  ataagcaacc  tcaacgtaag    2400
cctctgcgct  agatacccag  agaaacgatt  cgtcccggat  gggaatagaa  tttcctggga    2460
tagcaagaag  ggcttcacta  ttccgagcta  catgatatca  tacgcaggta  tggtgttctg    2520
cgaagcgaag  ataaacgatg  agagttatca  gtcaatcatg  tacatagtgg  tggtcgttgg    2580
gtacagaatt  tatgatgttg  tcctcagtcc  gtcccatggc  attgaactga  gtgtcgggga    2640
aaaattggtg  ctgaattgta  ccgctaggac  agaattgaac  gttggcattg  actttaactg    2700
ggagtatccg  agctcaaagc  accagcataa  aaagttggtt  aacagagatc  tgaaaaccca    2760
gtctggcagt  gaaatgaaaa  agttcctctc  tacgctgaca  atagacggtg  ttacgaggtc    2820
tgatcagggt  ttgtacacat  gtgctgcatc  ttccggtttg  atgacaaaga  aaaactccac    2880
gtttgttcgc  gtgcatgaga  agccgtttgt  ggcgttcggc  tcaggaatgg  agtccctcgt    2940
```

```
tgaagcgacg gtaggcgagc gggtccggat ccccgctaaa tacttgggct acccaccacc    3000
ggagataaaa tggtataaga atggtatacc gcttgagagt aatcatacga taaaagcggg    3060
tcatgtactc accataatgg aagtaagcga gagagatact ggaaattaca ccgttatcct    3120
gacaaatcca atatccaaag agaagcagtc acacgttgta tcactcgtgg tttatgtccc    3180
ccctcaaata ggagaaaagt cactcatcag tccggtggat agttatcaat acgggacgac    3240
ccagactctc acatgcacag tatatgccat ccctccaccc caccatattc attggtattg    3300
gcagcttgaa gaggaatgcg ccaatgagcc ttcacaggca gtgtcagtta caaatcctta    3360
cccttgtgag gaatggagga gcgtcgagga cttccagggg ggtaataaga tagaagtcaa    3420
taagaatcaa tttgcactca tagaaggaaa gaacaagacg gtttctactt tggtgataca    3480
agccgcaaat gtgtccgcac tctataagtg cgaggcagtc aacaaagttg gtcgcggcga    3540
gcgggtgata agcttccacg tcacgagggg accggaaatc actcttcaac ccgatatgca    3600
acccacggaa caggaatctg tttcactttg gtgtacggcg gataggagta cgtttgagaa    3660
cctcacatgg tataaattgg gaccgcagcc cttgcctatc cacgtggggg agcttcccac    3720
tcctgtttgc aagaatctgg atacactctg gaaactgaat gctactatgt tcagcaattc    3780
taccaatgac atactcatta tggaattgaa aaatgcgtca ctccaagatc agggagatta    3840
cgtatgcctc gctcaggacc gcaagactaa aaagaggcac tgtgttgtcc ggcagcttac    3900
agttcttgaa cgcgtggcgc ctaccattac cggcaatctg gagaatcaaa ctacgtcaat    3960
cggggagagc atcgaggtct catgcacggc cagcggcaat cctccgcccc agattatgtg    4020
gtttaaagac aatgagacgc tggtggagga tagtgggatt gtacttaagg atgggaatcg    4080
caacctcacc attcgaagag tgcgcaagga ggacgaaggg ttgtacacct gccaagcatg    4140
ctccgttctg ggatgcgcaa aagttgaagc attctttata accagatctc gcaagaagcg    4200
cagcaccaga tctcgcaaga agcgcagcgg ggcccccatg atatctctga tcgctgctct    4260
tgctgtggac tacgtgattg gtatggagaa tgctatgccc tggaatctgc ctgcagacct    4320
ggcatggttt aagaggaaca cccttaataa acctgtaatc atgggacgac atacatggga    4380
gagtatcggc aggccattgc ccgggaggaa gaatataatt ctgagttccc agccttctac    4440
tgatgatagg gtaacttggg tcaagagcgt cgacgaggcc atcgccgctt cggggatgt    4500 gcctgaaatc atggttatcg ggggcggacg ggtgattgag caatttctgc ccaaggcaca    4560
gaagctgtat ctgacccata tagacgccga ggtggaggga gatacacact ttcccgacta    4620
tgagcccgat gattgggaga gtgtctttag cgaatttcat gacgccgacg cacagaattc    4680
ccatagctac tgcttcgaaa ttctcgaacg gcgctaggcg gccgcgcgga tccagacatg    4740
ataagataca ttgatgagtt tggacaaacc acaactagaa tgcagtgaaa aaatgcttt    4800 atttgtgaaa tttgtgatgc tattgcttta tttgtaacca ttataagctg caataaacaa    4860
gttaacaaca acaattgcat tcattttatg tttcaggttc aggggaggt gtggaggtt    4920 ttttagtcga ctgggagag atctgaggaa ccccagtga tggagttggc cactccctct    4980
ctgcgcgctc gctcgctcac tgaggccgcc cggcaaagc ccggcgtcg gcgacctt    5040 ggtcgcccgg cctcagtgag cgagcgagcg cgcagagagg gagtggccaa c          5091
```

<210> SEQ ID NO 31
<211> LENGTH: 417
<212> TYPE: PRT
<213> ORGANISM: Artificial Sequence
<220> FEATURE:
<223> OTHER INFORMATION: Synthetic Polypeptide

<400> SEQUENCE: 31

```
Met Lys Val Leu Ala Ala Gly Val Val Pro Leu Leu Val Leu His
1               5                   10                  15

Trp Lys His Gly Ala Gly Asp Tyr Arg Ser Pro Phe Ile Ala Ser Val
            20                  25                  30

Ser Asp Gln His Gly Val Val Tyr Ile Thr Glu Asn Lys Asn Lys Thr
            35                  40                  45

Val Val Ile Pro Cys Leu Gly Ser Ile Ser Asn Leu Asn Val Ser Leu
        50                  55                  60

Cys Ala Arg Tyr Pro Glu Lys Arg Phe Val Pro Asp Gly Asn Arg Ile
65                  70                  75                  80

Ser Trp Asp Ser Lys Lys Gly Phe Thr Ile Pro Ser Tyr Met Ile Ser
                85                  90                  95

Tyr Ala Gly Met Val Phe Cys Glu Ala Lys Ile Asn Asp Glu Ser Tyr
                100                 105                 110

Gln Ser Ile Met Tyr Ile Val Val Val Gly Tyr Arg Ile Tyr Asp
            115                 120                 125

Val Val Leu Ser Pro Ser His Gly Ile Glu Leu Ser Val Gly Glu Lys
130                 135                 140

Leu Val Leu Asn Cys Thr Ala Arg Thr Glu Leu Asn Val Gly Ile Asp
145                 150                 155                 160

Phe Asn Trp Glu Tyr Pro Ser Ser Lys His Gln His Lys Lys Leu Val
                165                 170                 175

Asn Arg Asp Leu Lys Thr Gln Ser Gly Ser Glu Met Lys Lys Phe Leu
            180                 185                 190

Ser Thr Leu Thr Ile Asp Gly Val Thr Arg Ser Asp Gln Gly Leu Tyr
            195                 200                 205

Thr Cys Ala Ala Ser Ser Gly Leu Met Thr Lys Lys Asn Ser Thr Phe
210                 215                 220

Val Arg Val His Glu Lys Pro Phe Val Ala Phe Gly Ser Gly Met Thr
225                 230                 235                 240

Arg Ser Arg Lys Lys Arg Ser Thr Arg Ser Arg Lys Lys Arg Ser Gly
                245                 250                 255

Ala Pro Met Ile Ser Leu Ile Ala Ala Leu Ala Val Asp Tyr Val Ile
                260                 265                 270

Gly Met Glu Asn Ala Met Pro Trp Asn Leu Pro Ala Asp Leu Ala Trp
            275                 280                 285

Phe Lys Arg Asn Thr Leu Asn Lys Pro Val Ile Met Gly Arg His Thr
            290                 295                 300

Trp Glu Ser Ile Gly Arg Pro Leu Pro Gly Arg Lys Asn Ile Ile Leu
305                 310                 315                 320

Ser Ser Gln Pro Ser Thr Asp Asp Arg Val Thr Trp Val Lys Ser Val
            325                 330                 335

Asp Glu Ala Ile Ala Ala Cys Gly Asp Val Pro Glu Ile Met Val Ile
            340                 345                 350

Gly Gly Gly Arg Val Ile Glu Gln Phe Leu Pro Lys Ala Gln Lys Leu
            355                 360                 365

Tyr Leu Thr His Ile Asp Ala Glu Val Glu Gly Asp Thr His Phe Pro
            370                 375                 380

Asp Tyr Glu Pro Asp Asp Trp Glu Ser Val Phe Ser Glu Phe His Asp
385                 390                 395                 400

Ala Asp Ala Gln Asn Ser His Ser Tyr Cys Phe Glu Ile Leu Glu Arg
```

Arg

<210> SEQ ID NO 32
<211> LENGTH: 3549
<212> TYPE: DNA
<213> ORGANISM: Artificial Sequence
<220> FEATURE:
<223> OTHER INFORMATION: Synthetic Polynucleotide

<400> SEQUENCE: 32

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | gcggcctca | gtgagcgagc | gagcgcgcag | agagggagtg | 120 |
| gccaactcca | tcactagggg | ttcctcagat | ctgaattcgg | tacctagtta | ttaatagtaa | 180 |
| tcaattacgg | ggtcattagt | tcatagccca | tatatggagt | tccgcgttac | ataacttacg | 240 |
| gtaaatggcc | cgcctggctg | accgcccaac | gacccccgcc | cattgacgtc | aataatgacg | 300 |
| tatgttccca | tagtaacgcc | aatagggact | ttccattgac | gtcaatgggt | ggagtattta | 360 |
| cggtaaactg | cccacttggc | agtacatcaa | gtgtatcata | tgccaagtac | gccccctatt | 420 |
| gacgtcaatg | acggtaaatg | gcccgcctgg | cattatgccc | agtacatgac | cttatgggac | 480 |
| tttcctactt | ggcagtacat | ctacgtatta | gtcatcgcta | ttaccatggt | cgaggtgagc | 540 |
| cccacgttct | gcttcactct | ccccatctcc | cccccctccc | cacccccaat | tttgtattta | 600 |
| tttattttt | aattattttg | tgcagcgatg | ggggcggggg | ggggggggggg | gcgcgcgcca | 660 |
| ggcggggcgg | ggcggggcga | ggggcggggc | ggggcgaggc | ggagaggtgc | ggcggcagcc | 720 |
| aatcagagcg | gcgcgctccg | aaagtttcct | tttatggcga | ggcggcggcg | gcggcggccc | 780 |
| tataaaaagc | gaagcgcgcg | gcgggcggga | gtcgctgcgc | gctgccttcg | ccccgtgccc | 840 |
| cgctccgccg | ccgcctcgcg | ccgcccgccc | cggctctgac | tgaccgcgtt | actcccacag | 900 |
| gtgagcgggc | gggacggccc | ttctcctccg | ggctgtaatt | agcgcttggt | ttaatgacgg | 960 |
| cttgtttctt | ttctgtggct | gcgtgaaagc | cttgaggggc | tccgggaggg | ccctttgtgc | 1020 |
| gggggggagcg | gctcggggg | tgcgtgcgtg | tgtgtgtgcg | tggggagcgc | cgcgtgcggc | 1080 |
| tccgcgctgc | ccggcggctg | tgagcgctgc | gggcgcggcg | cggggctttg | tgcgctccgc | 1140 |
| agtgtgcgcg | aggggagcgc | ggccgggggc | ggtgccccgc | ggtgcggggg | gggctgcgag | 1200 |
| gggaacaaag | gctgcgtgcg | gggtgtgtgc | gtgggggggt | gagcagggggg | tgtgggcgcg | 1260 |
| tcggtcgggc | tgcaaccccc | cctgcacccc | cctccccgag | ttgctgagca | cggcccggct | 1320 |
| tcgggtgcgg | ggctccgtac | ggggcgtggc | gcggggctcg | ccgtgccggg | cgggggtgg | 1380 |
| cggcaggtgg | gggtgccggg | cggggcgggg | ccgcctcggg | ccggggaggg | ctcggggag | 1440 |
| gggcgcggcg | gccccggag | cgccggcggc | tgtcgaggcg | cggcgagccg | cagccattgc | 1500 |
| cttttatggt | aatcgtgcga | gagggcgcag | ggacttcctt | tgtcccaaat | ctgtgcggag | 1560 |
| ccgaaatctg | ggaggcgccg | ccgcaccccc | tctagcgggc | gcggggcgaa | gcggtgcggc | 1620 |
| gccggcagga | aggaaatggg | cggggagggc | cttcgtgcgt | cgccgcgccg | ccgtcccctt | 1680 |
| ctccctctcc | agcctcgggg | ctgtccgcgg | gggacggct | gccttcgggg | gggacggggc | 1740 |
| agggcgggggt | tcggcttctg | gcgtgtgacc | ggcggctcta | gagcctctgc | taaccatgtt | 1800 |
| catgccttct | tctttttcct | acagctcctg | ggcaacgtgc | tggttattgt | gctgtctcat | 1860 |
| cattttggca | aagaattcct | cgaagatcta | ggcaacgcgt | ctcgaggcgg | ccgccgccac | 1920 |
| catgaaagtc | cttgccgccg | gagttgtccc | tctcttgctt | gtactccact | ggaagcacgg | 1980 |

```
                                                -continued
tgcaggagat tatcgctcac catttatagc gagcgtgtca gatcaacatg gcgtggtcta    2040
tataactgag aataagaata aaacggtcgt tatccctgt ttgggtagca tatctaacct     2100
caacgttagt ttgtgcgctc gatacctga aaagcggttc gtacccgatg gcaatcggat     2160
cagttgggac agtaaaaaag gcttcactat tccgtcatac atgatcagct atgcagggat    2220
ggttttctgc gaagctaaaa tcaatgacga gagttatcag agcattatgt acatcgtagt    2280
tgtcgttggg tatcgaattt acgacgttgt gctgtcccct tctcacgaa ttgaactctc      2340 cgttggagaa aaactcgtat tgaactgtac ggcacgcacg gaattgaatg tagggataga    2400
tttcaactgg gagtatccat catctaaaca tcaacataaa aaacttgtaa atcgagacct    2460
gaagacacag agtgggtccg aaatgaaaaa atttcttagt actctgacta tcgacggggt    2520
aacaagatct gatcaagggc tgtacacctg tgcggccagc tcaggtctta tgacaaaaaa    2580
aaactccact tttgtcagag tgcatgaaaa gccgttcgtg gcatttggtt caggtatgac    2640
cagatctcgc aagaagcgca gcaccagatc tcgcaagaag cgcagcgggg ccccatgat    2700 atctctgatc gctgctcttg ctgtggacta cgtgattggt atggagaatg ctatgccctg    2760
gaatctgcct gcagacctgg catggtttaa gaggaacacc cttaataaac ctgtaatcat    2820
gggacgacat acatgggaga gtatcggcag gccattgccc gggaggaaga atataattct    2880
gagttcccag ccttctactg atgatagggt aacttgggtc aagagcgtcg acgaggccat    2940
cgccgcttgc ggggatgtgc ctgaaatcat ggttatcggg ggcggacggg tgattgagca    3000
atttctgccc aaggcacaga agctgtatct gacccatata gacgccgagg tggagggaga    3060
tacacacttt cccgactatg agcccgatga ttgggagagt gtctttagcg aatttcatga    3120
cgccgacgca cagaattccc atagctactg cttcgaaatt ctcgaacggc gctaggcggc    3180
cgcgcggatc cagacatgat aagatacatt gatgagtttg gacaaaccac aactagaatg    3240
cagtgaaaaa aatgctttat ttgtgaaatt tgtgatgcta ttgctttatt tgtaaccatt    3300
ataagctgca ataaacaagt taacaacaac aattgcattc attttatgtt tcaggttcag    3360
ggggaggtgt gggaggtttt ttagtcgact ggggagagat ctgaggaacc cctagtgatg    3420
gagttggcca ctccctctct gcgcgctcgc tcgctcactg aggccgcccg ggcaaagccc    3480
gggcgtcggg cgacctttgg tcgcccggcc tcagtgagcg agcgagcgcg cagagaggga    3540
gtggccaac                                                              3549
```

RETINAL PROTECTIVE FACTOR 2 (RPF2) PROTEIN DELIVERED BY ADENO-ASSOCIATED VIRUS EXPRESSION

RELATED APPLICATIONS

This Application is a national stage filing under 35 U.S.C. § 371 of international PCT application, PCT/US2019/020454, filed Mar. 2, 2019, which claims priority under 35 U.S.C. § 119(e) to U.S. provisional patent application, U.S. Ser. No. 62/637,485, filed Mar. 2, 2018, the entire contents of each of which are incorporated herein by reference.

FEDERALLY SPONSORED RESEARCH

This invention was made with government support under grant number EY016459 awarded by the National Institutes of Health. The government has certain rights in the invention.

BACKGROUND

Vision loss is often due to the loss of neurons that either initiate the visual response to light (photoreceptors), or the neurons that transmit the signal to the brain (bipolar cells, ganglion cells, etc.). To date, mutations in approximately 250 genes have been identified to cause inherited retinal diseases. For example, retinitis pigmentosa (RP) is a monogenetic disease and patients often have impaired night and peripheral vision beginning from childhood, which progressively worsens until central vision is lost. Other retinal degenerative disorders such as age-related macular degeneration (AMD) are caused by a multitude of factors such as polymorphisms in complement factor H, obesity, smoking and hypertension.

It has been observed that neuroprotective cytokines such as leukemia inhibitory factor (LIF) or ciliary neurotrophic factor (CNTF) can protect photoreceptors from a broad range of insults, including mechanical injury and multiple mutations that cause inherited retinal degeneration. However, long-term effects of highly-expressed neurotrophic factors (e.g., LIF, CNTF, etc.) have been shown to be detrimental to retinal function and may promote inflammation.

SUMMARY

Aspects of the disclosure relate to compositions and methods for delivering one or more transgenes (e.g., therapeutic proteins) to a subject, for example by adeno-associated virus (AAV)-based expression. The disclosure is based, in part, on expression vectors (e.g., AAV expression vectors) comprising a nucleic acid sequence encoding a fusion protein that includes a therapeutic protein and a drug-reactive domain (e.g., a drug-sensitive destabilization domain (DD), such as a dihydrofolate reductase (DHFR) protein). Without wishing to be bound by any particular theory, expression of therapeutic proteins comprising a DD may be controlled (e.g., induced or inhibited) by altering the amount of an agent, such as a small molecule, that interacts with the DD and prevents degradation of the therapeutic protein. Accordingly, compositions of the disclosure are useful, in some embodiments, for delivering and/or modulating expression of therapeutic transgenes in a cell or subject.

In some aspects, the disclosure provides an isolated nucleic acid that encodes a transgene comprising a fusion protein that includes a therapeutic protein and a destabilization domain (DD). In some embodiments, the therapeutic protein is selected from a neurotrophic factor (e.g., LIF, CNTF, EDN2, OSM, etc.), transcription factor (e.g., ASCL1, NRF2, STAT3, etc.), growth factor (e.g., HBEGF), protective factor, and a growth factor receptor subunit (e.g., VEGFR2, etc.). In some embodiments, the therapeutic protein is a recombinase (e.g., Cre recombinase).

In some embodiments, a fusion protein encodes an Achaete-scute homolog 1 (ASCL1) protein or a fragment thereof. In some embodiments, an ASCL1 protein comprises the amino acid sequence set forth in SEQ ID NO: 5. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 6.

In some embodiments, a fusion protein encodes a Ciliary neurotrophic factor (CNTF) protein or a fragment thereof. In some embodiments, a CNTF protein comprises the amino acid sequence set forth in SEQ ID NO: 7. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 8.

In some embodiments, a fusion protein encodes a Cre recombinase (Cre) protein or a fragment thereof. In some embodiments, an Cre protein comprises the amino acid sequence set forth in SEQ ID NO: 9. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 10.

In some embodiments, a fusion protein encodes a Endothelin 2 (EDN2) protein or a fragment thereof. In some embodiments, an EDN2 protein comprises the amino acid sequence set forth in SEQ ID NO: 11. In some embodiments, the destabilization domain (DD) is a DHFR protein. In some embodiments, a DD (e.g., DHFR protein or a fragment thereof) is capable of being bound by trimethoprim (TMP).

In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 12.

In some embodiments, a fusion protein encodes a Heparin-binding EGF-like growth factor (HBEGF) protein or a fragment thereof. In some embodiments, an HBEGF protein comprises the amino acid sequence set forth in SEQ ID NO: 13. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 14.

In some embodiments, a fusion protein encodes a Nuclear factor (erythroid-derived 2)-like 2 growth factor (NRF2) protein or a fragment thereof. In some embodiments, an NRF2 protein comprises the amino acid sequence set forth in SEQ ID NO: 15. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 16.

In some embodiments, a fusion protein encodes an Oncostatin M (OSM) protein or a fragment thereof. In some embodiments, an OSM protein comprises the amino acid sequence set forth in SEQ ID NO: 17. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 18.

In some embodiments, a fusion protein encodes an Oncostatin M (OSM) protein variant (e.g., OSM M2) or a fragment thereof. In some embodiments, an OSM M2 protein comprises the amino acid sequence set forth in SEQ ID NO: 19. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 20.

In some embodiments, a fusion protein encodes a Signal transducer and activator of transcription 3 (STAT3) protein or a fragment thereof. In some embodiments, an STAT3 protein comprises the amino acid sequence set forth in SEQ ID NO: 21. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 22.

In some embodiments, a fusion protein encodes a Signal transducer and activator of transcription 3 (STAT3) protein variant (e.g., STAT3 Y705F, STAT3 S727E, etc.) or a fragment thereof. In some embodiments, an STAT3 protein variant comprises the amino acid sequence set forth in SEQ ID NO: 23 or 25. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in SEQ ID NO: 24 or 26.

In some embodiments, a fusion protein encodes a vascular endothelial growth factor receptor 2 (VEGFR2) protein or a fragment thereof. In some embodiments, an VEGFR2 protein comprises one or more Ig-like loop regions, for example Ig-like regions 1-3, Ig-like regions 1-7, Ig-like regions 2-3, etc. In some embodiments, an VEGFR2 protein comprises the amino acid sequence set forth in any one of SEQ ID NOs: 27, 29, and 31. In some embodiments, the destabilization domain (DD) is a DHFR protein. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof. In some embodiments, a nucleic acid sequence encoding a protein is linked to a nucleic acid sequence encoding a DD by a linker sequence. In some embodiments, a linker sequence encodes one or more furin cleavage sites. In some embodiments, an isolated nucleic acid further comprises adeno-associated virus (AAV) inverted terminal repeats that flank the transgene. In some embodiments, an isolated nucleic acid comprises the nucleic acid sequence set forth in any one of SEQ ID NOs: 28, 30, or 32.

In some aspects, the disclosure provides recombinant adeno-associated virus (rAAV) particles comprising an isolated nucleic acid as described by the disclosure.

In some aspects, the disclosure provides methods of delivering a transgene to a cell or a subject comprising administering an rAAV comprising an isolated nucleic acid as described by the disclosure to a cell or subject.

In some aspects, the disclosure relates to compositions and methods useful for maintaining or improving retinal function and/or morphology. The disclosure is based, in part, on isolated nucleic acids encoding certain neurotrophic factors (e.g., leukemia inhibitory factor (LIF), etc.) and gene therapy vectors (e.g., recombinant adeno-associated virus (rAAV) vectors) encoding the same. In some embodiments, isolated nucleic acids and gene therapy vectors described by the disclosure are useful for treatment of certain diseases or disorders of the eye, for example retinal degeneration, retinitis pigmentosa (RP), age-related macular degeneration (AMD), glaucoma, etc.

Accordingly, in some aspects, the disclosure provides an isolated nucleic acid comprising a sequence that is at least 75% identical to SEQ ID NO: 1 and encodes a protein, wherein the protein binds to a Leukemia Inhibitory Factor Receptor subunit (LIFR) and/or a Glycoprotein 130 (gp130) subunit.

In some embodiments, the nucleic acid sequence encodes a protein that is at least 95% identical to the sequence set forth in SEQ ID NO: 2.

In some embodiments, the isolated nucleic acid comprises one or more adeno-associated virus (AAV) inverted terminal repeat (ITR) sequences. In some embodiments, the one or more AAV ITR sequences are AAV2 ITR sequences.

In some embodiments, an isolated nucleic acid comprises two AAV ITR sequences, wherein the ITR sequences flank a sequence encoding a protein.

In some embodiments, an isolated nucleic acid further comprises a CBA promoter operably linked to the sequence encoding the protein.

In some embodiments, an isolated nucleic acid further comprises a destabilization domain (DD). In some embodiments, a DD comprises a sequence encoding a dihydrofolate reductase (DHFR) protein, or a fragment thereof. In some embodiments, a DD (e.g., DHFR protein or a fragment thereof) is capable of being bound by trimethoprim (TMP). In some embodiments, a DHFR protein or fragment thereof is an *E. coli* DHFR protein, or a fragment thereof.

In some embodiments, a nucleic acid sequence encoding a protein is linked to a nucleic acid sequence encoding a DD by a linker sequence. In some embodiments, a linker sequence encodes one or more furin cleavage sites.

In some embodiments, an isolated nucleic acid described by the disclosure comprises the sequence set forth in SEQ ID NO: 3 or encodes the amino acid sequence set forth in SEQ ID NO: 4.

In some aspects, the disclosure provides a recombinant adeno-associated virus (rAAV) comprising: an expression cassette encoding a transgene comprising an isolated nucleic acid as described herein; and one or more adeno-associated virus (AAV) capsid proteins.

In some embodiments, one or more AAV capsid proteins is of a serotype selected from AAV2 or a variant thereof, and AAV6 or a variant thereof. In some embodiments, one or more capsid proteins is of an AAV2* serotype. In some embodiments, one or more capsid proteins is of an AAV6* serotype.

In some aspects, the disclosure provides a composition comprising an isolated nucleic acid as described herein or an rAAV as described herein, and a pharmaceutically acceptable excipient.

In some aspects, the disclosure provides a host cell comprising an isolated nucleic acid as described herein or an rAAV as described herein. In some embodiments, a host cell is a bacterial cell, a mammalian cell, or an insect cell. In some embodiments, a mammalian cell is a HEK293 cell. In some embodiments, an insect cell is an Sf9 cell.

In some aspects, the disclosure provides a method of delivering a transgene to the eye of a subject, the method comprising administering an isolated nucleic acid as described herein, or an rAAV as described herein, or a composition as described herein, to a subject.

In some aspects, the disclosure provides a method for treating a disease or disorder of the eye in a subject in need thereof, the method comprising administering an isolated nucleic acid as described herein, or rAAV as described herein, or composition as described herein, to a subject having or suspected of having a disease or disorder of the eye.

In some embodiments, a subject is a mammal. In some embodiments, a subject is a human or a mouse. In some embodiments, a subject has or is suspected of having retinal degeneration, retinitis pigmentosa (RP), age-related macular degeneration (AMD), or glaucoma.

In some embodiments, administration is intravitreal administration, topical administration, etc.

In some embodiments, methods described herein further comprise the step of administering trimethoprim (TMP) to a subject one or more times. In some embodiments, a subject has been administered TMP prior to administration of an isolated nucleic acid, rAAV, or composition. In some embodiments, a subject has been administered TMP after administration of the isolated nucleic acid, rAAV, or composition. In some embodiments, the concentration of TMP in each administration is between about 1 mg/kg and about 50 mg/kg of a subject.

In some embodiments, administration of an isolated nucleic acid as described herein, or rAAV as described herein, or composition as described herein, results in expression of the transgene in the eye of a subject. In some embodiments, expression of a transgene (e.g., a protein as described by the disclosure) does not result in edema and/or loss of function of retinal cells of the subject.

BRIEF DESCRIPTION OF DRAWINGS

FIG. 3A is a schematic depicting experimental design for NAIO₃) injection. FIG. 3B shows data indicating that LIF injection increases RPE resistance to NAIO₃.

FIG. 4A shows a schematic depicting signaling pathways associated with LIF/CNTF receptors. FIG. 4B shows microscopy data indicating loss of LIF-induced phosphorylated STAT3 (pSTST3) in gp130 targeted mice.

FIG. 5A shows loss of gp130 in rod photoreceptors accelerates photoreceptor cell death in a genetic model of retinal degeneration. FIG. 5B shows loss of STAT3 in rod photoreceptors accelerates photoreceptor cell death in a genetic model of retinal degeneration.

FIG. 6 shows AAV6 (3pMut) has improved targeting of cells in the inner nuclear layer.

FIG. 7A is a schematic depicting an AAV-hLIF expression construct. FIG. 7B is a schematic depicting a dosing schedule for AAV-hLIF and subsequent data analysis. FIG. 7C shows the OCT scoring system rubric. FIG. 7D shows OCT scores 7-weeks and 14-weeks post-injection of AAV-hLIF. FIG. 7E shows representative data of a-wave and b-wave detection. FIG. 7F shows a-wave amplitude measured 7-weeks and 14-weeks post-injection of AAV-hLIF.

FIG. 9A shows scoring of retinas with high titer AAV-CBA-hLIF. FIG. 9B shows levels of hLIF in the retina determined by ELISA. Between each serotype, levels of hLIF were equivalent. FIG. 9C shows activation of STAT3 as determined by ELISA.

FIG. 10A is a schematic of CBA-RPF iterations with no or one furin cleavage site (FCS). FIG. 10B shows levels of cytokine secreted by rMC-1 transfected cells into the conditioned media detected by ELISA. FIG. 10C shows activation of STAT3 in rMC-1 cells treated with conditioned media. FIG. 10D shows dose-dependent stabilization and maturation of RPF2 by TMP in transfected rMC-1 cells.

FIG. 11A is a schematic depicting one embodiment of a CBA-RPF2 rAAV vector. FIG. 11B is a schematic depicting stabilization of the RPF2 fusion protein in the presence of TMP. FIG. 11C shows cytokine secretion induced by TMP-stabilization of RPF2. FIG. 11D shows pSTAT3 activation induced by TMP-stabilization of RPF2.

FIG. 12A shows cytokine stabilization increases in a TMP-dose-dependent manner. FIG. 12B is a schematic depicting dosing schedule and sample analysis. FIG. 12C shows ONL thickness measured 7-weeks and 14-weeks post-administration of rAAV-CBA-RPF2. FIG. 12D shows a-wave amplitude measured 7-weeks and 14-weeks post-administration of rAAV-CBA-RPF2.

FIG. 15A is a schematic depicting dosing and data analysis schedules. FIG. 15B shows ONL thickness before and after Light Damage (LD) in control mice and mice administered AAV-CBA-RPF2. FIG. 15C shows a-wave amplitude measured before and after Light Damage (LD) in control mice and mice administered AAV-CBA-RPF2.

FIG. 17A is a schematic depicting a timeline of photoreceptor death and administration of AAV-CBA-RPF2. FIG. 17B shows ONL thickness measured between 3-weeks and 8-weeks of age. FIG. 17C shows preservation of cones in AAV-CBA-RPF2-injected mice. FIG. 17D shows cone number per 10 μm² in mock and AAV-CBA-RPF2-injected mice.

FIG. 18A shows b-wave amplitude measured between 3 and 8 weeks of age. FIG. 18B is a schematic depicting an OptoMotry assay. FIG. 18C shows visual acuity measurement in RPF2-treated rd10 mice.

DETAILED DESCRIPTION

Figure 1:
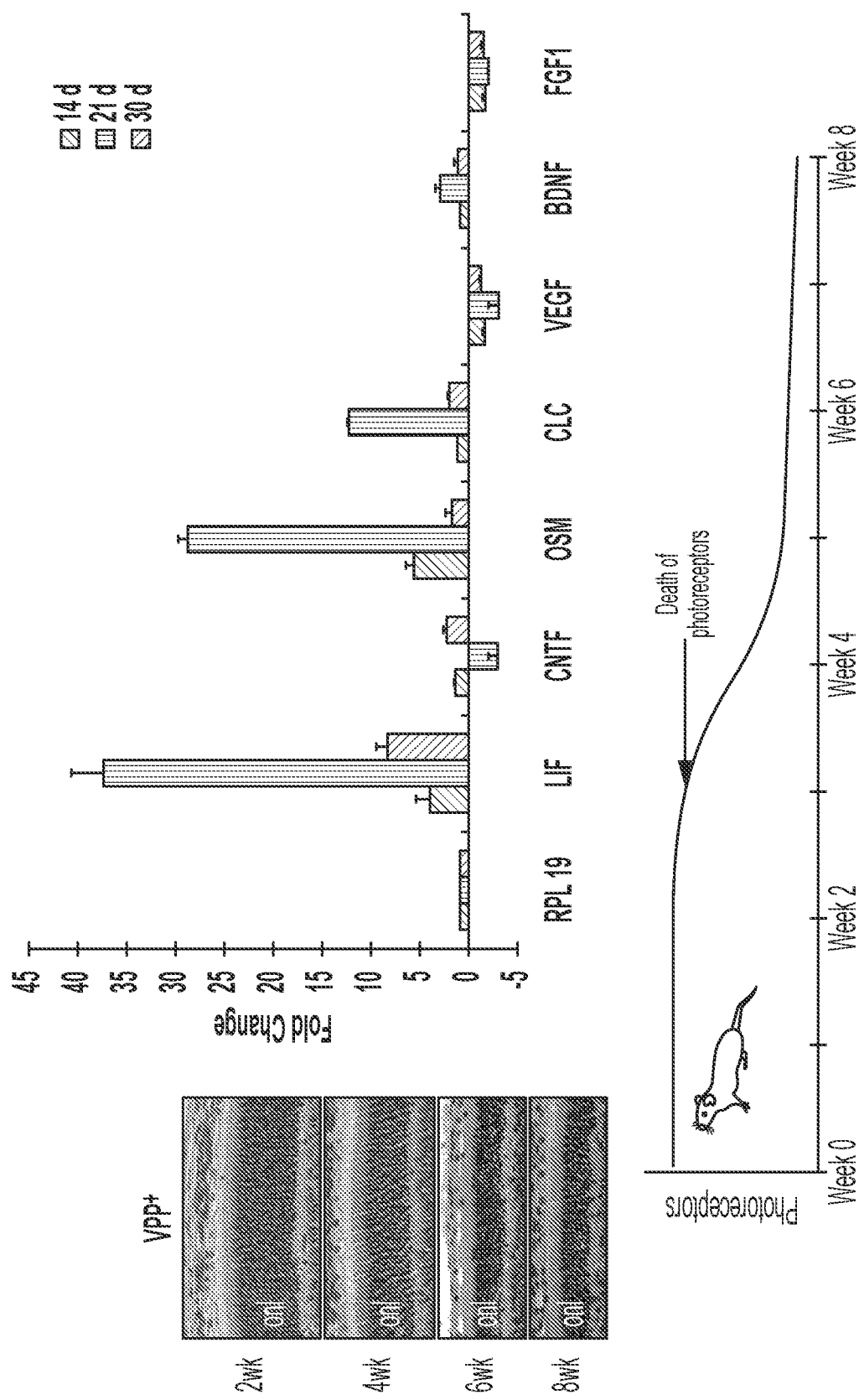
FIG. 1 shows up-regulation of leukemia inhibitory factor (LIF), Oncostatin M (OSM), and Eosinophil lysophospholipase (CLC), which are all gp130 ligands. Other genes assayed included Receptor-like protein 19 (RLP19), ciliary neurotrophic factor (CNTF), Vascular endothelial growth factor (VEGF), Brain-derived neurotrophic factor (BDNF), and Heparin-binding growth factor 1 (FGF1).

Aspects of the disclosure relate to compositions useful for delivering one or more transgenes (e.g., proteins, such as therapeutic proteins) to a subject, for example by adeno-associated virus (AAV)-based expression. The disclosure is based, in part, on expression vectors (e.g., AAV expression vectors) encoding fusion proteins comprising a destabilization domain (DD), which allows for control of protein expression in a cell (e.g., induction or inhibition) by altering the amount of an agent, such as a small molecule, that interacts with the DD. The disclosure relates, in some aspects, to methods for delivering and/or modulating expression of therapeutic transgenes in a cell or subject.

Isolated Nucleic Acids and Transgenes

In some aspects, the disclosure relates to isolated nucleic acids encoding one or more proteins (e.g., therapeutic proteins), or a portion thereof. Generally, an isolated nucleic acid may encode 1, 2, 3, 4, 5, or more than 5 (e.g., 10, 15, etc.) proteins, or portions thereof. A "portion" of a protein refers to a truncated amino acid sequence that retains the intended function of the full-length protein from which it is derived. A portion of a protein can be truncated at the N-terminus, C-terminus, or N- and C-termini relative to the protein from which the portion is derived. In some embodiments, a portion of a protein comprises an amino acid sequence comprising at least 20%, at least 30%, at least 40%, at least 50%, at least 60%, at least 70%, at least 80%, at least 90%, at least 95%, or at least 99% of the amino acids present in the protein from which the portion is derived.

In some embodiments, an isolated nucleic acid encodes a fusion protein. As used here, "fusion protein" refers to a protein that is produced by connecting two or more polypeptides which are derived from separate proteins to form a single, continuous polypeptide. In some embodiments, a fusion protein is produced by chemical conjugation (e.g., with or without a linker) between two polypeptides derived from separate proteins.

In some aspects, the disclosure relates to isolated nucleic acids comprising a transgene that encodes a protein selected from a neurotrophic factor, transcription factor, growth factor, protective factor, and a growth factor receptor subunit. Examples of neurotrophic factors include leukemia-inhibitory factor (LIF), Ciliary neurotrophic factor (CNTF), Endothelin 2 (EDN2), and Oncostatin M (OSM). Examples of transcription factors include ASCL1, NRF2, STAT3, etc. Examples of growth factors include VEGF, HBEGF, etc.

In some embodiments, a fusion protein encodes a Ciliary neurotrophic factor (CNTF) protein or a fragment thereof. CNTF is a polypeptide hormone and neurotrophic factor that promotes neurotransmitter synthesis and neurite outgrowth. Human CNTF is encoded by the CNTF gene, for example as set forth in NCBI Reference Sequence No. NM_000614. In some embodiments, a CNTF protein comprises the amino acid sequence set forth in SEQ ID NO: 7. In some embodiments, a CNTF protein comprises an amino acid sequence that is at least 70%, at least 80%, at least 90%, at least 95%, or at least 99% identical to the amino acid sequence set forth in SEQ ID NO: 7. In some embodiments, a CNTF protein is encoded by a nucleic acid sequence that encodes an amino acid sequence that is at least 70%, at least 80%, at least 90%, at least 95%, or at least 99% identical to the amino acid sequence set forth in SEQ ID NO: 7.

In some embodiments, a fusion protein encodes an Oncostatin M (OSM) protein or a fragment thereof. Oncostatin M is a pleiotropic cytokine that is part of the IL6 cytokine group, and signals through gp130 cell surface receptors (e.g., cell surface receptors comprising gp130 and LIFR or OSMR). Human OSM is encoded by the OSM gene, for example as set forth in NCBI Reference Sequence No. NM_020530. In some embodiments, an OSM protein comprises the amino acid sequence set forth in SEQ ID NO: 17. In some embodiments, a fusion protein encodes a variant of OSM protein, for example OSM M2 protein (e.g., as described by Chollangi et al. (2012) *J Biol Chem* 287(39): 32848-32859). In some embodiments, an OSM M2 protein comprises the amino acid sequence set forth in SEQ ID NO: 19. In some embodiments, an OSM protein comprises an amino acid sequence that is at least 70%, at least 80%, at least 90%, at least 95%, or at least 99% identical to the amino acid sequence set forth in SEQ ID NO: 17 or 19. In some embodiments, a OSM protein is encoded by a nucleic acid sequence that encodes an amino acid sequence that is at least 70%, at least 80%, at least 90%, at least 95%, or at least 99% identical to the amino acid sequence set forth in SEQ ID NO: 17 or 19.

In some embodiments, a fusion protein encodes a Endothelin 2 (EDN2) protein or a fragment thereof. Endothelin 2 (EDN2) protein is a member of the endothelin protein family of secretory vasoconstrictive peptides, and functions as a ligand for endothelin receptors that initiate intracellular signaling events. Human EDN2 is encoded by the EDN2 gene, for example as set forth in NCBI Reference Sequence No. NM_001956. In some embodiments, an EDN2 protein comprises the amino acid sequence set forth in SEQ ID NO: 11. In some embodiments, a EDN2 protein comprises an amino acid sequence that is at least 70%, at least 80%, at least 90%, at least 95%, or at least 99% identical to the amino acid sequence set forth in SEQ ID NO: 11. In some embodiments, a EDN2 protein is encoded by a nucleic acid sequence that encodes an amino acid sequence that is at least 70%, at least 80%, at least 90%, at least 95%, or at least 99% identical to the amino acid sequence set forth in SEQ ID NO: 11.

In some embodiments, a fusion protein encodes an Achaete-scute homolog 1 (ASCL1) protein or a fragment thereof. Achaete-scute homolog 1 is protein that is a member of the basic helix-loop-helix (BHLH) family of transcription factors. ASCL1 plays a role in the neuronal commitment and differentiation and in the generation of olfactory and autonomic neurons. Human ASCL1 is encoded by the ASCL1 gene, for example as set forth in NCBI Reference Sequence No. NM_004307. In some embodiments, an ASCL1 protein comprises the amino acid sequence set forth in SEQ ID NO: 5. In some embodiments, a ASCL1 protein comprises an amino acid sequence that is at least 70%, at least 80%, at least 90%, at least 95%, or at least 99% identical to the amino acid sequence set forth in SEQ ID NO: 5. In some embodiments, a ASCL1 protein is encoded by a nucleic acid sequence that encodes an amino acid sequence that is at least 70%, at least 80%, at least 90%, at least 95%, or at least 99% identical to the amino acid sequence set forth in SEQ ID NO: 5.

In some embodiments, a fusion protein encodes a Nuclear factor (erythroid-derived 2)-like 2 growth factor (NRF2) protein or a fragment thereof. NFR2 is transcription factor (a basic leucine zipper (bZIP) protein) that regulates the expression of antioxidant proteins that protect against oxidative damage triggered by injury and inflammation. Human NFR2 is encoded by the NFR2 gene, for example as set forth in NCBI Reference Sequence No. NM_006164. In some embodiments, an NRF2 protein comprises the amino acid sequence set forth in SEQ ID NO: 15. In some embodiments, a NRF2 protein comprises an amino acid sequence that is at least 70%, at least 80%, at least 90%, at least 95%, or at least 99% identical to the amino acid sequence set forth in SEQ ID NO: 15. In some embodiments, a NRF2 protein is encoded by a nucleic acid sequence that encodes an amino acid sequence that is at least 70%, at least 80%, at least 90%, at least 95%, or at least 99% identical to the amino acid sequence set forth in SEQ ID NO: 15.

In some embodiments, a fusion protein encodes a Signal transducer and activator of transcription 3 (STAT3) protein or a fragment thereof. STAT3 is a transcription factor that is phosphorylated in response to cytokines and growth factors, and plays important roles in regulation of gene expression during cell growth and apoptosis. Human STAT3 is encoded by the STAT3 gene, for example as set forth in NCBI Reference Sequence No. NM_003150. In some embodiments, an STAT3 protein comprises the amino acid sequence set forth in SEQ ID NO: 21. In some embodiments, a STAT3 protein comprises an amino acid sequence that is at least 70%, at least 80%, at least 90%, at least 95%, or at least 99% identical to the amino acid sequence set forth in SEQ ID NO: 21. In some embodiments, a STAT3 protein is encoded by a nucleic acid sequence that encodes an amino acid sequence that is at least 70%, at least 80%, at least 90%, at least 95%, or at least 99% identical to the amino acid sequence set forth in SEQ ID NO: 21.

In some embodiments, a fusion protein encodes a Signal transducer and activator of transcription 3 (STAT3) protein variant (e.g., STAT3 Y705F, STAT3 S727E, etc.) or a fragment thereof. A variant of STAT3 may have one or more (e.g., 2, 3, 4, 5, 6, 7, 8, 9, 10, or more) amino acid substitutions relative to a wild-type STAT3 protein (e.g., SEQ ID NO: 21). In some embodiments, at least one of the mutations results in the variant functioning as a phosphomimetic of STAT3 (e.g., the variant comprises one or more amino acid substitutions that mimic phosphorylaytion of the wild-type protein). In some embodiments, an STAT3 protein variant comprises an amino acid mutation at position 705 (e.g., Y705D) or position 772 (e.g., S727E). In some embodiments, a STAT3 protein variant comprises the amino acid sequence set forth in SEQ ID NO: 23 or 25.

In some embodiments, a fusion protein encodes a Heparin-binding EGF-like growth factor (HBEGF) protein or a fragment thereof. Heparin-binding EGF-like growth factor is a membrane-anchored mitogenic and chemotactic glycoprotein, and plays a role in wound healing, cardiac hypertrophy, and heart development and function. Human HBEGF is encoded by the HBEGF gene, for example as set forth in NCBI Reference Sequence No. NM_001945. In some embodiments, an HBEGF protein comprises the amino acid sequence set forth in SEQ ID NO: 13. In some embodiments, a HBEGF protein comprises an amino acid sequence that is at least 70%, at least 80%, at least 90%, at least 95%, or at least 99% identical to the amino acid sequence set forth in SEQ ID NO: 13. In some embodiments, a HBEGF protein is encoded by a nucleic acid sequence that encodes an amino acid sequence that is at least 70%, at least 80%, at least 90%, at least 95%, or at least 99% identical to the amino acid sequence set forth in SEQ ID NO: 13.

In some embodiments, a fusion protein encodes a vascular endothelial growth factor receptor 2 (VEGFR2) protein or a fragment thereof. Vascular endothelial growth factor receptor 2 is a tyrosine kinase receptor that functions on the cell surface, and plays a role in cell mitogenesis and cell migration. Human VEGFR2 is encoded by the VEGFR gene, for example as set forth in NCBI Reference Sequence No. NM_002253. VEGFR2 proteins typically comprise an extracellular portion consisting of 7 immunoglobulin-like (Ig) domains, a single transmembrane spanning region and an intracellular portion containing a split tyrosine-kinase domain. In some embodiments, a fusion protein encodes a truncated VEGFR2 protein, for example a protein that comprises one or more Ig-like loop regions, for example Ig-like regions 1-3, Ig-like regions 1-7, Ig-like regions 2-3, etc. of VEGFR2 but not other regions (e.g., the transmembrane spanning region). In some embodiments, an VEGFR2 protein comprises the amino acid sequence set forth in any one of SEQ ID NOs: 27, 29, and 31. In some embodiments, a VEGFR2 protein comprises an amino acid sequence that is at least 70%, at least 80%, at least 90%, at least 95%, or at least 99% identical to the amino acid sequence set forth in SEQ ID NO: 27. In some embodiments, a VEGFR2 protein is encoded by a nucleic acid sequence that encodes an amino acid sequence that is at least 70%, at least 80%, at least 90%, at least 95%, or at least 99% identical to the amino acid sequence set forth in SEQ ID NO: 27.

In some embodiments, a fusion protein encodes a Cre recombinase (Cre) protein or a fragment thereof. In some embodiments, an Cre protein comprises the amino acid sequence set forth in SEQ ID NO: 9. In some embodiments, a Cre protein comprises an amino acid sequence that is at least 70%, at least 80%, at least 90%, at least 95%, or at least 99% identical to the amino acid sequence set forth in SEQ ID NO: 9. In some embodiments, a Cre protein is encoded by a nucleic acid sequence that encodes an amino acid sequence that is at least 70%, at least 80%, at least 90%, at least 95%, or at least 99% identical to the amino acid sequence set forth in SEQ ID NO: 9.

The disclosure is based, in part, on the discovery that unregulated expression of certain proteins (e.g., growth factors, transcription factors, neurotrophic factors, etc.) in cells leads, in some embodiments, to cellular damage. Accordingly, in some embodiments, isolated nucleic acids described by the disclosure (e.g., isolated nucleic acids encoding proteins described herein) comprise one or more control elements that allow for regulation of gene expression (e.g., expression of ASCL1, CNTF, EDN2, HBEGF, NRF2, OSM, OSM-M2, STAT3, STAT3 Y705F, STAT3 S727E, Cre recombinase, VEGFR2, etc.). Non-limiting examples of control elements include promoters, insulators, silencers, response elements, introns, enhancers, initiation sites, termination signals, and poly(A) tails. Any combination of such control sequences is contemplated herein (e.g., a promoter and an enhancer).

In some embodiments, one or more promoters may be operably linked to a coding nucleotide sequence in the heterologous nucleic acid. A promoter is "operably linked" to a nucleotide sequence when the promoter sequence controls and/or regulates the transcription of the nucleotide sequence. A promoter may be a constitutive promoter, tissue-specific promoter, an inducible promoter, or a synthetic promoter. In some embodiments, a promoter comprises a β-actin promoter (e.g., chicken β-actin promoter, CBA. In some embodiments, a promoter is a chimeric viral/mammalian promoter, for example a chimeric CMV/chicken beta actin (CBA, CB or CAG) promoter.

The disclosure relates, in some aspects, to isolated nucleic acids encoding fusion proteins that comprise a destabilization domain (DD). As used herein, a "destabilization domain" or "DD" refers to a nucleic acid sequence encoding a protein (or a portion thereof) that, when fused to a sequence encoding a second protein, reversibly alters the stability of (e.g., destabilizes) the entire fusion protein (e.g., the DD and the second protein). Generally, the instability of the second protein caused by fusion to a DD can be reversed by addition of a small molecule that binds to the DD and re-stabilizes the fusion protein. The use of DDs to regulate protein expression from transgenes is known and described for example by Iwamoto et al. (2010) *Chem Biol.* 17(9)981-988. Non-limiting examples of DDs include but are not limited to FK506 binding protein (FKBP) destabilization domains and dihydrofolate reductase (DHFR) destabilization domains. In some embodiments, a DD comprises a sequence encoding a dihydrofolate reductase (DHFR) protein, or a fragment thereof.

Dihydrofolate reductase (DHFR) is an enzyme that catalyzes reduction of dihydrofolate to tetrahydrofolate. It has been observed that, in mammalian cells, fusion proteins containing bacterial DHFR protein (e.g., *E. coli* DHFR protein) are rapidly ubiquitinated and degraded by the proteasome system. However, binding of certain inhibitors of bacterial DHFR results in stabilization of the molecule and prevents degradation of the protein. Non-limiting examples of DHFR inhibitors include but are not limited to diaminoquinazolines, diaminopyrroloquinazolines, diaminopyrimidines, diaminopteridines, diaminotriazines, JP2056, piritrexim, cycloguanil, trimethoprim (TMP), iclaprim, tetrotoxoprim, etc. In some embodiments, an isolated nucleic acid encoding a fusion protein comprises a sequence encoding a DD (e.g., DHFR protein or a fragment thereof) is capable of being bound by trimethoprim (TMP).

Fusion of a DD directly to a protein, in some embodiments, prevents transit of the protein through cellular secretion pathways. The disclosure is based, in part, on the recognition that inclusion of a linker sequence between a sequence encoding a protein (e.g., a LIF protein) and a DD, in some embodiments, results in improved protein secretion. Thus, in some embodiments, a nucleic acid sequence encoding a protein (e.g., an LIF protein) is linked to a nucleic acid sequence encoding a DD by a linker sequence.

In some embodiments, a linker sequence encodes a peptide spacer, for example a glycine-rich and/or serine-rich peptide (e.g., GGGGS, (GGGGS)$_x$, where x is an integer between 1 and 20, etc.). The length of a linker can vary, for example from about 1 amino acid to about 500 amino acids (e.g., any integer between 1 and 500, inclusive). In some embodiments, a linker sequence comprises a cleavable linker sequence. Non-limiting examples of cleavable linkers include enzyme (e.g., protease) cleavable linkers and photocleavable linkers and are described for example in Leriche et al. (2012) *Bioorg Med Chem* 20(2):571-82. Examples of protease cleavable linkers include amino acid sequences that are substrates for cathepsin (e.g., cathepsin B), matrix metalloproteases (e.g., MMP1, MMP9, etc.), and furin. Generally, the number of protease cleavage substrates can vary. In some embodiments, a linker sequence encodes 1, 2, 3, 4, 5, 6, 7, 8, 9 or 10 protease cleavage sites. In some embodiments, the one or more protease cleavage sites are furin cleavage sites.

Furin is a member of the subtilisin-like proprotein convertase family and generally functions to process precursor proteins to their active forms by cleaving at a conserved dibasic amino acid consensus motif. In some embodiments, furin cleaves a sequence comprising RX(K/R)R, where X is any amino acid. Furin cleavage sites are known and described, for example by Tian et al. (2011) *Int. J Mol Sci.* 12(2):1060-1065.

The disclosure relates, in part, to recombinant adeno-associated virus vectors (rAAV vectors) comprising an isolated nucleic acid as described herein. Generally, an rAAV vector is an isolated nucleic acid sequence comprising an expression cassette engineered to express a transgene (e.g., an isolated nucleic acid encoding a LIF protein, and optionally, one or more furin cleavage sites and/or a DD) that is flanked by AAV inverted terminal repeat (ITR) sequences. The ITR sequences can be derived from any AAV serotype, including but not limited to AAV2, AAV3, AAV4, AAV5, AAV6, AAV7, AAV8, AAV9. In some embodiments, the AAV ITR sequences are AAV2 ITR sequences. In some embodiments, one of the ITR sequences in a rAAV vector is a truncated ITR (e.g., a ΔTRS ITR), which in some embodiments are useful for production of self-complementary rAAVs (scAAVs). In some embodiments, an rAAV vector is part of a plasmid (e.g., a bacterial plasmid).

In some embodiments, an isolated nucleic acid comprises AAV ITR sequences flanking a transgene that encodes a fusion protein (e.g., a fusion protein comprising a DD). ITR sequences and plasmids containing ITR sequences are known in the art and are commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. *Proc Natl Acad Sci*

*USA.* 1996 Nov. 26; 93(24):14082-7; and Curtis A. Machida. Methods in Molecular Medicine™. Viral Vectors for Gene Therapy Methods and Protocols. 10.1385/1-59259-304-6: 201© Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

Retinal Protective Factors

In some aspects, the disclosure relates to compositions and methods useful for maintaining or improving retinal function and/or morphology. The disclosure is based, in part, on isolated nucleic acids encoding certain neurotrophic factors (e.g., leukemia inhibitory factor (LIF), etc.) and gene therapy vectors (e.g., recombinant adeno-associated virus (rAAV) vectors) encoding the same. In some embodiments, isolated nucleic acids and gene therapy vectors described by the disclosure are useful for treatment of certain diseases or disorders of the eye, for example retinal degeneration, retinitis pigmentosa (RP), age-related macular degeneration (AMD), glaucoma, etc.

In some aspects, the disclosure provides isolated nucleic acids encoding transgenes encoding molecules (e.g., proteins, interfering nucleic acids, etc.) that bind to receptors located in the eye of a subject. In some embodiments, an isolated nucleic acid described by the disclosure encodes a protein, for example a protein that binds to a receptor. Generally, a protein that binds to a receptor can bind to a G-protein coupled receptor (GPCR), an ion channel (e.g., a ligand-gated ion channel), a cytokine receptor, an enzyme-linked receptor, an intracellular receptor, etc.

In some embodiments, a protein as described by the disclosure binds to a cytokine receptor. Examples of cytokine receptors include but are not limited to Type I cytokine receptors, Type II cytokine receptors, Immunoglobulin receptors, Tumor Necrosis Factor receptors, chemokine receptors, etc. In some embodiments, nucleic acid encodes a protein that binds to a Type I cytokine receptor, for example a cytokine receptor comprising a gp130 subunit and/or a leukemia inhibitory factor receptor (LIFR) subunit. Type I cytokine receptors comprising LIFR subunits are generally know and are described, for example, in Giese et al. (2005) *J. Cell Sci* 118:5129-5140.

Typically, proteins that bind to LIFRs are IL-6 type cytokines, including but not limited to Leukemia inhibitory factor (LIF), ciliary neurotrophic factor (CNTF), Cardiotrophin-1 (CT-1), Eosinophil lysophospholipase (CLC), oncostatin M (OSM), etc. Thus, in some embodiments, a nucleic acid described by the disclosure encodes a protein selected from LIF, CNTF, CT-1, CLC, OSM, or a portion thereof.

A "portion" of a protein refers to a truncated amino acid sequence that retains the intended function of the full-length protein from which it is derived. For example, a truncated IL-6 type cytokine, in some embodiments, retains the function of binding to receptors comprising a gp130 subunit and/or a LIFR subunit. A portion of a protein can be truncated at the N-terminus, C-terminus, or N- and C-termini relative to the protein from which the portion is derived. In some embodiments, a portion of a protein comprises an amino acid sequence comprising at least 20%, at least 30%, at least 40%, at least 50%, at least 60%, at least 70%, at least 80%, at least 90%, at least 95%, or at least 99% of the amino acids present in the protein from which the portion is derived.

In some embodiments, an isolated nucleic acid encodes a Leukemia inhibitory factor (LIF) protein, or a portion thereof. LIF is an IL-6 type cytokine that is generally involved with control of cell differentiation and signaling through the Jak/STAT pathway and the MAPK signaling cascade. In some embodiments, the LIF is mammalian LIF, for example human LIF (e.g., hLIF) or mouse LIF. In some embodiments, LIF comprises a sequence set forth in SEQ ID NO: 1. In some embodiments, an isolated nucleic acid described by the disclosure comprises a sequence that is that is at least 75% (e.g., at least 75%, at least 80%, at least 85%, at least 90%, at least 95%, or at least 99%) identical to SEQ ID NO: 1. In some embodiments, an isolated nucleic acid described by the disclosure comprises a sequence that encodes a codon-optimized LIF. Codon optimization is well-known in the art and is described, for example by Quax et al. (2015) *Molecular Cell* 59:149-161.

The disclosure is based, in part, on the discovery that unregulated expression of LIF proteins in the eye leads, in some embodiments, to cellular damage of retinal cells. Accordingly, in some embodiments, isolated nucleic acids described by the disclosure (e.g., isolated nucleic acids encoding LIF or a portion thereof) comprise one or more control elements that allow for regulation of gene expression (e.g., expression of LIF). Non-limiting examples of control elements include promoters, insulators, silencers, response elements, introns, enhancers, initiation sites, termination signals, and poly(A) tails. Any combination of such control sequences is contemplated herein (e.g., a promoter and an enhancer).

In some embodiments, one or more promoters may be operably linked to a coding nucleotide sequence in the heterologous nucleic acid. A promoter is "operably linked" to a nucleotide sequence when the promoter sequence controls and/or regulates the transcription of the nucleotide sequence. A promoter may be a constitutive promoter, tissue-specific promoter, an inducible promoter, or a synthetic promoter.

For example, constitutive promoters of different strengths can be used. A nucleic acid described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A cytomegalovirus (CMV) promoters. Non-limiting examples of constitutive mammalian promoters include various housekeeping gene promoters, as exemplified by the β-actin promoter (e.g., chicken β-actin promoter) and human elongation factor-1α (EF-1α) promoter. In some embodiments, chimeric viral/mammalian promoters may include a chimeric CMV/chicken beta actin (CBA, CB or CAG) promoters.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. In some embodiments, it may be beneficial to combine an isolated nucleic acid (e.g., an isolated nucleic acid encoding LIF protein) as disclosed herein, with a promoter that targets the cells, tissue, or organ where expression of LIF is desired. For example, if LIF expression is desired in the eye of a subject, a nucleic acid may comprise a promoter that targets photoreceptor cells or the retina as a whole. In some embodiments, a cell-type-specific promoter targeting the retina is human rhodopsin kinase promoter (hGRK1). Non-limiting examples of hGRK1 promoter can be found in Beltran et al., 2010, Gene Ther. 17:1162, Zolotukhin et al., 2005, Hum Gene Ther. 16:551, and Jacobson et al., Mol Ther. 13:1074. In some embodiments, a retina-specific promoter is a Pleiades Mini-promoter (for example Ple155). In some embodiments, a retina-specific promoter is glial fibrillary acidic protein promoter. Other non-limiting examples of promoters that can be used as retinal cell-type-specific promoters include red opsin promoter "PR2.1" (which targets M and L cones), chimeric 'IRBPe-GNAT2' promoter (which targets all cones), IRBP promoter (which targets rods), Grm6-SV40 enhancer/promoter (which targets bipolar cells), Thy1 (which targets RGCs), other Pleiades promoters, rod opsin promoter (which targets rods), cone arrestin promoters (which targets all cones), VMD2 or Bestrophin promoter (which targets RPE cells).

Several promoters are publically available or described. For example, Ple155 promoter is available through Addgene plasmid repository (Addgene plasmid #29011, addgene.org/29011/) and is described in Scalabrino et al. (Hum Mol Genet. 2015, 24(21):6229-39). Ye et al. (Hum Gene Ther.; 27(1):72-82) describes a shorter version of this promoter called PR1.7. A Thy1 promoter construct is also available through Addgene plasmid repository (Addgene plasmid #20736, addgene.org/20736/). A GRM6 promoter construct is also available through Addgene plasmid repository (Addgene plasmid #66391, addgene.org/66391/). Guziewicz et al. (PLoS One. 2013 Oct. 15; 8(10):e75666) and Esumi et al (J Biol Chem. 2004, 279(18):19064-73) provide examples of the use of VMD2 promoter. Dyka et al. (Adv Exp Med Biol. 2014; 801: 695-701) describes cone specific promoters for use in gene therapy, including IRBP and IRBPe-GNAT2 promoter. The use of PR2.1 promoter has been demonstrated in Komáromy et al. (Gene Ther. 2008 July; 15(14):1049-55) and its characterization in Karim et al. (Tree Physiol. 2015 October; 35(10):1129-39). Aartsen et al. (PLoS One, 5(8): e12387) describes the use of GFAP promoter to drive GFP expression in Muller glial cells. Other examples of Muller glia specific promoters are RLBP1 and GLAST (Vázquez-Chona, Invest Ophthalmol Vis Sci. 2009, 50(8):3996-4003; Regan et al., Journal of Neuroscience, 2007, 27(25): 6607-6619).

Synthetic promoters are also contemplated herein. A synthetic promoter may comprise, for example, regions of known promoters, regulatory elements, transcription factor binding sites, enhancer elements, repressor elements, and the like.

It is to be understood that a promoter may be a fragment of any one of the promoters disclosed herein, or one that retains partial promoter activity (e.g., 10-90, 30-60, 50-80, 80-99 or 90-99.9% of the activity) of a whole promoter.

The disclosure relates, in some aspects, to isolated nucleic acids encoding LIF proteins and further comprising a destabilization domain (DD). As used herein, a "destabilization domain" or "DD" refers to a nucleic acid sequence encoding a protein (or a portion thereof) that, when fused to a sequence encoding a second protein, reversibly alters the stability of (e.g., destabilizes) the entire fusion protein (e.g., the DD and the second protein). Generally, the instability of the second protein caused by fusion to a DD can be reversed by addition of a small molecule that binds to the DD and re-stabilizes the fusion protein. The use of DDs to regulate protein expression from transgenes is known and described for example by Iwamoto et al. (2010) Chem Biol. 17(9)981-988. Non-limiting examples of DDs include but are not limited to FK506 binding protein (FKBP) destabilization domains and dihydrofolate reductase (DHFR) destabilization domains. In some embodiments, a DD comprises a sequence encoding a dihydrofolate reductase (DHFR) protein, or a fragment thereof.

Dihydrofolate reductase (DHFR) is an enzyme that catalyzes reduction of dihydrofolate to tetrahydrofolate. It has been observed that, in mammalian cells, fusion proteins containing bacterial DHFR protein (e.g., E. coli DHFR protein) are rapidly ubiquitinated and degraded by the proteasome system. However, binding of certain inhibitors of bacterial DHFR results in stabilization of the molecule and prevents degradation of the protein. Non-limiting examples of DHFR inhibitors include but are not limited to diaminoquinazolines, diaminopyrroloquinazolines, diaminopyrimidines, diaminopteridines, diaminotriazines, JP2056, piritrexim, cycloguanil, trimethoprim (TMP), iclaprim, tetrotoxoprim, etc. In some embodiments, an isolated nucleic acid encoding LIF comprises a sequence encoding a DD (e.g., DHFR protein or a fragment thereof) is capable of being bound by trimethoprim (TMP).

Fusion of a DD directly to a LIF protein, in some embodiments, prevents transit of the LIF protein through cellular secretion pathways. The disclosure is based, in part, on the recognition that inclusion of a linker sequence between a sequence encoding a protein (e.g., a LIF protein) and a DD, in some embodiments, results in improved LIF protein secretion. Thus, in some embodiments, a nucleic acid sequence encoding a protein (e.g., an LIF protein) is linked to a nucleic acid sequence encoding a DD by a linker sequence.

In some embodiments, a linker sequence encodes a peptide spacer, for example a glycine-rich and/or serine-rich peptide (e.g., GGGGS, (GGGGS)$_x$, where x is an integer between 1 and 20, etc.). The length of a linker can vary, for example from about 1 amino acid to about 500 amino acids (e.g., any integer between 1 and 500, inclusive). In some embodiments, a linker sequence comprises a cleavable linker sequence. Non-limiting examples of cleavable linkers include enzyme (e.g., protease) cleavable linkers and photocleavable linkers and are described for example in Leriche et al. (2012) Bioorg Med Chem 20(2):571-82. Examples of protease cleavable linkers include amino acid sequences that are substrates for cathepsin (e.g., cathepsin B), matrix metalloproteases (e.g., MMP1, MMP9, etc.), and furin. Generally, the number of protease cleavage substrates can vary. In some embodiments, a linker sequence encodes 1, 2, 3, 4, 5, 6, 7, 8, 9 or 10 protease cleavage sites. In some embodiments, the one or more protease cleavage sites are furin cleavage sites.

Furin is a member of the subtilisin-like proprotein convertase family and generally functions to process precursor proteins to their active forms by cleaving at a conserved dibasic amino acid consensus motif. In some embodiments, furin cleaves a sequence comprising RX(K/R)R, where X is any amino acid. Furin cleavage sites are known and described, for example by Tian et al. (2011) Int. J Mol Sci. 12(2):1060-1065.

The disclosure relates, in part, to recombinant adeno-associated virus vectors (rAAV vectors) comprising an isolated nucleic acid as described herein. Generally, an rAAV vector is an isolated nucleic acid sequence comprising an expression cassette engineered to express a transgene (e.g., an isolated nucleic acid encoding a LIF protein, and optionally, one or more furin cleavage sites and/or a DD) that is flanked by AAV inverted terminal repeat (ITR) sequences. The ITR sequences can be derived from any AAV serotype, including but not limited to AAV2, AAV3, AAV4, AAV5, AAV6, AAV7, AAV8, AAV9. In some embodiments, the AAV ITR sequences are AAV2 ITR sequences. In some embodiments, one of the ITR sequences in a rAAV vector is a truncated ITR (e.g., a ΔTRS ITR), which in some embodiments are useful for production of self-complementary rAAVs (scAAVs). In some embodiments, an rAAV vector is part of a plasmid (e.g., a bacterial plasmid).

In some embodiments, an isolated nucleic acid described by the disclosure comprises the sequence set forth in SEQ ID NO: 3 or encodes the amino acid sequence set forth in SEQ ID NO: 4.

Recombinant Adeno-Associated Viruses

In some aspects, the disclosure provides recombinant AAVs (rAAVs) comprising an isolated nucleic acid as described herein.

The AAV genome is built of single-stranded deoxyribonucleic acid (ssDNA), which is either positive- or negative-sensed. At each end of the DNA strand is an inverted terminal repeat (ITR). Between the ITRs are two open reading frames (ORFs): rep and cap. The rep ORF is composed of four overlapping genes encoding Rep proteins required for the AAV life cycle. The cap ORF contains overlapping nucleotide sequences of capsid proteins: VP1, VP2 and VP3, which interact together to form a capsid of an icosahedral symmetry.

The capsid proteins, which are controlled by the same promoter, designated p40, are translated from the same mRNA. The molecular weights of VP1, VP2 and VP3 are 87, 72 and 62 kiloDaltons, respectively. The AAV capsid is composed of 60 capsid protein subunits, VP1, VP2, and VP3, that are arranged in an icosahedral symmetry in a ratio of 1:1:10.

In some embodiments, a rAAV particle comprises a rAAV vector comprising an isolated nucleic acid as described herein flanked by ITRs of serotype 2. In some embodiments, a rAAV particle is a pseudotyped rAAV particle, which comprises (a) a capsid comprised of capsid proteins derived from a serotype other than serotype 2 (e.g., serotype 3, 4, 5, 6, 7, 8, 9, etc.), and (b) a rAAV vector comprising ITRs from serotype 2. For example, a particle may have ITRs of serotype 2 and a capsid of serotype 6. Such a pseudotyped rAAV particle would be designated AAV2/6.

In some embodiments, a rAAV particle comprises (a) a capsid comprised of capsid proteins derived from a serotype selected from serotype 2, 3, 4, 5, 6, 7, 8, 9, and 10, and (b) a rAAV vector comprising ITRs from serotype 2 flanking an expression cassette comprising an isolated nucleic acid as described herein.

Generally, a rAAV as described herein may comprise capsid proteins of any serotype (e.g., 2, 3, 4, 5, 6, 7, 8, 9, 10, and variants thereof, or certain non-human capsid protein serotypes, such as rh10, rh39, etc.). In some preferred embodiments, rAAV particles have one or more capsid proteins of serotype 2 or variants thereof. Examples of serotype 2 capsid variants are described, for example by Kay et al. (2013) *PLoS ONE* 8(4): e62097 and Boye et al. (2016) *J Virol.* 90(8):4215-31. In some embodiments, an rAAV comprises an AAV2 variant having one or more of the following mutations: Y272F, Y444F, Y500F, Y730F, and T491V. In some embodiments, an rAAV comprises an AAV2 variant having the following mutations: Y272F, Y444F, Y500F, Y730F, and T491V (e.g., AAV2*).

In some preferred embodiments, rAAV particles have one or more capsid proteins of serotype 6 or variants thereof. In some embodiments, an rAAV comprises an AAV6 variant having one or more of the following mutations: Y705F, Y731F, and T492V. In some embodiments, an rAAV comprises an AAV6 variant having the following mutations: Y705F, Y731F, and T492V (e.g., AAV6*).

Various methods of producing rAAV particles and nucleic acid vectors are known (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). In some embodiments, a vector (e.g., a plasmid) comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP region as described herein), and transfected into a recombinant cells, called helper or producer cells, such that the nucleic acid vector is packaged or encapsidated inside the capsid and subsequently purified.

Non-limiting examples of mammalian helper cells include HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). A non-limiting example of an insect helper cells is Sf9 cells (see, e.g., ATCC® CRL-1711™). A helper cell may comprises rep and/or cap genes that encode the Rep protein and/or Cap proteins. In some embodiments, the packaging is performed in vitro (e.g., outside of a cell).

In some embodiments, a nucleic acid vector (e.g., a plasmid) containing the gene of interest is combined with one or more helper plasmids, e.g., that contain a rep gene of a first serotype and a cap gene of the same serotype or a different serotype, and transfected into helper cells such that the rAAV particle is packaged. In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, *Human Gene Therapy*, Vol. 9, 2745-2760; Kern, A. et al. (2003), Identification of a Heparin-Binding Motif on Adeno-Associated Virus Type 2 Capsids, *Journal of Virology*, Vol. 77, 11072-11081; Grimm et al. (2003), Helper Virus-Free, Optically Controllable, and Two-Plasmid-Based Production of Adeno-associated Virus Vectors of Serotypes 1 to 6, *Molecular Therapy*, Vol. 7, 839-850; Kronenberg et al. (2005), A Conformational Change in the Adeno-Associated Virus Type 2 Capsid Leads to the Exposure of Hidden VP1 N Termini, *Journal of Virology*, Vol. 79, 5296-5303; and Moullier, P. and Snyder, R. O. (2008), International efforts for recombinant adeno-associated viral vector reference standards, *Molecular*

*Therapy*, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), *J Virology*, 6:3096-3101).

ITR sequences and plasmids containing ITR sequences are known in the art and are commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. *Proc Natl Acad Sci USA*. 1996 Nov. 26; 93(24):14082-7; and Curtis A. Machida. Methods in Molecular Medicine™. Viral Vectors for Gene Therapy Methods and Protocols. 10.1385/1-59259-304-6:201© Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

Genebank reference numbers for sequences of AAV serotypes 1, 2, 3, 3B, 4, 5, 6, 7, 8, 9, 10, 11, 12, and 13 are listed in patent publication WO2012064960, which is incorporated herein by reference in its entirety.

A non-limiting method of rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes, cap genes, and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. As an example, HEK293 cells (available from ATCC®) are transfected via CaPO4-mediated transfection, lipids or polymeric molecules such as Polyethylenimine (PEI) with the helper plasmid(s) and a plasmid containing a nucleic acid vector. The HEK293 cells are then incubated for at least 60 hours to allow for rAAV particle production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

Methods for large-scale production of AAV using a herpesvirus-based system are also known. See for example, Clement et al. (*Hum Gene Ther.* 2009, 20(8):796-806). Methods of producing exosome-associated AAV, which can be more resistant to neutralizing anti-AAV antibodies, are also known (Hudry et al., *Gene Ther.* 2016, 23(4):380-92; Macguire et al., *Mol Ther.* 2012, 20(5):960-71).

Methods for producing and using pseudotyped rAAV vectors are also known in the art (see, e.g., Duan et al., J. Virol., 75:7662-7671, 2001; Halbert et al., J. Virol., 74:1524-1532, 2000; Zolotukhin et al., *Methods*, 28:158-167, 2002; and Auricchio et al., *Hum. Molec. Genet.*, 10:3075-3081, 2001).

Compositions

Various formulations have been developed to facilitate rAAV particle use. For example, for administration of an injectable aqueous solution of rAAV particles, the solution may be suitably buffered, if necessary, and the liquid diluent first rendered isotonic with sufficient saline or glucose. In some embodiments, a composition as provided herein comprises a plurality of any one of the rAAV particles disclosed herein. In some embodiments, a composition comprises pluralities of more than one of the rAAV particles disclosed herein. In some embodiments, "administering" or "administration" means providing a material to a subject in a manner that is pharmacologically useful.

Accordingly, in some embodiments, a composition of variant rAAV particles comprises a pharmaceutically acceptable carrier. The term "carrier" refers to a diluent, adjuvant, excipient, or vehicle with which the rAAV particle is administered. Such pharmaceutical carriers can be sterile liquids (e.g., water, oils, saline solutions, aqueous dextrose and glycerol solutions), suspending agents, preserving agents (e.g., methyl-, ethyl-, and propyl-hydroxy-benzoates), and pH adjusting agents (such as inorganic and organic acids and bases). In some embodiments, carriers include buffered saline solutions (e.g., phosphate buffered saline, HEPES-buffered saline). USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

In some embodiments, a composition comprising any one of the rAAV particles disclosed herein comprises Balanced Salt Solution (BSS) supplemented with 0.014% Tween 20 (polysorbate 20).

Typically, compositions may contain at least about 0.1% of the therapeutic agent (e.g., rAAV particle) or more, although the percentage of the active ingredient(s) may be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms of rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. In some embodiments, the form is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

Preparation of compositions for administration to a subject are known in the art. For example, a dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Methods

In some aspects, the disclosure relates to methods for delivering an isolated nucleic acid or rAAV to a cell or cells (e.g., a cell or cells of a subject). In some aspects, the disclosure relates to the recognition that incorporation of a DD into certain fusion proteins, in some embodiments, prevents transit of the protein through cellular secretion pathways. The disclosure is based, in part, on the recognition that inclusion of a linker sequence between a sequence encoding a protein (e.g., a LIF protein) and a DD, in some embodiments, results in improved protein secretion.

Accordingly, in some embodiments the disclosure relates to methods of increasing secretion of a transgene product from a cell. In some embodiments, the method comprises introducing into a cell an isolated nucleic acid or rAAV as described by the disclosure (e.g., encoding a fusion protein comprising a protein coding sequence linked to a DD by a linker sequence), and an agent that binds to the DD. In some embodiments, the linker sequence comprises a furin cleavage sequence. In some embodiments, the agent is TMP.

The amount of increased secretion (e.g., increased secretion of the protein relative to secretion from a cell transfected with a sequence coding for the protein that does not include a linker sequence and/or DD) may vary. In some embodiments, secretion of the protein is increased 2-fold, 3-fold, 5-fold, 10-fold, 20-fold, 50-fold, 100-fold, 200-fold, 500-fold, 1000-fold, or more than 1000-fold.

Methods described by the disclosure are useful, in some embodiments, for the treatment of certain diseases or disorders (e.g., diseases and disorders of the eye, for example, retinal degeneration, retinitis pigmentosa (RP), age-related macular degeneration (AMD), glaucoma, etc.). In some embodiments, the disclosure provides a method for treating a disease or disorder in a subject in need thereof, the method comprising administering to the subject an rAAV encoding an isolated nucleic acid as described by the disclosure (e.g., an isolated nucleic acid encoding one or more of LIF, ASCL1, CNTF, EDN2, HBEGF, NRF2, OSM, OSM-M2, STAT3, STAT3 Y705F, STAT3 S727E, Cre recombinase, VEGFR2 IgG loops 1-3, VEGFR2 IgG loops 1-7, and VEGFR2 IgG loops 2-3 of VEGFR2.

As shown in the Examples, a neurotrophic factor-DD fusion protein (e.g., Retinal Protective Factor 2 (RPF2)) was produced. It was observed that, in some embodiments, TMP can be used to regulate RPF2 production in vitro and in vivo in a dose-dependent manner, and that expression was reversible by TMP withdrawal. It was also observed that, in some embodiments, long-term expression of RPF2 did not alter retinal function or morphology and rescued photoreceptors from an acute light-induced degeneration model as well as preserved cone vision in an rd10 inherited retinal degeneration model.

Accordingly, in some aspects, the disclosure provides a method for delivering a transgene to the eye of a subject, the method comprising administering an isolated nucleic acid as described herein, or rAAV as described herein, or composition as described herein, to the eye of a subject (e.g., a subject having or suspected of having a disease or disorder of the eye).

A subject is generally a mammal, for example a human, mouse, dog, cat, pig, horse, or non-human primate. In some embodiments, a subject is a human. In some embodiments, a subject in which a cell, tissue or organ is transduced is a vertebrate animal (e.g., a mammal or reptile). In some embodiments, a mammalian subject is a human, a non-human primate, a dog, a cat, a hamster, a mouse, a rat, a pig, a horse, a cow, a donkey or a rabbit. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, a subject is a model for a particular disease or used to study the pharmacokinetics and/or pharmacokinetics of a protein or siRNA encoded by a gene of interest.

A subject "having" a disease generally refers to a subject who exhibits one or more signs and/or symptoms of a particular disease. For example, a subject "having retinitis pigmentosa" may be a subject who exhibits one or more of the following signs and/or symptoms: trouble seeing at night, decreased peripheral vision, tunnel vision, photophobia, development of bone spicules in the fundus, blurring of vision, etc. In some embodiments, a subject "having" a disease has been diagnosed as having the disease by a medical professional (e.g., a medical doctor). In some embodiments, the diagnosis has been confirmed by a laboratory assay.

In some embodiments, a subject "suspected of having" a disease refers to a subject who is genetically predisposed (e.g., has one or more genetic factors, such as mutations) associated with increased risk of developing a particular disease. A subject "suspected of having" a disease may or may not exhibit one or more signs and/or symptoms of that disease. For example, a subject "suspected having retinitis pigmentosa" may be a subject who does not exhibit the following signs and/or symptoms—trouble seeing at night, decreased peripheral vision, tunnel vision, photophobia, development of bone spicules in the fundus, blurring of vision, etc.—but does have a mutation associated with development of RP in one of the following genes: RP1, RP2, RPGR, PRPH2, RP9, IMPDH1, PRPF31, CRB1, PRPF8, TULP1, CA4, HPRPF3, ABCA4, EYS, CERKL, FSCN2, TOPORS, SNRNP200, SEMA4A, PRCD, NR2E3, MERTK, USH2A, PROM1, KLHL7, CNGB1, BEST1, TTC8, C2Orf71, ARL6, ZFN516, DHDDS, LRAT, SPATA7, CRX, PAP1, etc.

In some embodiments, a subject "having" a disease has been diagnosed as having the disease by a medical professional (e.g., a medical doctor). In some embodiments, the diagnosis has been confirmed by a laboratory assay. In some embodiments, a subject "suspected of having" a disease has been diagnosed as having the disease by a medical professional but the diagnosis has not been confirmed by a laboratory assay.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host cell, tissue or organ. A therapeutically acceptable amount may be an amount that is capable of treating a disease, e.g., retinal degeneration or retinitis pigmentosa (RP). As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

In some embodiments, a specific tissue in the eye is targeted. For example, the retina or one or more cell type of the retina may be targeted (e.g., photoreceptors (PR), retinal ganglion cells (RGC), bipolar cells, retinal pigment epithelium (RPE) cells, amacrine cells, astrocytes, horizontal cell, microglia, Muller glia, etc.).

Some non-limiting examples of retinal diseases that may be treated using any one of the compositions provided herein include age-related macular degeneration, choroidermia, color blindness, Leber's congenital amaurosis, reitinitis pigmentosa, Stargardt's disease, Acromatopsia, Blue cone monochromacy, Cone-rod dystrophy, congenital stationary night-blindness, Leber's hereditary Optic Neuropathy, Glaucoma, and retinal degeneration (e.g., retinal degeneration due to light damage).

In some embodiments, a composition comprising any one or more of the variant rAAV particles disclosed herein is provided to photoreceptor cells (PRs). In some embodiments, a composition comprising any one or more of the rAAV particles disclosed herein is provided to retinal ganglion cells (RGCs). In some embodiments, a composition comprising rAAV particles is provided to a PR and/or RGC via an intravitreal injection to the subject carrying the PR and/or RGC. In some embodiments, a composition is provided via subretinal injection. Other non-limiting examples of routes to administrate a composition as disclosed herein to the eye include intracameral, periocular and subconjunctival injections. In some embodiments, a composition may be injected into the lateral geniculate nucleus of a subject. Such a method may be used to target RGCs. In some embodiments, a composition may be administered topically to an eye (e.g., in eye drops).

EXAMPLES

Example 1

Role of gp130 Ligands in Autosomal Retinitis Pigmentosa (RP)

Gene expression in retinas with autosomal dominant retinitis pigmentosa (RP) was investigated in a VPP transgenic mouse model. FIG. 1 shows up-regulation of leukemia inhibitory factor (LIF), Oncostatin M (OSM), and Eosinophil lysophospholipase (CLC), which are all gp130 ligands. Other genes assayed included Receptor-like protein 19 (RLP19), ciliary neurotrophic factor (CNTF), Vascular endothelial growth factor (VEGF), Brain-derived neurotrophic factor (BDNF), and Heparin-binding growth factor 1 (FGF1).

Figure 2:
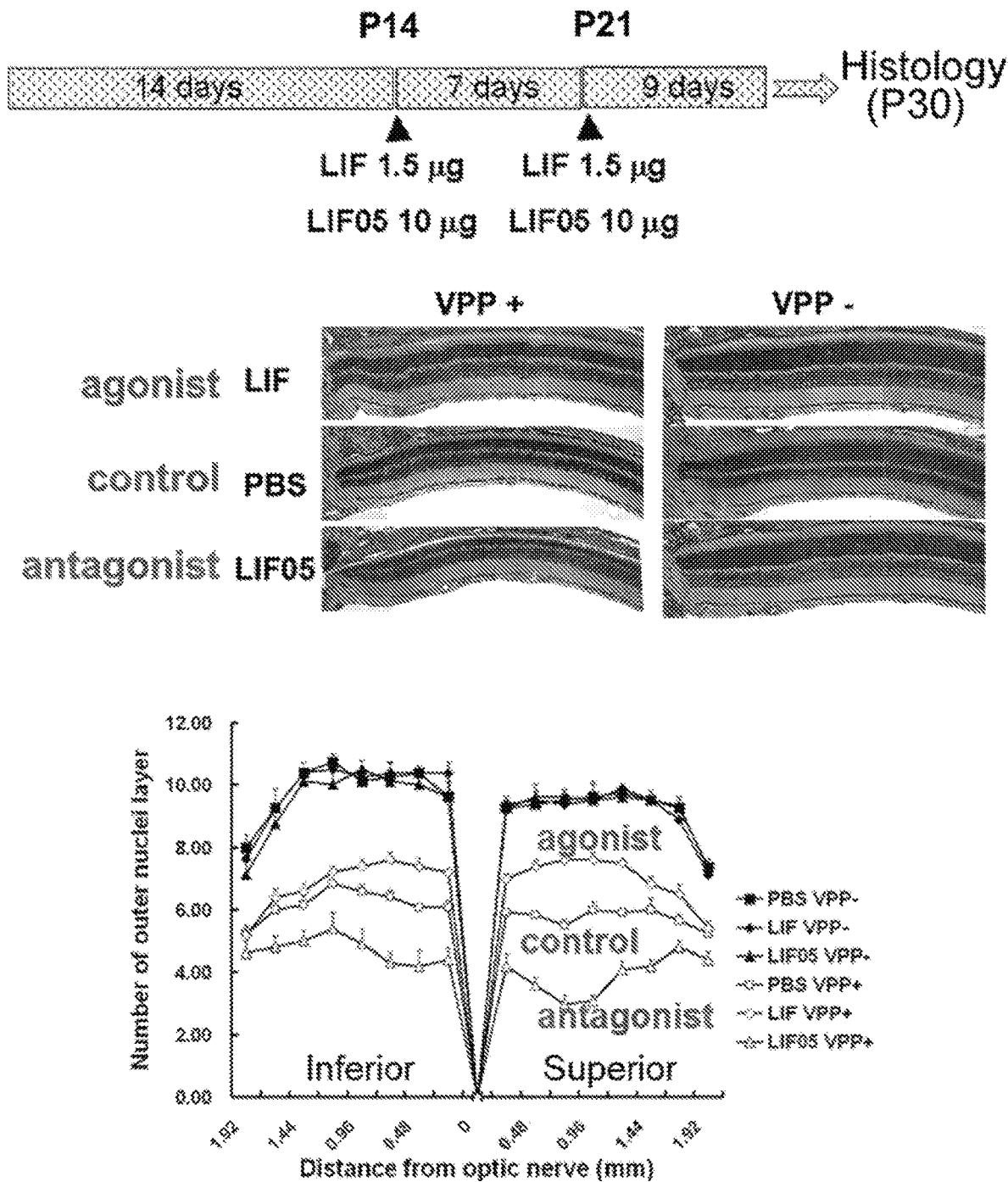
FIG. 2 shows injection of LIF delays photoreceptor degeneration in mice with autosomal dominant RP. On the contrary, injection of LIF05, an antagonist of LIF receptor, accelerates degeneration.

FIG. 2 shows injection of LIF delays photoreceptor degeneration in mice with autosomal dominant RP. On the contrary, injection of LIF05, an antagonist of LIF receptor, accelerates degeneration.

Figure 3A:
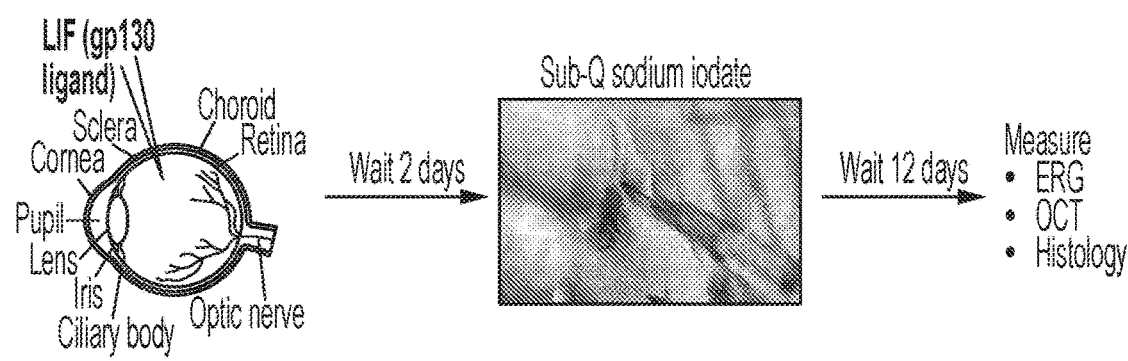
FIGS. 3A-3B show LIF injection protects retinal pigment epithelium (RPE) from degeneration caused by sodium iodate ($NAIO_3$) injection.
Figure 3A:
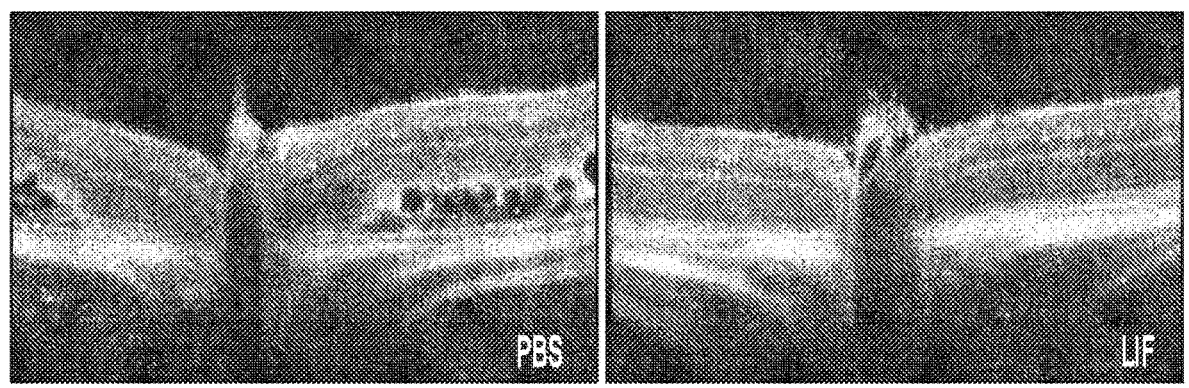
Figure 3B:
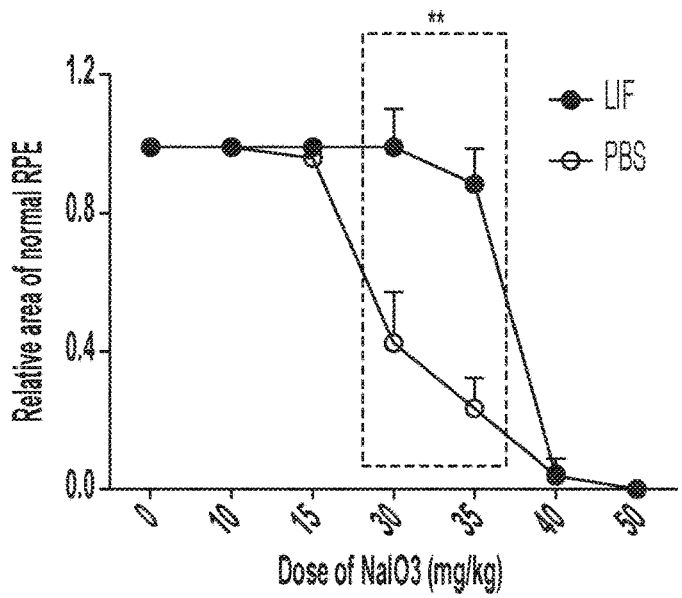

FIG. 3A shows LIF injection protects retinal pigment epithelium (RPE) from degeneration caused by sodium iodate ($NAIO_3$) injection. FIG. 3B shows data indicating that LIF injection increases RPE resistance to $NAIO_3$.

Figure 4A:
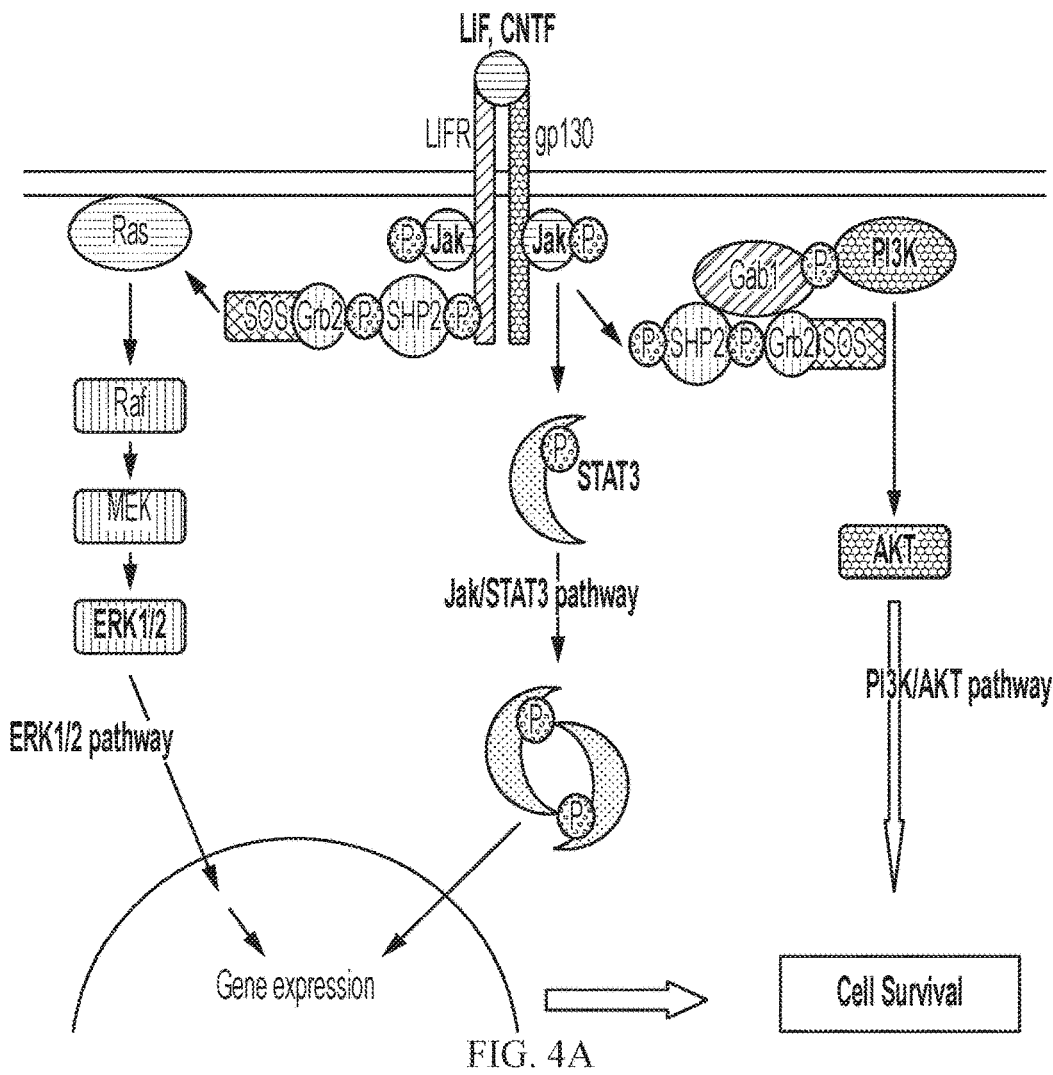
FIGS. 4A-4B show LIF and STAT3 signaling pathways.
Figure 4B:
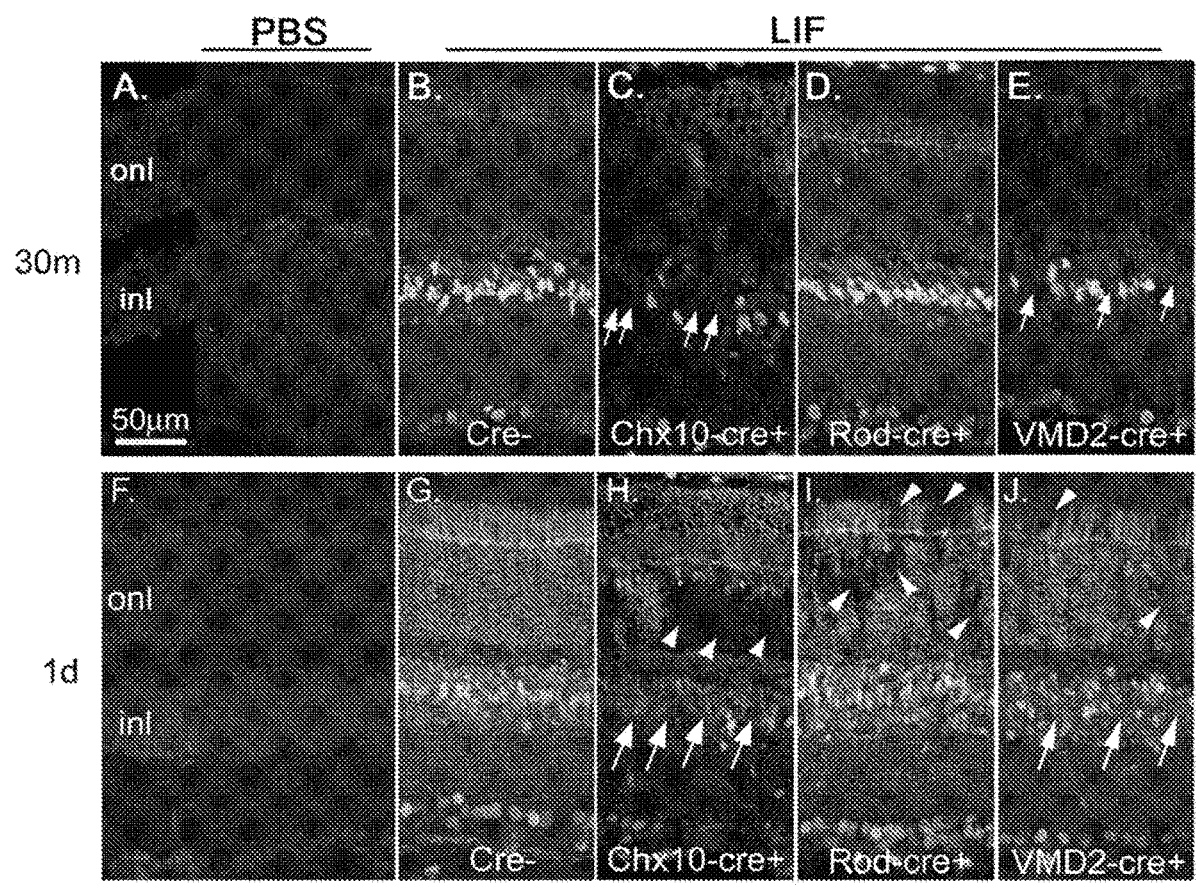

FIG. 4A shows a schematic depicting signaling pathways associated with LIF/CNTF receptors. FIG. 4B shows microscopy data indicating loss of LIF-induced phosphorylated STAT3 (pSTST3) in gp130 targeted mice.

Figure 5A:
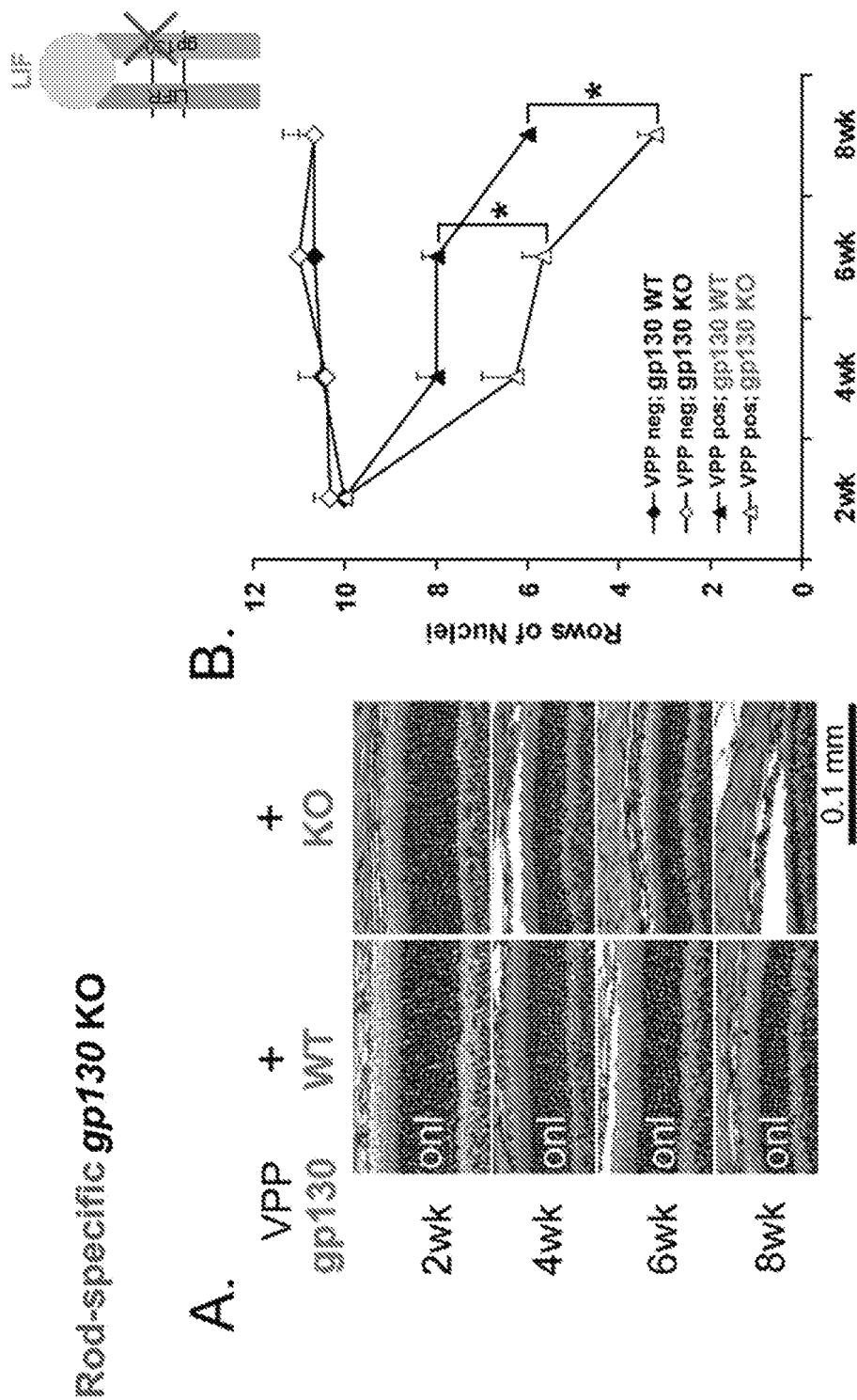
FIGS. 5A-5B show the role of gp130 and STAT3 in a genetic model of retinal degeneration.
Figure 5B:
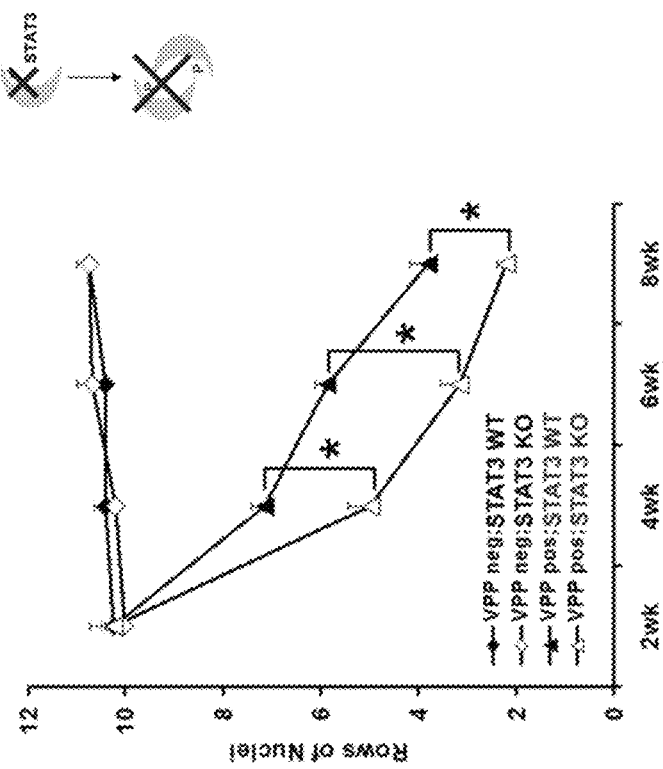
Figure 5B:
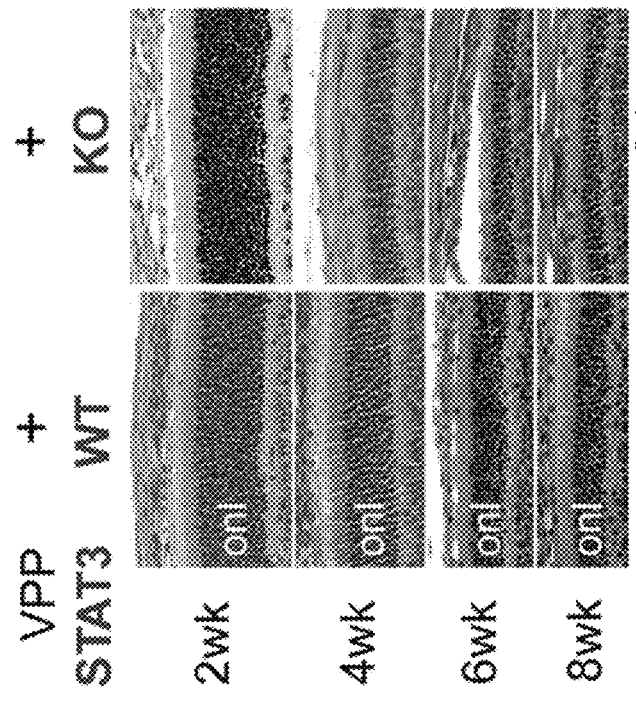

FIG. 5A shows loss of gp130 in rod photoreceptors accelerates photoreceptor cell death in a genetic model of retinal degeneration. FIG. 5B shows loss of STAT3 in rod photoreceptors accelerates photoreceptor cell death in a genetic model of retinal degeneration.

In summary, the data described in this example indicate the following regarding protection induced by LIF:

1. In some embodiments, cytokines protect photoreceptors from LD and inherited mutations ($Opsin^{VPP}$ and $PDE6B^{RD10}$).

2. In some embodiments, cytokines protect RPE from sodium iodate.

3. In some embodiments, LIF-induced protection requires GP130 and STAT3 expression in protected cells.

4. In some embodiments, part of LIF-induced protection is mediated by downregulation of phototransduction in PR and the visual cycle in RPE.

5. In some embodiments, part of LIF-induced protection is mediated by protecting mitochondria.

6. In some embodiments, STAT3 regulates NRF2 pathway including oxidative defense, DNA repair, and increasing proteostasis.

Example 2

LIF Expression Vectors
Materials and Methods
Mice

BALB/cJ, C57BL/6, and rd10 breeders were obtained and colonies were established. All mice were reared in 12 hour cyclic dim light (<100 lux)/dark conditions (6 AM-6 PM) in the University of Florida animal housing facility and provided water and food ad libitum.

Vector Production

The AAV vector plasmid, 'Sc-smCBA-mCherry', contains a chimeric CMV/chicken beta-actin promoter driving expression of the mCherry cDNA. The AAV terminal repeat (ITR) contained a mutated terminal resolution site to enable packaging of a self-complementary vector genome. The AAV vector plasmid, 'pTR-UF11' contains the full chimeric CMV/chicken beta-actin promoter (CBA) driving green fluorescent protein (GFP) cDNA. The AAV vector plasmid 'pTR-CBA-hLIF' contains the CBA promoter driving human LIF cDNA. The AAV vector plasmid 'pTR-CBA-RPF2' contains the CBA promoter driving the RPF2 cDNA.

The RPF2 cDNA was created by de-novo synthesis from Genscript (Piscataway, NJ). For packaging of AAV6 (trp Mut) an AAV2 rep-AAV6 cap plasmid containing substitutions resulting in a tyrosine to phenylalanine substitution at amino acid position 705 and 731 (Y705+731F) and threonine to valine substitution at position 492 (T492V). The rep-cap plasmid contains AAV2 cap with Y272F, Y444F, Y500F, Y730F and T491V mutations. Vector plasmids, AAV rep-cap and Ad helper plasmid were co-transfected into HEK293T cells and the virus was harvested and purified. Purified viruses were resuspended in balanced salt solution (BSS) (Alcon, Ft. Worth TX) supplemented with Tween-20 (0.014%) and stored at −80° C. until use. All viruses were titered by qPCR and tested for endotoxin.

Cell Culture Transfections, Trimethoprim Treatment, and Conditioned Media Experiments The rat müller glial-like cell line (rMC-1) was used in this example. The cells were cultured in high glucose Dulbecco's minimal essential medium (DMEM) supplemented with 10% fetal bovine serum 100 U/mL penicillin, and 100 µg/mL streptomycin and 1× GlutaMax (Thermo Fisher Scientific Inc., Waltham, MA). At 80% confluence, the cells were transfected with a purified plasmid using the standard Lipofectamine 3000 protocol (Thermo Fisher Scientific Inc., Waltham, MA). 24 hours after transfection, the media was replaced with serum-free DMEM. The cells were then dosed overnight with varying concentrations of trimethoprim or control vehicle (20% DMSO). The conditioned media was then collected for ELISA or STAT3 activation studies. For conditioned media experiments, rMC-1 cells were grown in 6-well plates. The serum-deprived cells were incubated for 30 minutes with conditioned media collected from transfected rMC-1 cells treated with trimethoprim. The cells were then washed with cold PBS and harvested for analysis by immunoblotting.

Immunoblotting

Retinal tissue or rMC-1 cells were homogenized in RIPA buffer (Sigma-Aldrich, St. Louis, MO) containing a protease inhibitor cocktail (Merck Millipore, Billerica, MA) supplemented with sodium fluoride and sodium orthovanadate (New England BioLabs Inc., Ipswich, MA). Protein lysate concentration was quantified by BCA assay (Thermo Fisher Scientific Inc., Waltham, MA) before boiling and subjecting to SDS-PAGE. Lysates were run on 4%-20% polyacrylamide gel (Thermo Fisher Scientific Inc., Waltham, MA) and transferred onto polyvinylidene fluoride membranes (Merck Millipore, Billerica, MA). Membranes were blocked with Odyssey blocking buffer (LI-COR Biosciences, Lincoln, NE) and incubated overnight with primary antibodies. Secondary antibodies conjugated with IRDyes were used. Signals were detected using the Odyssey CLx Imaging System (LI-COR Biosciences, Lincoln, NE). Intensities of the protein bands were quantified using Image Studio 5 (LI-COR Biosciences, Lincoln, NE).

Enzyme-Linked Immunosorbent Assay (ELISA)

LIF and RPF-2 levels were detected in retinal tissue lysates and rMC-1 conditioned media. For tissue lysates, the retinas were prepared in an ELISA lysis buffer (1% IGEPAL-CA 630, 135 mM NaCl, 20 mM Tris and 2 mM EDTA). Lysates or conditioned media was incubated for 2 hours on plates containing pre-blocked capture antibodies followed by 1-hour incubations with biotinylated detection antibody and streptavidin conjugated to horseradish peroxidase. Signals were developed using the Substrate Reagent Pack (R&D Systems, Inc., Minneapolis, MN) and read at 450 nm wavelength using the CLARIOstar microplate reader (BMG LABTECH GmbH, Ortenberg, Germany).

Trimethoprim (TMP) Delivery

For the in vivo dose response, varying concentrations of TMP was resuspended in a solution of 20% DMSO. The mice were intraperitoneally injected once per day for seven days with equal volumes of the varying TMP dosage or vehicle. For the reversal study, mice were injected once per day for seven days followed by no administration of the drug for a subsequent seven days before the retinas were harvested for ELISA analysis. For the TMP food supplement, 600 ppm of trimethoprim was added to the Teklad LM-485 mouse diet (Envigo, Huntingdon, United Kingdom). The TMP food was provided ad libitum to the mice.

Intravitreal Injections

Mice were anesthetized with ketamine (70-100 mg/kg) and xylazine (5-10 mg/kg). The eyes were dilated with a single drop of tropicamide and phenylephrine (Alcon, Ft. Worth TX). 1 µl of viral vector or Balanced Saline Solution (Alcon, Ft. Worth TX) were separately injected into the vitreous through the temporal limbus of the eye using a syringe with a 33-gauge needle (Hamilton Company, Reno, NV) AK-Poly-Bac ophthalmic medication (Alcon, Ft. Worth TX) was used to prevent post-surgical infections and suppress inflammation. Eyes were evaluated by OCT one week post-injection, and any animals with unresolved surgical trauma were excluded from the study.

Electroretinography (ERG)

Mice were anesthetized with ketamine (70-100 mg/kg) and xylazine (5-10 mg/kg). The eyes were dilated with a single drop of tropicamide and phenylephrine (Alcon, Ft. Worth TX). Retinal function was measured using the Colordome ERG system (Diagnosys, Dorset, United Kingdom). To record electrical responses from both eyes, gold wire electrodes were placed on the corneas, the platinum reference electrode was placed in the mouth and the platinum ground electrode was attached to the tail. The body temperature was maintained at 37° C. throughout the experiment using the built-in heating pad of the ERG system. For scotopic ERGs, the animals were dark adapted for at least 12 hours. A series of increasing light flash intensities ranging from 0.0001-180 cd·s/m$^2$ were used. The a-wave was determined as the trough of the negative deflection from the baseline while the b-wave was measured from the a-wave to the peak of the positive deflection. For photopic ERGs, to prevent rod photoreceptor contribution to the recording, a background illumination of 30 cd·s/m$^2$ was used to bleach the rods. A series of increasing light flash intensities above the background illumination (photopic 1.875-60 cd·s/m$^2$) were used to generate a cone response.

Spectral Domain-Optical Coherence Tomography (OCT) and Scoring

For in vivo retinal imaging, Spectral Domain-OCT images were obtained using the Envisu C-Class OCT system (Leica Microsystems, Wetzlar, Germany) Mice were first anesthetized with ketamine (70-100 mg/kg) and xylazine (5-10 mg/kg), followed by dilation with a single drop of tropicamide and phenylephrine (Alcon, Ft. Worth TX). Cornea clarity was maintained using GenTeal lubricating eye gel (Novartis Pharmaceuticals Corp., Basil, Switzerland). The mice were placed on a custom-built stage secured with a bite bar to allow free rotation for imaging. The stage was adjusted manually to center the image of the retina at the optic nerve head. Cross-sectional images were generated using 425 rectangular volume scans, which were averaged every five scans prior to image analysis. Images were acquired for both eyes. Averaged OCT images were analyzed using InVivoVue 2.4 (Leica Microsystems, Wetzlar, Germany). Outer nuclear layer (ONL) thickness was measured using the linear caliper function in the software by a masked observer using a pre-established uniform grid. The OCT images were also graded utilizing a scoring system ranging from 1 to 3 by a masked observer (FIG. 7C). A score of 3 was used to indicate a healthy-normal retina with no thinning and little to no inflammation. A scoring of 2 indicated a retina with slight edema, minor thinning, or inflammation. A scoring of 1 signified a degenerated retina with severe thinning, severe inflammation, missing external limiting membrane, or visible retinal detachment.

Immunohistochemistry

To obtain retinal tissue sections, mouse eyes were enucleated with forceps and placed in cold PBS. Under a dissecting microscope, the cornea and lens were dissected away and the remaining eye cup was processed for cryosectioning. In additional eyes, retinal flat-mounts were made by gently dissecting the retina from the eyecup. Four incisions were made from the periphery to the center of the retina, to flatten the retina unto a microscope slide. Eyecups and flat mounts were fixed in 4% paraformaldehyde for 30 minutes at room temperature. The fixed eyecups were cryopreserved in 30% sucrose in PBS overnight at 4° C. The samples were embedded in Tissue-Tek OCT Compound (Sakura Fintek USA Inc., Torrance, CA) and immediately frozen in liquid nitrogen. Tissue sections were cut at a thickness of 16 μm on a cryostat and placed onto glass slides. Slides were stored at −20° C. until needed for immunostaining. For IHC, the flat mount retinas or eyecup sectioned slides were washed with PBS containing 1% Triton X-100 (PBS-T). To prevent nonspecific binding, the tissue was blocked with 10% horse serum in PBS-T for at least 1 hour at room temperature. Primary antibody was applied to each sample for incubation overnight at 4° C. Samples were washed with PBS-T before incubating with secondary antibody for 1 hour at room temperature. Nuclei were counter-stained with 4-6-Diamidino-2-phenylindole (DAPI) before mounting on glass coverslip with 60% glycerol. Imaging was performed using the BZ-9000 fluorescence microscope (Keyence Corp., Osaka, Japan). The exposure time of each fluorescent channel was kept constant between samples for a given antibody. For flat mount counting of cone outer segments, a 250 $mm^2$ grid was superimposed over five different areas of each flat mount image. Cells within the grid were counted. All data collection was done by a masked observer.

Light Damage

Mice 2-3 months old were exposed to varying intensities of light for a set amount of time. For light experiments, mice are placed (2 mice per cage) in a cage with a lid equipped with LED lights (white light). Light intensity can be adjusted using a connected dimmer switch, and a timer is set for the appropriate amount of time for each experiment. A light meter is used to measure the desired light intensity inside the cage. The mice are kept in a ventilated rack for the entire length of the experiment. At the end of the experiment, mice cages are replaced with a normal cage lid and moved back into dim light conditions for a one week wait until downstream structural and functional analysis.

OptoMotry

To test the visual acuity of mice the OptoMotry system was used. The system consists of 4 computer screens that display alternating vertical light and dark bar that appear as a virtual rotating 3D cylinder. The mouse is placed on a non-rotating pedestal in the middle of the enclosure. The 3D cylinder pattern was rotated at a fixed speed of 12 degrees per second and the contrast was maintained at 100%. Head tracking was monitored using an overhead camera, and recorded by a masked observer. The staircase method was used to determine visual acuity by establishing the threshold of spatial frequency that the animal can track. An animal was considered to be tracking if its head followed the direction of the stimulus with a speed similar to the pattern movement.

Fundus Imaging

For fundus imaging, a Micron III camera (Phoenix Research Labs, Pleasanton, CA) was used. Mice were anesthetized with ketamine (70-100 mg/kg) and xylazine (5-10 mg/kg) and dilated with a single drop of tropicamide and phenylephrine (Alcon, Ft. Worth TX). Corneal clarity was maintained using GenTeal lubricating eye gel (Novartis Pharmaceuticals Corp., Basil, Switzerland). The mice were stabilized on a custom holder that allowed adjustments to center the image of the retina at the optic nerve head. Imaging was performed in under brightfield illumination, and using filtered red, and green channels. Images were acquired for both eyes.

Statistical Analysis

Statistical analysis was carried out using Prism 6 (GraphPad Software Inc., La Jolla, CA). Statistical significance between multiple groups was determined by using Analysis of Variance (ANOVA) followed by Holm-Sidak post hoc test. p-value<0.05 was considered to be significant.

Unregulated, Long-Term Cytokine Expression is Detrimental to the Retina

Figure 6A:
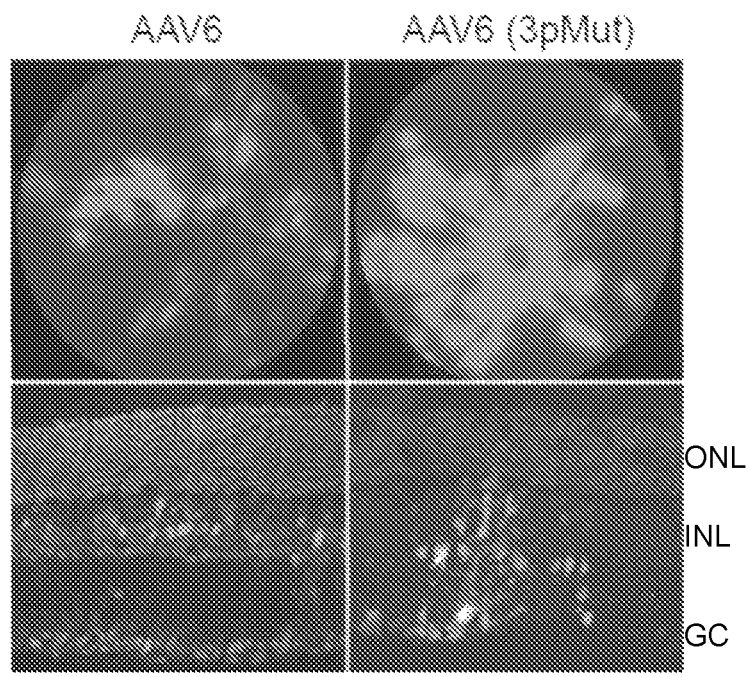
FIG. 6A (top panel) shows fundus images of the retina comparing mCherry expression in AAV6 and AAV6 (3pMut); (bottom panel) immunohistochemistry cross section of retinas injected intravitreally with AAV6 or AAV6 (3pMut) showing mCherry expression and DAPI stained nuclei.
Figure 6B:
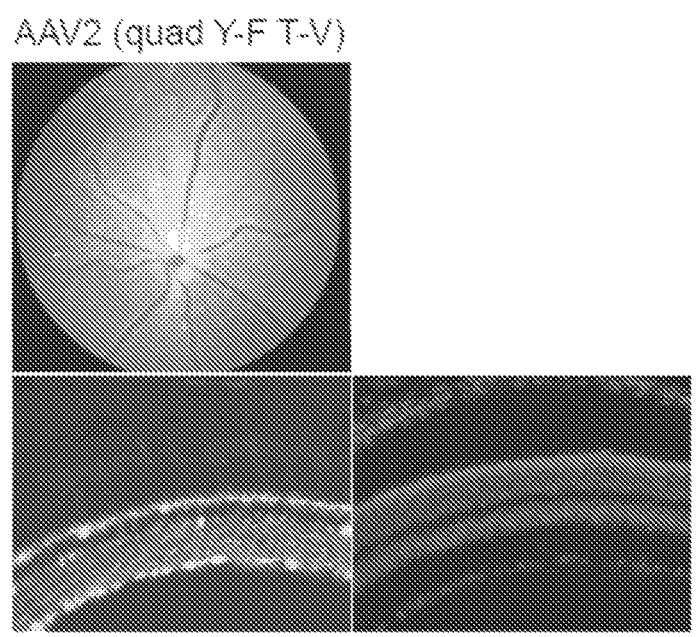
FIG. 6B (top panel) shows fundus images of the retina injected with AAV2-CBA-GFP; (bottom panel): immunohistochemistry cross section of the same retina showing GFP expression. ONL=Outer nuclear layer, INL=Inner nuclear layer and GC=Ganglion cell layer.

Two AAV serotypes were used to deliver the human LIF (hLIF) transgene to the retina by intravitreal injection, each with a unique tropism for retinal cells. AAV2 quadYF+TV (referred to as AAV2*) was selected since it can efficiently transduce a broad range of cells types in the murine retina by intravitreal injections. A triple mutant AAV6 serotype (referred to as AAV6*) was also investigated. This mutant serotype, in some embodiments, has increased transduction of cells in the inner nuclear layer, particularly Müller glial cells, compared to the wild-type AAV6 serotype via intravitreal delivery (FIGS. 6A-6B).

Figure 7A:
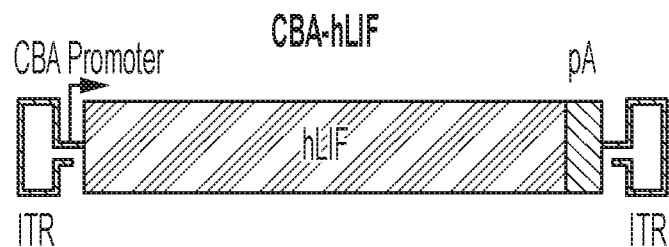
FIGS. 7A-7F show long term constitutive expression of AAV-hLIF can have adverse effects on retinal morphology and function.
Figure 7B:
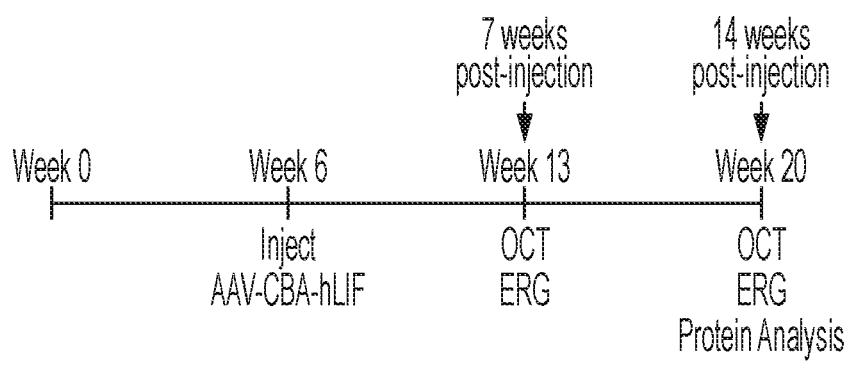
Figure 7C:
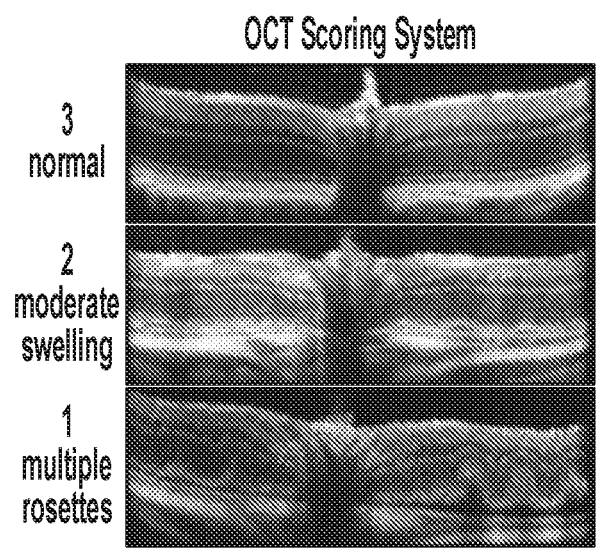
Figure 7D:
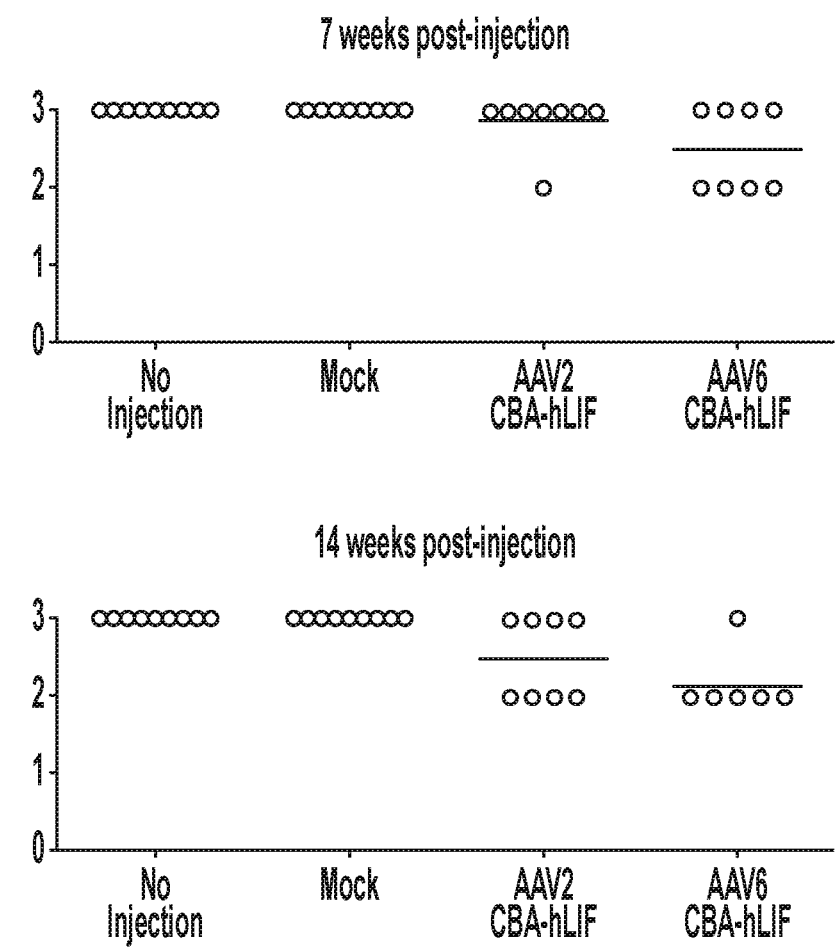
Figure 7E:
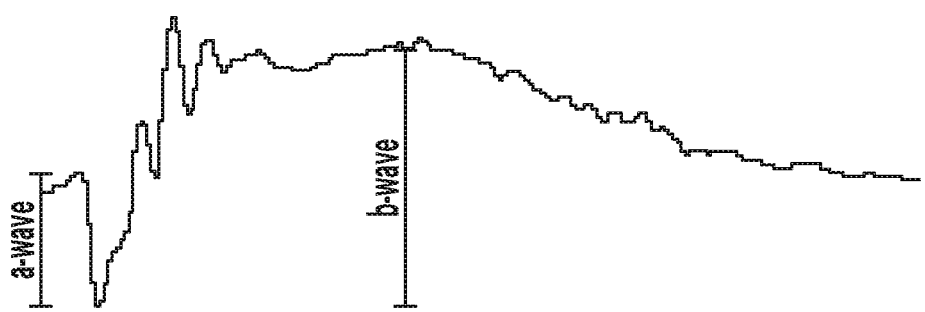
Figure 7F:
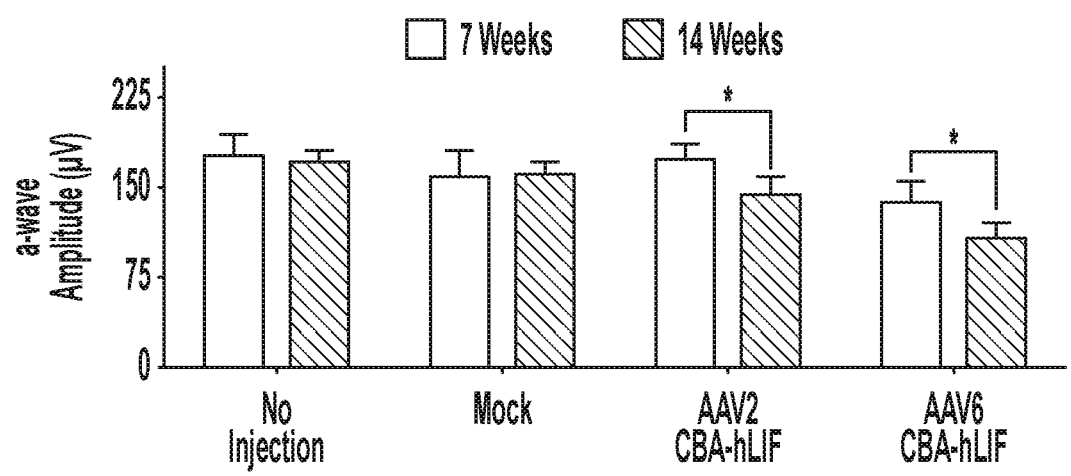
Figure 8:
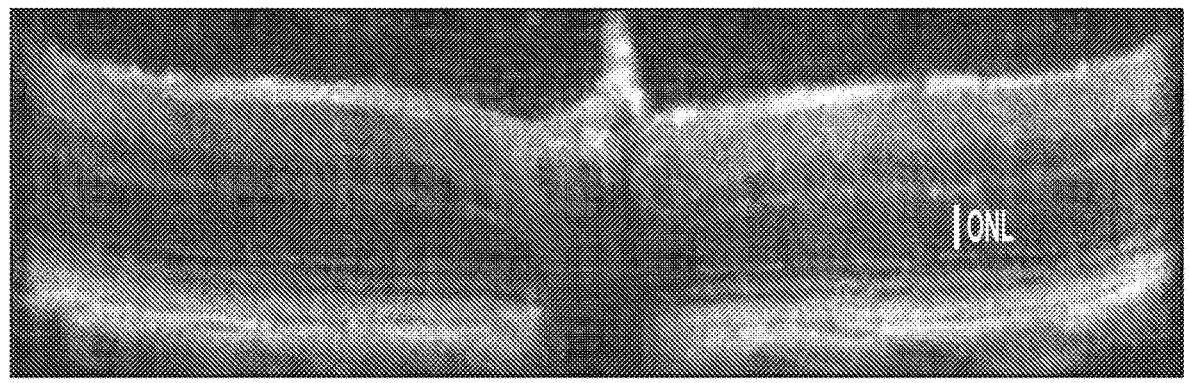
FIG. 8 shows AAV delivery of hLIF protects the retina from light damage. Top: Representative OCT image showing how the outer nuclear layer (ONL) thickness is measured. Thickness was measured from superior to inferior retina 500 μm from the optic nerve. Bottom: Spider plot of the ONL thickness of light damaged retinas treated with AAV-CBA-hLIF. No treatment and mock injected were used as controls.
Figure 8:
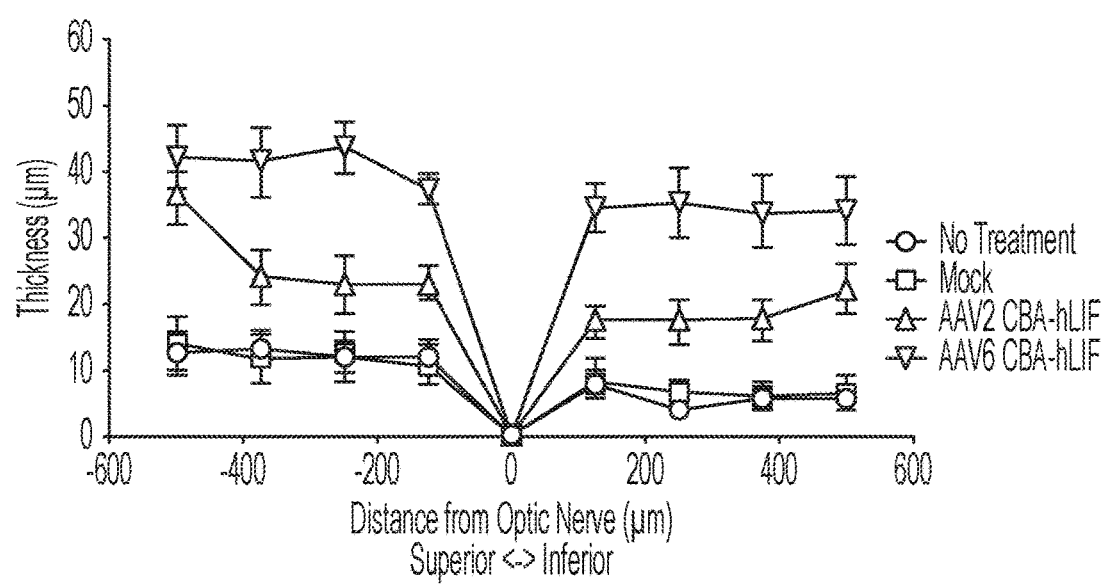
Figure 9A:
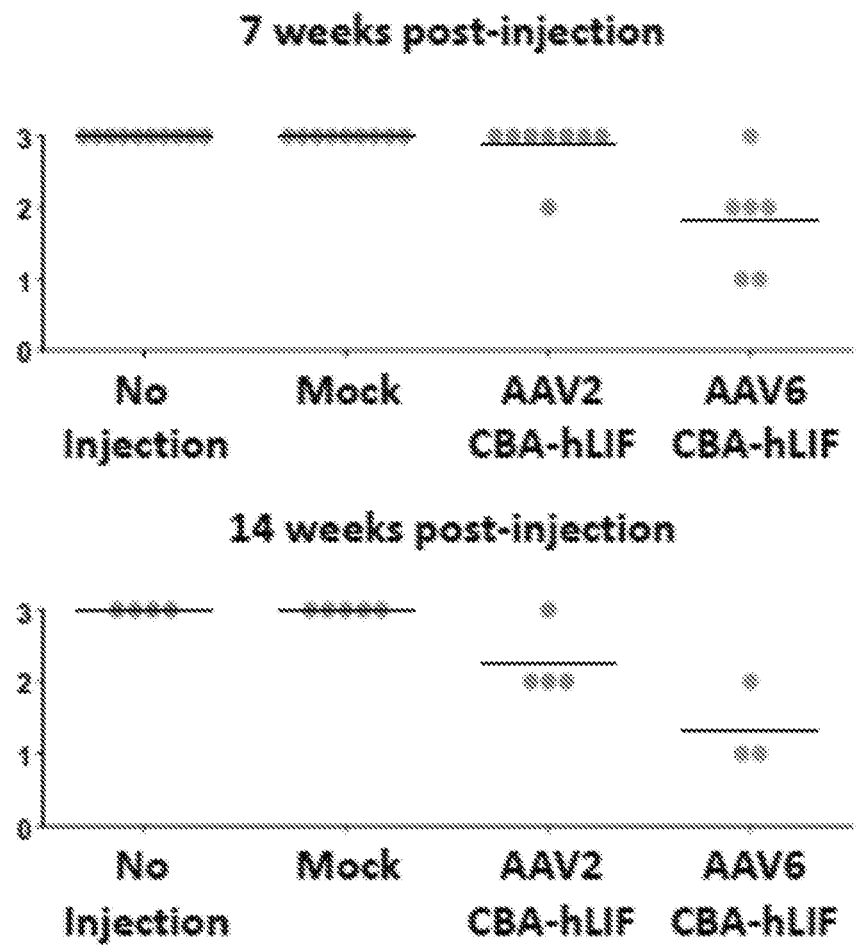
FIGS. 9A-9C show characterization of AAV-CBA-hLIF delivery in the mouse retina.
Figure 9B:
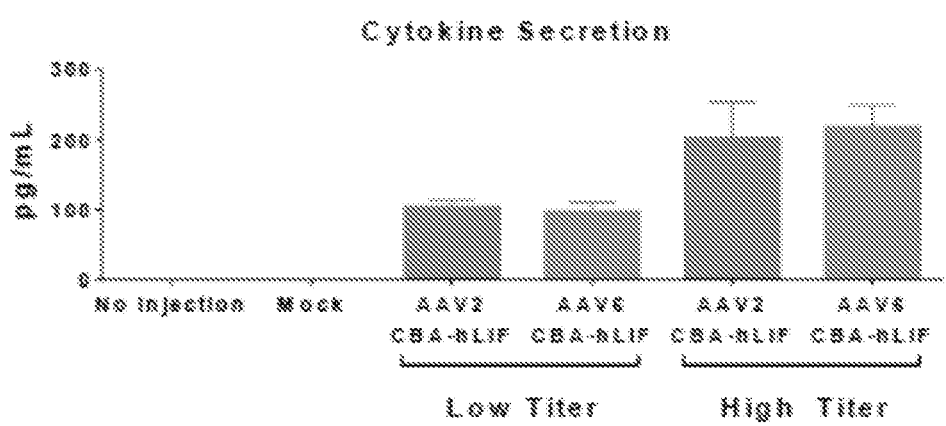
Figure 9C:
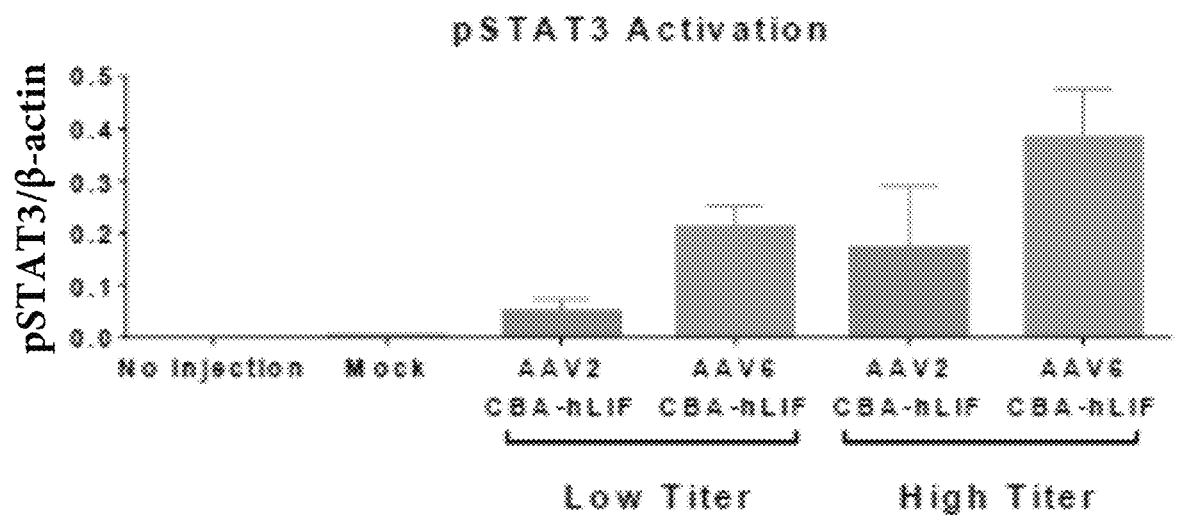

AAV2* and AAV6* vectors expressing the human leukemia inhibitory factor (hLIF) transgene under the control of the chicken beta-actin promoter (CBA) were injected into the vitreous of Balb/cJ mice at two titers ($1\times10^8$ viral genomes/pt for low titer, $1\times10^9$ viral genomes/pt for high titer) (FIG. 7A). After seven weeks, mice were exposed to damaging bright light that was calibrated to synchronously kill approximately 50% of photoreceptors in a well-established light damage model (LD). Mice injected with either serotype of AAV-hLIF had significant preservation of photoreceptors in the outer nuclear (ONL) compared to controls (FIG. 8). However, despite this protective activity, long-term studies on treated mice not exposed to damaging light had progressive abnormal retinal structures consistent with edema, as seen by optical coherence tomography (OCT) imaging (FIGS. 7B-7D). Long-term expression also caused a reduction in photoreceptor light responses as measured by electroretinography (ERG) (FIGS. 7E-7F). The edema in AAV6*-treated mice was slightly worse than in AAV2*-treated mice at low titers (FIGS. 7D-7F). At high titers, the edema was significantly worse in both serotype groups. (FIG. 9A). The severity of adverse retinal changes (edema and loss of function) correlated with the level of LIF protein expression and activation of STAT3 (FIGS. 9B-9C). Overall, these results indicate that unregulated, high LIF expression is detrimental to the retina.

Retinal Protective Factor 2

Figure 10A:
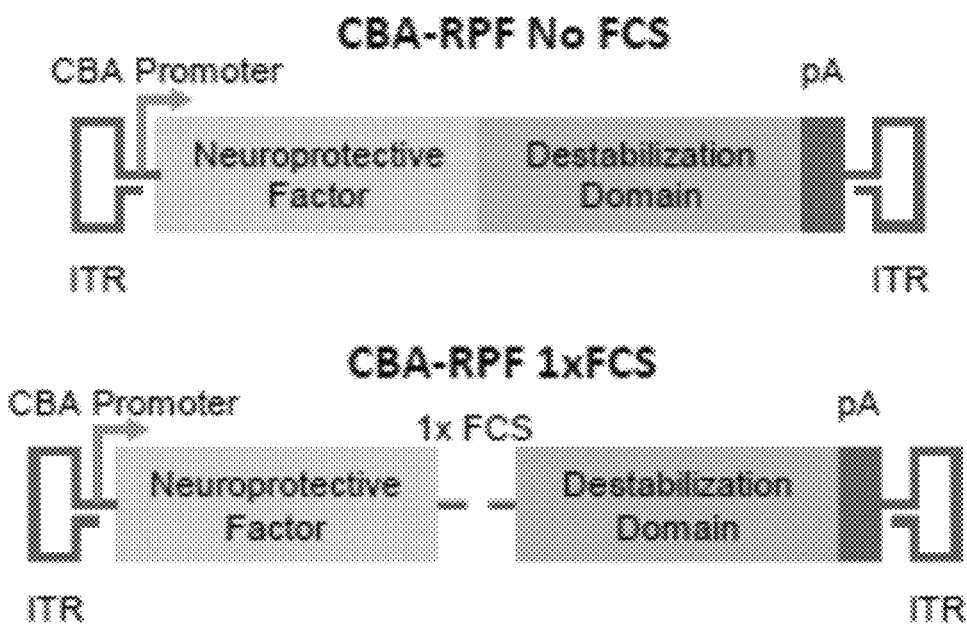
FIGS. 10A-10D show iterations of RPF2 development.
Figure 10B:
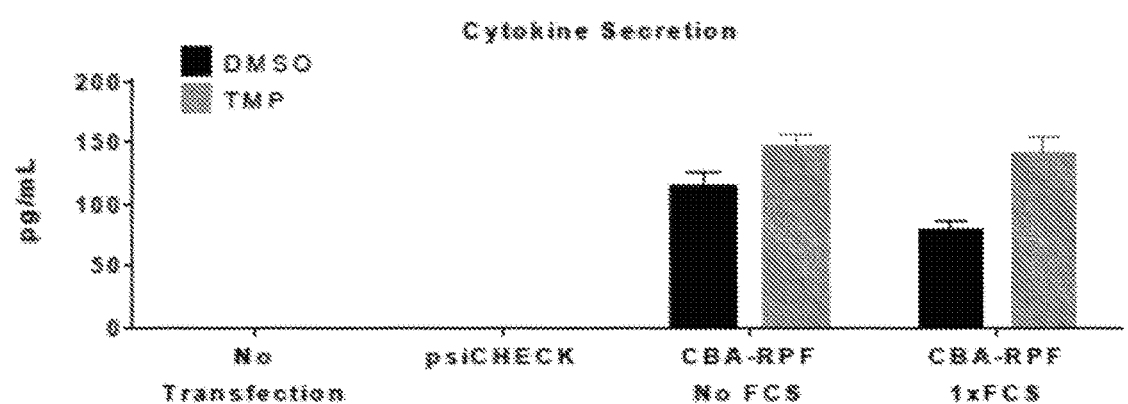
Figure 10C:
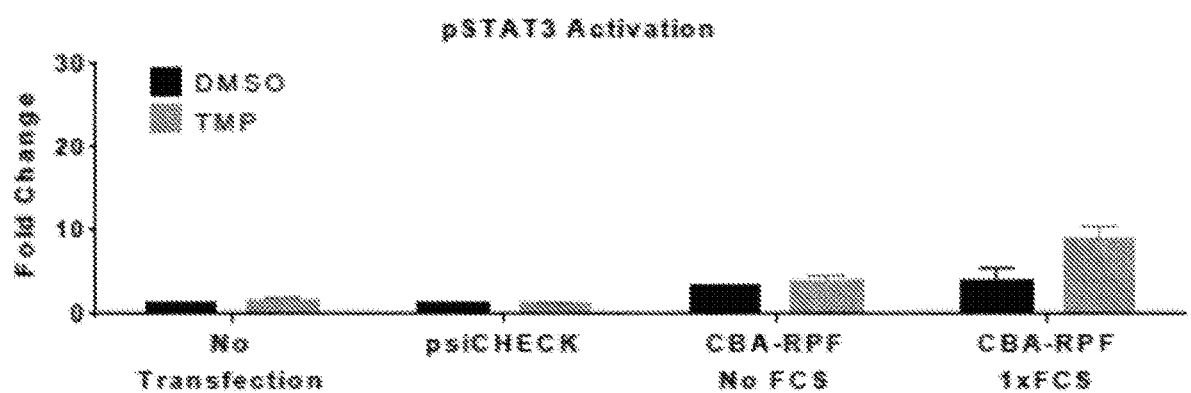
Figure 10D:
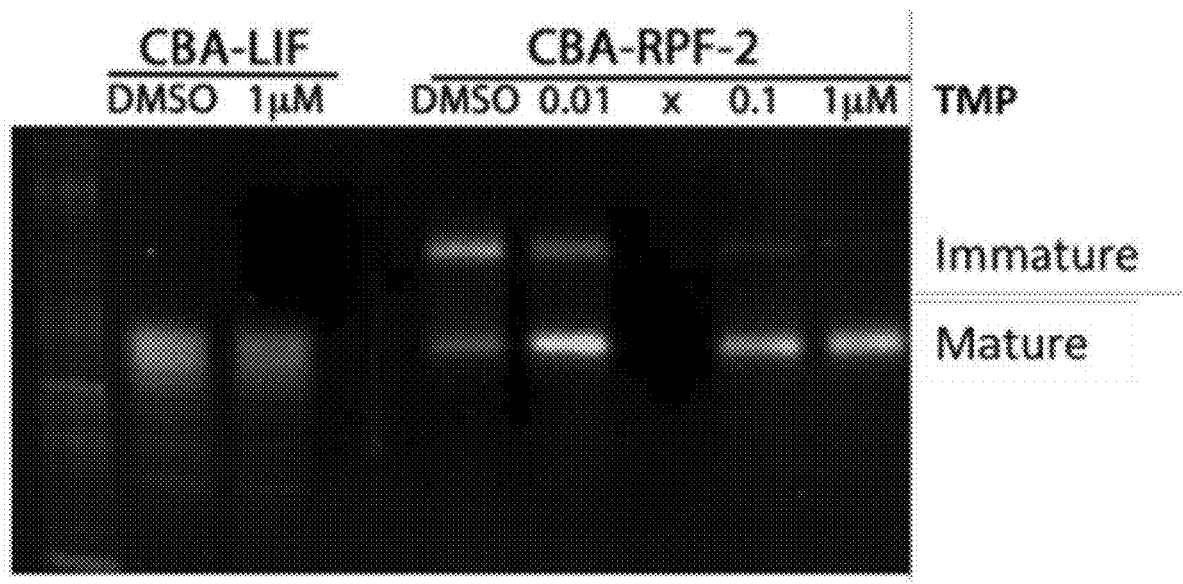
Figure 11A:
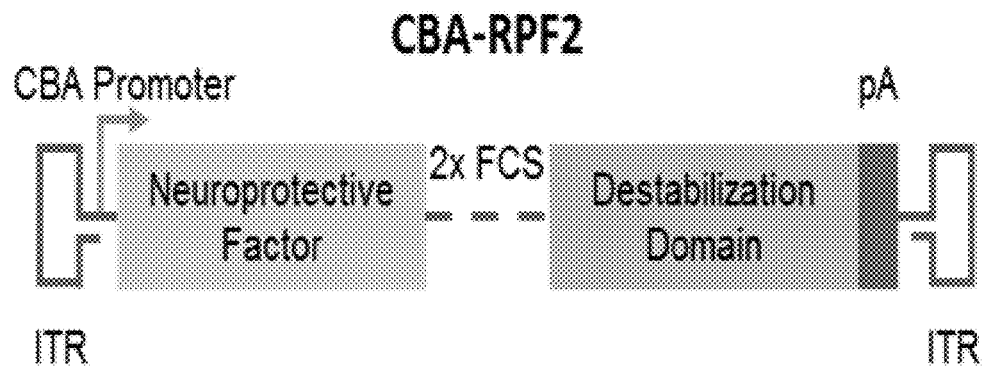
FIGS. 11A-11D show in vitro characterization of RPF2 TMP-dependent stability.
Figure 11B:
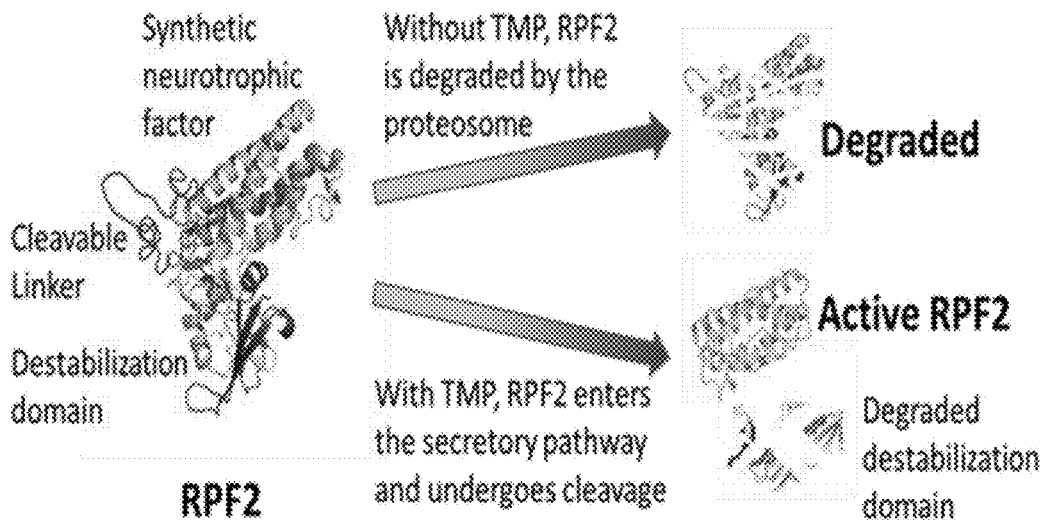
Figure 11C:
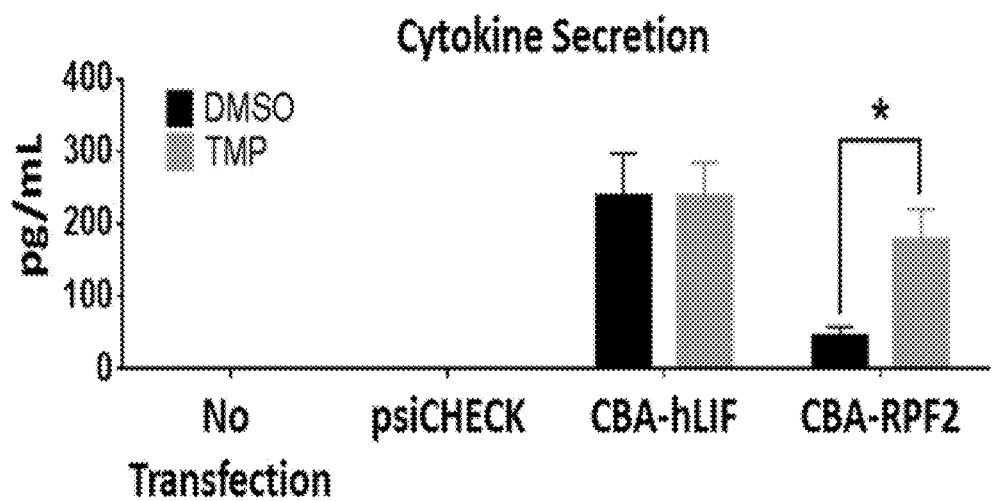

This example describes a synthetic and codon optimized *E. coli* dihydrofolate reductase cDNA (e.g., a destabilization domain, "DD") fused to an hLIF cDNA (FIG. 10A). While the resulting fusion protein was expressed in cell culture, it was not regulated by TMP and was unable to activate STAT3 downstream of its receptor (FIG. 10C), likely because each domain in the fusion protein inhibited the activity of the other. Sequences encoding an eight amino acid linker with one furin cleavage site (FCS) were added between LIF and DD, or sequences encoding a twelve amino acid linker with two FCS (FIG. 10; FIG. 11A). This strategy takes advantage of the furin protease system which will cleave the domains as they transit the secretory pathway (FIG. 11B). The fusion proteins were tested in vitro, and the 12 amino acid linker containing two FCS produced the highest levels of cleaved cytokine with TMP treatment and had minimally detectable levels of cytokine in the absence of TMP (FIGS. 11C; 10B and 10D). In addition, the expression of cleaved and secreted cytokine was regulated by TMP in a dose-dependent manner (FIG. 10). The effects of TMP required the DD fusion since TMP did not alter the expression of cytokine in the hLIF-transfected group.

Figure 11D:
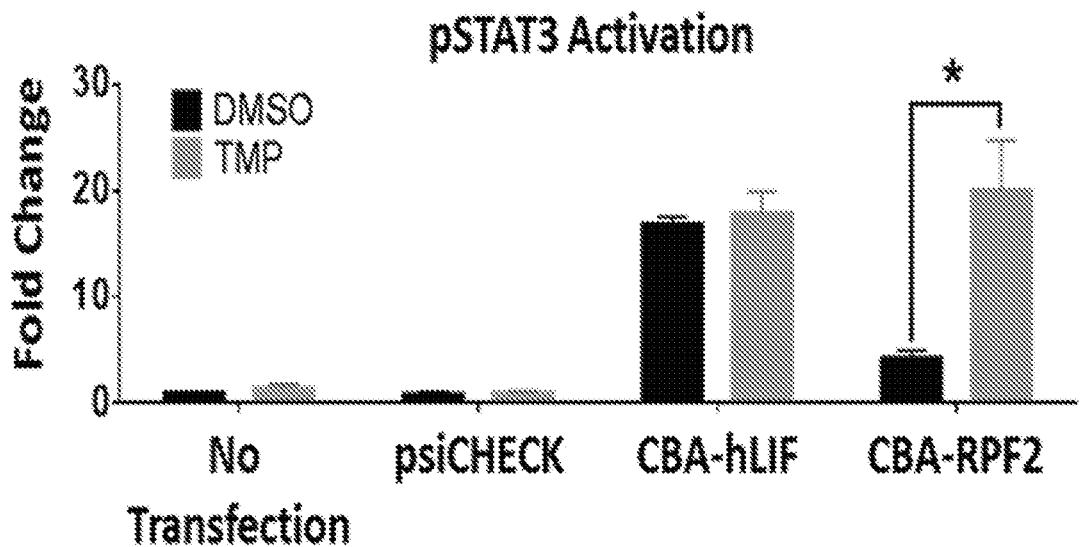

To determine whether the secreted RPF2 was functional, the conditioned media from transfected cells were collected and used to stimulate STAT3 in untransfected rMC-1 cells. Only conditioned media from TMP treated cells led to a significant increase in STAT3 activation (FIG. 11D). These levels were comparable to that of the hLIF-transduced group. In vitro data indicate that RPF2 is regulated in a dose-dependent manner and is secreted in its functional form to activate STAT3. The fusion protein with two FCS was used in AAV vector development and was named Retina Protective Factor 2 (RPF2).

AAV Expression of RPF2 is Regulated by TMP in a Dose-Dependent Manner In Vivo

Figure 12A:
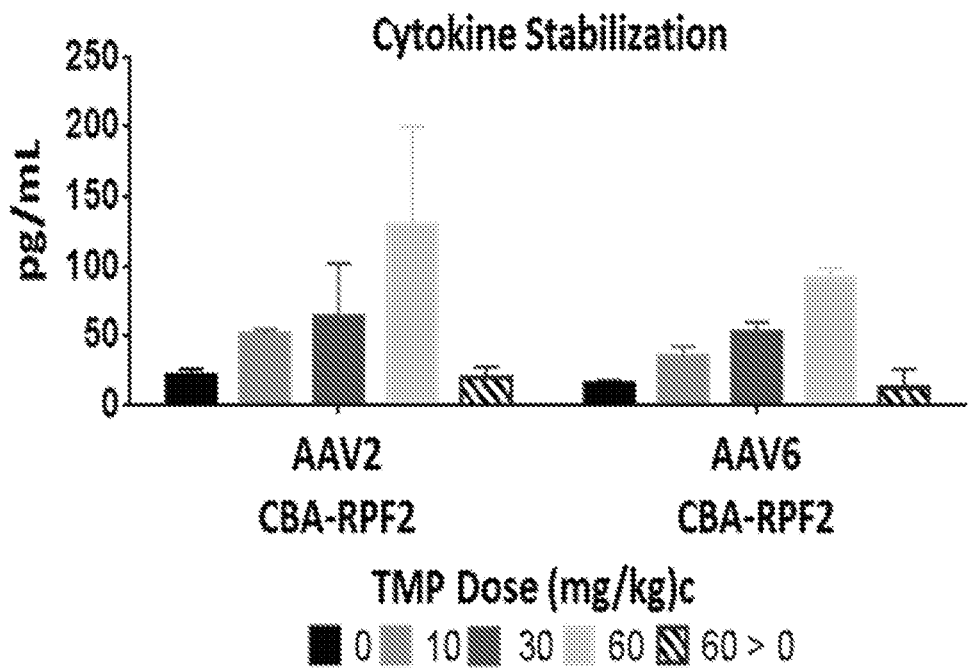
FIGS. 12A-12D show RPF2 is regulated in a dose-dependent manner and demonstrates no toxicity in vivo.
Figure 12B:
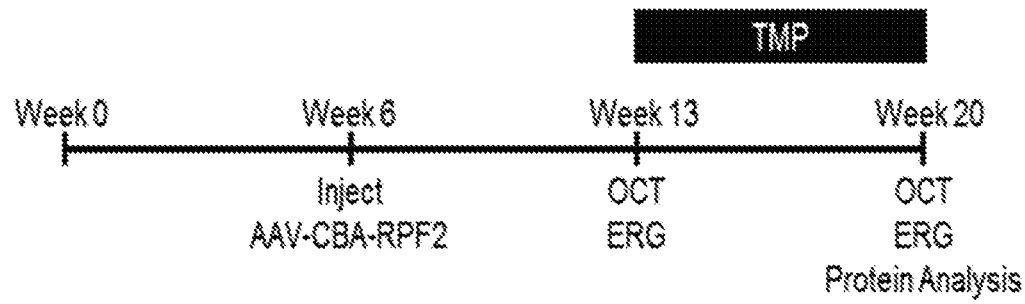
Figure 12C:
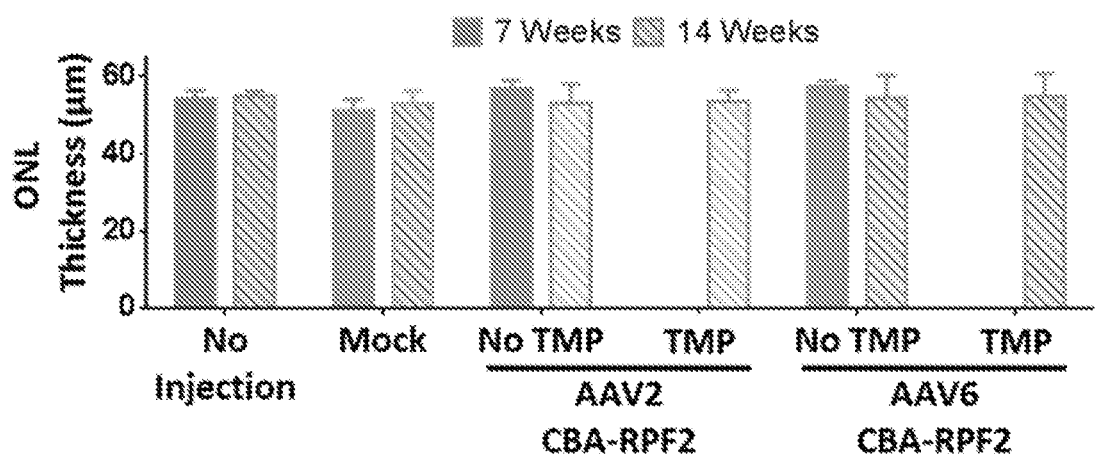
Figure 12D:
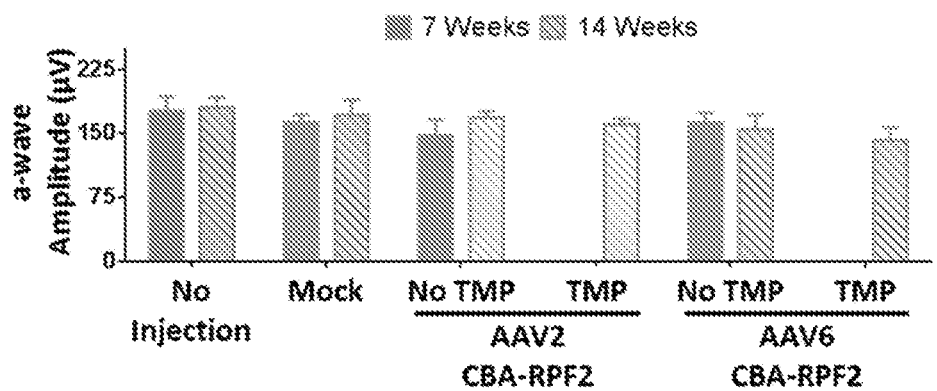
Figure 13:
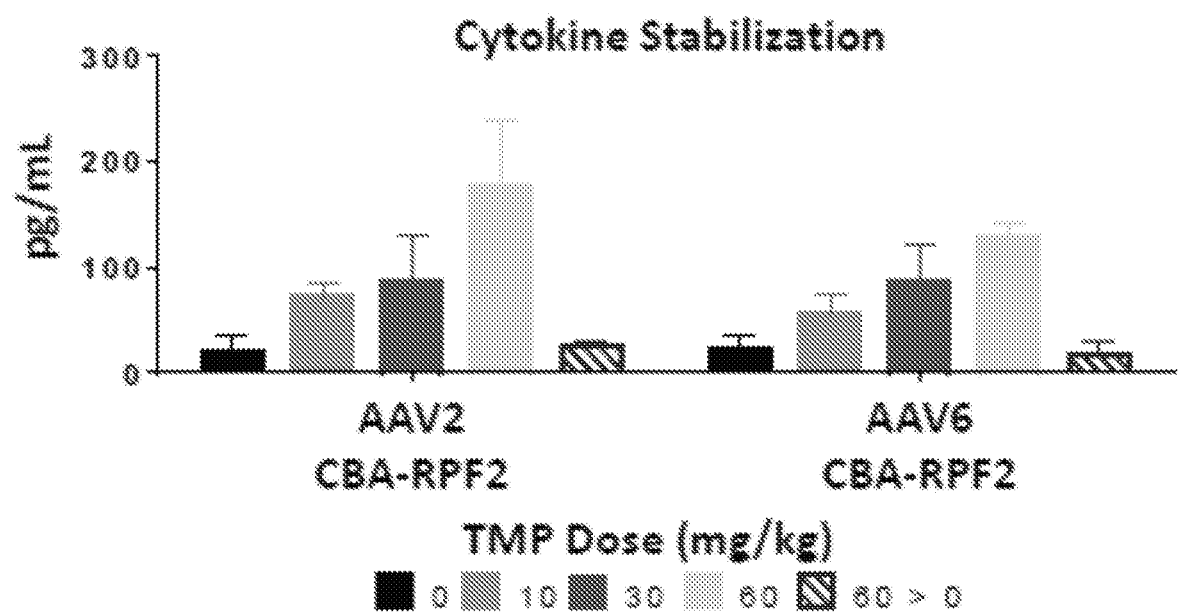
FIG. 13 shows characterization of RPF2 in vivo. Top panel shows levels of RPF2 in the retina of animals injected with the high titer dose. Bottom panel shows levels of RPF2 in the retina when TMP is administered in the food. Cytokine levels were detected by ELISA after one week of TMP treatment.
Figure 13:
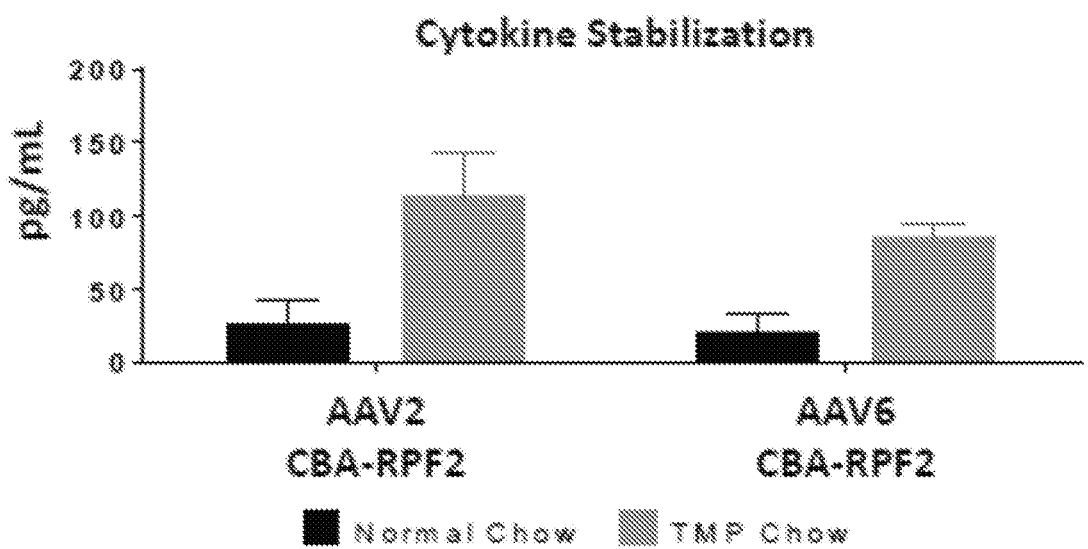
Figure 14:
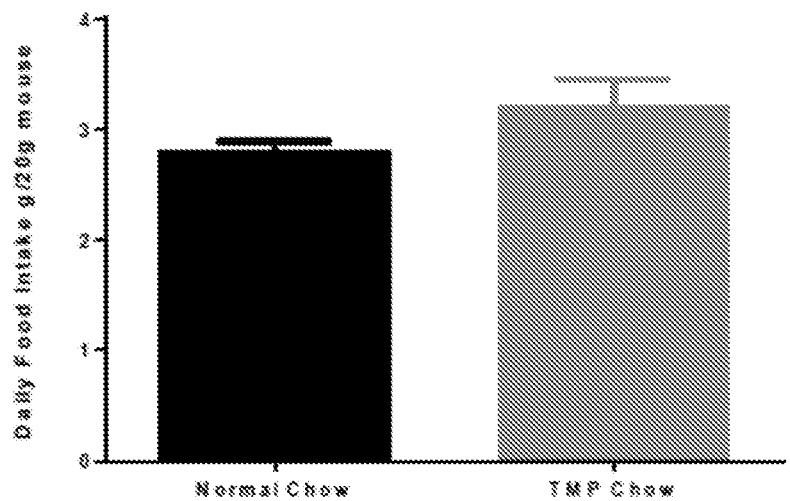
FIG. 14 shows mouse daily food intake is unchanged with TMP supplemented chow. Food intake was measured for one week for mice on normal and TMP chow.

RPF2 was packaged into both AAV2* and AAV6* serotypes and intravitreally injected into Balb/cJ mice at high and low titers. Six weeks after AAV injections, mice were given six daily IP injections of the indicated doses of TMP. RPF2 levels rose dramatically with increasing doses of TMP and fell to baseline following a 7 day TMP withdrawal (FIG. 12A). Cytokine levels for both the 0 mg/kg dose and TMP withdrawal groups were below the limit of detection for the assay. The expressed cytokine was also functional since STAT3 activation in the retina was higher in animals treated with TMP. To characterize the long-term effects of the AAV-RPF2 therapies, retinal structure and function were monitored over time following viral delivery (FIG. 12B). Animals were placed on chow containing TMP starting 7 weeks post-injection. This route of drug administration yielded RPF2 stabilization at levels comparable to that of the 60 mg/kg systemic TMP delivery and did not affect the animal's daily food intake (FIGS. 13 and 14). At the highest dose of TMP, the cytokine levels were comparable but lower than the AAV-hLIF injected group (FIG. 8). After 7 weeks of TMP treatment, mice given AAV-RPF2 had normal retinal morphology and clearly lacked the edema observed in the AAV-hLIF treated mice (FIG. 12C; FIG. 13). Mice also had normal photoreceptor function as reflected in scotopic ERG responses (FIG. 12D). These data indicate that AAV-RPF2 therapies are regulated by TMP in a dose-dependent manner in vivo, and long-term therapy did not result in the negative outcomes observed using high expression of AAV-hLIF.

AAV-Expressed RPF2 Can Protect Photoreceptors from Acute Light Injury

Figure 15A:
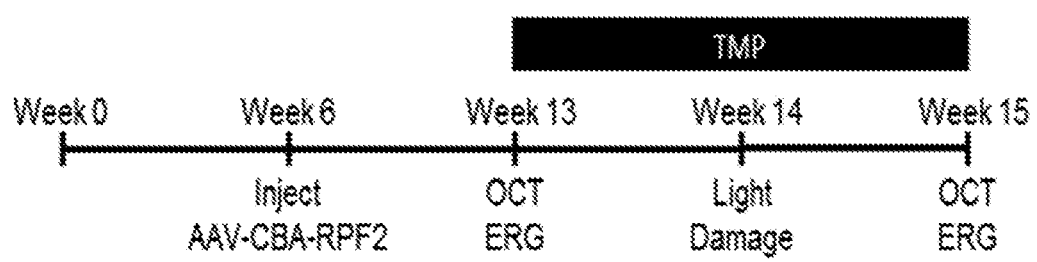
FIGS. 15A-15C show RPF2 reduces retinal degeneration in an acute light damage mouse model.
Figure 15B:
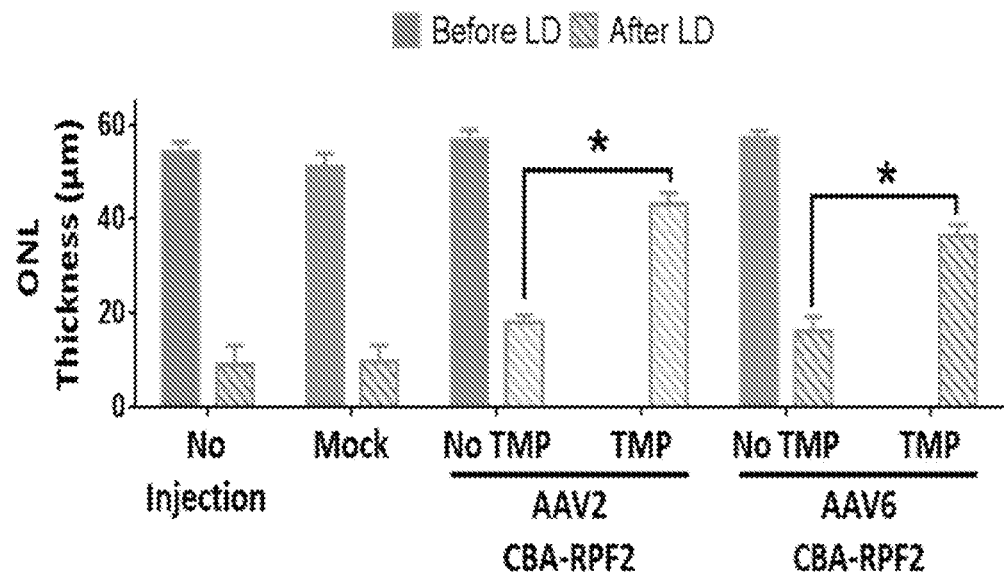
Figure 15C:
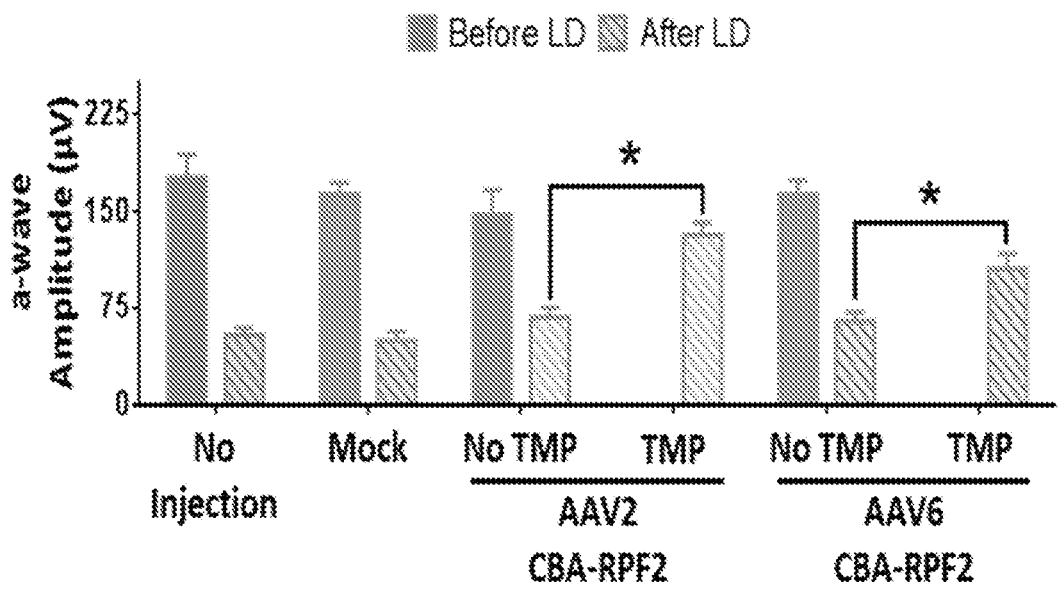
Figure 16:
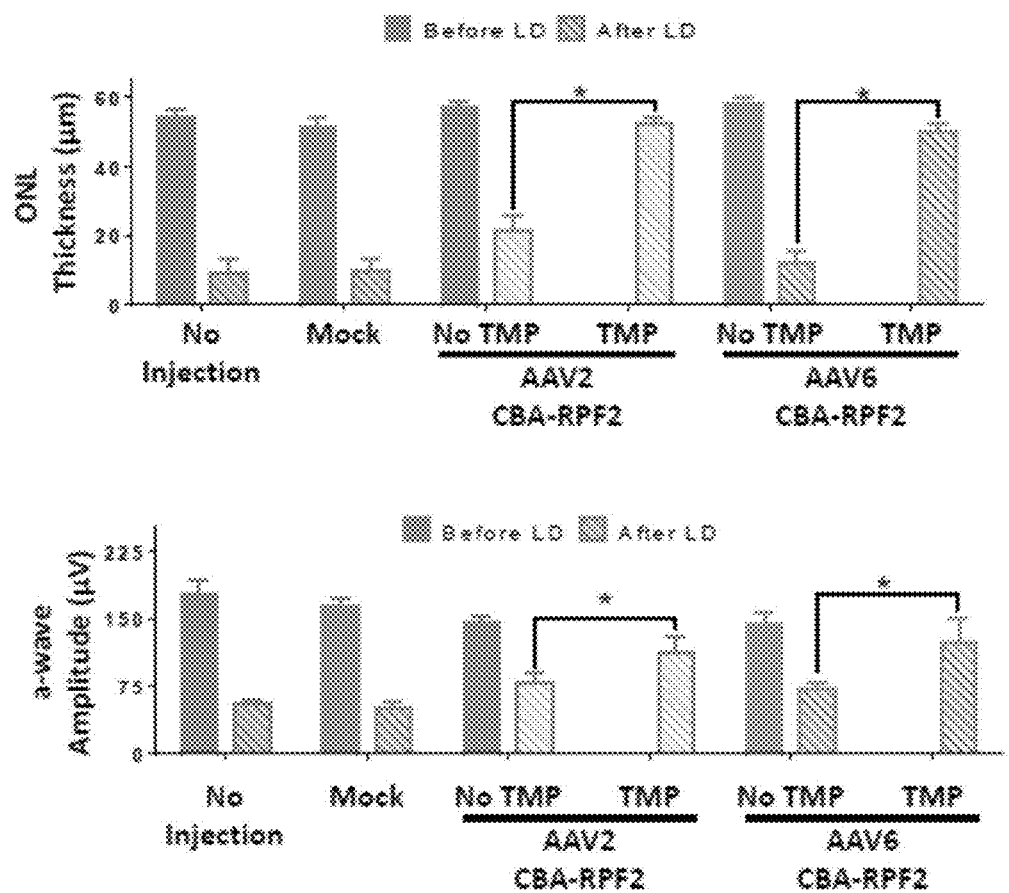
FIG. 16 shows RPF2 treated retinas show improved retinal structure and function after bright light exposure. Top panel shows averaged thickness of the retinal outer nuclear layer and retinal function by ERG after RPF2 stabilization in high titer treated animals. Bottom panel shows low titer and high titer RPF2-treated animals showed less signs of edema, rosette formation and infiltrating immune cells compared to the control groups.
Figure 16:
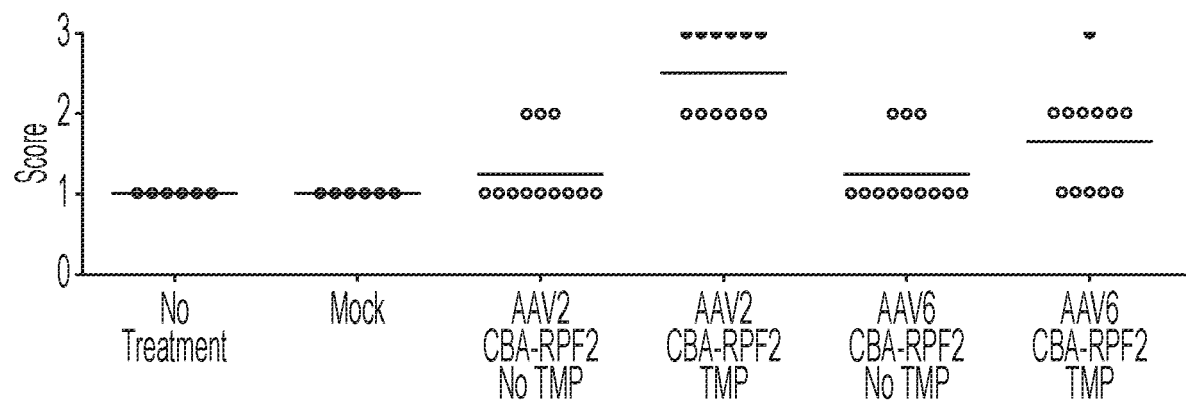
Figure 16:
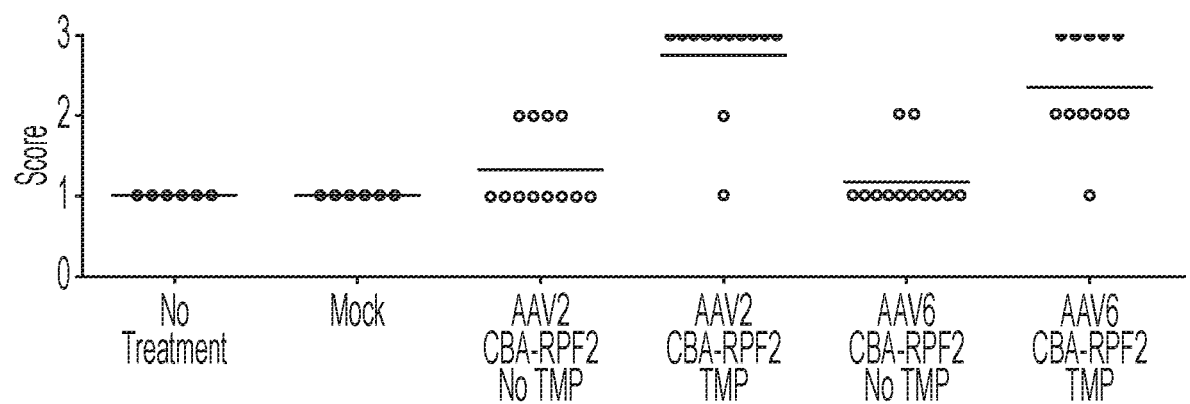

To determine whether AAV-RPF2 therapy can protect photoreceptors from light damage (LD), six-week-old mice were injected with AAV-RPF2 containing virus at low and high titers. After 7 weeks, mice were given TMP in mouse chow for 7 days prior to exposure to damaging bright light (FIG. 15A). In the presence of TMP, animals injected with either AAV-RPF2 serotypes showed significant preservation of ONL thickness compared to mock-injected or no TMP control groups, indicating that TMP-induced cytokine protected photoreceptors (FIG. 15B; FIG. 16). TMP induced RPF2 not only preserved structure but also preserved photoreceptor function as well (FIG. 15C; FIG. 16). High-titer AAV-RPF2 groups had greater preservation of the ONL than the low titer groups (FIG. 16).

AAV-RPF2 Protects Photoreceptors in a Model of Inherited Retinal Degeneration

Figure 17A:
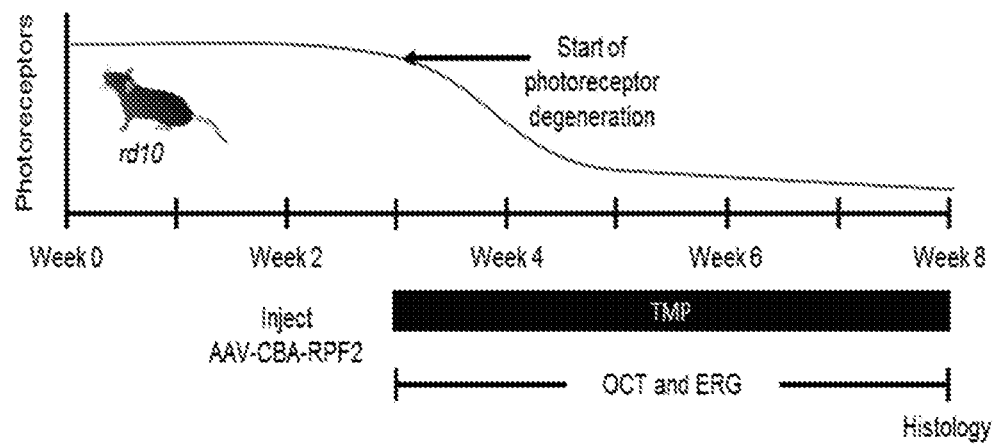
FIGS. 17A-17D show RPF2 preserves cone morphology in the inherited rd10 retinal degeneration model.
Figure 17B:
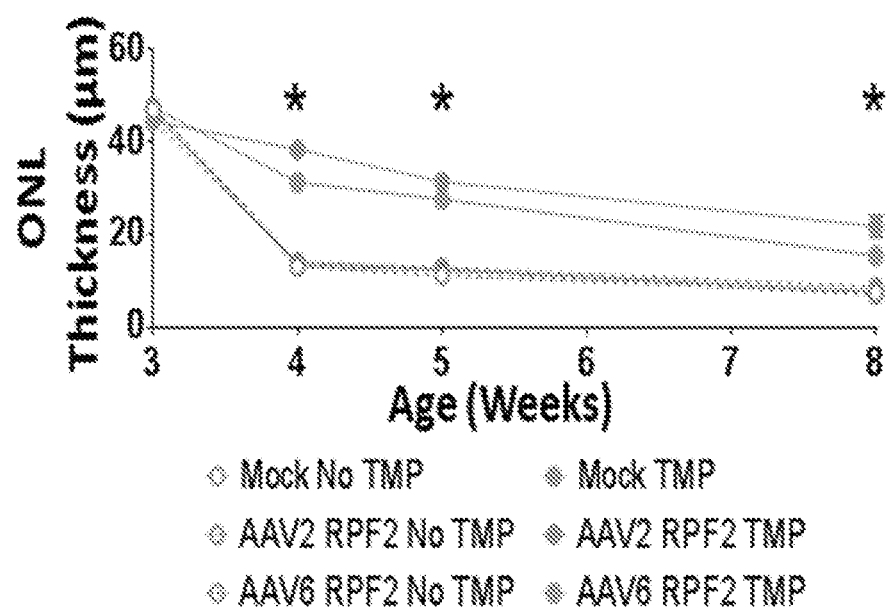
Figure 17C:
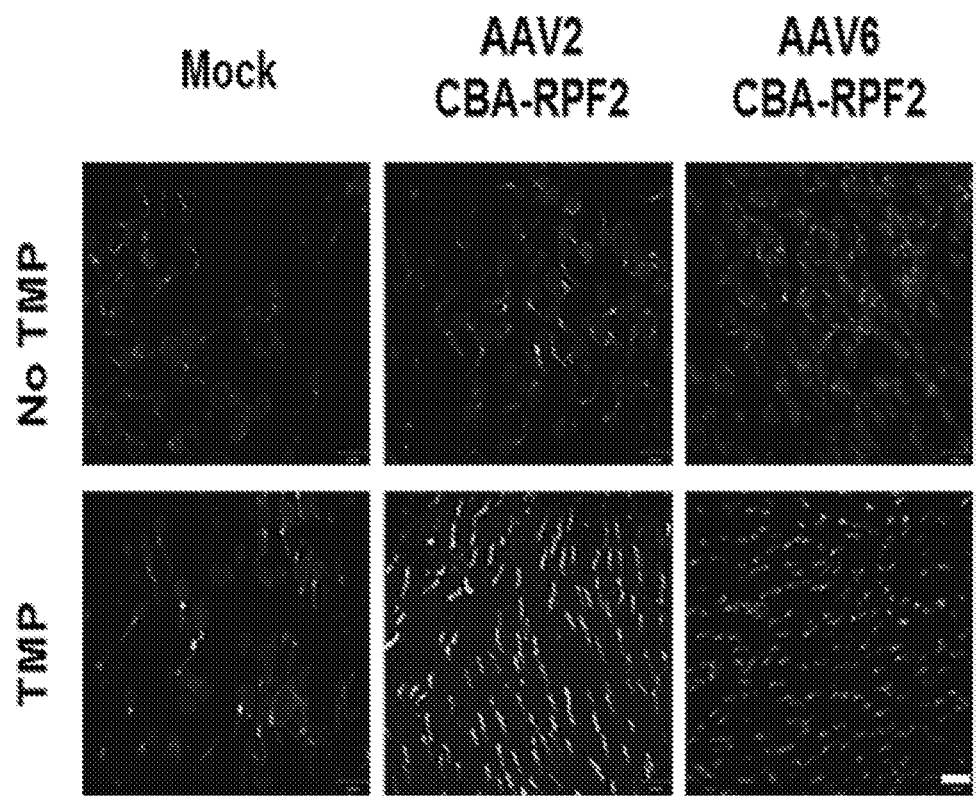
Figure 17D:
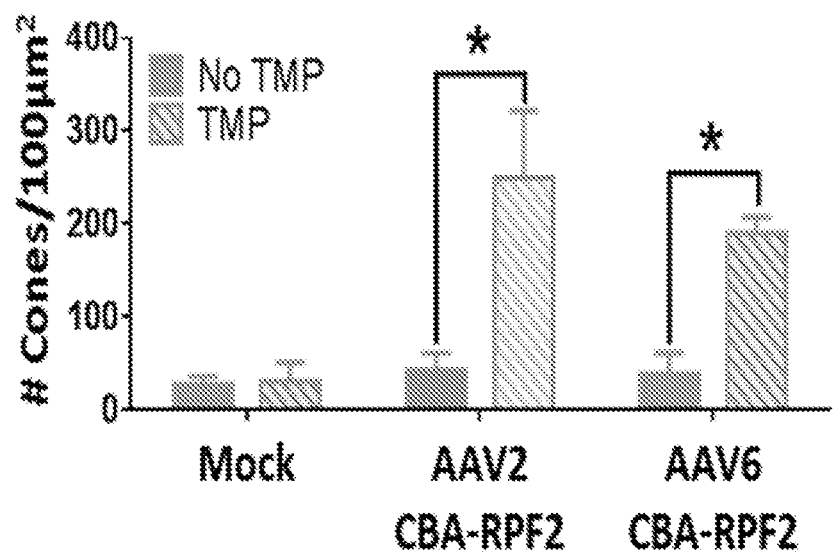
Figure 18A:
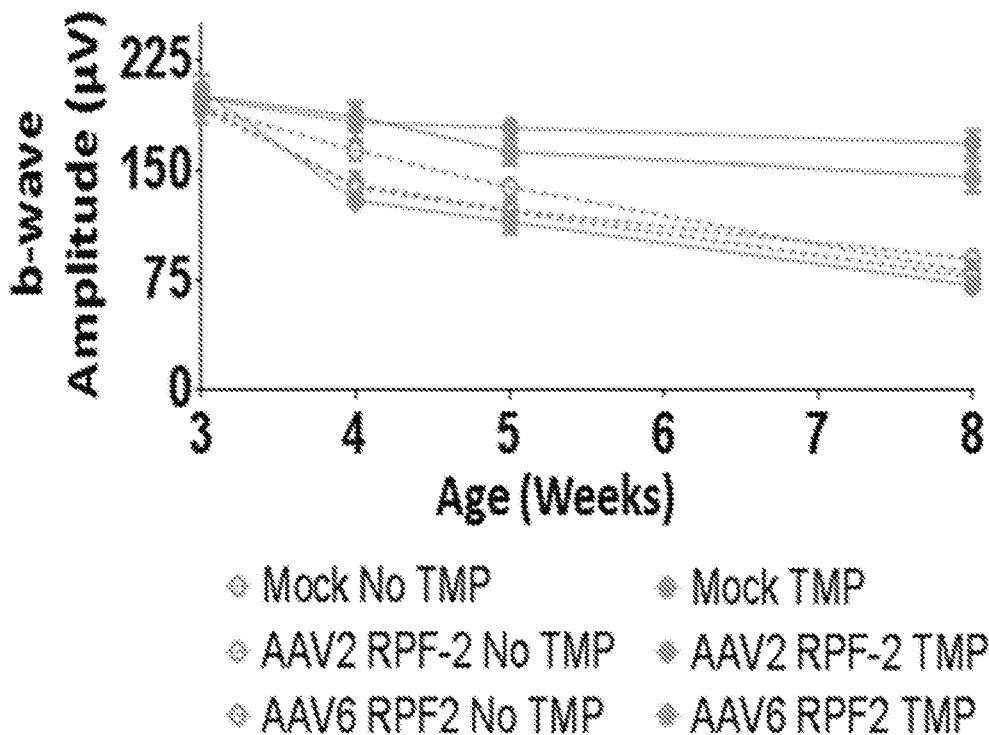
FIGS. 18A-18C show RPF2-treated rd10 mice maintain long-term cone-dependent vision.
Figure 18B:
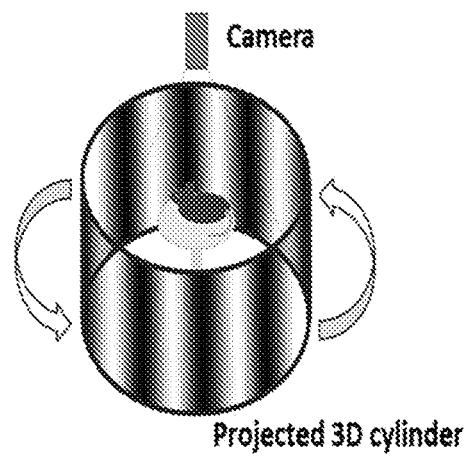
Figure 18C:
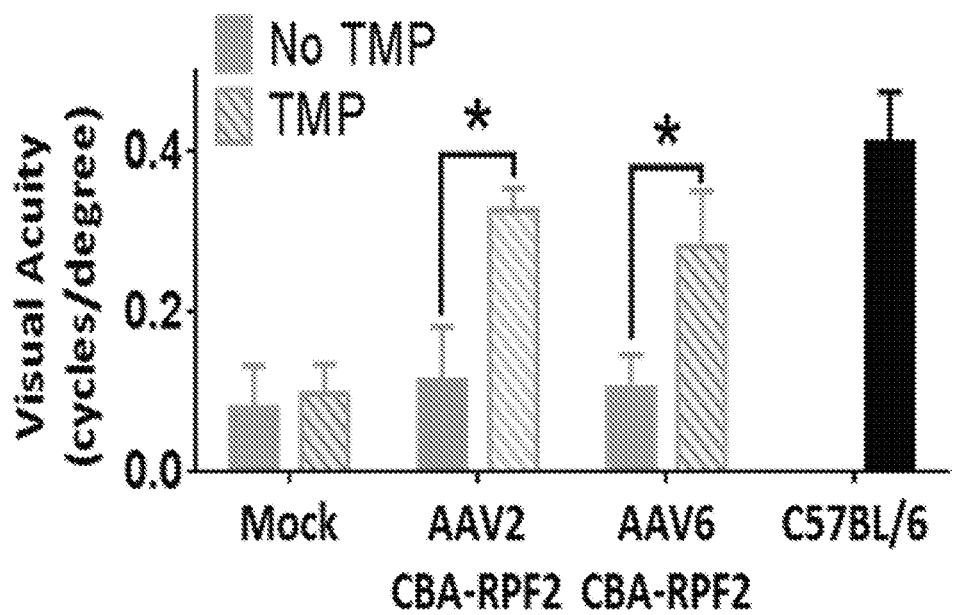
Figure 19:
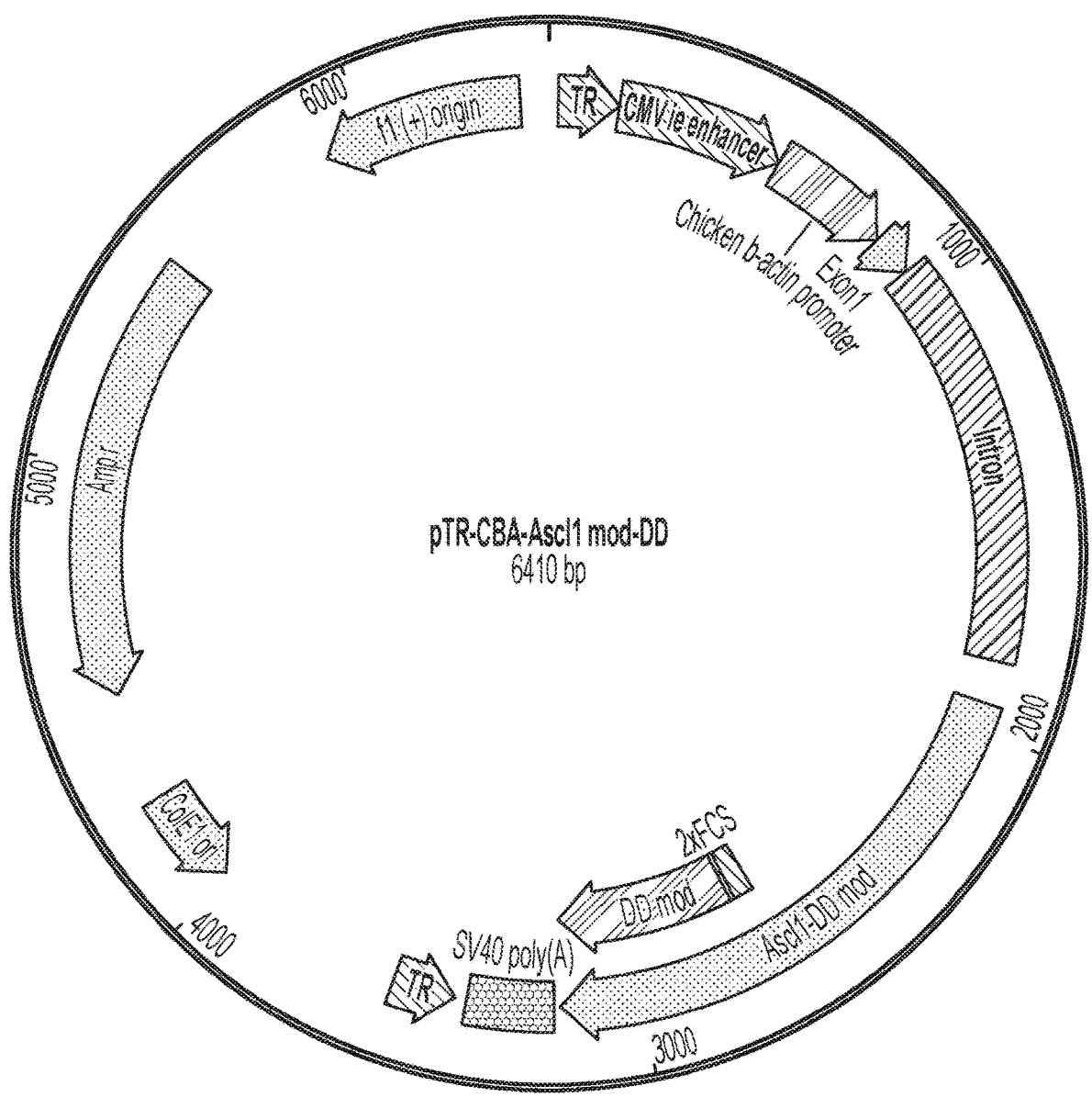
FIG. 19 is a schematic depicting one embodiment of a plasmid comprising an rAAV vector encoding ASCL1 fused to a destabilization domain (DD). Presence of the DD allows for regulation of expression by TMP.
Figure 20:
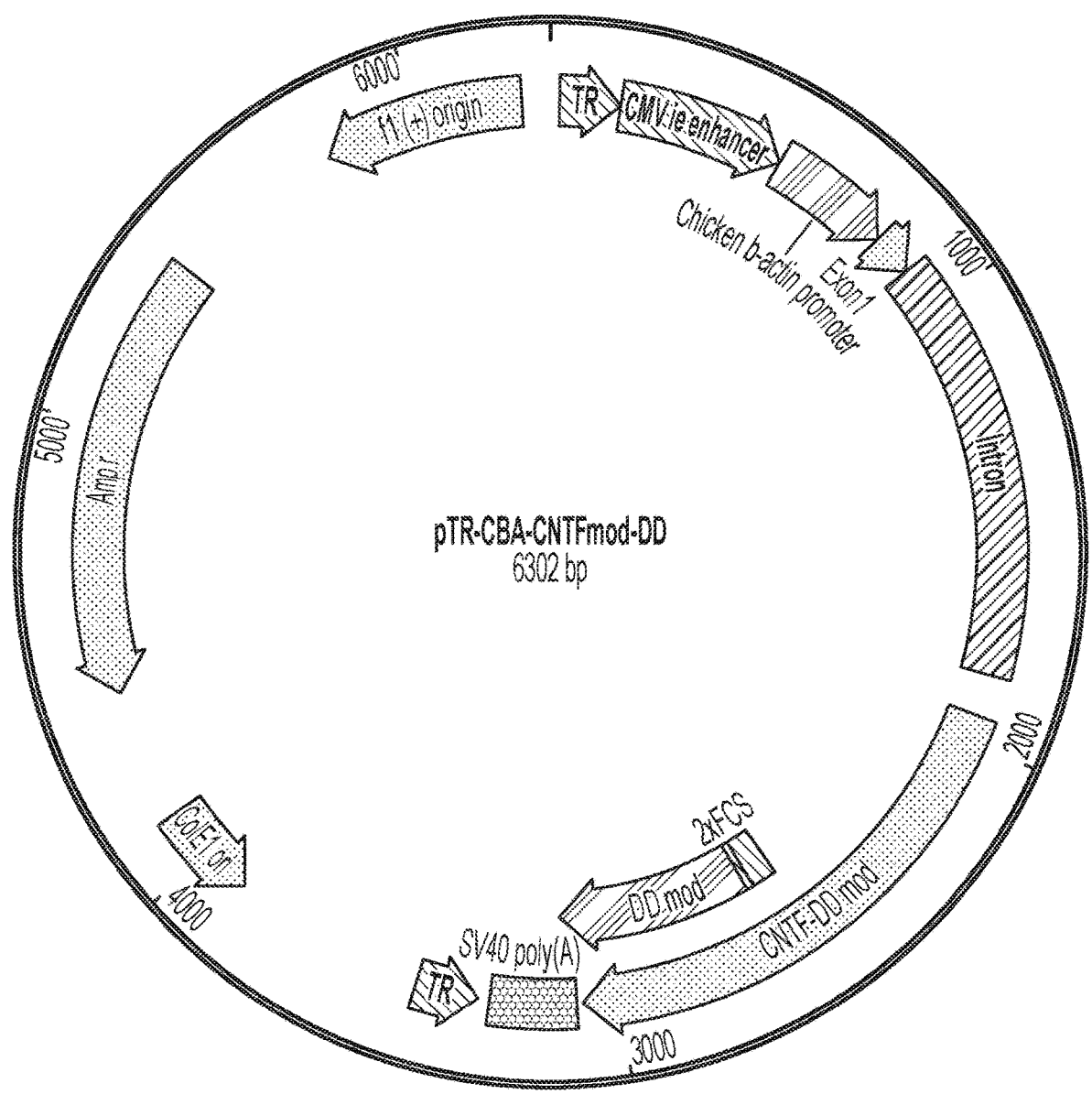
FIG. 20 is a schematic depicting one embodiment of a plasmid comprising an rAAV vector encoding CNTF fused to a destabilization domain (DD). Presence of the DD allows for regulation of expression by TMP.
Figure 21:
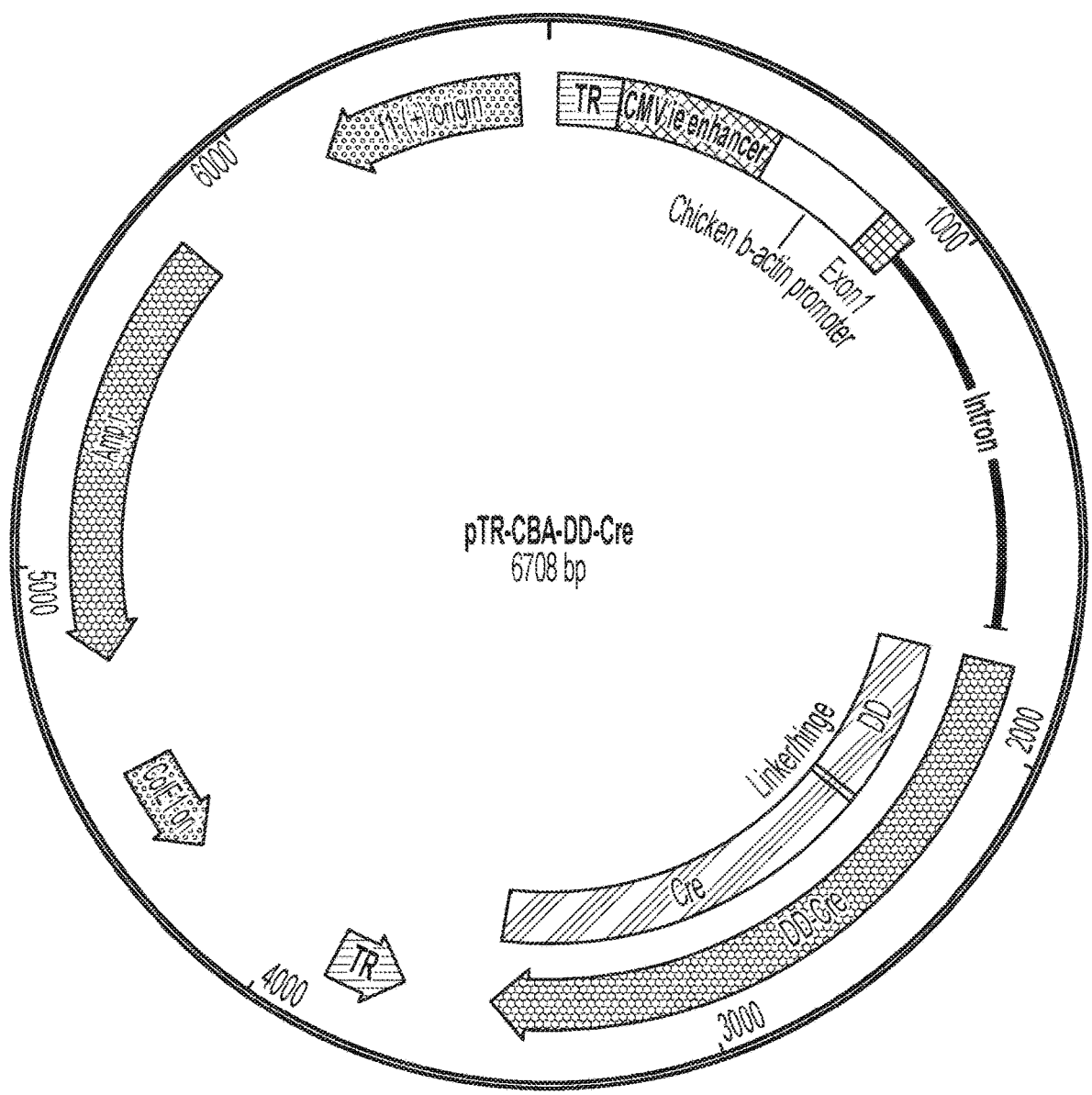
FIG. 21 is a schematic depicting one embodiment of a plasmid comprising an rAAV vector encoding Cre recombinase fused to a destabilization domain (DD). Presence of the DD allows for regulation of expression by TMP.
Figure 22:
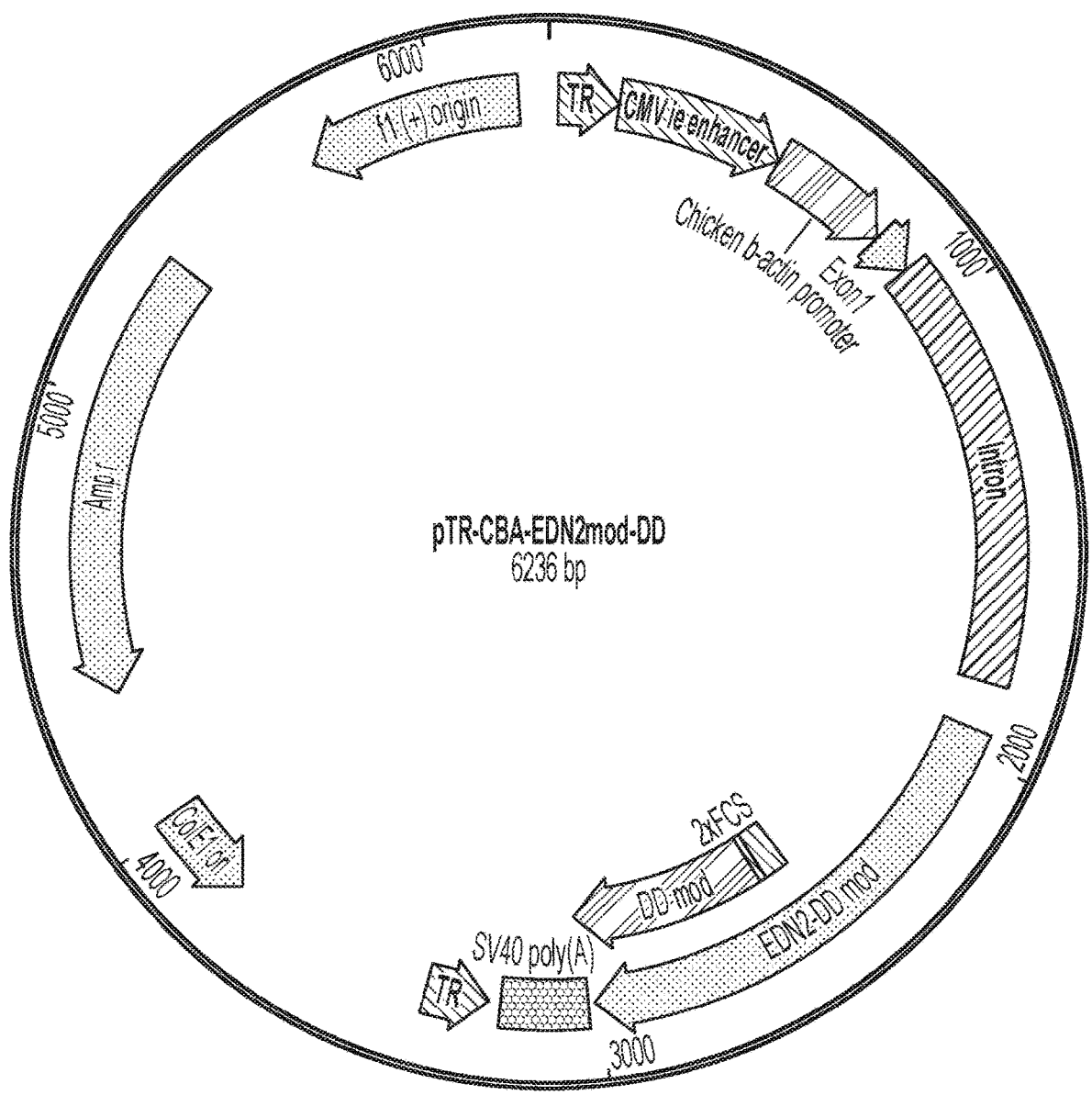
FIG. 22 is a schematic depicting one embodiment of a plasmid comprising an rAAV vector encoding EDN2 fused to a destabilization domain (DD). Presence of the DD allows for regulation of expression by TMP.
Figure 23:
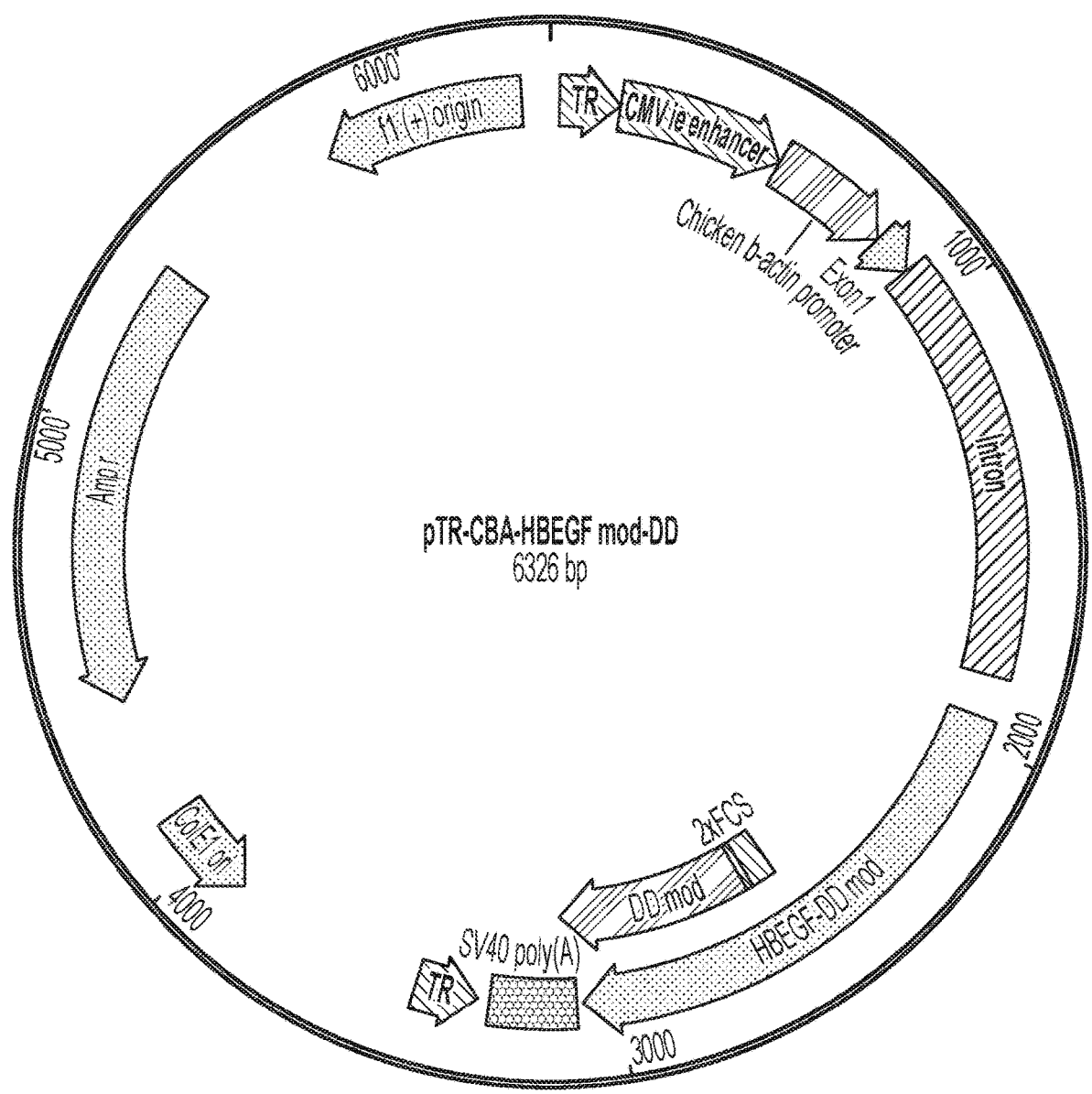
FIG. 23 is a schematic depicting one embodiment of a plasmid comprising an rAAV vector encoding HBEGF fused to a destabilization domain (DD). Presence of the DD allows for regulation of expression by TMP.
Figure 24:
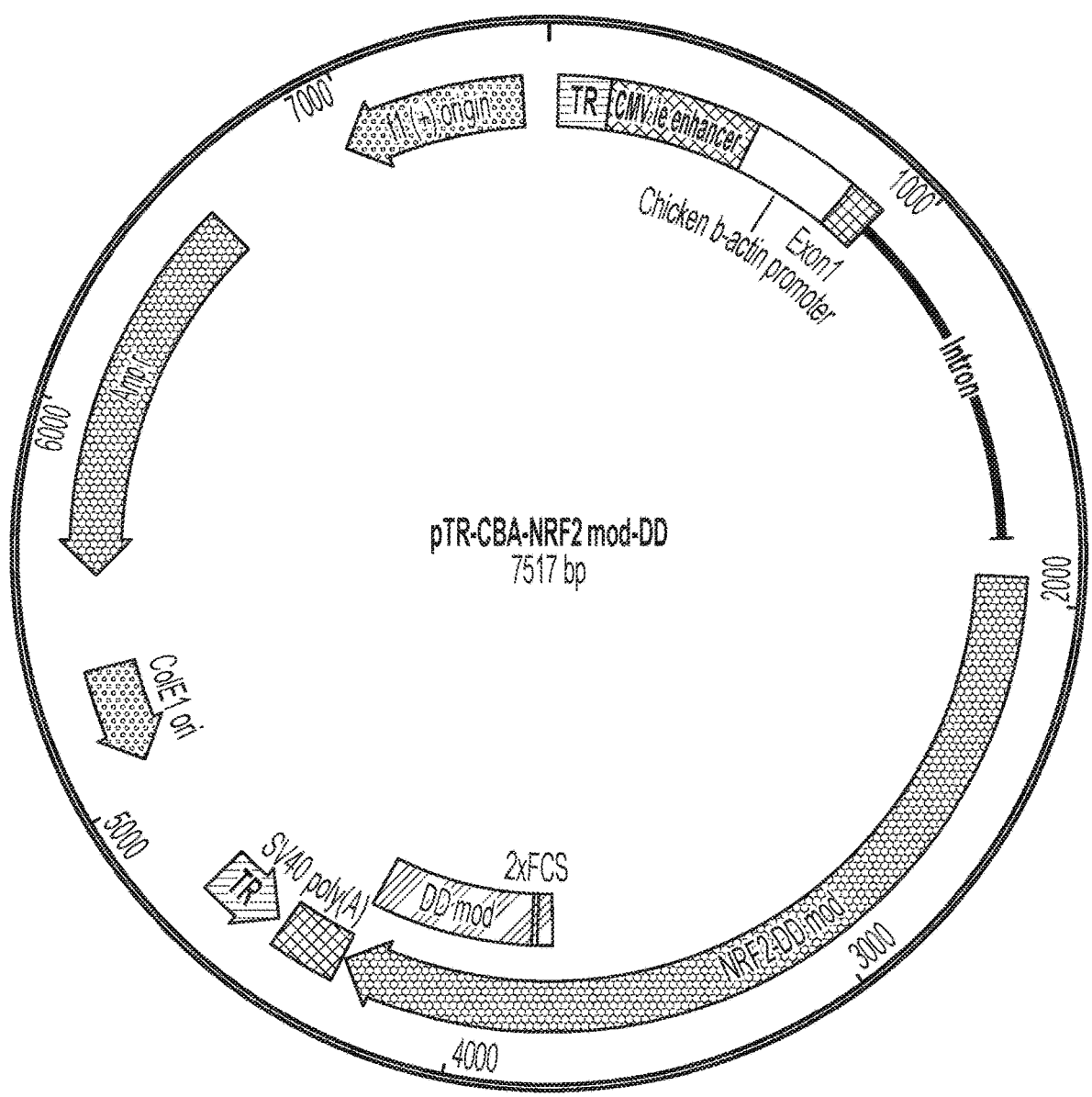
FIG. 24 is a schematic depicting one embodiment of a plasmid comprising an rAAV vector encoding NRF2 fused to a destabilization domain (DD). Presence of the DD allows for regulation of expression by TMP.
Figure 25:
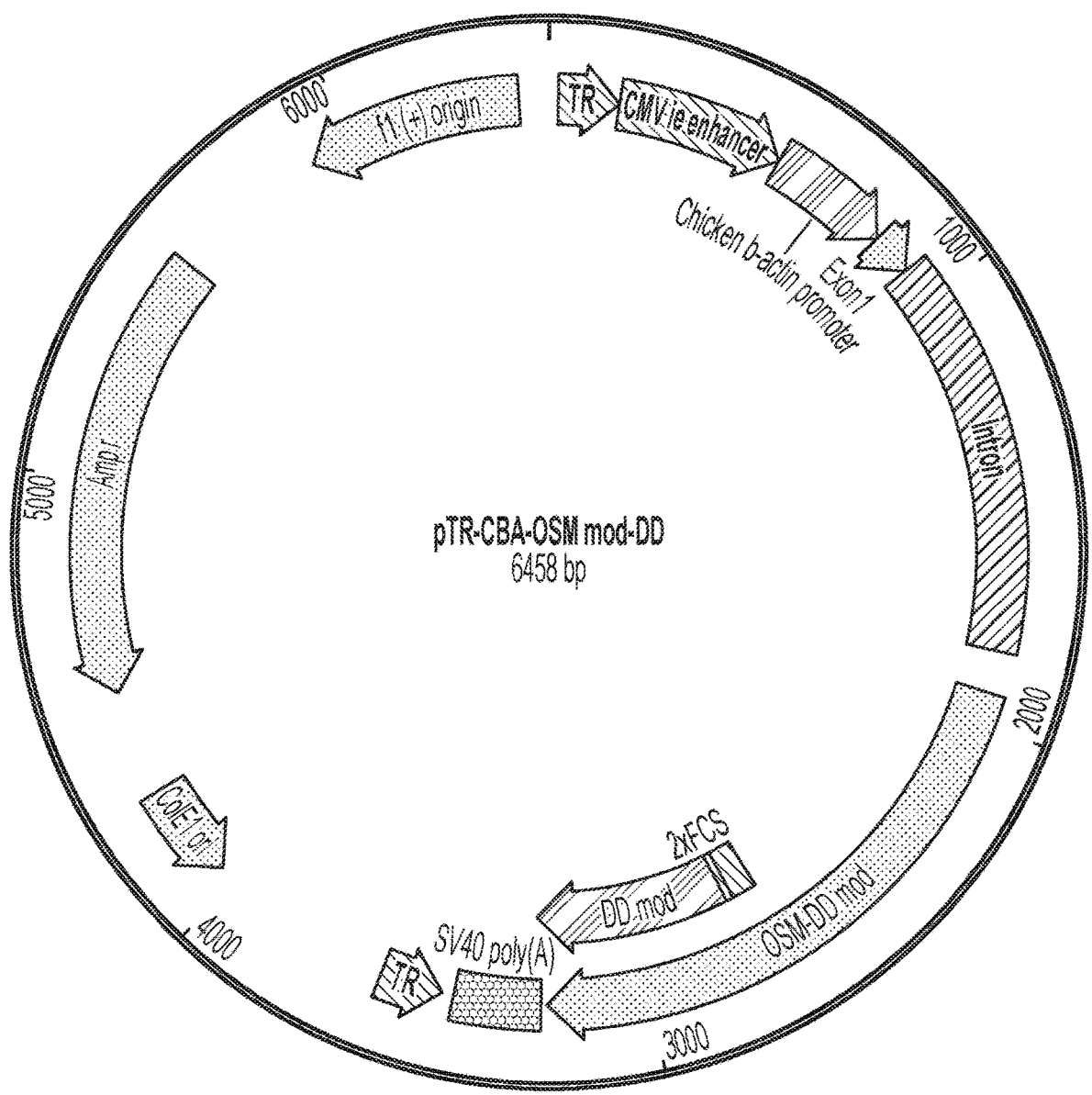
FIG. 25 is a schematic depicting one embodiment of a plasmid comprising an rAAV vector encoding OSM fused to a destabilization domain (DD). Presence of the DD allows for regulation of expression by TMP.
Figure 26:
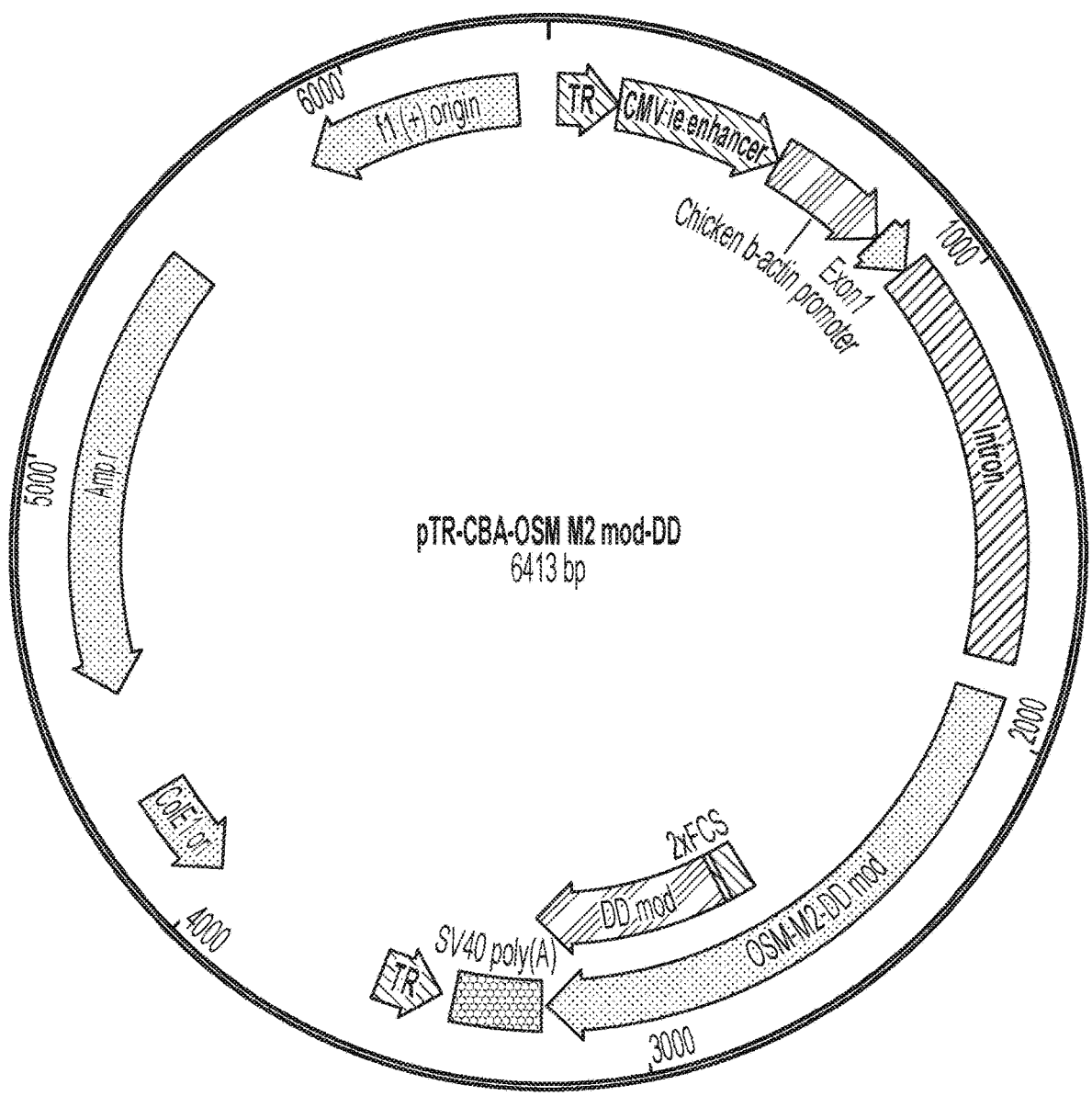
FIG. 26 is a schematic depicting one embodiment of a plasmid comprising an rAAV vector encoding OSM-M2 fused to a destabilization domain (DD). Presence of the DD allows for regulation of expression by TMP.
Figure 27:
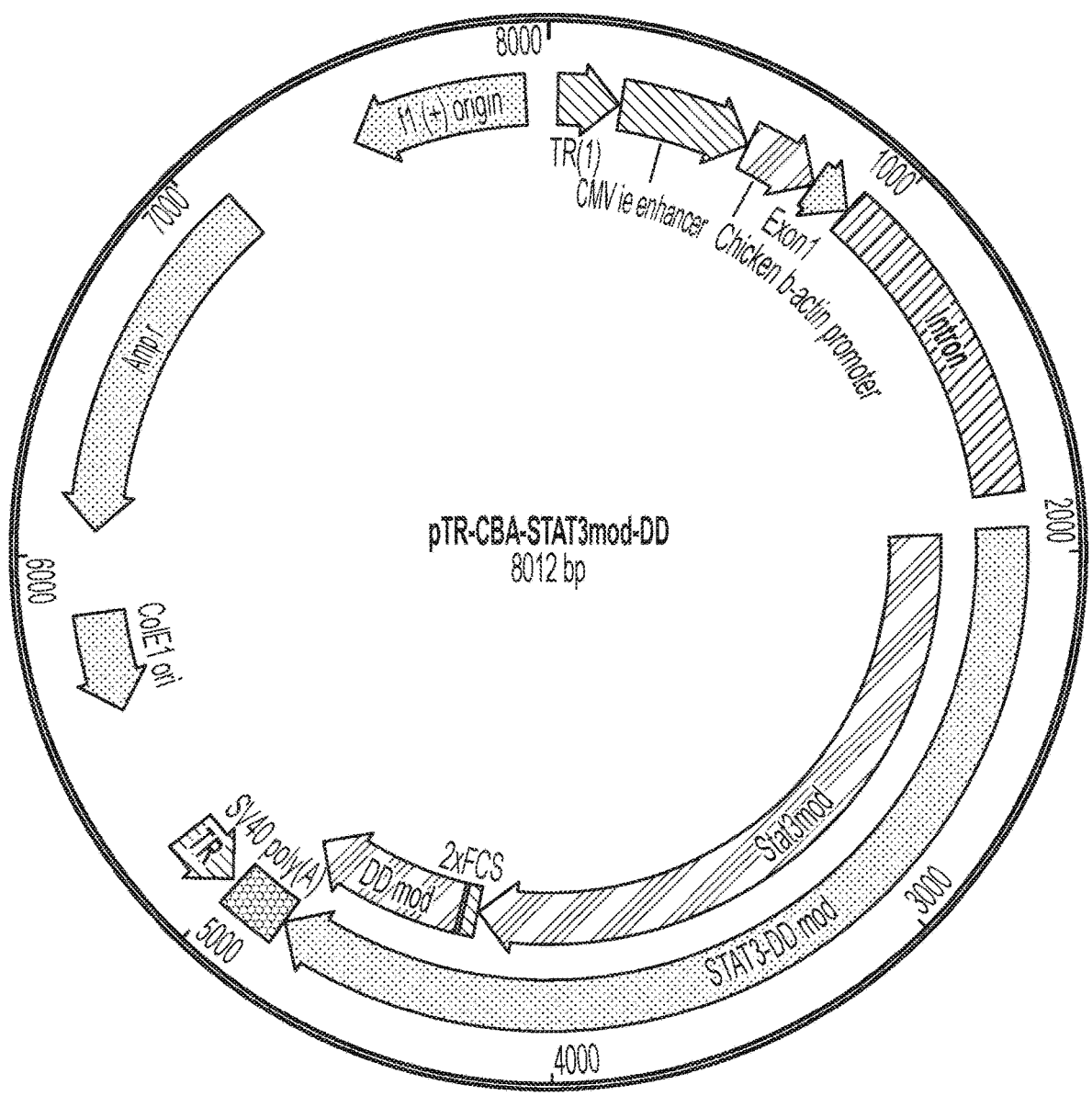
FIG. 27 is a schematic depicting one embodiment of a plasmid comprising an rAAV vector encoding STAT3 fused to a destabilization domain (DD). Presence of the DD allows for regulation of expression by TMP.
Figure 28:
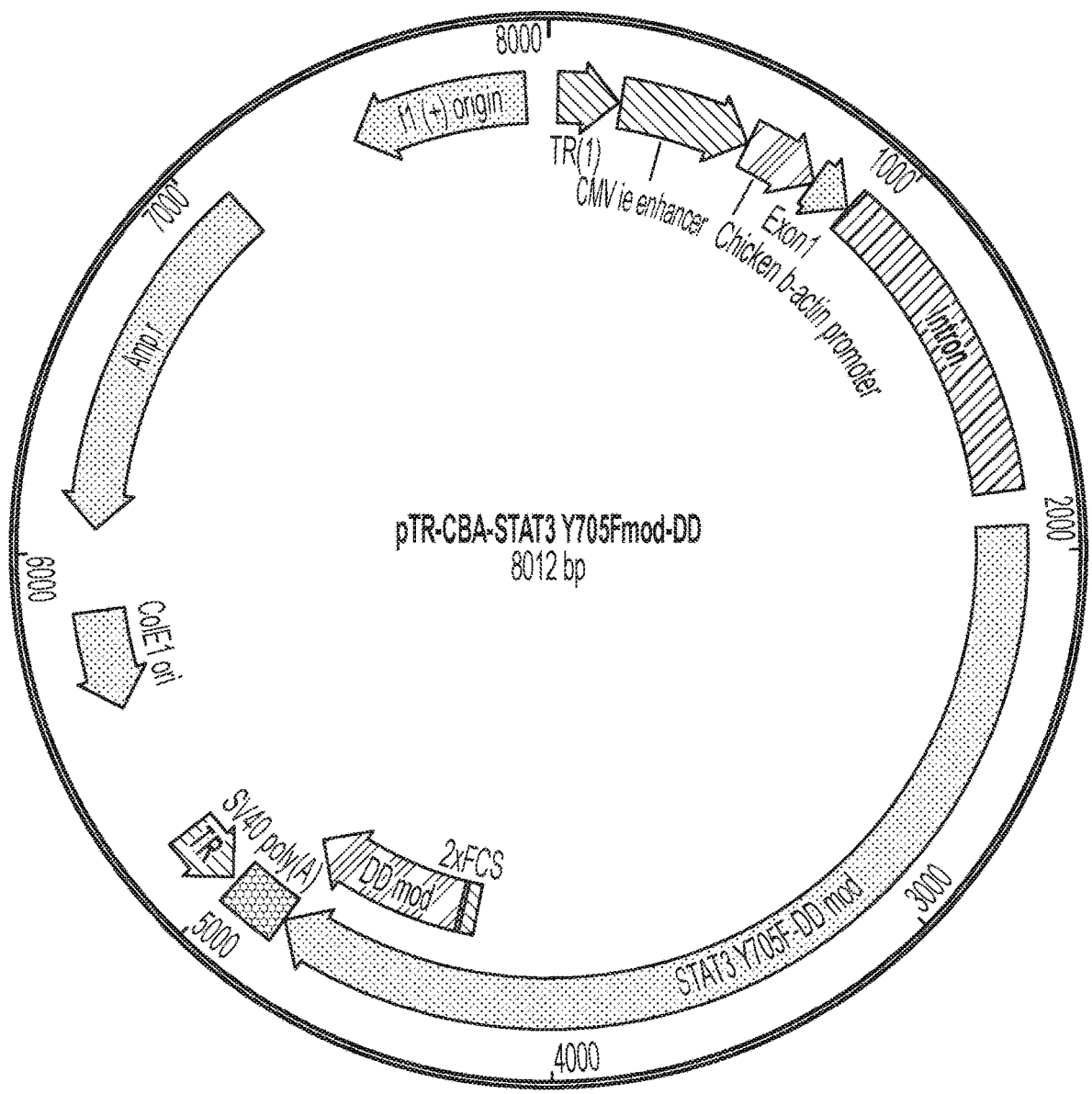
FIG. 28 is a schematic depicting one embodiment of a plasmid comprising an rAAV vector encoding STAT3 variant Y705F fused to a destabilization domain (DD). Presence of the DD allows for regulation of expression by TMP.
Figure 29:
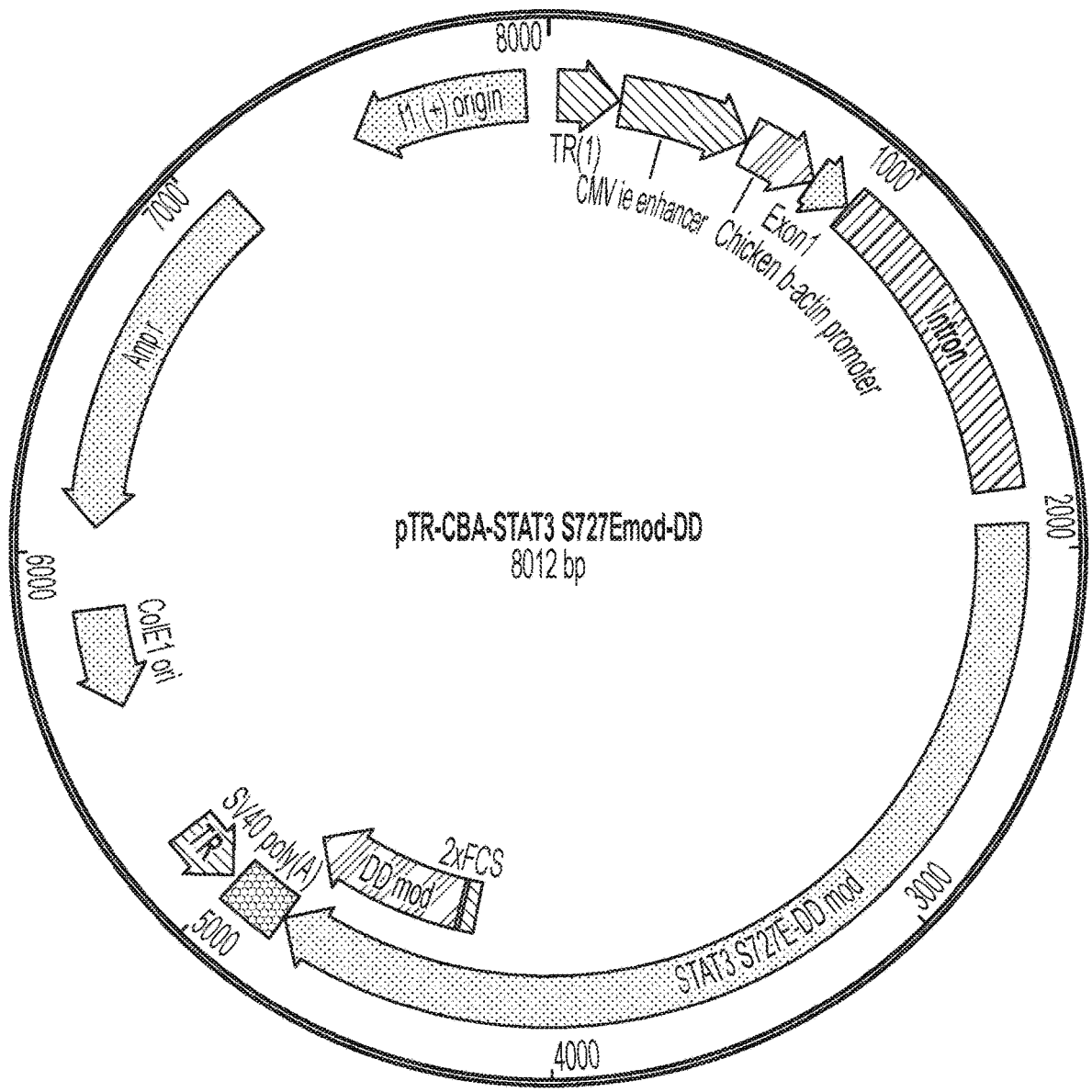
FIG. 29 is a schematic depicting one embodiment of a plasmid comprising an rAAV vector encoding STAT3 variant S727E fused to a destabilization domain (DD). Presence of the DD allows for regulation of expression by TMP.
Figure 30:
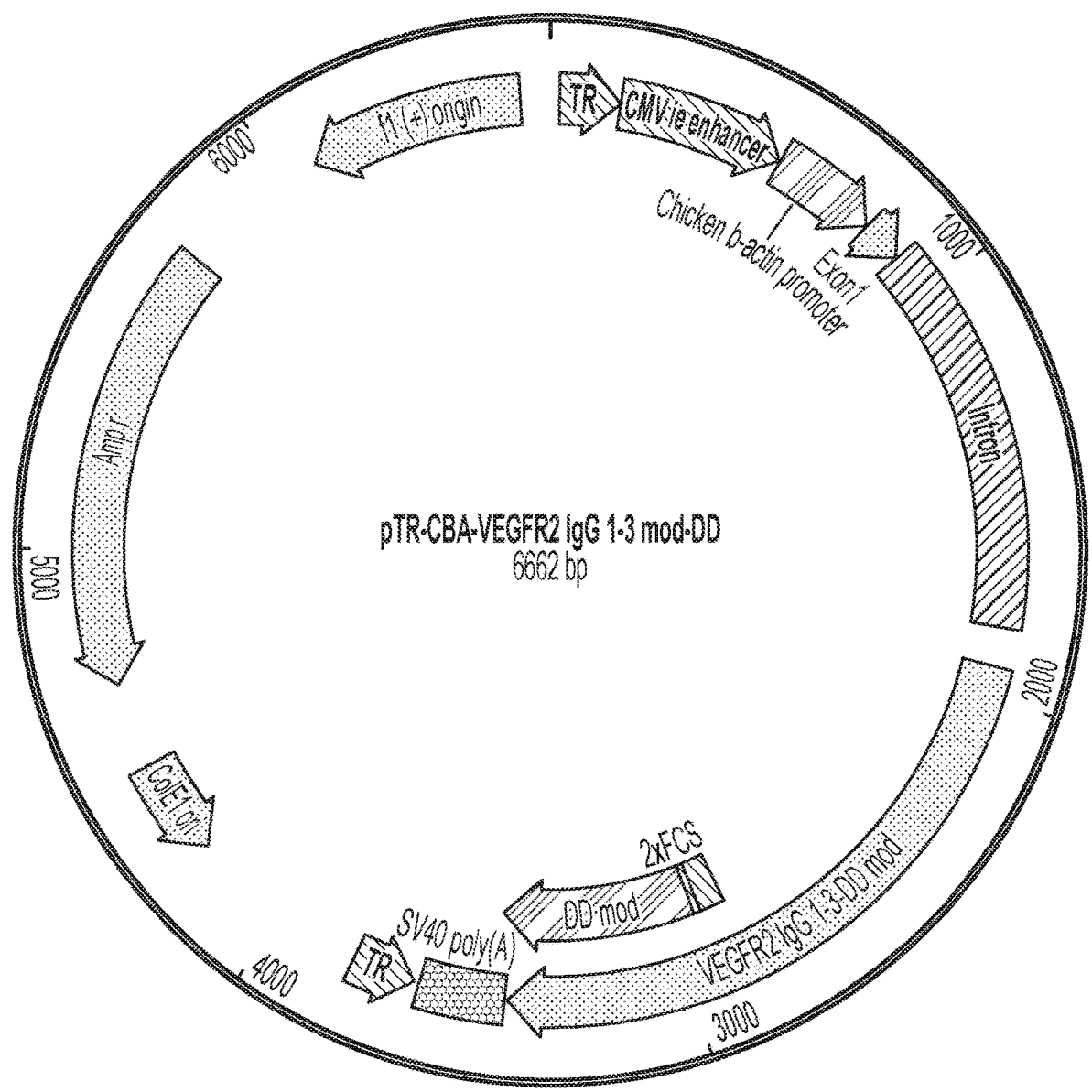
FIG. 30 is a schematic depicting one embodiment of a plasmid comprising an rAAV vector encoding VEGFR2 IgG 1-3 (e.g., loops 1-3 of VEGFR2) fused to a destabilization domain (DD). Presence of the DD allows for regulation of expression by TMP.
Figure 31:
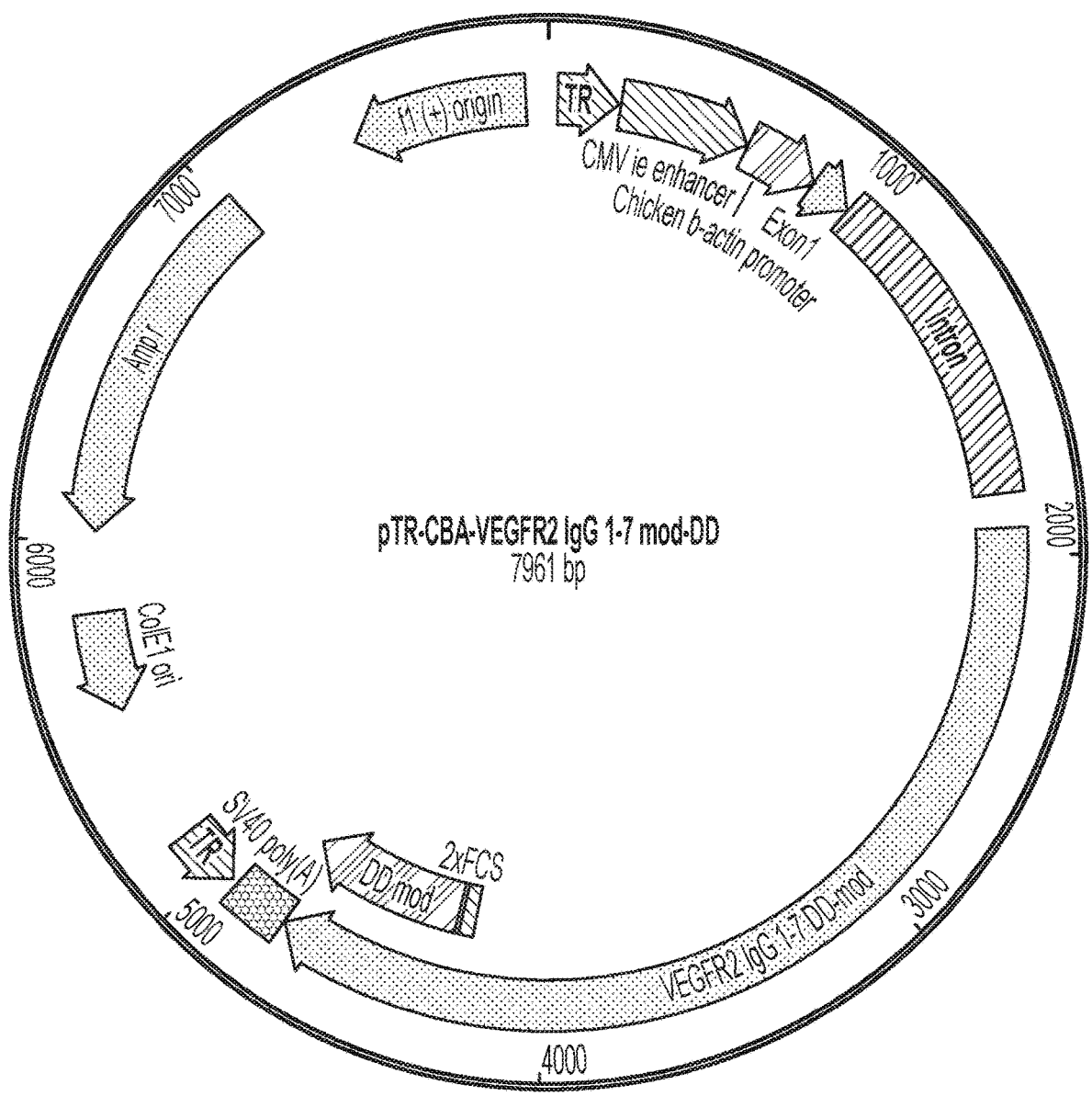
FIG. 31 is a schematic depicting one embodiment of a plasmid comprising an rAAV vector encoding VEGFR2 IgG 1-7 (e.g., loops 1-7 of VEGFR2) fused to a destabilization domain (DD). Presence of the DD allows for regulation of expression by TMP.
Figure 32:
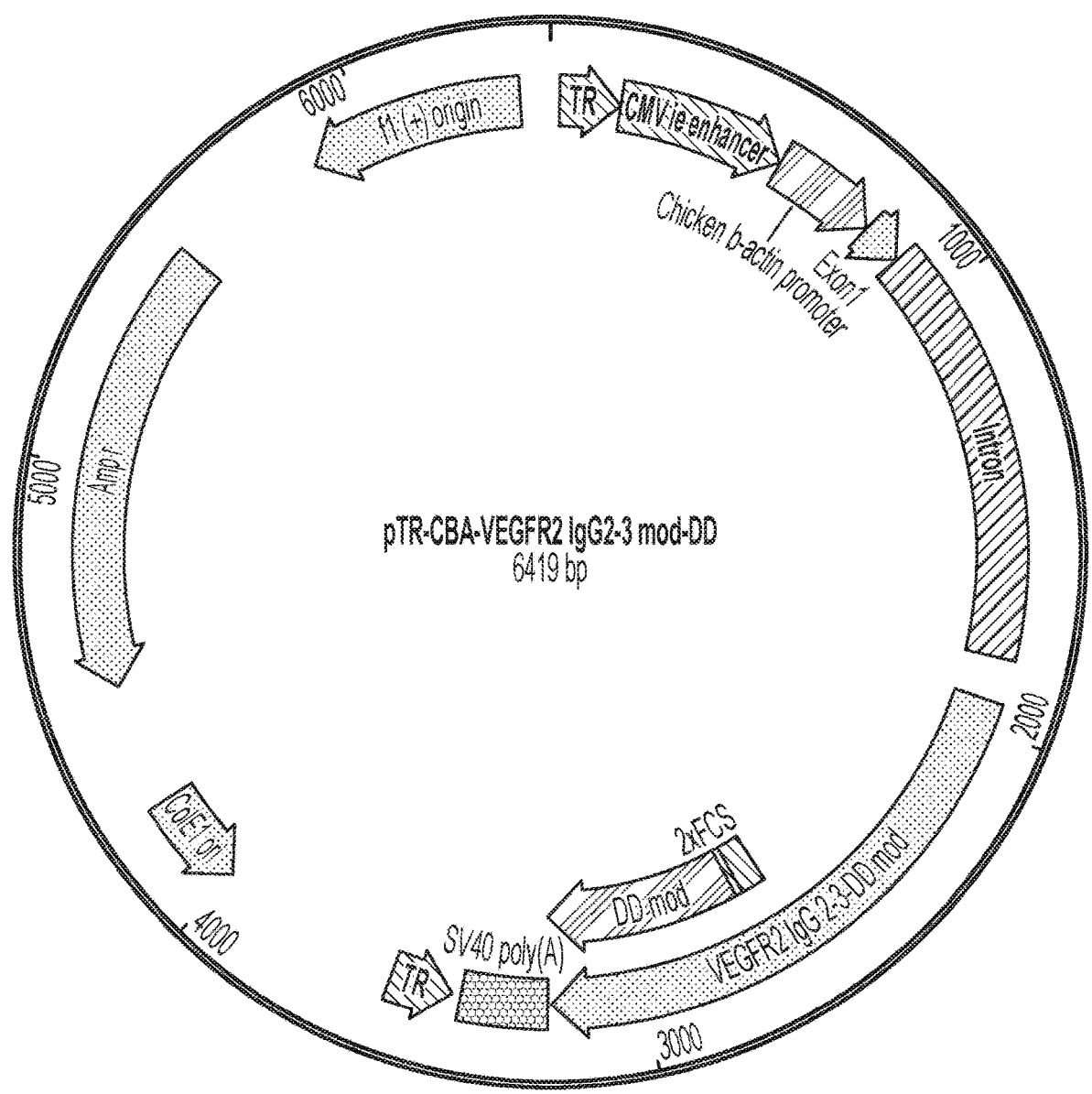
FIG. 32 is a schematic depicting one embodiment of a plasmid comprising an rAAV vector encoding VEGFR2 IgG 2-3 (e.g., loops 2-3 of VEGFR2) fused to a destabilization domain (DD). Presence of the DD allows for regulation of expression by TMP.

The rd10 mouse is a widely used model to study inherited retinal degeneration. To determine whether TMP-induced RPF2 expression can preserve photoreceptors in rd10 retinas, AAV-RPF2 vectors were delivered at high titer to the animals prior to any degeneration at week 2 (FIG. 17A). At week 3 (weaning age), TMP was administered and the animals were monitored by OCT and ERG over time (FIG. 17A). The TMP-treated AAV-RPF2 groups had significant preservation of the ONL compared to no TMP controls (FIG. 17B). Retinas were also collected at week 8 to measure preservation of cones, which normally die subsequent to rod loss. In the AAV-RPF2 groups treated with TMP, cones were markedly preserved compared to mock-infected mice or no TMP controls (FIGS. 17C-17D). The preserved cones maintained 80% of their function in the TMP-treated AAV-RPF2 groups, as measured by photopic ERG responses (FIG. 18A). To quantify functional vision in treated mice, OptoMotry was used to measure visual acuity (FIG. 18B). AAV-RPF2 groups treated with TMP showed significant preservation of visual acuity compared to mock-injected or no-TMP groups. The visual acuity in TMP treated mice was comparable to that of C57BL/6J wild-type control mice (FIG. 18C). Overall, data indicate AAV-RPF2 therapy protects rods and cones and preserves cone vision in an aggressive model of inherited retinal degeneration.

Example 3: Additional Expression Vectors

Additional rAAV vectors targeting ASCL1, CNTF, EDN2, HBEGF, NRF2, OSM, OSM-M2, STAT3, STAT3 Y705F, STAT3 S727E, Cre recombinase, VEGFR2 IgG loops 1-3, VEGFR2 IgG loops 1-7, and VEGFR2 IgG loops 2-3 of VEGFR2 were produced. Each rAAV vector comprises a DHFR destabilization domain (DD), which allows for tunable expression based on the presence or absence of TMP in a cell. FIGS. 19-32 show schematics depicting plasmids encoding the rAAV vectors.

SEQUENCES

>Human Leukemia Inhibitory Factor (hLIF) Nucleic Acid Sequence (SEQ ID NO: 1)
ATGAAGGTCTTGGCGGCAGGAGTTGTGCCCCTGCTGTTGGTTCTGCACTGGAAACATGGGGCGGGGAGCCCCCTCCCCATCACCCCTGTC
AACGCCACCTGTGCCATACGCCACCCATGTCACAACAACCTCATGAACCAGATCAGGAGCCAACTGGCACAGCTCAATGGCAGTGCCAAT
GCCCTCTTTATTCTCTATTACACAGCCCAGGGGGAGCCGTTCCCCAACAACCTGGACAAGCTATGTGGCCCCAACGTGACGGACTTCCCG
CCCTTCCACGCCAACGGCACGGAGAAGGCCAAGCTGGTGGAGCTGTACCGCATAGTCGTGTACCTTGGCACCTCCCTGGGCAACATCACC

| SEQUENCES |
|---|
| CGGGACCAGAAGATCCTCAACCCCAGTGCCCTCAGCCTCCACAGCAAGCTCAACGCCACCGCCGACATCCTGCGAGGCCTCCTTAGCAAC<br>GTGCTGTGCCGCCTGTGCAGCAAGTACCACGTGGGCCATGTGGACGTGACCTACGGCCCTGACACCTCGGGTAAGGATGTCTTCCAGAAG<br>AAGAAGCTGGGCTGTCAACTCCTGGGGAAGTATAAGCAGATCATCGCCGTGTTGGCCCAGGCCTTCTAG<br><br>>Human Leukemia Inhibitory Factor (hLIF) Amino Acid Sequence (SEQ ID NO: 2)<br>MKVLAAGVVPLLLVLHWKHGAGSPLPITPVNATCAIRHPCHNNLMNQIRSQLAQLNGSANALFILYYTAQGEPFPNNLDKLCGPNVTDFP<br>PFHANGTEKAKLVELYRIVVYLGTSLGNITRDQKILNPSALSHSKLNATADILRGLLSNVLCRLCSKYHVGHVDVTYGPDTSGKDVFQK<br>KKLGCQLLGKYKQIIAVLAQAF<br><br>>RPF2 Nucleic Acid Sequence (SEQ ID NO: 3); (Bold: Destabilization domain; Italic: 2xFCS linker)<br>atgaaagtgctggctgccggcgtggttcctctgctgctggtacttcactggaagcacggtgccggctcaccactcccatcaccccagta<br>aacgcgacctgcgctattagacacccatgtcacaacaacctgatgaaccagattcgctcccaactggcccagctgaacgggagtgctaat<br>gctctgttcatcttgtattacacagcccaaggagaacccttccaataaccttgataaactgtgcggccccaatgtgaccgatttcccc<br>cccttccatgctaacgggacggagaaagctaaactggtcgagctgtaccggatagttgtgtacttgggcacatcactcggcaacattaca<br>cgggatcagaagatcctgaacccttctgcccttctttgcatagcaagctgaacgccacggctgacatactgagggggtctgctttctaat<br>gtgttgtgccggctttgctctaagtaccatgtaggccatgtagatgtgacgtacggtccggatacttcagggaaagacgtattccagaaa<br>aagaagttggggtgccagctgctggggaaatataagcagatcatagccgttctggcccaggctttt*accagatctcgcaagaagcgcagc*<br>*accagatctcgcaagaagcgcagcggggccccc*atgatatctctgatcgctgctcttgctgtggactacgtgattggtatggagaatgct*<br>*atgccctggaatctgcctgcagacctggcatggtttaagaggaacacccttaataaacctgtaatcatgggacgacatacatgggagagt*<br>*atcggcaggccattgcccgggaggaagaatataattctgagttcccagccttctactgatgatagggtaacttgggtcaagagcgtcgac*<br>*gaggccatcgccgcttgcggggatgtgcctgaaatcatggttatcgggggcggacgggtgattgagcaatttctgcccaaggcacagaag*<br>*ctgtatctgacccatatagacgccgaggtggagggagatacacactttcccgactatgagcccgatgattgggagagtgtctttagcgaa*<br>*tttcatgacgccgacgcacagaattcccatagctactgcttcgaaattctcgaacggcgctag*<br><br>>RPF2 Amino Acid Sequence (SEQ ID NO: 4); (Bold: Destabilization domain; Italic: 2xFCS linker)<br>MKVLAAGVVPLLLVLHWKHGAGSPLPITPVNATCAIRHPCHNNLMNQIRSQLAQLNGSANALFILYYTAQGEPFPNNLDKLCGPNVTDFP<br>PFHANGTEKAKLVELYRIVVYLGTSLGNITRDQKILNPSALSHSKLNATADILRGLLSNVLCRLCSKYHVGHVDVTYGPDTSGKDVFQK<br>KKLGCQLLGKYKQIIAVLAQAF*TRSRKKRSTRSRKKRSGAP*MISLIAALAVDYVIGMENAMPWNLPADLAWFKRNTLNKPVIMGRHTWES<br>IGRPLPGRKNIILSSQPSTDDRVTWVKSVDEAIAACGDVPEIMVIGGGRVIEQFLPKAQKLYLTHIDAEVEGDTHFPDYEPDDWESVFSE<br>FHDADAQNSHSYCFEILERR***<br><br>> ASCL1-DD amino acid sequence (SEQ ID NO: 5)<br>MESSAKMESGGAGQQPQPQQPFLPPAACFFATAAAAAAAAAAAAAQSAQQQQQQQQQQQAPQLRPAADGQPSGGGHKSAPKQVKRQR<br>SSSPELMRCKRRLNFSGFGYSLPQQQPAAVARRNERERNRVKLVNLGFATLREHVPNGAANKKMSKVETLRSAVEY1RALQQLLDEHDAV<br>SAAFQAGVLSPTISPNYSNDLNSMAGSPVSSYSSDEGSYDPLSPEEQELLDFTNWFTRSRKKRSTRSRKKRSGAPMISLIAALAVDYVIG<br>MENAMPWNLPADLAWFKRNTLNKPVIMGRHTWESIGRPLPGRKNIILSSQPSTDDRVTWVKSVDEAIAACGDVPEIMVIGGGRVIEQFLP<br>KAQKLYLTHIDAEVEGDTHFPDYEPDDWESVFSEFHDADAQNSHSYCFEILERR*<br><br>> rAAV vector encoding ASCL1 (TMP-regulated transcription factor ASCL1) (SEQ ID NO: 6)<br>ttggccactccctctctgcgcgctcgctcgctcactgaggccgggcgaccaaaggtcgcccgacgcccgggctttgcccgggcggcctca<br>gtgagcgagcgagcgcgcagagagggagtggccaactccatcactagggggttcctcagatctgaattcggtacctagttattaatagtaa<br>tcaattacggggtcattagttcatagcccatatatggagttccgcgttacataacttacggtaaatggcccgcctggctgaccgcccaac<br>gacccccgcccattgacgtcaataatgacgtatgttcccatagtaacgccaatagggactttccattgacgtcaatgggtggagtattta<br>cggtaaactgcccacttggcagtacatcaagtgtatcatatgccaagtacgccccctattgacgtcaatgacggtaaatggcccgcctgg<br>cattatgcccagtacatgaccttatgggactttcctacttggcagtacatctacgtattagtcatcgctattaccatggtcgaggtgagc<br>cccacgttctgcttcactctccccatctcccccccctccccaccccaattttgtatttatttattttttaatattttttgtgcagcgatg<br>ggggcggggggggggggggcgcgcgccaggcgggcggggcgggcggggcgaggcggaggcggggcgaggcggagaggtcggcggcagcc<br>aatcagagcggcgcgctccgaaaagttttccttttatggcgaggcggcggcggcggcggcggcccctataaaaagcgaagcgcgcggcggg<br>gtcgctgcgcgctgccttcgccccgtgccccgctccgccgccgccgcctcgccgccgcccgccccggctctgactgaccgcgttactcccacag<br>gtgagcgggcgggacggcccttctcctccgggctgtaattagcgcttggtttaatgacggcttgtttcttttctgtggctgcgtgaaagc<br>cttgagggctccgggagggccctttgtgcgggggagcggctcgggggtgcgtgcgtgtgtgtgcgtggggagcgccgcgtgcggc<br>tccgcgctgcccggcggctgtgagcgctgcgggcggcgcgggctttgtgcgctccgcagtgtgcgcgaggggagcgcggccgggggcggc<br>ggtgcccgcggtcgggggggctgcgagggaacaaaggctcgtgcgggggtgtgtgcgtgggggggtgagcaggggtgtgggcgcg<br>tcggtcgggctgcaaccccccctgcacccccctcccgagttgctgagcacggcccggcttcgggtgcgggctccgtacggggcgtggc<br>gcgggctcgccgtgccggcgggggtggcggcaggtggggtgccggcggggcggggccgcctcggccgggagggctcggggag<br>gggcgcggcggccccgagcgccggcggcgctgtcgaggcggcgagccgcagccattgcctttatggtaatcgtgcgagaggcgcag<br>ggacttcctttgtcccaaatctgtgcggagccgaaatctggaggcgccgccgcaccccctctagcggcgcggggcgaagcggtcgcgc<br>gccgcaggaaggaaatgggcgggagggccttcgtgcgtcgccgcgccgccgtcccttctccctctcagcctcggggctgtccgcgg<br>ggggacggctgccttcggggggacggggcagggcggggttcggcttctggcgtgtgaccggcggctctagagcctctgctaaccatgtt<br>catgccttcttcttttttcctacagctcctgggcaacgtgctggttattgtgctgtctcatcattttggcaaagaattcctcgaagatcta<br>ggcaacgcgtctcgaggcggccgccgccaccatggagtcttctgctaaaatggaaagcggaggagcaggtcagcagcccagccacagcc<br>ccaacagccgtttctccctccggccgcatgcttttcgcaacagcagccgcagctcggccgctgccgctgctgccgctcaatcagc<br>ccaacagcagcaacaacaacagcaacagcagcaacaggccccacaactgagaccagcagctgacgggcaaccctcagggggtggacataa<br>gagtgccccaaagcaagttaagcgccaacgctcaagttccccggagctgatgcggtgtaagagacgcctgaactttagcgggttcggcta<br>cagcctgccccaacagcaaccagcagccgtagccaggagaattgaaagggagcgcaatcgggttaagctcgtcaactcggcttcgcaac<br>tctgcgcgaacacgtcccaaatggagcggctaacaagaaaatgagtaaagttgagactctccgcagtgctgtcgaatatattcgggcgct<br>tcaacaacttctcgatgagcacgatgcagtgtctgccgcgtttcaggccggggtcttgtctccgaccattccccgaactactccaatga<br>cctgaactctatggcaggttctcccgtctcttcctattcttctgatgaaggctcatacgatcctctgagtcctgaggaacaggaattgtt<br>ggatttcacgaactggttcaccagatctcgcaagaagcgcagcaccagatctcgcaagaagcgcagcggggcccccatgatatctctgat<br>cgctgctcttgctgtggactacgtgattggtatggagaatgctatgccctggaatctgcctgcagacctggcatggtttaagaggaacac<br>ccttaataaacctgtaatcatgggacgacatacatgggagagtatcggcaggccattgcccgggaggaagaatataattctgagttccca<br>gccttctactgatgatagggtaacttgggtcaagagcgtcgacgaggccatcgccgcttgcggggatgtgcctgaaatcatggttatcgg<br>gggcggacgggtgattgagcaatttctgcccaaggcacagaagctgtatctgacccatatagacgccgaggtggagggagatacacactt<br>tcccgactatgagcccgatgattgggagagtgtctttagcgaatttcatgacgccgacgcacagaattcccatagctactgcttcgaaat<br>tctcgaacggcgctaggcggccgcgcggatccagacatgataagatacattgatgagtttggacaaaccacaactagaatgcagtgaaaa |

| SEQUENCES |
| --- |
| aaatgctttatttgtgaaatttgtgatgctattgctttatttgtaaccattataagctgcaataaacaagttaacaacaacaattgcatt<br>catttttatgtttcaggttcaggggggaggtgtgggaggttttttagtcgactggggagagatctgaggaacccctagtgatggagttggcc<br>actccctctctgcgcgctcgctcgctcactgaggccgcccgggcaaagcccgggcgtcgggcgacctttggtcgcccggcctcagtgagc<br>gagcgagcgcgcagagagggagtggccaac |

>CNTF-DD amino acid sequence (SEQ ID NO: 7)
MAFTEHSPLTPHRRDLCSRSIWLARKIRSDLTALTESYVKHQGLNKNINLDSADGMPVASTDQWSELTEAERLQENLQAYRTFHVLLARL
LEDQQVHFTPTEGDFHQAIHTLLLQVAAFAYQIEELMILLEYKIPRNEADGMPINVGDGGLFEKKLWGLKVLQELSQWTVRSIHDLRFIS
SHQTGIPARGSHYIANNKKMTRSRKKRSTRSRKKRSGAPMISLIAALAVDYVIGMENAMPWNLPADLAWFKRNTLNKPVIMGRHTWESIG
RPLPGRKNIILSSQPSTDDRVTWVKSVDEAIAACGDVPEIMVIGGGRVIEQFLPKAQKLYLTHIDAEVEGDTHFPDYEPDDWESVFSEFH
DADAQNSHSYCFEILERR*

>rAAV vector encoding CNTF (TMP-regulated protective factor CNTF) (SEQ ID NO: 8)
ttggccactccctctctgcgcgctcgctcgctcactgaggccgggcgaccaaaggtcgcccgacgcccgggctttgcccgggcggcctca
gtgagcgagcgagcgcgcagagagggagtggccaactccatcactagggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc
cccacgttctgcttcactctccccatctcccccccctccccaccccccaatttttgtatttatttatttttttaattttttttgtgcagcgatg
ggggcggggggggggggggcgcgcgccaggcggggcggggcggggcgaggggcggggcggggcgaggcggagaggtgcggcggcagcc
aatcagagcggcgcgctccgaaagtttccttttatggcgaggcggcggcggcggcggccctataaaaagcgaagcgcgcggcgggcggga
gtcgctgcgcgctgcctcgccccgtgccccgctccgccgccgcctcgccgcccgccccggctctgactgaccgcgttactcccacag
gtgagcgggcgggacggcccttctcctccggggctgtaattagcgcttggtttaatgacggcttgtttcttttctgtggctgcgtgaaagc
cttgaggggctccgggagggccctttgtgcgggggagcggctcgggggggtgcgtgcgtgtgtgtgtgcgtggggagcgccgcgtgcgc
tccgcgctgcccggcggctgtgagcgctgcgggcgcggcgcgggcttttgtgcgctccgcagtgtgcgcgagggagcgcggccgggggc
ggtgcccgcggtgcgggggggctgcgaggggaacaaaggctgcgtgcggggtgtgtgcgtgggggggtgagcagggggtgtgggcgcg
tcggtcgggctgcaacccccctgcacccccctccccgagttgctgagcacggcccggcttcgggtgcggggctccgtacggggcgtggc
gcggggctcgccgtgccgggcggggggtggcggcaggtggggtgccgggcggggcgggccgcctcgggccgggagggctcggggggag
gggcgcggcggccccggagcgccggcggctgtcgaggcggcgagccgcagccattgccttttatggtaatcgtgcgagagggcag
ggacttcctttgtcccaaatctgtgcggaccgaaatctgggaggcgccgccgcaccccctctagcgggcgcggggcgaagcggtgcggc
gccggcaggaaggaaatgggcgggaggggccttcgtgcgtcgccgcgccgccgtccccttctccctctccagcctcggggcgtgtccgcgg
ggggacggctgccttcggggggggacagggcgggtcgggtctcggcgtgtgaccggcggctctagagcctctgctaaccatgtt
catgccttcttctttttcctacagtcctgggcaacgtgctggttattgtgctgtctcatcattttggcaaagaattcctcgaagatcta
ggcaacgcgtctcgaggcggccgccgccaccatggcctttactgagcatagccccttgacaccgcacagaagggatcttgctccaggtc
catctggctcgcacggaagatcaggtcagacctgacagccctgaccgaatcatatgtaaagcaccagggcctgaataaaaacattaacct
cgacagcgcagacgaatgccggtggcctcaacagatcagtggtccgaactgacggaggcggacggtgcaagaaaacttgcaggcgta
tcgaacgtttcacgtcctgcttgcccggcttcttgaagaccagcaggttcattcacgcctacagagggagatttccatcaagcaatcca
cactttgctcctgcaagtcgcggcctttgcctatcagattgaggaactcatgattcttctcgaatataagattccacggaatgaggcgga
tgggatgccgattaacgtgggcgacggagggttgtttgagaaaaaactctggggtttgaaagttctgcaagaattgagtcagtggactgt
gcgatctatccacgacttgaggttcatctcatcccatcaaacagggataccttgcaagaggctctcattatatagcgaataataaaaaaat
gaccagatctcgcaagaagcgcagcaccagatctcgcaagaagcgcagcgggccccatgatatctctgatcgctgctcttgctgtgga
ctacgtgattggtatggagaatgctatgccctggaatctgcctgcagacctggcatggtttaagaggaacacccttaataaacctgtaat
catgggacgacatacatgggagagtatcggcaggccattgcccgggaggaagaatataattctgagttcccagccttctactgatgatag
ggtaacttgggtcaagagcgtcgacgaggccatcgccgcttgcggaggtgtcctgaaatcatggttatcgggggcggacggggtgattga
gcaatttctgcccaaggcacagaagctgtatctgacccatatagacgccgaggtggaggggagatacacactttcccgactatgagcccga
tgattgggagagtgtctttagcgaatttcatgacgccgacgcacagaattcccatagctactgctttgaaattctcgaacggcgctaggc
ggccgcgcggatccagacatgataagatacattgatgagtttggacaaaccacaactagaatgcagtgaaaaaaatgctttatttgtgaa
atttgtgatgctattgctttatttgtaaccattataagctgcaataaacaagttaacaacaacaattgcattcattttatgtttcaggtt
caggggggaggtgtgggaggttttttagtcgactggggagagatctgaggaacccctagtgatggagttggccactccctctctgcgcgct
cgctcgctcactgaggccgcccgggcaaagcccgggcgtcgggcgacctttggtcgcccggcctcagtgagcgagcgagcgcgcagagag
ggagtggccaac >Cre recombinase-DD amino acid sequence (SEQ ID NO: 9)
MISLIAALAVDYVIGMENAMPWNLPADLAWFKRNTLNKPVIMGRHTWESIGRPLPGRKNIILSSQPSTDDRVTWVKSVDEAIAACGDVPE
IMVIGGGRVIEQFLPKAQKLYLTHIDAEVEGDTHFPDYEPDDWESVFSEFHDADAQNSHSYCFEILERRGAPKKKRKVSNLLTVHQNLPA
LPVDATSDEVRKNLMDMFRDRQAFSEHTWKMLLSVCRSWAAWCKLNNRKWFPAEPEDVRDYLLYLQARGLAVKTIQQHLGQLNMLHRRSG
LPRPSDSNAVSLVMRRIRKENVDAGERAKQALAFERTDFDQVRSLMENSDRCQDIRNLAFLGIAYNTLLRIAEIARIRVKDISRTDGGRM
LIHIGRTKTLVSTAGVEKALSLGVTKLVERWISVSGVADDPNNYLFCRVRKNGVAAPSATSQLSTRALEGIFEATHRLIYGAKDDSGQRY
LAWSGHSARVGAARDMARAGVSIPEIMQAGGWTNVNIVMNYIRNLDSETGAMVRLLEDGD*

>rAAV vector encoding Cre (TMP-Regulated Cre recombinase) (SEQ ID NO: 10)
ttggccactccctctctgcgcgctcgctcgctcactgaggccgggcgaccaaaggtcgcccgacgcccgggctttgcccgggcggcctca
gtgagcgagcgagcgcgcagagagggagtggccaactccatcactagggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatggtggagtattta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc
cccacgttctgcttcactctccccatctcccccccctccccaccccccaatttttgtatttatttatttttttaattttttttgtgcagcgatg
ggggcggggggggggggggcgcgcgccaggcggggcggggcggggcgaggggcggggcggggcgaggcggagaggtgcggcggcagcc
aatcagagcggcgcgctccgaaagtttccttttatggcgaggcggcggcggcggcggccctataaaaagcgaagcgcgcggcgggcggga
gtcgctgcgcgctgcctcgccccgtgccccgctccgccgccgcctcgccgcccgccccggctctgactgaccgcgttactcccacag
gtgagcgggcgggacggcccttctcctccggggctgtaattagcgcttggtttaatgacggcttgtttcttttctgtggctgcgtgaaagc
cttgaggggctccgggagggccctttgtgcgggggagcggctcgggggggtgcgtgcgtgtgtgtgtgcgtggggagcgccgcgtgcgc
tccgcgctgcccggcggctgtgagcgctgcgggcgcggcgcgggcttttgtgcgctccgcagtgtgcgcgagggagcgcggccgggggc
ggtgcccgcggtgcgggggggctgcgaggggaacaaaggctgcgtgcggggtgtgtgcgtgggggggtgagcagggggtgtgggcgcg
tcggtcgggctgcaacccccctgcacccccctccccgagttgctgagcacggcccggcttcgggtgcggggctccgtacggggcgtggc -continued

| SEQUENCES |
|---|
| gcggggctcgccgtgccgggcgggggtggcggcaggtggggtgccgggcggggcgggcggggccgcctcgggccggggagggctcggggag |
| gggcgcggcggcccccggagcgccggcggctgtcgaggcgcggcgagccgcagccattgcctttatggtaatcgtgcgagagggcgcag |
| ggacttcctttgtcccaaatctgtgcggagccgaaatctgggaggcgccgccgcaccccctctagcgggcgcggggcgaagcggtgcggc |
| gccggcaggaaggaaatgggcggggagggccttcgtgcgtcgccgccgccgtcccttctccctctccagcctcggggctgtccgcgg |
| ggggacggctgccttcgggggggacggggcagggcggggttcggcttctggcgtgtgaccggcggctctagagcctctgctaaccatgtt |
| catgccttcttcttttcctacagctcctgggcaacgtgctggttattgtgctgtctcatcatttggcaaagaattcctcgaagatcta |
| ggcctgcaggcggccgccgccaccatgatctctctgattgccgctctggccgtggactacgtgatcgggatggaaaacgctatgccatgg |
| aatctgcccgccgatctggcttggttcaagagggaacaccctgaacaagccagtgatcatgggcagacacacttgggagtccattggccgg |
| ccctgcctggacgcaagaacatcattctgagctcccagccctctaccgacgacagggtgacatgggtgaaaagtgtggacgaagccatt |
| gccgcttgcggagatgtgcccgagatcatggtcatcggcggaggggagagtgatcgagcagttcctgcctaaggcccagaaactgtacctg |
| actcacattgacgctgaggtggaagggacacccattttcctgattatgagccagacgattgggaaagcgtgttctccgagtttcacgac |
| gccgatgctcagaattctcatagttattgctttgagatcctggaaaggagaggcgcgcctaagaagaagaggaaggtgccaatttactg |
| accgtacaccaaaatttgcctgcattaccggtcgatgcaacgagtgatgaggttcgcaagaacctgatggacatgttcagggatcgccag |
| gcgtttctgagcatacctggaaaatgcttctgtccgtttgccggtcgtgggcggcatggtgcaagttgaataaccggaaatggtttccc |
| gcagaacctgaagatgttcgcgattatcttctatatcttcaggcgcgcggtctggcagtaaaaactatccagcaacatttgggccagcta |
| aacatgcttcatcgtcggtccgggctgccacgaccaagtgacagcaatgctgtttcactggttatgcggcggatccgaaaagaaaacgtt |
| gatgccggtgaacgtgcaaaacaggctctagcgttcgaacgcactgatttcgaccaggttcgttcactcatggaaaatagcgatcgctgc |
| caggatatacgtaatctggcatttctggggattgcttataacaccctgttacgtatagccgaaattgccaggatcagggttaaagatatc |
| tcacgtactgacggtggggagaatgttaatccatattggcagaacgaaaacgctggttagcaccgcaggtgtagagaaggcacttagcctg |
| ggggtaactaaactggtcgagcgatggatttccgtctctggtgtagctgatgatccgaataactacctgttttgccgggtcagaaaaaat |
| ggtgttgccgcgccatctgccaccagccagctatcaactcgcgccctggaagggatttttgaagcaactcatcgattgatttacggcgct |
| aaggatgactctggtcagagataccttggcctggtctggacacagtgaccgttgtcggagccgcgcggagatatggcccgccgctggagttca |
| ataccggagatcatgcaagctggtggctggaccaatgtaaatattgtcatgaactatatccgtaacctggatagtgaaacagggggcaatg |
| gtgcgcctgctggaagatggcgattaggtcgactagagctcgctgatcagcctcgactgtgccttctagttgccagccatctgttgtttg |
| cccctcccccgtgccttccttgaccctggaaggtgccactcccactgtcctttcctaataaaatgaggaaattgcatcgcattgtctgag |
| taggtgtcattctattctggggggtggggtggggcaggacagcaaggggggaggattgggaagacaatagcaggcatgctggggagagatc |
| tgaggaaccccagtgatggagttggccactccctctctgcgcgctcgctcgctcactgaggccgcccgggcaaagcccgggcgtcgggc |
| gacctttggtcgcccggcctcagtgagcgagcgagcgcgcagagagggagtggccaac |

>EDN2-DD amino acid sequence (SEQ ID NO: 11)
MVSVPTTWCSVALALLVALHEGKGQAAATLEQPASSSHAQGTHLRLRRCSCSSWLDKECVYFCHLDIIWVNTPEQTAPYGLGNPPRRRRR
SLPRRCQCSSARDPACATFCLRRPWTEAGAVPSRKSPADVFQTGKTGATTGELLQRLRDISTVKSLFAKRQQEAMREPRSTHSRWRKRTR
SRKKRSTRSRKKRSGAPMISLIAALAVDYVIGMENANPWNLPADLAWFKRNTLNKPVIMGRHTWESIGRPLPGRKNIILSSQPSTDDRVT
WVKSVDEAIAACGDVPEIMVIGGGRVIEQFLPKAQKLYLTHIDAEVEGDTHFPDYEPDDWESVFSEFHDADAQNSHSYCFEILERR*

>rAAV vector encoding EDN2 (TMP-regulated protective factor EDN2) (SEQ ID NO: 12)
ttggccactccctctctgcgcgctcgctcgctcactgaggccgggcgaccaaaggtcgcccgac -continued

SEQUENCES

>HBEGF-DD amino acid sequence (SEQ ID NO: 13)
MKLLPSVVLKLFLAAVLSALVTGESLERLRRGLAAGTSNPDPPTVSTDQLLPLGGGRDRKVRDLQEADLDLLRVTLSSKPQALATPNKEE
HGKRKKKGKGLGKKRDPCLRKYKDFCIHGECKYVKELRAPSCICHPGYHGERCHGLSLPVENRLYTYDHTTILAVVAVVLSSVCLLVIVG
LLMFRYHRRGGYDVENEEKVKLGMTNSHTRSRKKRSTRSRKKRSGAPMISLIAALAVDYVIGMENAMPWNLPADLAWFKRNTLNKPVIMG
RHTWESIGRPLPGRKNIILSSQPSTDDRVTWVKSVDEAIAACGDVPEIMVIGGGRVIEQFLPKAQKLYLTHIDAEVEGDTHFPDYEPDDW
ESVFSEFHDADAQNSHSYCFEILERR*

>rAAV vector encoding HBEGF (TMP-regulated growth factor HBEGF) (SEQ ID NO: 14)
ttggccactccctctctgcgcgctcgctcgctcactgaggccgggcgaccaaaggtcgcccgacgcccgggctttgcccgggcggcctca
gtgagcgagcgagcgcgcagagagggagtggccaactccatcactagggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc
cccacgttctgcttcactctccccatctccccccccctcccaccccccaatttttgtatttatttattttttaattattttgtgcagcgatg
ggggcggggggggggggggggcgcgcgccaggcggggcggggcggggcgagggggcggggcggggcgaggcggagaggtgcggcggcagcc
aatcagagcggcgcgctccgaaagtttccttttatggcgaggcggcggcggcggcggccctataaaaagcgaagcgcgcggcgggcggga
gtcgctgcgcgctgccttcgcccgtgccccgctccgccgccgcctcgccgccccgccccggctctgactgaccgcgttactcccacag
gtgagcgggcgggacggcccttctcctccgggctgtaattagcgcttggtttaatgacggcttgttttcttttctgtggctgcgtgaaagc
cttgagggggctccgggaggggcccttttgtgcgggggagcggctcggggggtgcgtgcgtgtgtgtgtgcgtggggagcgccgcgtgcgc
tccgcgctgcccggcggctgtgagcgctgcgggcgcggcgcgggcttttgtgcgctccgcagtgtgcgcgaggggagcgcggccggggc
ggtgccccgcggtgcggggggggctgcgagggaacaaaggctgcgtgcggggtgtgtgcgtgggggggtgagcaggggggtgtgggcgcg
tcggtcgggctgcaaccccccctgcaccccctccccgagttgctgagcacggcccggcttcgggtgcggggctccgtacggggcgtggc
gcggggctcgccgtgccggcgggggtggcggcaggtggggggtgccgggcggggcggggccgcctcgggccgggagggctcggggag
gggcgcggcggccccggagccgcggcggctgtcgaggcgcggcgagccgcagccattgccttttatggtaatcgtgcgagagggcgcag
ggacttcctttgtcccaaatctgtgcggagccgaaatctgggaggcgccgccgcaccccctctagcgggcgcggggcgaagcggtgcggc
gccggcaggaaggaaatgggcggggaggggccttcgtgcgtcgccgccgcccgctcccctccctctccagcctcggggcctgtccgcgg
ggggacggctgccttcgggggggacggggcagggcgggtttcggcttctggcgtgtgaccggcggctctagagcctctgctaaccatgtt
catgccttcttcttttttcctacagctcctgggcaacgtgctggttattgtgctgtctcatcattttggcaaagaattcctcgaagatcta
ggcaacgcgtctcgaggcggccgccgccaccatgaaactcctgccgtctgtagtcctgaaactgtttctggctgctgtgttgagtgctct
cgttacgggagagtccttggagagggcttcgacgcggtttggcagcaggtacgtcaaacccagatcccccctaccgtgagtacggatcagct
tctgccgctcggcggaggaagggaccgcaaggtgcgcgatctgcaggaggcggaccttgacctgctcgagttacattgtcctctaagcc
tcaagctctggcgacgccgaacaaagaggagcatggtaagcgaaagaagaaaggcaaaggggctgggaaaaaaacgcgaccctgtcttcg
caagtataaggacttctgtattcatggagagtgtaagtatgttaaagagcttcgagctcccagttgcatttgccaccctgggtatcacgg
ggaacgctgtcatggcttgtcattgccagttgaaaatcgcttgtatacgtatgaccataccactatcctcgcagtagtagctgttgtcct
ttccagcgtttgtttgctggtcatcgtcggcttgctgatgtttcggtaccaccgacggggaggttacgatgtagagaacgaggagaaagt
caagctgggcatgacaaatagccataccagatctcgcaagaagcgcagcaccagatctcgcaagaagcgcagcggggcccccatgatatc
tctgatcgctgctcttgctgtggactacgtgattggtatggagaatgctatgccctggaatctgcctgcagacctggcatggtttaagag
gaacacccttaataaacctgtaatcatgggacgacatacatgggagagtatcggcaggccattgcccgggaggaagaatataattctgag
ttcccagccttctactgatgataggtaacttgggtcaagagcgtcgacgaggccatcgccgctgcggggatgtgcctgaaatcatggt
tatcgggggcggacgggtgattgagcaatttctgcccaaggcacagaagctgtatctgacccatatagacgccgaggtggagggagatac
acactttcccgactatgagcccgatgattgggagagtgtctttagcgaatttcatgacgccgacgcacagaattcccatagctactgctt
cgaaattctcgaacggcgctaggcggccgcgcggatccagacatgataagatacattgatgagtttggacaaaccacaactagaatgcag
tgaaaaaaatgcttatttgtgaaatttgtgatgctattgcttttatttgtaaccattataagctgcaataaacaagttaacaacaacaat
tgcattcatttttatgtttc aggttcaggggggaggtgtgggaggttattagtcgactgggggagagatctgaggaaccccctagtgatggag
ttggccactccctctctgcgcgctcgctcgctcactgaggccgcccgggcaaagcccgggcgtcgggcgacctttggtcgcccggcctca
gtgagcgagcgagcgcgcagagagggagtggccaac >NRF2-DD amino acid sequence (SEQ ID NO: 15)
MMDLELPPPGLPSQQDMDLIDILWRQDIDLGVSREVFDFSQRRKEYELEKQKKLEKERQEQLQKEQEKAFFAQLQLDEETGEFLPIQPAQ
HIQSETSGSANYSQVAHIPKSDALYFDDCMQLLAQTFPFVDDNEVSSATFQSLVPDIPGHIESPVFIATNQAQSPETSVAQVAPVDLDGM
QQDIEQVWEELLSIPELQCLNIENDKLVETTMVPSPEAKLTEVDNYHFYSSIPSMEKEVGNCSPHFLNAFEDSFSSILSTEDPNQLTVNS
LNSDATVNTDFGDEFYSAFIAEPSISNSMPSPATLSHSLSELLNGPIDVSDLSLCKAFNQNHPESTAEFNDSDSGISLNTSPSVASPEHS
VESSSYGDTLLGLSDSEVEELDSAPGSVKQNGPKTPVHSSGDMVQPLSPSQGQSTHVHDAQCENTPEKELPVSPGHRKTPFTKDKHSSRL
EAHLTRDELRAKALHIPFPVEKIINLPVVDFNEMMSKEQFNEAQLALIRDIRRRGKNKVAAQNCRKRKLENIVELEQDLDHLKDEKEKLL
KEKGENDKSLHLLKKQLSTLYLEVFSMLRDEDGKPYSPSEYSLQQTRDGNVFLVPKSKKPDVKKNTRSRKKRSTRSRKKRSGAPMISLIA
ALAVDYVIGMENAMPWNLPADLAWFKRNTLNKPVIMGRHTWESIGRPLPGRKNIILSSQPSTDDRVTWVKSVDEAIAACGDVPEIMVIGG
GRVIEQFLPKAQKLYLTHIDAEVEGDTHFPDYEPDDWESVFSEFHDADAQNSHSYCFEILERR*

>rAAV vector encoding NRF2 (TMP-regulated transcription factor NRF2) (SEQ ID NO: 16)
ttggccactccctctctgcgcgctcgctcgctcactgaggccgggcgaccaaaggtcgcccgacgcccgggctttgcccgggcggcctca
gtgagcgagcgagcgcgcagagagggagtggccaactccatcactagggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc
cccacgttctgcttcactctccccatctccccccccctcccaccccccaatttttgtatttatttattttttaattattttgtgcagcgatg
ggggcggggggggggggggcgcgcgccaggcggggcggggcggggcgagggggcggggcggggcgaggcggagaggtgcggcggcagcc
aatcagagcggcgcgctccgaaagtttccttttatggcgaggcggcggcggcggcggccctataaaaagcgaagcgcgcggcgggcggga
gtcgctgcgcgctgccttcgcccgtgccccgctccgccgccgcctcgccgccccgccccggctctgactgaccgcgttactcccacag
gtgagcgggcgggacggcccttctcctccgggctgtaattagcgcttggtttaatgacggcttgttttcttttctgtggctgcgtgaaagc
cttgagggggctccgggaggggcccttttgtgcgggggagcggctcggggggtgcgtgcgtgtgtgtgtgcgtggggagcgccgcgtgcgc
tccgcgctgcccggcggctgtgagcgctgcgggcgcggcgcgggcttttgtgcgctccgcagtgtgcgcgaggggagcgcggccggggc
ggtgccccgcggtgcggggggggctgcgagggaacaaaggctgcgtgcggggtgtgtgcgtgggggggtgagcaggggggtgtgggcgcg
tcggtcgggctgcaaccccccctgcaccccctccccgagttgctgagcacggcccggcttcgggtgcggggctccgtacggggcgtggc
gcggggctcgccgtgccggcgggggtggcggcaggtggggggtgccgggcggggcggggccgcctcgggccgggagggctcggggag -continued

| SEQUENCES |
|---|
| gggcgcggcggcccccggagcgccggcggctgtcgaggcgcggcgagccgcagccattgccttttatggtaatcgtgcgagagggcgcag
ggacttcctttgtcccaaatctgtgcggagccgaaatctggaggcgccgccgcaccccctctagcgggcgcggggcgaagcggtgcggc
gccggcaggaaggaaatgggcggggagggccttcgtgcgtcgccgccgccgtcccctttctccctctccagcctcggggctgtccgcgg
ggggacggctgccttcgggggggacggggcagggcggggttcggcttctggcgtgtgaccggcggctctagagcctctgctaaccatgtt
catgccttcttcttttttcctacagctcctgggcaacgtgctggttattgtgctgtctcatcattttggcaaagaattcctcgaagatcta
ggcaacgcgtctcgaggcggccgccgccaccatgatggatctcgaacttccccctccaggcctgcctagccagcaagacatggacctttat
cgacatcctgtggcgccaggatattgatctcggtgtgtctagggaagtctttgacttttcccaaaggaggaaggaaatatgagcttgagaa
acaaaagaagcttgaaaaggaacggcaagagcagcttcaaaaggagcaggaaaaaagcattcttttgcgcaattgcagcttgatgaagaaac
cggcgaattccttccaatacaaccagctcaacatatccaatccgagacctcaggttccgcaaattactcccaagtggcacatataccgaa
atccgacgcgttgtacttcgacgattgtatgcagctgctcgcacaaacgttcccttcgtggacgataacgaagtgagttctgctacttt
ccagtcacttgttccagacatccccggacatattgaatccccagtgtttatagcgacaaaccaagcccaatcacctgagacgagtgtcgc
ccaagtagccccagtcgatctggatggtatgcaacaggacattgaacaagtctgggaagagctgcttagcattcctgaactgcagtgcct
gaacatcgaaaacgacaaattggtagagacaactatggtaccctcacctgaggcaagttgaccgaggtggacaattatcatttttactc
ttcaatacctagtatggagaaagaagtcggtaattgttcccctcatttcctgaacgcgttcgaagacagctttagcagcatcttgtccac
agaagacccaaatcaattgacggtaaactccttgaactcagacgcgacagtgaataccgattttggtgatgaattttattcagcatttat
agccggccaagcatcagtaattctatgcccagccccgcaactctctcccacagtctttcagaattgctcaacggaccatcgatgtgag
tgatctgtccctctgcaaagcgtttaaccaaaaccatccggagagtacggccgagttcaacgacagtgatagtggtatttcactcaatac
ctcaccctccgtggccagtccggagcacagtgttgaatcaagctcctacggggacacattgctgggcctctcagacagcgaagtcgaaga
acttgacagcgcccccggatccgtaaagcaaatgggccgaaaactccggtgcattcatcaggtgatatggtacagccactttcaccaag
tcagggacaaagtacgcacgtccatgacgcgcaatgtgaaaatactcctggagaaagactcccggtatcaccggggcaccggaagaccc
tttactaaggacaaacatagtagtcgcttggaggctcatttgactcgagatgagctccgcgcaaaagcactccatattccatttcccgt
tgaaaagattattaaccctcccggtagtggacttcaacgagatgatgtctaaggagcagttaatgaggcgcagcttgcactgataaggga
catacgacgcagaggtaagaataaggtggctgcccaaaactgcaggaagcgaaagctcgagaacattgtagaacttgagcaggaccttga
tcacctgaaagatgagaaggaaaaattgcttaaagagaaaggtgagaagcttgcatcttctcaaaaaaacagctgagcacatt
gtatcttgaggtcttcagcatgctcagagatgaagatgggaaaccgtattctccgagcgaatacagtctgcagcagaccgggatggcaa
tgtgttcctcgtacccaaaagcaaaaaacctgatgttaagaagaataccagatctcgcaagaagcgcagcaccagatctcgcaagaagcg
cagcggggccccatgatatctctgatcgctgctcttgctgtggactacgtgattggtatggagaatgctatgccctggaatctgcctgc
agacctgcatggtttaagaggaacacccttaataaacctgtaatcatgggacgacatacatgggagagtgtctttagcgaatttcatgacgccgacgcaca
gaattcccatagctactgcttcgaaattctcgaacggcgctaggcggccgcgcgatccagacatgataagatacattgatgagtttgga
caaaccacaactagaatgcagtgaaaaaaatgctttatttgtgaaatttgtgatgctattgcttttatttgtaaccattataagctgcaat
aaacaagttaacaacaacaattgcattcattttatgtttcaggttcagggggaggtgtgggaggttttttagtcgactggggagagatct
gaggaaccctagtgatggagttggccactccctctctgcgcgctcgctcgctcactgaggccgggcgaccaaaggtcgcccgacgcccgggctttgcccgggcggcctca
gtgagcgagcgagcgcgcagagagggagtggccaac |

>OSM-DD amino acid sequence (SEQ ID NO: 17)
MGVLLTQRTLLSLVLALLFPSMASMAAIGSCSKEYRVLLGQLQKQTDLMQDTSRLLDPYIRIQGLDVPKLREHCRERPGAFPSEETLRGL
GRRGFLQTLNATLGCVLHRLADLEQRLPKAQDLERSGLNIEDLEKLQMARPNILGLRNNIYCMAQLLDNSDTAEPTKAGRGASQPPTPTP
ASDAFQRKLEGCRFLHGYHRFMHSVGRVFSKWGESPNRSRRHSPHQALRKGVRRTRPSRKGKRLMTRGQLPRTRSRKKRSTRSRKKRSGA
PMISLIAALAVDYVIGMENAMPWNLPADLAWFKRNTLNKPVIMGRHTWESIGRPLPGRKNIILSSQPSTDDRVTWVKSVDEAIAACGDVP
EIMVIGGGRVIEQFLPKAQKLYLTHIDAEVEGDTHFPDYEPDDWESVFSEFHDADAQNSHSYCFEILERR*

>rAAV vector encoding OSM (TMP-regulated protective factor OSM) (SEQ ID NO: 18)
ttggccactccctctctgcgcgctcgctcgctcactgaggccgggcgaccaaaggtcgcccgac -continued

SEQUENCES tatcggcaggccattgcccgggaggaagaatataattctgagttcccagccttctactgatgatagggtaacttgggtcaagagcgtcga
cgaggccatcgccgcttgcggggatgtgcctgaaatcatggttatcgggggcggacgggtgattgagcaatttctgcccaaggcacagaa
gctgtatctgacccatatagacgccgaggtggagggagatacacactttcccgactatgagcccgatgattgggagagtgtctttagcga
atttcatgacgccgacgcacagaattcccatagctactgcttcgaaattctcgaacggcgctaggcggccgcgcggatccagacatgata
agatacattgatgagtttggacaaaccacaactagaatgcagtgaaaaaaatgctttatttgtgaaatttgtgatgctattgctttattt
gtaaccattataagctgcaataaacaagttaacaacaacaattgcattcattttatgtttcaggttcagggggaggtgtgggaggtttttt
tagtcgactggggagagatctgaggaacccctagtgatggagttggccactccctctctgcgcgctcgctcgctcactgaggccgcccgg
gcaaagcccgggcgtcgggcgacctttggtcgcccggcctcagtgagcgagcgagcgcgcagagagggagtggccaac >OSM M2-DD variant amino acid sequence (SEQ ID NO: 19)
MGVLLTQRTLLSLVLALLFPSMASMAAIGSCSKEYRVLLGQLQKQTDLMQDTSRLLDPYIRIQGLDVPKLREHCRERPGAFPSEETLRGL
GRRGFLQTLNATLGCVLHRLADLEQRLGGGNIEDLEKLQMARPNILGLRNNIYCMAQLLDNSDTAEPTKAGRGASQPPTPTPASDAFQRK
LEGCRFLHGYHRFMHSVGRVFSKWGESPNRSRRHSPHQALRKGVRRTRPSRKGKRLMTRSRKKRSTRSRKKRSGAPMISLIAALAVDYVI
GMENAMPWNLPADLAWFKRNTLNKPVIMGRHTWESIGRPLPGRKNIILSSQPSTDDRVTWVKSVDEAIAACGDVPEIMVIGGGRVIEQFL
PKAQKLYLTHIDAEVEGDTHFPDYEPDDWESVFSEFHDADAQNSHSYCFEILERR*

>rAAV vector encoding OSM-M2 (TMP regulated protective factor OSM-M2) (SEQ ID NO: 20)
aggccactccctctctgcgcgctcgctcgctcactgaggccgggcgaccaaaggtcgcccgacgcccgggctagcccgggcggcctcagt
gagcgagcgagcgcgcagagagggagtggccaactccatcactaggggacctcagatctgaattcggtacctagttattaatagtaatca
attacggggtcattagacatagcccatatatggagaccgcgttacataacttacggtaaatggcccgcctggctgaccgcccaacgaccc
ccgcccattgacgtcaataatgacgtatgacccatagtaacgccaatagggactaccattgacgtcaatgggtggagtatttacggtaaa
ctgcccacaggcagtacatcaagtgtatcatatgccaagtacgcccccctattgacgtcaatgacggtaaatggcccgcctggcattatgc
ccagtacatgaccttatgggactacctacaggcagtacatctacgtattagtcatcgctattaccatggtcgaggtgagccccacgactg
cacactctccccatctcccccccctccccacccccaattagtatttatttattattaattattagtgcagcgatgggggcggggggggggg
gggggg1cgcgcgccaggcggggcggggcggggcgaggggcggggcggggcgaggcggagaggtgcggcggcagccaatcagagcggcgc
gctccgaaagtaccattatggcgaggcggcggcggcggcggccctataaaaagcgaagcgcgcggcgggcgggagtcgctgcgcgctgcc
acgccccgtgccccgctccgccgccgcctcgcgccgcccgccccggctctgactgaccgcgttactcccacaggtgagcgggcgggacgg
cccactcctccgggctgtaattagcgcaggataatgacggcttgatcattctgtggctgcgtgaaagccagaggggctccgggagggccc
tagtgcgggggggagcggctcgggggggtgcgtgcgtgtgtgtgtgcgtggggagcgccgcgtgcggctccgcgctgcccggcggctgtgag
cgctgcgggcgcggcgcggggctagtgcgctccgcagtgtgcgcgaggggagcgcggccgggggcggtgccccgcggtgcgggggggggct
gcgaggggaacaaaggctgcgtgcggggtgtgtgcgtgggggggtgagcagggggtgtgggcgcgtcggtcgggctgcaacccccccctgc
acccccctccccgagagctgagcacggcccggcttcgggtgcggggctccgtacggggcgtggcgcggggctcgccgtgccgggcggggg
gtggcggcaggtgggggtgccgggcggggcggggccgcctcgggccggggagggctcgggggaggggcgcggcggcccccggagcgccgg
cggctgtcgaggcgcggcgagccgcagccattgccattatggtaatcgtgc1gagagggcgcagggacacctagtcccaaatctgtgcgg
agccgaaatctgggaggcgccgccgcacccccctctagcgggcgcggggcgaagcggtgcggcgccggcaggaaggaaatgggcggggagg
gccacgtgcgtcgccgcgccgccgtccccactccctctccagcctcggggctgtccgcgggggggacggctgccacggggggggacggggca
gggcggggacggcactggcgtgtgaccggcggctctagagcctctgctaaccatgacatgccacttcatacctacagctcctgggcaacg
tgctggttattgtgctgtctcatcattaggcaaagaattcctcgaagatctaggcaacgcgtctcgaggcggccgccgccaccatgggtg
tgagctcactcaaaggaccagagtccctggtcctggcactcagacccatctatggcgagtatggcggctattggctcatgctctaaagag
tacagagactgctcggtcaactgcaaaagcaaacggacctgatgcaagatacgtccaggagctcgacccttatattaggatccagggact
cgacgaccgaagcttagagagcactgtcgcgagcgaccaggtgccatcccagtgaagaaacactgaggggtagggcaggcgcggatcagc
agacccttaatgctacattggggtgcgtattgcatcgcctggcagatctcgagcaaagactcggaggtggcaatatcgaggatcagaaaa
gctccagatggctcgcccgaacatactcgggctgaggaataatatatattgtatggctcaactcctcgacaactcagacactgcggagcc
tacgaaagcaggaaggggcgcatcacaaccacctalcacctactcctgccagtgatgccatcagcgcaagcttgagggctgccgatactc
cacggctatcatcggacatgcactccgaggccgagtgattcaaaatgggggaatctcctaaccgatctagaaggcactcacctcaccag
gcactgcggaaaggcgttaggagaacccggccaagccgcaaaggaaagcgcctgatgaccagatctcgcaagaagcgcagcaccagatct
cgcaagaagcgcagcggggcccccatgatatctctgatcgctgctcttgctgtggactacgtgattggtatggagaatgctatgccctgg
aatctgcctgcagacctggcatggtttaagaggaacacccttaataaacctgtaatcatgggacgacatacatgggagagtatcggcagg
ccattgcccgggaggaagaatataattctgagttcccagccttctactgatgatagggtaacttgggtcaagagcgtcgacgaggccatc
gccgcttgcggggatgtgcctgaaatcatggttatcgggggcggacgggtgattgagcaatttctgcccaaggcacagaagctgtatctg
acccatatagacgccgaggtggagggagatacacactttcccgactatgagcccgatgattgggagagtgtctttagcgaatttcatgac
gccgacgcacagaattcccatagctactgcttcgaaattctcgaacggcgctaggcggccgcgcggatccagacatgataagatacattg
atgagtttggacaaaccacaactagaatgcagtgaaaaaaatgctttatttgtgaaatttgtgatgctattgctttatttgtaaccatta
taagctgcaataaacaagttaacaacaacaattgcattcattttatgtttcaggttcagggggaggtgtgggaggttttttagtcgactg
gggagagatctgaggaacccctagtgatggagttggccactccctctctgcgcgctcgctcgctcactgaggccgcccgggcaaagcccg
ggcgtcgggcgacctttggtcgcccggcctcagtgagcgagcgagcgcgcagagagggagtggccaac >STAT3-DD amino acid sequence (SEQ ID NO: 21)
MAQWNQLQQLDTRYLEQLHQLYSDSFPMELRQFLAPWIESQDWAYAASKESHATLVFHNLLGEIDQQYSRFLQESNVLYQHNLRRIKQFL
QSRYLEKPMEIARIVARCLWEESRLLQTAATAAQQGGQANHPTAAVVTEKQQMLEQHLQDVRKRVQDLEQKMKVVENLQDDFDFNYKTLK
SQGDMQDLNGNNQSVTRQKMQQLEQMLTALDQMRRSIVSELAGLLSAMEYVQKTLTDEELADWKRRQQIACIGGPPNICLDRLENWITSL
AESQLQTRQQIKKLEELQQKVSYKGDPIVQHRPMLEERIVELFRNLMKSAFVVERQPCMPMHPDRPLVIKTGVQFTTKVRLLVKFPELNY
QLKIKVCIDKDSGDVAALRGSRKFNILGTNTKVMNMEESNNGSLSAEFKHLTLREQRCGNGGRANCDASLIVTEELHLITFETEVYHQGL
KIDLETHSLPVVVISNICQMPNAWASILWYNMLTNNPKNVNFFTKPPIGTWDQVAEVLSWQFSSTTKRGLSIEQLTTLAEKLLGPGVNYS
GCQITWAKFCKENMAGKGFSFWVWLDNIIDLVKKYILALWNEGYIMGFISKERERAILSTKPPGTFLLRFSESSKEGGVTFTWVEKDISG
KTQIQSVEPYTKQQLNNMSFAEIIMGYKIMDATNILVSPLVYLYPDIPKEEAFGKYCRPESQEHPEADPGSAAPYLKTKFICVTPTTCSN
TIDLPMSPRTLDSLMQFGNNGEGAEPSAGGQFESLTFDMELTSECATSPMTRSRKKRSTRSRKKRSGAPMISLIAALAVDYVIGMENAMP
WNLPADLAWFKRNTLNKPVIMGRHTWESIGRPLPGRKNIILSSQPSTDDRVTWVKSVDEAIAACGDVPEIMVIGGGRVIEQFLPKAQKLY
LTHIDAEVEGDTHFPDYEPDDWESVFSEFHDADAQNSHSYCFEILERR*

>rAAV vector encoding STAT3 (TMP-regulated transcription factor STAT3) (SEQ ID NO: 22)
ttggccactccctctctgcgcgctcgctcgctcactgaggccgggcgaccaaaggtcgcccgacgcccgggctttgcccgggcggcctca
gtgagcgagcgagcgcgcagagagggagtggccaactccatcactaggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc -continued

SEQUENCES cccacgttctgcttcactctccccatctccccccctccccaccccaattttgtatttatttattttttaattattttgtgcagcgatg
ggggcggggggggggggggcgcgcgccaggcggggcggggcggggcgagggcggggcggggcgaggcggagaggtgcggcggcagcc
aatcagagcggcggcgctccgaaagtttccttttatggcgaggcggcggcggcggcggcccctataaaaagcgaagcgcgcggcggcggga
gtcgctgcgcgctgccttcgccccgtgccccgctccgccgccgcctcgcgccgcccgccccggctctgactgaccgcgttactcccacag
gtgagcgggcgggacggcccttctcctccgggctgtaattagcgcttggtttaatgacggcttgtttcttttctgtggctgcgtgaaagc
cttgaggggctccgggagggcccttttgtgcggggggagcggctcggggggtgcgtgcgtgtgtgtgcgtggggagcgccgcgtgcggc
tccgcgctgcccggcggctgtgagcgctgcgggcgcggcgcggggcttttgtgcgctccgcagtgtgcgcgagggggagcgggccggggggc
ggtgccccgcggtgcggggggggctgcgaggggaacaaagggctgcgtgcggggtgtgtgcgtgggggggtgagcaggggggtgtgggcgcg
tcggtcgggctgcaaccccccctgcaccccctccccgagttgctgagcacggcccggcttcgggtgcggggctccgtacggggcgtggc
gcggggctcgccgtgccggcgggggtggcggcaggtgggggtgccggcggggcggggccgcctcgggccggggagggctcggggggag
gggcgcggcggccccggagcgccggcggctgtcgaggcgcggcgagccgcagccattgccttttatggtaatcgtgcgagagggcgcag
ggacttccttttgtcccaaatctgtgcggagccgaaatctgggaggcgccgccgcaccccctctagcgggcgcggggcgaagcggtgcggc
gccggcaggaaggaaatgggcggggagggccttcgtgcgtcgccgccgccgccgtcccctctccctctccagcctcggggctgtccgcgg
ggggacggctgccttcggggggggacggggcagggcggggttcggcttctggcgtgtgaccggcggctctagagcctctgctaaccatgtt
catgccttcttcttttttcctacagctcctgggcaacgtgctggttattgtgctgtctcatcatttttggcaaagaattcctcgaagatcta
ggcaacgcgtctcgaggcggccgccgccaccatggctcaatggaacaattgcaacaacttgatactcgatacctggagcaactccatca
gctgtactcagattcatttccgatggagctccggcagtttctggctccatggataagaatcacaggattgggcctacgcggcttcaaagga
aagtcacgcgaccctcgtatttcacaaccctcctggggaaattgatcagcaatatagtcggtttctgcaagaaagcaacgtcttgtacca
acataacttgaggaggattaagcaatttctccaaagccggtacttggagaagcctatggaaatcgctcgcattgtagcgaggtgcctgtg
ggaggagagtcgccttctgcagaccgccgccacagccgctcaacaaggtgggcaggctaatcatcccaccgctgctgtggtcaccgaaaa
gcagcagatgctcgagcaacacctcaggacgtcagaaagagggttcaggatctgaacaaaagatgaaagtcgtggagaattgcagga
tgattttgattttaactacaagaccttgaaatcccaaggcgatatgcaagatcttaatgaaacaaccagtcagtgaccaggcagaagat
gcaacaacttgaacaaatgttgactgccctcgatcaaatgagacgcagtatagtaagcgagttggccggtcttctctcagcgatggagta
cgtacagaaaacgctgactgatgaagagctggctgactggaagcggcggcagcgatgctttgcatcggtgggccccccaaatatatgcct
ggatcgcctggagaactggataacgagtcttggccgagagtcagctgcagactcgccagcagatcaaaaaactggaagaactccagcaaaa
agtttcatacaagggagatccgattgtacagcatcgcccatgctggaagagcgaattgttgaactcttagaaatttgatgaagagcgc
gttcgttgtagagcggcagccgtgtatgcctatgcacccggaccggccacttgtgataaagaccggagttcagtttacaacaaaggtccg
actgcttgtcaaatttccggaattgaactatcaattgaagatcaaggtttgcatcgataaggattctggcgatgttgcggcgttgcgcgg
cagccgcaagtttaacatacttggcactaataccaaggttatgaacatggaggagtccaacaacggctcactcagtgctgaattcaagca
ccttacgctgagagaacagagatgcggtaacggggacgcgccaactgtgatgcctcacttattgtcactgaagagcttcacctgataac
gttcgaaactgaggtttaccatcaaggcctgaaaatagatctggagactcattctctgcccgttgtcgttatttctaacatttgccagat
gcccaatgcatgggcgagcattctgtggtataatatgctgacaaacaatccgaagaacgtcaacttcttcacgaagcgccgatcggtac
ctgggatcaggtggcggaagtccttagctggcagttcagctccaccaccaagagggttttgtcaatagagcaattgactacgttggctga
gaagctcctgggacctggagtaaattacagtgggtgtcgatcacatgggctaaattttgcaaggaaaacatggcaggtaagggttttc
cttttgggtctggcttgataacataatagatctcgtcaaaaagtacatactcgcgctgtggaacgagggttacataatgggttttatatc
taaagaaagggagagagcgattttgtccactaaaccaccgggcacgtttcttctccgattttccgagtcaagcaaagaaggtggcgtaac
atttacctgggtcgaaaaggacattagtggaaagacgcaaattcaaagtgtgaacttatacgaaacagcaactgaataacatgtcctt
tgcggagataataatggggtacaaaattatggatgctactaatatactcgttagccctctggtctacctttacccagacatccccaagga
ggaggcgttcggaaagtattgccgaccggaatcccaagagcatcccgaagcggacccaggtagtgccgcaccctaccttaaaactaagtt
catttgcgtcacccaacgacgtcagcaacacaatagacttgccgatgagtccccgaacgctcgatagtctcatgcagttcggaaacaa
tggcgaggggagctgagccctccgccggcggacaatttgagagcctcaccttttgacatggagctttacatcagagtgcgcgacaagcccgat
gaccagatctcgcaagaagcgcagcaccagatctcgcaagaagcgcagcggggccccatgatatctctgatcgtgctcttgctgtgga
ctacgtgattggtatggagaatgctatgccctggaatctgcctcagacctggcatggtttaagaggaacacccttaataaacctgtaat
catgggacgacatacatgggagagtatcggcaggccattgcccgggaggaagaatataattctgagttcccagccttctactgatgatag
ggtaacttgggtcaagagcgtcgacgaggccatcgccgcttgcggagctgtgcctgaaatcatggttatcggggggcgggtgattga
gcaatttctgcccaaggcacagaagctgtatctgacccatatagacgccgaggtggagggagatacacacttcccgactatgagcccga
tgattgggagagtgtctttagcgaatttcatgacgccgacgcacagaattcccatagctactgcttcgaaattctcgaacggcgctaggc
ggccgcgcggatccagacatgataagatacattgatgagtttggacaaaccacaactagaatgcagtgaaaaaaatgctttatttgtgaa
atttgtgatgctattgctttatttgtaaccattataagctgcaataaacaagttaacaacaattgcattcattttatgtttcaggtt
cagggggaggtgtgggaggttttttagtcgactggggagagatctgaggaaccccagtgatggagttggccactccctctctgcgcgct
cgctcgctcactgaggccgggcgaccaaaggtcgcccgacgcccgggctttgcccgggcggcctcagtgagcgagcgagcgcgcagagag
ggagtggccaac >STAT3 Y705F-DD amino acid sequence (SEQ ID NO: 23)
MAQWNQLQQLDTRYLEQLHQLYSDSFPMELRQFLAPWIESQDWAYAASKESHATLVFHNLLGEIDQQYSRFLQESNVLYQHNLRRIKQFL
QSRYLEKPMEIARIVARCLWEESRLLQTAATAAQQGGQANHPTAAVVTEKQQMLEQHLQDVRKRVQDLEQKMKVVENLQDDFDFNYKTLK
SQGDMQDLNGNNQSVTRQKMQQLEQMLTALDQMRRSIVSELAGLLSAMEYVQKTLTDEELADWKRRQQIACIGGPPNICLDRLENWITSL
AESQLQTRQQIKKLEELQQKVSYKGDPIVQHRPMLEERIVELFRNLMKSAFVVERQPCMPMHPDRPLVIKTGVQFTTKVRLLVKFPELNY
QLKIKVCIDKDSGDVAALRGSRKFNILGTNTKVMNMEESNNGSLSAEFKHLTLREQRCGNGGRANCDASLIVTEELHLITFETEVYHQGL
KIDLETHSLPVVVISNICQMPNAWASILWYNMLTNNPKNVNFFTKPPIGTWDQVAEVLSWQFSSTTKRGLSIEQLTTLAEKLLGPGVNYS
GCQITWAKFCKENMAGKGFSFWVWLDNIIDLVKKYILALWNEGYIMGFISKERERAILSTKPPGTFLLRFSESSKEGGVTFTWVEKDISG
KTQIQSVEPYTKQQLNNMSFAEIIMGYKIMDATNILVSPLVYLYPDIPKEEAFGKYCRPESQEHPEADPGSAAPFLKTKFICVTPTTCSN
TIDLPMSPRTLDSLMQFGNNGEGAEPSAGGQFESLTFDMELTSECATSPMTRSRKKRSTRSRKKRSGAPMISLIAALAVDYVIGMENAMP
WNLPADLAWFKRNTLNKPVIMGRHTWESIGRPLPGRKNIILSSQPSTDDRVTWVKSVDEAIAACGDVPEIMVIGGGRVIEQFLPKAQKLY
LTHIDAEVEGDTHFPDYEPDDWESVFSEFHDADAQNSHSYCFEILERR*

>rAAV vector encoding STAT3 Y705F (TMP-regulated phosphomemetic of the transcription
factor STAT3 at amino acid 705) (SEQ ID NO: 24)
ttggccactccctctctgcgcgctcgctcgctcactgaggccgggcgaccaaaggtcgcccgacgcccgggctttgcccgggcggcctca
gtgagcgagcgagcgcgcagagagggagtggccaactccatcactaggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtatttta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc
cccacgttctgcttcactctccccatctccccccctccccaccccaatttttgtatttatttattttttaattattttgtgcagcgatg
ggggcggggggggggggggcgcgcgccaggcggggcggggcggggcgagggcggggcggggcgaggcggagaggtgcggcggcagcc
aatcagagcggcgcgctccgaaagtttccttttatggcgaggcggcggcggcggcggcccctataaaaagcgaagcgcgcggcgggcggga -continued

SEQUENCES gtcgctgcgcgctgccttcgcccgtgccccgctccgccgccgcctcgcgccgcccgccccggctctgactgaccgcgttactcccacag
gtgagcgggcgggacggcccttctcctccgggctgtaattagcgcttggtttaatgacggcttgtttcttttctgtggctgcgtgaaagc
cttgagggctccgggagggcccttttgtgcgggggggagcggctcgggggtgcgtgcgtgtgtgtgcgtggggagcgccgcgtgcggc
tccgcgctgcccggcggctgtgagcgctgcgggcgcggcgcggggctttgtgcgctccgcagtgtgcgcgagggggagcgcggcggggggc
ggtgccccgcggtgcgggggggctgcgaggggaacaaaggctgcgtgcggggtgtgtgcgtgggggggtgagcagggggtgtgggcgcg
tcggtcgggctgcaacccccctgcaccccctccccgagttgctgagcacggcccggcttcgggtgcgggctccgtacggggcgtggc
gcggggctcgccgtgccggcggggggtggcggcaggtgggggtgccggcggggcggggccgcctcgggccggggagggctcggggggag
gggcgcggcggccccgagcgccggcggctgtcgaggcgcggcgagccgcagccattgccttttatggtaatcgtgcgagaggggcag
ggacttcctttgtcccaaatctgtgcggagccgaaatctgggaggcgccgccgcaccccctctagcgggcgcggggcgaagcggtgcggc
gccggcaggaaggaaatgggcggggagggccttcgtgcgtcgccgcgccgccgtccccttctccctctccagcctcggggctgtccgcgg
ggggacggctgccttcggggggggacggggcagggcggggttcggcttctggcgtgtgaccggcggctctagagcctctgctaaccatgtt
catgccttcttcttttttcctacagctcctgggcaacgtgctggttattgtgctgtctcatcattttggcaaagaattcctcgaagatcta
ggcaacgcgtctcgaggcggccgccgccaccatggccagtggaatcaactcaacaacttgatacccgctacctggaacaacttcatca
actctacagtgatagctttcctatggagctcagacagttcctcgcgccgtggattgaaagccaggactgggcgtatgctgcttcaaagga
gagtcatgcaactctcgtattccataatctgctcggagagatcgtcaacaatacagcaggtttctgcaggaatctaacgtgctttatca
acacaatctgaggcggattaaacaattcctgcaatctcgatatcttgaaaaaccatggagattgcccggatcgtcgcacgctgtctgtg
ggaagagagtcgactgttgcagacggcagctactgctgcccagcagggcggacaggcgaatcatccgactgccgctgtagtgacggaaaa
acaacaaatgctggagcaacatctgcaagacgtcagaaaacgagtacaggacctcgaacagaagatgaaagtggtcgaaaacttgcaaga
cgacttcgatttttaattataaaacgctgaaatcccaggggggatatgcaagaccttaacgcaataatcagtctgttaccagacagaaaat
gcagcagctcgagcaaatgctgacggctcttgaccaagtcagacatagtctcagaattggcaggcctcctctctgccatggagta
cgtacagaagacgttgacagatgaggaactcgctgattggaagagacgccaacagattgcttgcataggggtccacctaatatatgcct
cgaccggttggaaaactggataacatctttggctgaatctcagctccaaacacgccagcaaataaaaaagcttgaggagttgcagcagaa
ggttagttacaaggagatcccattgtgcagcataggccaatgctggaagagaggattgttgagctgtttaggaatctgatgaaagtgc
cttcgtagtggagagacagccatgcatgccaatgcatcctgacagaccactggttataaagactggagttcaatttacaacaaaagttag
actcctggtcaagttcccggagctcaactatcaactgaagataaaagtctgtattgacaaggatagtggcgatgttgcagccttgagggg
tagccgaaaatttaacattctcggaacgaacacaaaagtgatgaacatggaggaatcaaataatggttctctctccgcagagtttaagca
ccttactctgcgcgaacaacgctgcggaaacggcggccgggccaattgcgatgccagcctatagtgacggaagagctgcatctgataac
tttcgagacggaagtctcatcaagggcctcaaaattgacttggagactcactccttgcccgtagtggttatttcaaatatatgccaaat
gcctaatgcatgggcatcaatccttttggtacaatatgcttactaataacccaaagaacgttaattcttcactaaacctccaattggtac
ttgggaccaagttgccgaggtattgagttggcagttttcctcaacaactaagagagggttgagcatagaacagctgaccacactggcgga
gaaacttctgggacccggcgtcaactattctggatgtcagattacctgggccaaattctgcaaagaaaatatggctggcaagggtttcag
cttctgggtatggcttgacaatataattgacctcgtaaaaaagtacatcctcgctctttggaatgaagtttatattatgggctttataag
taaagagcgagagcgggctatcttgtcaacgaagccccgggtacgttcctgttgcgattctcagagagctctaaggaggggtggcgtgac
tttcacgtgggtagagaaagacatctctggtaagactcaaatccaatcagttgaaccgtacacaaagcaacaactgaataacatgtcctt
cgcagaaattatcatggggtacaagattatggacgcgaccaacatcctggtcagtccgctcgtttatctctatcccgatatacctaaaga
agaagcatttggaaagtactgccggccagaatcacaagagcatcctgaggctgatcctggttccgctgcaccgttcttgaaaacgaaatt
catatgtgtcactcctacaacctgttcaaacacgatagaccttccaatgtctcctaggacgttggacagccttatgcagtttggtaataa
tggggaggggccgagccgtccgcgggggtcagtttgagagcctacattcgatatggagctgacctctgagtgtgcaacttctccgat
gaccagatctcgcaagaagcgcagcaccagatctcgcaagaagcgcagcggggcccccatgatatctctgatcgctgctcttgctgtgga
ctacgtgattggtatggagaatgctatgccctggaatctgctgcagacctggcatggtttaagaggaacacccttaataaacctgtaat
catgggagcacatcatgggagactatcggcaggccattgcccgggagggaagaatataattctgagttcccagccttctactgatgatag
ggtaacttgggtcaagagcgtcgacgaggccatcgccgcttgcggggatgtgcctgaaatcatggttatcggggggcggacgggtgattga
gcaatttctgcccaaggcacagaagctgtatctgacccatatagacgccgaggtggagggagatacacactttcccgactatgagcccga
tgattgggagagtgtctttagcgaatttcatgacgccgacgcacagaattcccatagctactgcttcgaaattctcgaacggcgctaggc
ggccgcgcggaatccagactgataagatacttgagtttggacaaaccacaactagaatgcagtgaaaaaaatgctttatttgtgaa
atttgtgatgctattgctttatttgtaaccattataagctgcaataaacaagttaacaacaacaattgcattcattttatgtttcaggtt
cagggggaggtgtgggaggttttttagtcgactggggagagatctgaggaaccctagtgatggagttggccactccctctctgcgcgct
cgctcgctcactgaggccgcccgggcaaagcccgggcgtcgggcgacctttggtcgcccggcctcagtgagcgagcgagcgcgcagagag
ggagtggccaac >STAT3 S727E-DD amino acid sequence (SEQ ID NO: 25)
MAQWNQLQQLDTRYLEQLHQLYSDSFPMELRQFLAPWIESQDWAYAASKESHATLVFHNLLGEIDQQYSRFLQESNVLYQHNLRRIKQFL
QSRYLEKPMEIARIVARCLWEESRLLQTAATAAQQGGQANHPTAAVVTEKQQMLEQHLQDVRKRVQDLEQKMKVVENLQDDFDFNYKTLK
SQGDMQDLNGNNQSVTRQKMQQLEQMLTALDQMRRSIVSELAGLLSAMEYVQKTLTDEELADWKRRQQIACIGGPPNICLDRLENWITSL
AESQLQTRQQIKKLEELQQKVSYKGDPIVQHRPMLEERIVELFRNLMKSAFVVERQPCMPMHPDRPLVIKTGVQFTTKVRLLVKFPELNY
QLKIKVCIDKDSGDVAALRGSRKFNILGTNTKVMNMEESNNGSLSAEFKHLTLREQRCGNGGRANCDASLIVTEELHLITFETEVYHQGL
KIDLETHSLPVVVISNICQMPNAWASILWYNMLTNNPKNVNFFTKPPIGTWDQVAEVLSWQFSSTTKRGLSIEQLTTLAEKLLGPGVNYS
GCQITWAKFCKENMAGKGFSFWVWLDNIIDLVKKYILALWNEGYIMGFISKERERAILSTKPPGTFLLRFSESSKEGGVTFTWVEKDISG
KTQIQSVEPYTKQQLNNMSFAEIIMGYKIMDATNILVSPLVYLYPDIPKEEAFGKYCRPESQEHPEADPGSAAPYLKTKFICVTPTTCSN
TIDLPMEPRTLDSLMQFGNNGEGAEPSAGGQFESLTFDMELTSECATSPMTRSRKKRSTRSRKKRSGAPMISLIAALAVDYVIGMENAMP
WNLPADLAWFKRNTLNKPVIMGRHTWESIGRPLPGRKNIILSSQPSTDDRVTWVKSVDEAIAACGDVPEIMVIGGGRVIEQFLPKAQKLY
LTHIDAEVEGDTHFPDYEPDDWESVFSEFHDADAQNSHSYCFEILERR*

>rAAV vector encoding STAT3 S727E (TMP-regulated phosphomemetic of the transcription
factor STAT3 at amino acid 727) (SEQ ID NO: 26)
ttggccactcctctctgcgcgctcgctcgctcactgaggccgggcgaccaaaggtcgcccgacgcccgggctttgcccggcggcctca
gtgagcgagcgagcgcgcagagaggggagtggccaactccatcactaggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc
cccacgttctgcttcactctccccatctccccccccctccccacccccaattttgtatttatttattttttaattattttgtgcagcgatg
ggggcggggggggggggggcgcgcgccaggcgggggcggggcgagggcgggcgggggcgaggcggagaggtgcggcggcagcc
aatcagagcggcgcgctccgaaagtttccttttatggcgaggcggcggcggcggcggccctataaaaagcgaagcgcgcggcgggcgga
gtcgctgcgcgctgccttcgccccgtgccccgctccgccgccgcctcgcgccgcccgccccggctctgactgaccgcgttactcccacag
gtgagcgggcgggacggcccttctcctccgggctgtaattagcgcttggtttaatgacggcttgtttcttttctgtggctgcgtgaaagc
cttgagggctccgggagggccctttgtgcgggggagcggctcgggggtgcgtgcgtgtgtgtgtgcgtggggagcgccgcgtgcggc

| SEQUENCES |
|---|
| tccgcgctgcccggcggctgtgagcgctgcgggcgcggcgcggggctttgtgcgctccgcagtgtgcgcgaggggagcgcggccggggc |
| ggtgccccgcggtgcgggggggctgcgagggaacaaaggctgcgtgcggggtgtgtgcgtgggggggtgagcaggggtgtgggcgcg |
| tcggtcgggctgcaaccccctgcacccccctccccgagttgctgagcacggccggcttcgggtgcggggctccgtacggggcgtggc |
| gcggggctcgccgtgccggcggggggtggcggcaggtgggggtgccggcggggcggggccgcctcgggcggggagggctcggggggag |
| gggcgcggcggccccggagcgccggcggctgtcgaggcgcggcgagccgcagccattgcctttatggtaatcgtgcgagagggcgcag |
| ggacttcctttgtcccaaatctgtgcggagccgaaatctgggaggcgccgccgcaccccctagcgggcgcggggcgaagcggtgcggc |
| gccggcaggaaggaaatgggcggggagggccttcgtgcgtcgccgcgccgccgtcccctttctccctctccagcctcggggcgtccgcgg |
| ggggacggctgccttcggggggacgggcagggcggggttcggcttctggcgtgtgaccggcggctctagagcctctgctaaccatgtt |
| catgccttcttcttttcctacagctcctgggcaacgtgctggttattgtgctgtctcatcattttggcaaagaattcctcgaagatcta |
| ggcaacgcgtctcgaggcggccgccgccaccatggctcaatggaaccagctccaacagctcgacaccaggtacctggagcaattgcatca |
| actctatagtgatagcttccccatggaactgagacaattccttcgcaccatggatagagtcacaggattgggcgtacgctgcaagcaaaga |
| atctcatgcaaccctcgtatttcataatctcctcggtgagatcgaccagcaatactcacggttccttcaggagtctaatgtgctttatca |
| acacaaccttcgccggattaagcagttcttgcagagccgatatctcgagaagcctatggaaatagctaggatcgttgcaaggtgcttgtg |
| ggaagaaagtagacttctccaaactgcagcaacggctgcgcagcagggtggccaggccaaccacccgacagccgccgtggtaacggaaaa |
| acagcagatgcttgaacaacaccttcaggacgtccgcaaaagagtacaggacctggaacaaaaaatgaaggtcgtcgaaaaccttcagga |
| tgacttcgattttaactataaaacccctcaaatctcagggagatatgcaagacctcaagacctaatcagagcgtcactgcacgagaagat |
| gcagcaacttgagcaaatgcttacgcactggatcagatgcgaaggtccattgtctccgaacttgccgggctcctgtcagccatggagta |
| tgtacagaaaactttgaccgacgaggagttggcagactggaagaggaggcaacagatagcctgcattggcgggcccctaacatttgcct |
| tgacaggttggaaaactggattacatctctggcggagagtcaactgcagacacggcagcaaataaaaaaactggaagagctccagcagaa |
| ggtgagttacaagggggacccaattgtgcagcatcgcccaatgctggaagaacgggattgttgaattgtttaggaacctcatgaaatccgc |
| gtttgtcgtagagagacagccctgtatgccgatgcatcctgatcgaccctcgtgatcaaaactggtgtacaattcacaacaaaagtgag |
| gttgctggtcaagttccctgaactcaactaccaactgaagattaaagtgtgcattgacaaggattctggagacgtggcggcacttcgcgg |
| ttcaagaaagtttaacatactcggcactaatacaaaagttatgaatatggaggagtccaacaacgggtcactgtccgccgaatttaagca |
| cttgacgcttcgcgagcaacgatgtggcaatggggggcagagcaaattgtgcaggagaacatggcggggaaaggtttcag |
| cttttgggtttggttggataacataattgatctcgtaaagaaatacatactggccctctggaatgaaggttatatcatgggcttcattag |
| taaagaacgggagagggccatacttagcactaagcctccaggaacgttcttctcagattttctgagtcttcaaaggagggaggcgtgac |
| cttcacctgggttgaaaaagatatctcaggaaagacacagattcagtccgtcgaaccatatacgaaacagcaactcaataacatgagttt |
| cgcagaaataatcatgggatataagattatgacgcaactaatatactggtgagtccactcgtttatctctacccccgatatcccgaagga |
| ggaagcattcggaaaatactgcagacctgaatcccaggaacatccagaggcgacccaggcctctgccgctccatatttgaaaactaaatt |
| tatctgcgtaacacctacaacttgcagcaatacgatcgatttgcccatggaaccacgcaccctcgatagccttatgcaattcgggaataa |
| tggggaaggagcagaaccctctgcaggaggacaatttgagagcctcacattcgatatggagttgacgtcagaatgcgcaaccagtccaat |
| gaccagatctcgcaagaagcgcagcaccagatctcgcaagaagcgcagcggggccccatgatatctctgatcgctgctcttgctgtgga |
| ctacgtgattggtatggagaatgctatgccctggaatctgccctcgagacctggcatggtttaagaggaacacccttaataaacctgtaat |
| catgggacgacatacatgggagagtatcggcaggccattgcccgggaggaagaataatattctgagttcccagccttctactgatgatag |
| ggtaacttgggtcaagagcgtcgacgaggccatcgccgcttgcggggatgtgcctgaaatcatggttatcgggggcggacgggtgattga |
| gcaatttctgcccaaggcacagaagctgtatctgacccatatagacgccgaggtggagggagatacacactttcccgactatgagcccga |
| tgattgggagagtgtctttagcgaatttcatgacgcccgacgacagaattcccatagctactgcttcgaaattctcgaacggcgctagc |
| ggccgcgcggatccagacatgataagatacattgatgagtttggacaaaccacaactagaatgcagtgaaaaaaatgctttatttgtgaa |
| atttgtgatgctattgctttatttgtaaccattataagctgcaataaacaagttaacaacaacaattgcattcatttatgtttcaggtt |
| cagggggaggtgtgggaggttttttagtcgactggggagagatctgaggaacccctagtgatggagttggccactccctctctgcgcgct |
| cgctcgctcactgaggccgcccgggcaaagcccgggcgtcgggcgacctttggtcgcccggcctcagtgagcgagcgagcgcgcagagag |
| ggagtggccaac |

>VEGFR2 IgG 1-3-DD amino acid sequence (SEQ ID NO: 27)
MQSKVLLAVALWLCVETRAASVGLPSVSLDLPRLSIQKDILTIKANTTLQITCRGQRDLDWLWPNNQSGSEQRVEVTECSDGLFCKTLTI
PKVIGNDTGAYKCFYRETDLASVIYVYVQDYRSPFIASVSDQHGVVYITENKNKTVVIPCLGSISNLNVSLCARYPEKRFVPDGNRISWD
SKKGFTIPSYMISYAGMVFCEAKINDESYQSIMYIVVVVGYRIYDVVLSPSHGIELSVGEKLVLNCTARTELNVGIDFNWEYPSSKHQHK
KLVNRDLKTQSGSEMKKFLSTLTIDGVTRSDQGLYTCAASSGLMTKKNSTTRSRKKRSTRSRKKRSGAPMISLIAALAVDYVIGMENAMP
WNLPADLAWFKRNTLNKPVIMGRHTWESIGRPLPGRKNIILSSQPSTDDRVTWVKSVDEAIAACGDVPEIMVIGGGRVIEQFLPKAQKLY
LTHIDAEVEGDTHFPDYEPDDWESVFSEFHDADAQNSHSYCFEILERR*

>rAAV vector encoding VEGFR2 IgG 1-3 (TMP-regulated IgG loops 1-3 of VEGFR2)
(SEQ ID NO: 28)
| |
|---|
| ttggccactccctctctgcgcgctcgctcgctcactgaggccgggcg -continued

SEQUENCES catgccttcttcttttcctacagctcctgggcaacgtgctggttattgtgctgtctcatcattttggcaaagaattcctcgaagatcta
ggcaacgcgtctcgaggcggccgccgccaccatgcaatcaaaggtgttgctggcggtggccctttggttgtgtgtcgagacccgagcggc
ctccgtgggtcttccctccgtttctctcgatctccctcggttgagcatccaaaaagacatccttaccataaaagcaaacactaccttgca
gatcacatgcagaggtcagagagatctcgattggttgtggcccaataatcagagcgggtccgaacagcgggttgaggtgaccgagtgctc
agatggacttttctgtaagaccctcacgatacccaaagttataggcaacgatactggtgcctacaagtgcttctaccgagaaacggattt
ggcctcagttatatacgtttatgtgcaagattaccgctcccattcatagcgtcagtcagcgaccaacacggcgttgtctacattacgga
aaacaagaataagacggtcgtgataccgtgtctcggaagcatctcaaatctgaatgtctccctgtgcgctcgctacccgtgagaaaaggtt
tgttcctgacggtaacagaatatcctgggatagtaaaaaaggttttacgattccctcctatatgattagttatgctggcagtggttttg
cgaggctaaaatcaacgatgagtcctaccagtcaataatgtatattgtggtggttgtgggctacaggatctacgatgtggttttgtctcc
cagccatggaatcgagttgtctgtaggggaaaaactggtgcttaactgcacagcgagaaccgaactcaacgttgaatagacttcaactg
ggagtacccgagttccaaacaccaacacaaaaaactcgtaaacagggatctgaagacccagtcagggtctgagatgaaaaatttctttc
tactctgacaatagatggagtcacccgctccgatcaagggctctacacttgtgcggcttcctcagggctgatgaccaaaaaaaatcaac
taccagatctcgcaagaagcgcagcaccagatctcgcaagaagcgcagcggggcccccatgatatctctgatcgctgctcttgctgtgga
ctacgtgattggtatggagaatgctatgcctggaatctgcctgcagacctggcatggttaagaggaacacccttaataaacctgtaat
catgggacgacatacatgggagagtatcggcaggccattgcccgggaggaagaatataattctgagttcccagccttctactgatgatag
ggtaacttgggtcaagagcgtcgacgaggccatcgccgcttgcggggatgtgcctgaaatcatggttatcgggggcggacgggtgattga
gcaatttctgcccaaggcacagaagctgtatctgacccatatagacgccgaggtggagggagatacacactttcccgactatgagcccga
tgattgggagagtgtctttagcgaatttcatgacgccgacgcacagaattcccatagctactgcttcgaaattctcgaacggcgctaggc
ggccgcgcggatccagacatgataagatacattgatgagtttggacaaaccacaactagaatgcagtgaaaaaaatgctttatttgtgaa
atttgtgatgctattgctttatttgtaaccattataagctgcaataaacaagttaacaacaattgcattcatttttatgtttcaggtt
caggggaggtgtgggaggttttttagtcgactggggagagatctgaggaacccctagtgatggagttggccactccctctctgcgcgct
cgctcgctcactgaggccgcccgggcaaagcccgggcgtcgggcgacctttggtcgcccggcctcagtgagcgagcgagcgcgcagagag
ggagtggccaac >VEGFR2 IgG 1-7-DD amino acid sequence (SEQ ID NO: 29)
MQSKVLLAVALWLCVETRAASVGLPSVSLDLPRLSIQKDILTIKANTTLQITCRGQRDLDWLWPNNQSGSEQRVEVTECSDGLFCKTLTI
PKVIGNDTGAYKCFYRETDLASVIYVYVQDYRSPFIASVSDQHGVVYITENKNKTVVIPCLGSISNLNVSLCARYPEKRFVPDGNRISWD
SKKGFTIPSYMISYAGMVFCEAKINDESYQSIMYIVVVVGYRIYDVVLSPSHGIELSVGEKLVLNCTARTELNVGIDFNWEYPSSKHQHK
KLVNRDLKTQSGSEMKKFLSTLTIDGVTRSDQGLYTCAASSGLMTKKNSTFVRVHEKPFVAFGSGMESLVEATVGERVRIPAKYLGYPPP
EIKWYKNGIPLESNHTIKAGHVLTIMEVSERDTGNYTVILTNPISKEKQSHVVSLVVYVPPQIGEKSLISPVDSYQYGTTQTLTCTVYAI
PPPHHIHWYWQLEEECANEPSQAVSVTNPYPCEEWRSVEDFQGGNKIEVNKNQFALIEGKNKTVSTLVIQAANVSALYKCEAVNKVGRGE
RVISFHVTRGPEITLQPDMQPTEQESVSLWCTADRSTFENLTWYKLGPQPLPIHVGELPTPVCKNLDTLWKLNATMFSNSTNDILIMELK
NASLQDQGDYVCLAQDRKTKKRHCVVRQLTVLERVAPTITGNLENQTTSIGESIEVSCTASGNPPPQIMWFKDNETLVEDSGIVLKDGNR
NLTIRRVRKEDEGLYTCQACSVLGCAKVEAFFITRSRKKRSTRSRKKRSGAPMISLIAALAVDYVIGMENAMPWNLPADLAWFKRNTLNK
PVIMGRHTWESIGRPLPGRKNIILSSQPSTDDRVTWVKSVDEAIAACGDVPEIMVIGGGRVIEQFLPKAQKLYLTHIDAEVEGDTHFPDY
EPDDWESVFSEFHDADAQNSHSYCFEILERR*

>rAAV vector encoding VEGFR2 IgG 1-7 (TMP-regulated IgG loops 1-7 of VEGFR2)
(SEQ ID NO: 30)
ttggccactcc -continued

SEQUENCES aagaatcaatttgcactcatagaaggaaagaacaagacggtttctactttggtgatacaagccgcaaatgtgtccgcactctataagtgc
gaggcagtcaacaaagttggtcgcggcgagcgggtgataagcttccacgtcacgaggggaccggaaatcactcttcaacccgatatgcaa
cccacggaacaggaatctgtttcactttggtgtacggcggataggagtacgtttgagaacctcacatggtataaattgggaccgcagccc
ttgcctatccacgtgggggagcttcccactcctgtttgcaagaatctggatacactctggaaactgaatgctactatgttcagcaattct
accaatgacatactcattatggaattgaaaaatgcgtcactccaagatcagggagattacgtatgcctcgctcaggaccgcaagactaaa
aagaggcactgtgttgtccggcagcttacagttcttgaacgcgtggcgcctaccattaccggcaatctggagaatcaaactacgtcaatc
ggggagagcatcgaggtctcatgcacggccagcggcaatcctccgccccagattatgtggtttaaagacaatgagacgctggtggaggat
agtgggattgtacttaaggatgggaatcgcaacctcaccattcgaagagtgcgcaaggaggacgaagggttgtacacctgccaagcatgc
tccgttctgggatgcgcaaaagttgaagcattctttataaccagatctcgcaagaagcgcagcaccagatctcgcaagaagcgcagcggg
gcccccatgatatctctgatcgctgctcttgctgtggactacgtgattggtatggagaatgctatgccctggaatctgcctgcagacctg
gcatggtttaagaggaacacccttaataaacctgtaatcatgggacgacatacatgggagagtatcggcaggccattgcccgggaggaag
aatataattctgagttcccagccttctactgatgatagggtaacttgggtcaagagcgtcgacgaggccatcgccgcttgcggggatgtg
cctgaaatcatggttatcgggggcggacgggtgattgagcaatttctgcccaaggcacagaagctgtatctgacccatatagacgccgag
gtggagggagatacacactttcccgactatgagcccgatgattgggagagtgtctttagcgaatttcatgacgccgacgcacagaattcc
catagctactgcttcgaaattctcgaacggcgctaggcggccgcgcggatccagacatgataagatacattgatgagtttggacaaacca
caactagaatgcagtgaaaaaaatgctttatttgtgaaatttgtgatgctattgctttatttgtaaccattataagctgcaataaacaag
ttaacaacaacaattgcattcattttatgtttcaggttcagggggaggtgtgggaggttttttagtcgactggggagagatctgaggaac
ccctagtgatggagttggccactccctctctgcgcgctcgctcgctcactgaggccgcccgggcaaagcccgggcgtcgggcgacctttg
gtcgcccggcctcagtgagcgagcgagcgcgcagagagggagtggccaac >VEGFR2 IgG 2-3-DD amino acid sequence (SEQ ID NO: 31)
MKVLAAGVVPLLLVLHWKHGAGDYRSPFIASVSDQHGVVYITENKNKTVVIPCLGSISNLNVSLCARYPEKRFVPDGNRISWDSKKGFTI
PSYMISYAGMVFCEAKINDESYQSIMYIVVVVGYRIYDVVLSPSHGIELSVGEKLVLNCTARTELNVGIDFNWEYPSSKHQHKKLVNRDL
KTQSGSEMKKFLSTLTIDGVTRSDQGLYTCAASSGLMTKKNSTFVRVHEKPFVAFGSGMTRSRKKRSTRSRKKRSGAPMISLIAALAVDY
VIGMENAMPWNLPADLAWFKRNTLNKPVIMGRHTWESIGRPLPGRKNIILSSQPSTDDRVTWVKSVDEAIAACGDVPEIMVIGGGRVIEQ
FLPKAQKLYLTHIDAEVEGDTHFPDYEPDDWESVFSEFHDADAQNSHSYCFEILERR*

>rAAV vector encoding VEGFR2 IgG 2-3 (TMP-regulated IgG loops 2-3 of VEGFR2)
(SEQ ID NO: 32)
ttggccactccctctctgcgcgctcgctcgctcactgaggccgggcgaccaaaggtcgcccgacgcccgggctttgcccgggcggcctca
gtgagcgagcgagcgcgcagagagggagtggccaactccatcactaggggttcctcagatctgaattcggtacctagttattaatagtaa
tcaattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattta
cggtaaactgcccacttggcagtacatcaagtgtatcatatgccaagtacgccccctattgacgtcaatgacggtaaatggcccgcctgg
cattatgcccagtacatgaccttatgggactttcctacttggcagtacatctacgtattagtcatcgctattaccatggtcgaggtgagc
cccacgttctgcttcactctccccatctcccccccctccccacccccaattttgtatttatttattttttaattattttgtgcagcgatg
ggggcgggggggggggggggcgcgcgccaggcggggcggggcggggcgaggggcggggcggggcgaggcggagaggtgcggcggcagcc
aatcagagcggcgcgctccgaaagtttccttttatggcgaggcggcggcggcggcggccctataaaaagcgaagcgcgcggcgggcggga
gtcgctgcgcgctgccttcgccccgtgccccgctccgccgccgcctcgcgccgcccgccccggctctgactgaccgcgttactcccacag
gtgagcgggcgggacggcccttctcctccgggctgtaattagcgcttggtttaatgacggcttgtttcttttctgtggctgcgtgaaagc
cttgaggggctccgggagggccctttgtgcggggggagcggctcgggggggtgcgtgcgtgtgtgtgtgcgtggggagcgccgcgtgcggc
tccgcgctgcccggcggctgtgagcgctgcgggcgcggcgcggggctttgtgcgctccgcagtgtgcgcgaggggagcgcggccgggggc
ggtgccccgcggtgcggggggggctgcgaggggaacaaaggctgcgtgcggggtgtgtgcgtgggggggtgagcagggggtgtgggcgcg
tcggtcgggctgcaaccccccctgcacccccctccccgagttgctgagcacggcccggcttcgggtgcggggctccgtacggggcgtggc
gcggggctcgccgtgccgggcggggggtggcggcaggtgggggtgccgggcggggcggggccgcctcgggccggggagggctcgggggag
gggcgcggcggcccccggagcgccggcggctgtcgaggcgcggcgagccgcagccattgccttttatggtaatcgtgcgagagggcgcag
ggacttcctttgtcccaaatctgtgcggagccgaaatctgggaggcgccgccgcaccccctctagcgggcgcggggcgaagcggtgcggc
gccggcaggaaggaaatgggcggggagggccttcgtgcgtcgccgcgccgccgtccccttctccctctccagcctcggggctgtccgcgg
ggggacggctgccttcgggggggacggggcagggcggggttcggcttctggcgtgtgaccggcggctctagagcctctgctaaccatgtt
catgccttcttctttttcctacagctcctgggcaacgtgctggttattgtgctgtctcatcattttggcaaagaattcctcgaagatcta
ggcaacgcgtctcgaggcggccgccgccaccatgaaagtccttgccgccggagttgtccctctcttgcttgtactccactggaagcacgg
tgcaggagattatcgctcaccatttatagcgagcgtgtcagatcaacatggcgtggtctatataactgagaataagaataaaacggtcgt
tatcccctgtttgggtagcatatctaacctcaacgttagtttgtgcgctcgataccctgaaaagcggttcgtacccgatggcaatcggat
cagttgggacagtaaaaaaggcttcactattccgtcatacatgatcagctatgcagggatggttttctgcgaagctaaaatcaatgacga
gagttatcagagcattatgtacatcgtagttgtcgttgggtatcgaatttacgacgttgtgctgtccccttctcacggaattgaactctc
cgttggagaaaaactcgtattgaactgtacggcacgcacggaattgaatgtagggatagatttcaactgggagtatccatcatctaaaca
tcaacataaaaaacttgtaaatcgagacctgaagacacagagtgggtccgaaatgaaaaaatttcttagtactctgactatcgacggggt
aacaagatctgatcaagggctgtacacctgtgcggccagctcaggtcttatgacaaaaaaaaactccacttttgtcagagtgcatgaaaa
gccgttcgtggcatttggttcaggtatgaccagatctcgcaagaagcgcagcaccagatctcgcaagaagcgcagcggggcccccatgat
atctctgatcgctgctcttgctgtggactacgtgattggtatggagaatgctatgccctggaatctgcctgcagacctggcatggtttaa
gaggaacacccttaataaacctgtaatcatgggacgacatacatgggagagtatcggcaggccattgcccgggaggaagaatataattct
gagttcccagccttctactgatgatagggtaacttgggtcaagagcgtcgacgaggccatcgccgcttgcggggatgtgcctgaaatcat
ggttatcgggggcggacgggtgattgagcaatttctgcccaaggcacagaagctgtatctgacccatatagacgccgaggtggagggaga
tacacactttcccgactatgagcccgatgattgggagagtgtctttagcgaatttcatgacgccgacgcacagaattcccatagctactg
cttcgaaattctcgaacggcgctaggcggccgcgcggatccagacatgataagatacattgatgagtttggacaaaccacaactagaatg
cagtgaaaaaaatgctttatttgtgaaatttgtgatgctattgctttatttgtaaccattataagctgcaataaacaagttaacaacaac
aattgcattcattttatgtttcaggttcagggggaggtgtgggaggttttttagtcgactggggagagatctgaggaacccctagtgatg
gagttggccactccctctctgcgcgctcgctcgctcactgaggccgcccgggcaaagcccgggcgtcgggcgacctttggtcgcccggcc
tcagtgagcgagcgagcgcgcagagagggagtggccaac

What is claimed is:

1. An isolated nucleic acid comprising an expression cassette flanked by adeno-associated virus (AAV) inverted terminal repeats (ITRs), wherein the expression cassette encodes a fusion protein comprising:
   (i) a Retinal protective factor 2 (RPF2) protein;
   (ii) a destabilization domain (DD); and
   (iii) an amino acid linker comprising two furin cleavage sites, each furin cleavage site positioned between the RPF2 protein and the DD.

2. The isolated nucleic acid of claim 1, wherein the AAV ITRs are AAV2 ITRs.

3. The isolated nucleic acid of claim 1, wherein at least one of the AAV ITRs comprises a mutated terminal resolution site.

4. The isolated nucleic acid of claim 1, wherein the destabilization domain comprises an FK506 binding protein (FKBP) destabilization domain or a dihydrofolate reductase (DHFR) destabilization domain.

5. The isolated nucleic acid of claim 4, wherein the DHFR destabilization domain is capable of binding to trimethoprim (TMP).

6. The isolated nucleic acid of claim 4, wherein the DHFR destabilization domain is an *E. coli* destabilization domain.

* * * * *